United States Patent [19]
Kalindjian et al.

[11] Patent Number: 5,514,683
[45] Date of Patent: May 7, 1996

[54] BICYCLO[2,2,2]OCTANE DERIVATIVES

[75] Inventors: Sarkis B. Kalindjian, Banstead; Caroline M. R. Low, Croydon; Iain M. McDonald, Paddock Wood; Robert A. D. Hull, Tonbridge; Nigel P. Shankley, Nr. Edenbridge; Ildiko M. Buck, London; Katherine I. M. Steel, Beckenham; Jonathan M. R. Davies, Beckenham; David J. Dunstone, London; Elaine A. Harper, London; Michael J. Pether, London; Michael J. Bodkin, London; Matthew J. Tozer, London; Martin L. Hudson, Brighton, all of Great Britain

[73] Assignee: James Black Foundation Limited, Dulwich, United Kingdom

[21] Appl. No.: 288,185

[22] Filed: Aug. 9, 1994

Related U.S. Application Data

[63] Continuation-in-part of PCT/GB93/00346, Feb. 19, 1993.

[30] Foreign Application Priority Data

| Feb. 20, 1992 | [GB] | United Kingdom | 9203608 |
| Jun. 19, 1992 | [GB] | United Kingdom | 9213093 |
| Nov. 24, 1992 | [GB] | United Kingdom | 9224629 |
| Aug. 12, 1993 | [GB] | United Kingdom | 9316722 |

[51] Int. Cl.$^6$ .............. A61K 31/435; A61K 31/41; A61K 31/38; A61K 31/34

[52] U.S. Cl. .......... 514/277; 514/359; 514/438; 514/461; 514/617; 514/620; 514/619; 546/348; 548/250; 548/254; 548/400; 548/566; 548/567; 549/61; 549/74; 549/29; 549/426; 549/356; 549/429; 549/491; 549/497; 560/10; 560/21; 560/25; 560/28; 560/56; 560/80; 562/427; 562/434; 562/443; 562/444; 562/448; 562/452; 562/466; 564/164; 564/165; 564/166; 564/172; 564/180; 558/388; 558/411

[58] Field of Search ............... 562/442, 443, 562/427, 434, 443, 444, 448, 452, 466; 514/620, 277, 359, 438, 461, 617, 619; 560/10, 21, 25, 28, 56, 80; 564/164, 165, 166, 172, 180; 558/388, 411; 548/250, 254, 400, 566, 567; 549/61, 74, 29, 426, 356, 429, 491, 497; 546/348

[56] References Cited

U.S. PATENT DOCUMENTS

| 3,422,104 | 1/1969 | Schroter et al. | 260/247.1 |
| 3,577,366 | 5/1971 | Klandermann et al. | 260/618 |
| 3,950,407 | 4/1976 | Hammar | 260/515 |
| 4,306,063 | 12/1981 | Umen | 544/130 |
| 5,055,468 | 10/1991 | Gray et al. | 514/249 |
| 5,332,820 | 7/1994 | Duncia | 546/118 |

FOREIGN PATENT DOCUMENTS

| 0405537 | 1/1991 | European Pat. Off. . |
| 0532178 | 3/1993 | European Pat. Off. . |
| 0532177 | 3/1993 | European Pat. Off. . |
| 482642  | 1/1970 | Switzerland . |
| 1262972 | 2/1972 | United Kingdom . |

OTHER PUBLICATIONS

Weber et al., "Design of Roof–Shaped Clathrate Hosts. Inclusion Properties and X–ray Crystal Structures of a Free Host and of Inclusion Compounds . . . " *J. Org. Chem.* 53:5831–5839 (Dec. 9, 1988).

Czugler et al., "Selective Clathrate Formation with the New Host Systems cis– and trans–9,10–Dihydro–9,10–ethanoanthracene–11,12–dicarboxylic Acid . . . " *J. Chem. Soc. Chem. Comm.* 23:1632–1634 (1984).

Singh et al., "PMR Spectral Studies of Diels–Alder Adducts: Anthracene–Coronic Acid, Anthracene–Fumaric Acid & β–Naphthol–Fumaric Acid," *Indian J. Chem.* 23B:631–634 (Jul. 1984).

Russell et al., "Aliphatic Semidiones. XIX. Polycyclic Derivatives of Cyclobutanesemidione," *J. Am. Chem. Soc.* 94:1693–1698 (Mar. 8, 1972).

Tolbert et al., "Transition States in Catalyzed and Uncatalyzed Diels–Alder Reactions. Cooperativity as a Probe of Geometry," *J. Am. Chem. Soc.* 106:3806–3810 (1984).

Thebtaranonth, "The Use of Anthracene Adducts in the Synthesis of Natural Products," *Proc. Asian Symp. Med. Plants Species* 1:321–329 (1981).

Leclerco et al., "Etude Des Melanges D'Antipodes Optiques–XII," *Tetrahedron* 32:821–828 (1976).

Brienne et al., "No. 14.–Étude des mélanges d'antipodes optiques. VI.–Dérivés du dihydro–9,10 éthano–9,10anthracéne," *Bull. Soc. Chim.*, Fr. 1:190–197 (1973).

Hagishita et al., "Optical Activity of $C_2$ Symmetrical 9,10–Dihydro–9,10–Ethanoanthracenes," *Tetrahedron* 28:1435–1467 (1972).

Cristol et al., "Bridged Polycyclic Compounds. 83. Steric and Bromine Substituent Acceleration in Bromination Reactions". *J. Org. Chem.* 41:1919–1926 (1976).

Boissier et al., "Synthesis and Pharmacological Properties of New 9,10–Dihydro–9,10–ethanoanthracene Derivatives," *J. Med. Chem.* 10:86–91 (Jan. 1967).

Nanu et al., "Esters of 9,10–dihydroanthracene–endo–α, β–succinic acid as models for the study of large–molecule plasticizers," *Chem. Abs.* 73:3680, abstract no. 3689Z (Jul. 6, 1970).

*Primary Examiner*—José G. Dees
*Assistant Examiner*—Joseph M. Conrad, III
*Attorney, Agent, or Firm*—Foley & Lardner

[57] ABSTRACT

The compounds of the formula I

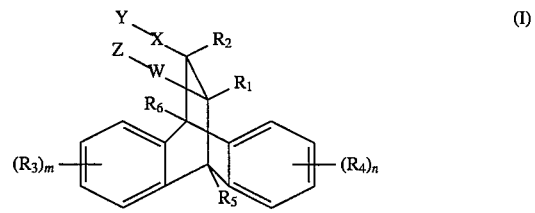

and their pharmaceutical acceptable salts, which are defined herein, are ligands for cholecystokinin and/or gastrin receptors.

19 Claims, No Drawings

BICYCLO[2,2,2] OCTANE DERIVATIVES

This application is a continuation-in-part of PCT/GB93/00346 filed Feb. 19, 1993. The benefit is hereby claimed of the right to an earlier effective filing date based on PCT/GB93/00346 as provided for in 35 USC §120.

This invention relates to bicyclo [2.2.2]octane derivatives, and more particularly to bicyclo [2.2.2]octane derivatives which bind to cholecystokinin and/or gastrin receptors. The invention also relates to methods for preparing such bicyclo [2.2.2]octane derivatives and to compounds which are useful as intermediates in such methods.

Gastrin and CCK's are structurally-related neuropeptides which exist in gastrointestinal tissue and in the CNS (see Mutt V., *Gastrointestinal Hormones*, Glass G. B. J., ed., Raven Press, N.Y., p 169 and Nisson G., ibid, p. 127).

Gastrin is one of the three primary stimulants of gastric acid secretion. Several forms of gastrin are found including 34-, 17-, and 14-amino acid species with the minimum active fragments being the C-terminal tetrapeptide (TrpMetAsp-Phe-$NH_2$) which is reported in the literature to have full pharmacological activity (see Tracey H.J. and Gregory R.A., Nature (London), 1964, 204, 935). Much effort has been devoted to the synthesis of analogues of this tetrapeptide (and the N-protected derivative Boc-TrpMetAspPhe-$NH_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal motility, gall bladder contraction, pancreatic enzyme secretion, and are known to have a trophic action on the pancreas. They also inhibit gastric emptying and have various effects in the CNS.

Compounds which bind to cholecystokinin and/or gastrin receptors are important because of their potential pharmaceutical use as antagonist of the natural peptides.

A number of gastrin antagonists have been proposed for various therapeutic applications, including the prevention of gastrin-related disorders, gastrointestinal ulcers, Zollinger-Ellison syndrome, antral G Cell hyperplasia and other conditions in which lowered gastrin activity is desirable. The hormone has also been shown to have a trophic action on cells and so an antagonist may be expected to be useful in the treatment of cancers, particularly in the stomach and the colon.

Possible therapeutic uses for cholecystokinin antagonists include the control of appetite disorders such as anorexia nervosa, and the treatment of pancreatic inflammation, biliary tract disease and various psychiatric disorders. Other possible uses are in the potentiation of opiate (e.g. morphine) analgesia, and in the treatments of cancers, especially of the pancreas. Moreover, ligands for cholecystokinin receptors in the brain (so-called $CCK_B$ receptors) have been claimed to posses anxiolytic activity.

According to the present invention, there is provided a method for counteracting an effect of cholecystokinin or gastrin in a patient, said method comprising administering to said patient an effective amount of a compound of the formula

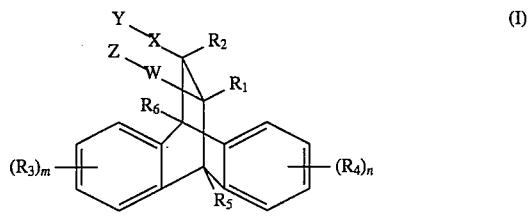

wherein

W is a carbonyl, sulphonyl or sulphinyl group, and X is a carbonyl, sulphonyl or sulphinyl group or -C(O)-$CH_2$- (in which the carbonyl group is bonded to Y), provided that at least one of W and X contains carbonyl, Y is $R_7$—O— or $R_7$—N($R_8$)— (wherein $R_7$ is H or $C_1$ to $C_{15}$ hydrocarbyl, up to two carbon atoms of the hydrocarbyl moiety optionally being replaced by a nitrogen, oxygen or sulphur atom provided that Y does not contain a —O—O— group, and $R_8$ is H, $C_1$ to $C_3$ alkyl, carboxymethyl or esterified carboxymethyl), Z is selected from
i) —O—$R_9$
   wherein $R_9$ is H, $C_1$ to $C_5$ alkyl, phenyl, substituted phenyl, benzyl or substituted benzyl;
ii)

wherein Q is H, $C_1$ to $C_5$ hydrocarbyl, or —$R_{10}$—U, wherein $R_{10}$ is bond or $C_1$ to $C_3$ alkylene and U is aryl, substituted aryl, heterocyclic, substituted heterocyclic or cycloalkyl;

iii)

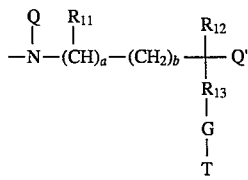

wherein a is 0 or 1 and b is from 0 to 3,
$R_{11}$ is H or methyl,
$R_{12}$ is H or $C_1$ to $C_3$ alkyl; or $R_{12}$ is $CH_2$= and Q' is absent; or $R_{11}$ and $R_{12}$ are linked to from a 3- to 7-membered ring,
$R_{13}$ is a bond or $C_1$ to $C_5$ hydrocarbylene,
G is a bond, —CHOH— or —C(O)—
Q' is recited above for Q or —$R_{10}$—(C(O))$_d$—L—(C(O))$_e$—$R_9$ (wherein $R_9$ and $R_{10}$ are as defined above, L is O, S or —N($R_{14}$)—, in which $R_{14}$ is as defined above for $R_8$, and d and e are 0 or 1, provided that d+e<2); or Q' and $R_{12}$, together with the carbon atom to which they are attached, from a 3 to 7-membered ring,
Q is defined above, or Q and $R_{12}$ together form a group of the formula —(CH$_2$)$_f$—V—(CH$_2$)$_g$— wherein V is —S—, —S(O)—, —S(O)$_2$—, —$CH_2$—, —CHOH— or —C(O)—, f is from 0 to 2 and g is from 0 to 3; or when Q' is —$R_{10}$—U and U is an aromatic group, Q may additionally represent a methylene link to U, which link is ortho to the $R_{10}$ link to U,
T is H, cyano, $C_1$ to $C_4$ alkyl, —$CH_2$OH, carboxy, esterified carboxy or amidated carboxy; or iv)

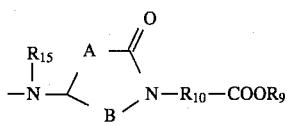

wherein A and B are independently a bond or $C_1$ to $C_3$ alkylene, provided that A and B together provide from 2 to 4 carbon atoms in the ring, $R_9$ and $R_{10}$ are as defined above, and $R_{15}$ is as defined above for $R_8$ or Z is absent and W is H, $R_1$ is H, methyl, halo, carboxy, esterified carboxy, amidated carboxy, carboxymethyl, esterified carboxymethyl or amidated carboxymethyl, $R_2$ is selected from the groups recited above for $R_1$; or, when Z is absent and W is H, $R_2$ may additionally represent —C(O)—Z' wherein Z' is selected from the groups recited above for Z; or $R_1$ and $R_2$ together form a second bond between the carbon atoms to which they are attached, $R_3$ $R_4$ (or each $R_3$ and $R_4$ group, when m or n is 2 or more) are independently selected from halo, amino, nitro, cyano, sulphamoy, sulphonyl, trifluoromethyl, $C_1$ to $C_3$ alkyl, $C_1$ to $C_3$ alkoxy, hydroxy, $C_1$ to $C_3$ hydroxyalkyl, $C_1$ to $C_3$ alkylcarboxyamino, carboxy, esterified carboxy and amidated carboxy $R_5$ and $R_6$ are independently selected from H and the groups recited above for $R_3$ m is from 0 to 4, provided that m is not more than 2 unless $R_3$ is exclusively halo, n is from 0 to 4, provided that n is not more than 2 unless $R_4$ is exclusively halo, or a pharmaceutically acceptable salt thereof.

A number of compounds falling within the above definition are known from U.S. Pat. No. 3,950,407; Weber et al, J. Org. Chem. 53, 5831–9 (1988); Czugler et al, J. Chem. Soc., Chem Commun. (23), 1632–4 (1984); Russell et al, J. Am. Chem. Soc. 94(5), 1693–8 (1972); Chem. Abs. 73, no. 3689z (1970); and Singh et al, Ind. J. Chem. 23B, 631–4 (1984). However, compounds according to the above definition are believed to be novel per se, provided that if one (but only one) of $R_1$ and $R_2$ is methyl, m and n are not both 0, Z is not hydroxy or methoxy when Y is hydroxy or methoxy, Z and Y are not trans to each other when Z is $R_8$—O— and Y is $R_7$—O—, —X—Y does not equal —W—Z when $R_1$=$R_2$=H and m=n=0, and if Z is absent and $R_1$ and $R_2$ are both H, Y is not $R_7$—O— and further provided that the compounds are not 7-(N,N-dimethylaminocarbonyl)-8-methyl-2,3,5,6-dibenzobicyclo[2.2.2]octane or 7-(N-methyl-N-phenylaminocarbonyl)-8-methyl-2,3,5,6-dibenzobicyclo[2.2.2]octane.

CCK inhibitors of different structures are disclosed in EP-A-0405537 and U.S. Pat. No. 3,577,366.

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al, "Prodrugs", *Drug Delivery Systems*, pp. 112–176 (1985), and *Drugs*, 29, pp. 445–473 (1985).

Pro-drug forms of the pharmacologically-active compounds of the invention include compounds according to formula (I) in which Y and/or Z include an esterified or amidated acid group.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups, A "carbocyclic" group, as the term is used herein, comprises one or more closed chains or rings, which consist entirely of carbon atoms. Included in such groups are alicyclic groups (such as cyclopropyl, cyclobutyl, cyclopentyl, cyclohexyl and adamantyl), groups containing both alkyl and cycloalkyl moieties (such as methyl adamantyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above.

A "heterocyclic" group comprises one or more closed chains or rings which have at least one atom other than carbon in the closed chain or ring. Examples include benzimidazolyl, thienyl, furanyl, pyrrolyl, imidazolyl, pyrazolyl, thiazolyl, isothiazolyl, oxazolyl, pyrrolinyl, pyrrolinyl, imidazolidinyl, imidazolinyl, pyrazolindinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

The term "halogen", as used herein, refers to any of fluorine, chlorine, bromine and iodine. Most usually, however, halogen substituents in the compounds of the invention are chlorine or fluorine substituents.

Preferably, m and n are both O. However, when m and n are not both 0, $R_3$ and $R_4$ are preferably selected from halo, hydroxy, amino, nitro, cyano, sulphamoyl, $C_1$ to $C_3$ alkyl and $C_1$ and $C_3$ alkoxy. As mentioned above, when m or n is 2 or more, each $R_3$ and $R_4$ group is independent of the others. For example, the compounds of the invention may include two different $R_3$ groups.

Particularly preferred groups for $R_5$ and $R_6$ are hydrogen and the groups just recited for $R_3$, and especially hydrogen, methyl and fluoro.

When reference is made herein to a "substituted" aromatic group, the substituents will generally be from 1 to 3 in number (and more usually 1 or 2 in number), and generally selected from the groups recited above for $R_3$. However, halo substituents may be up to 5 in number.

An "esterified" carboxy group, as the term is used herein, is preferably of the form —$COOR_{16}$, wherein $R_{16}$ is $C_1$ to $C_5$ alkyl, phenyl, substituted phenyl, benzyl, substituted benzyl, heteroaryl or one of the following:

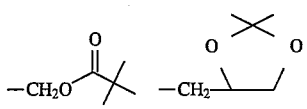

Most commonly, $R_{16}$ is $C_1$ to $C_5$ alkyl, benzyl or substituted benzyl, and particularly $C_1$–$C_5$ alkyl. Similarly, an "amidated" carboxy group is preferably of the form —$CONR_{17}R_{18}$ wherein $R_{17}$ is H, $C_1$ to $C_5$ alkyl, phenyl, substituted phenyl, benzyl or substituted benzyl, and $R_{18}$ is —OH or one of the groups just recited for $R_{17}$.

In the case of the group T, preferred amidated carboxy groups take the form —$CONR_{17}R_{18}$ (wherein $R_{17}$ and $R_{18}$ are as defined above) or

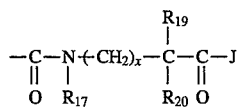

wherein $R_{17}$ is as defined above, $R_{19}$ and $R_{20}$ are independently H or methyl, or $R_{19}$ and $R_{20}$ (together with the carbon atom to which they are attached) for a 3- to 7-membered carbocyclic group, J is —OH, —O—$R_{16}$ or —$NHR_{18}$, wherein $R_{16}$ and $R_{18}$ are as defined above, and x is 0 to 3.

When $R_{11}$ and $R_{12}$ are linked to form a ring, such ring will generally be saturated, and usually also carbocyclic. Similarly, when Q' and $R_{12}$ are linked to form a ring, this will also usually be saturated and carbocyclic.

Exemplary carbocyclic and heterocyclic groups which may form the group U include:

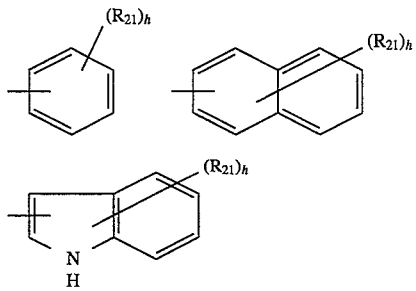

wherein $R_{21}$ is as defined above for $R_3$, and h is from 0 to 3, and

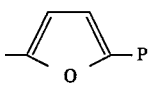

wherein P is H or —$COOR_{22}$, in which $R_{22}$ is as defined above for $R_{17}$.

In a preferred embodiment, Z is —$NH_2$, —O—$R_9$ or

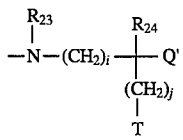

wherein i is from 0 to 4, j is from 0 to 3, $R_{23}$ and $R_{24}$ are independently H or methyl, or $R_{23}$ and $R_{24}$ together form a group of the formula —$(CH_2)_k$—V'—$CH_2$— (wherein V' is —$CH_2$—, —CHOH— or —C(O)—, and k is 0 to 2). Most commonly, i is 0 or 1 and j is 0 to 2.

When W is sulphinyl, Y is preferably $R_7$—NH—.

Preferably, $R_7$ is $C_6$ to $C_8$ straight or branched chain alkyl or cycloalkyl, or $R_{25}$—$(CH_2)_p$—, wherein $R_{25}$ is selected from phenyl, 1-naphthyl, 2-naphthyl, indolyl, norbornyl, 1-adamantyl, 2-adamantyl, cyclohexyl or cycloheptyl, and p is from 0 to 3.

Most preferably, the compounds of the invention are of the formula

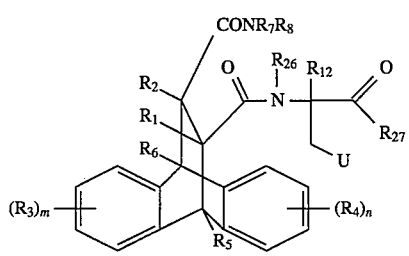

wherein $R_1$, $R_2$, $R_3$, $R_4$, $R_5$, $R_6$, $R_7$, $R_8$, $R_{12}$ and U are as defined above, $R_{26}$ is H or $C_1$ to $C_3$ alkyl, and $R_{27}$ is

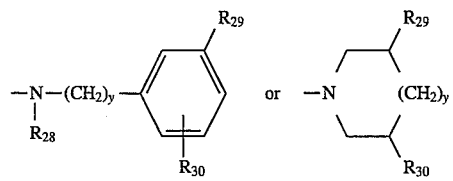

(wherein $R_{28}$ is H or $C_1$ to $C_3$ alkyl, $R_{29}$ is —$CO_2H$ or tetrazolyl, $R_{30}$ is H, —$CO_2H$, tetrazolyl, —$CH_2OH$, —$CO_2Me$ or —$CONH_2$, and y is from 0 to 2).

Pharmaceutically acceptable salts of the acidic compounds of the invention include salts with alkali metals and alkaline earth metals, such as sodium, potassium, calcium and magnesium, and salts with organic bases. Suitable organic bases include amines such as N-methyl-D-glucamine.

Pharmaceutically acceptable salts of the basic compounds of the invention include salts derived from organic or inorganic acids. Suitable acids include hydrochloric acid, phosphoric acid, oxalic acid, maleic acid, succinic acid and citric acid.

The compounds of the invention exist in various enantiomeric and diastereomeric forms as a result of the asymmetric carbon atoms to which W and X are attached. It will be understood that the invention comprehends the different enantiomers and diastereomers in isolation from each other, as well as mixtures of enantiomers and diastereomers. Also, the structural formulae herein show the groups W and X arranged cis to each other, but it will be appreciated that the invention includes the corresponding trans isomers.

Compounds according to the present invention in which W is a carbonyl group, X is carbonyl or sulphonyl, and Z is OH may conveniently be made by the process depicted in Reaction Scheme A.

Reaction Scheme A

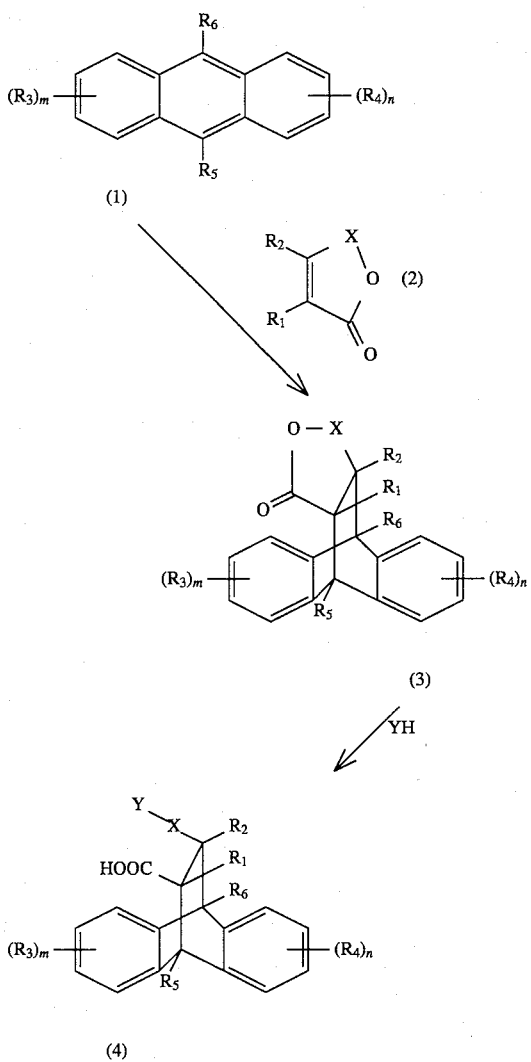

In this scheme, anthracene or an anthracene derivative (1) is reacted with the acid anhydride (2) in a Diels-Alder reaction. The reactants are conveniently refluxed together in a suitable solvent such as toluene to form the adduct (3). In some cases, it may be appropriate to conduct the reaction at elevated pressure and/or in the presence of a Lewis acid catalyst. The adduct (3) is then reacted with a compound of the formula YH (ie. either an alcohol or an amine) to form the acid compound (4). If YH is an amine, the reaction is suitably carried out in a solvent such as THF in the presence of a catalytic amount of DMAP. If YH is an alcohol, the reaction may be conducted in pyridine at elevated temperature.

The invention therefore also provides a method of making compounds wherein W is carbonyl and X is carbonyl or sulphonyl, said method including the step of reacting a compound of the formula

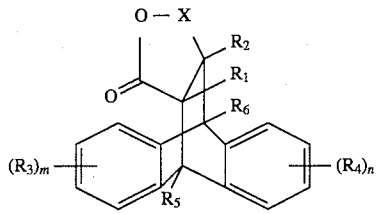

with a compound of formula YH.

The equivalent trans adducts can be prepared using a suitably differentiated fumaric acid (e.g. the mono methyl mono benzyl diester), which, after addition to anthracene or an anthracene derivative (1), allows independent elaboration of the two sidechains.

Compounds in which Z is other than OH may of course be made from the acid compound (4) by conventional esterification or amidation reactions. Suitable amidation methods are described in detail in "The Peptides, Vol. 1", Gross and Meinenhofer, Eds., Academic Press, New York, 1979. These include the carbodiimide method (using, for example, 1,3-dicyclohexylcarbodiimide [DCC] or 1-(3-dimethylaminopropyl)-3-ethylcarbodiimide hydrochloride [EDCI], and optionally an additive such as 1-hydroxybenzotriazole [HOBT] to prevent racemization), the azide method, the mixed anhydride method, the symmetrical anhydride method, the acid chloride method, the use of bis (2-oxo-3-oxazolidinyl) phosphinic chloride [BOP-Cl], the use of PyBOP or PyBrOP, the use of the isopropenylsuccinimido carbonate method and the active ester method (using, for example, N-hydroxysuccinimide esters, 4-nitrophenyl esters or 2,4,5-trichlorophenol esters).

The coupling reactions are generally conducted under an inert atmosphere, such as an atmosphere of nitrogen or argon. Suitable solvents for the reactants include methylene chloride, tetrahydrofuran [THF], dimethoxyethane [DME] and dimethylformamide [DMF].

When both W and X are carbonyl, and Z is other than OH, it is of course possible to open the adduct (3) by reacting it with a compound of the formula ZH (suitably protected, if necessary), rather than YH, and then esterifying or amidating the free carboxyl group of the resulting compound using YH.

A procedure analogous to that shown in reaction scheme A may also be used as the basis for preparing the compounds of the invention in which W is sulphonyl and Y is $R_7$—O—, as depicted in reaction scheme B below:

Reaction Scheme B

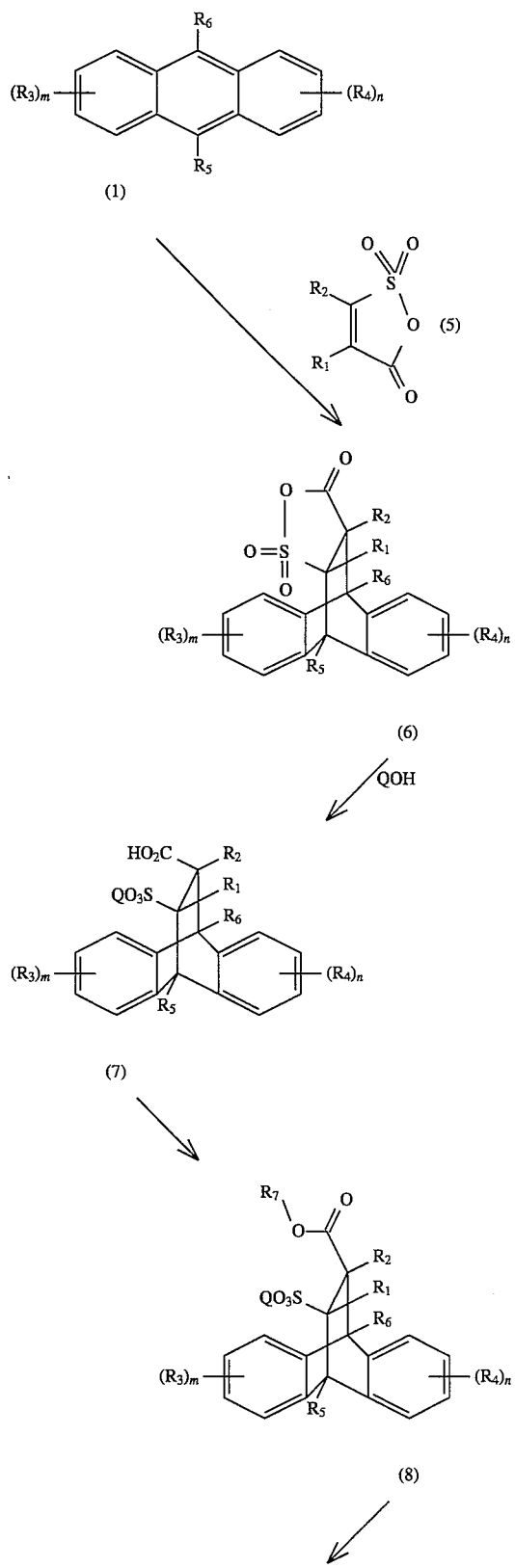

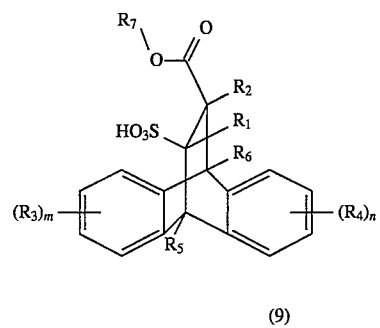

In this case, the Diels-Alder adduct (6) is opened with an alcohol such as benzyl alcohol (represented as QOH), so that product (7) is the corresponding sulphonyl ester. The free carboxylic acid group of this sulphonyl ester may then be esterified by conventional methods, followed by hydrogenolysis of the product (8) to yield the desired sulphonic acid carboxylic ester (9).

The compounds of the invention in which W is sulphonyl and Y is $R_7$—NH— may be prepared by analogous means, in which compound (7) is amidated (rather than esterified) prior to hydrogenolysis. Alternatively, a process such as is depicted in reaction scheme C may be employed:

Reaction Scheme C

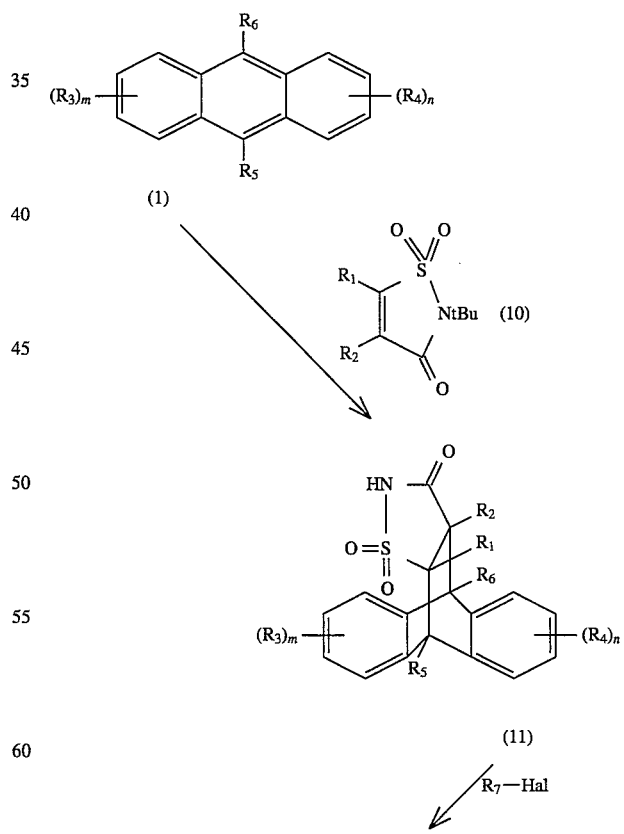

-continued
Reaction Scheme C

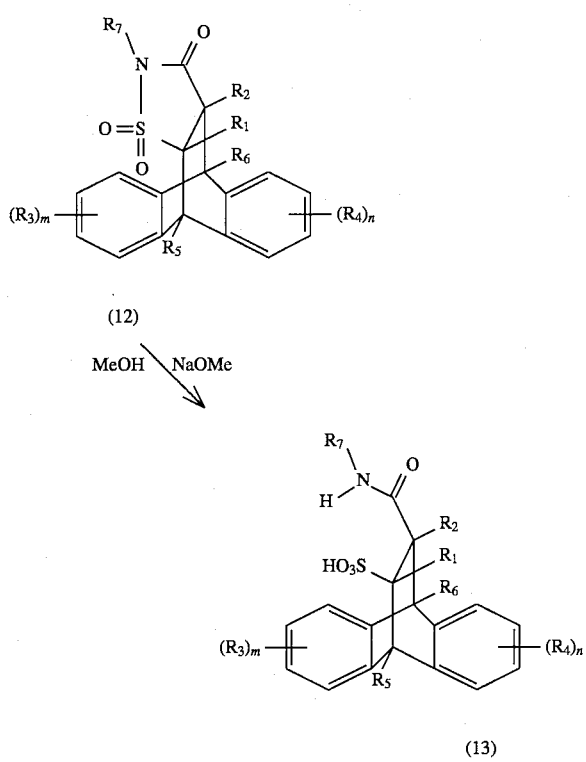

(12)

MeOH, NaOMe (13)

In this scheme, anthracene or an anthracene derivative (1) is reacted with the N-protected compound (10) in a Diels-Alder reaction analogous to that of the first step in reaction scheme A. The deprotected product Diels-Alder Adduct (11) is then reacted with a compound of the formula $R_7$-Hal (wherein Hal represents a halogen atom) to form compound (12). The N-containing ring may then be opened using an alkoxide (eg. sodium methoxide in methanol) to produce the target compound (13).

The invention therefore also provides a method of making compounds wherein W is sulphonyl and Y is $R_7$—NH—, said method comprising the step of reacting a compound of the formula

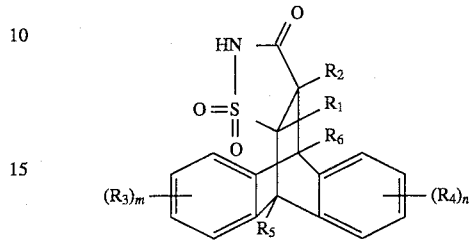

with a compound of the formula $R_7$-Hal, and then reacting the product with an alkoxide.

Compounds of the invention wherein W or X is a sulphinyl group may conveniently be prepared by the route shown in reaction scheme D:

Reaction Scheme D

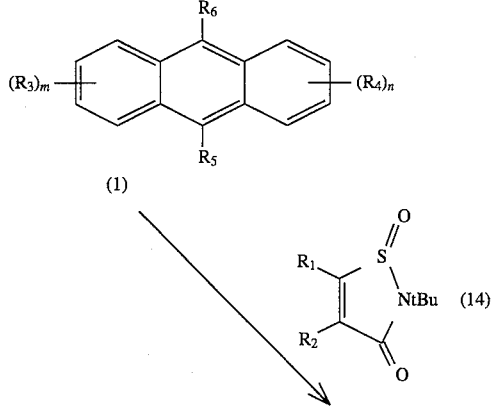

-continued
Reaction Scheme D

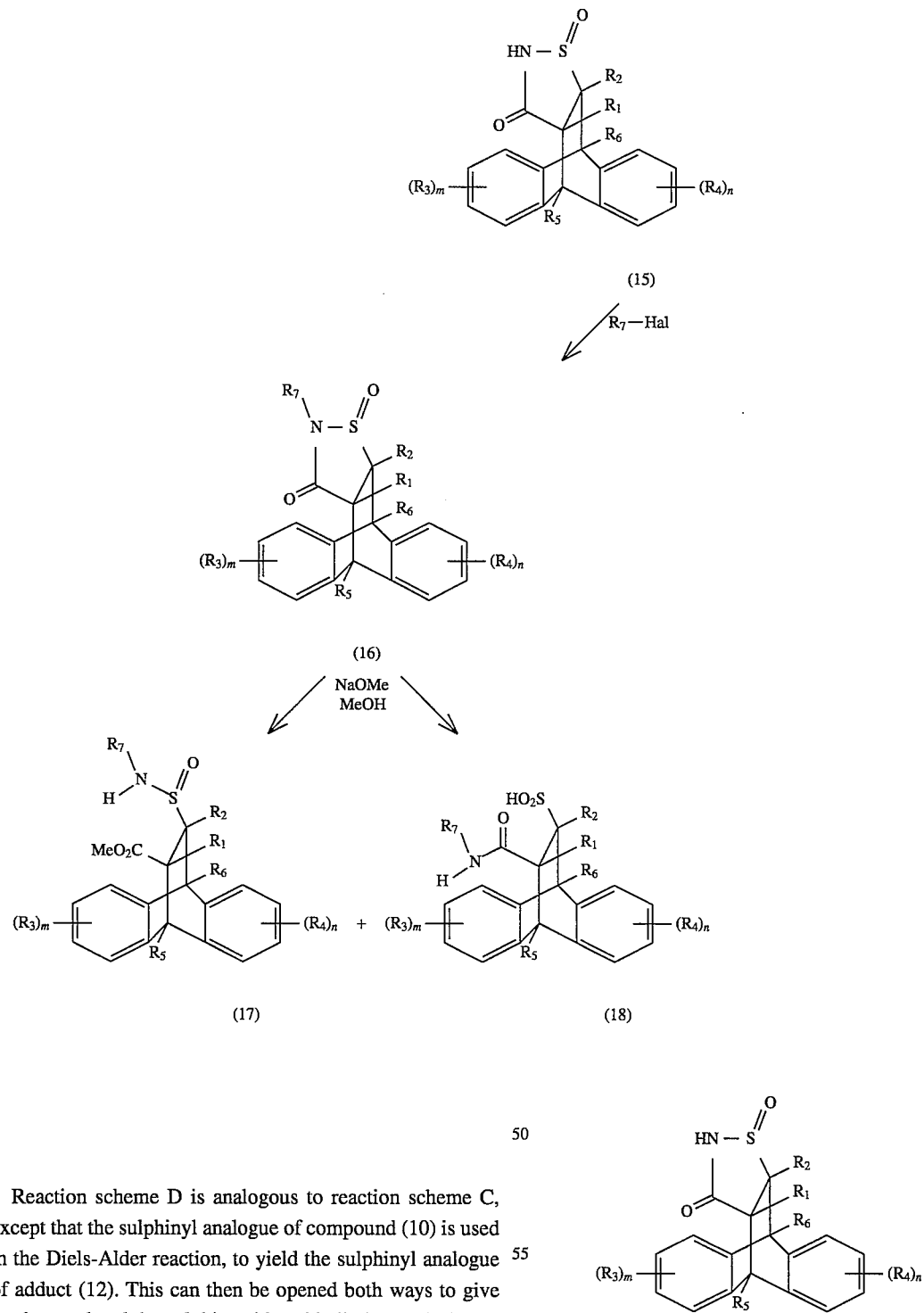

Reaction scheme D is analogous to reaction scheme C, except that the sulphinyl analogue of compound (10) is used in the Diels-Alder reaction, to yield the sulphinyl analogue of adduct (12). This can then be opened both ways to give on the one hand the sulphinamide acid alkyl ester (17), and on the other the sulphinic acid amide (18). The free sulphinamide acid can of course be obtained from the alkyl ester (12) by conventional methods.

Accordingly, the invention also provides a method of making compounds wherein W or X is sulphinyl, said method comprising the step of reacting a compound of the formula:

with a compound of the formula $R_7$-Hal, and then reacting the product with an alkoxide.

While reaction schemes C and D above led to the free sulphonic or sulphinic acid compounds, it will be appreciated that the corresponding ester or amide derivatives can be prepared from the free acid compounds by conventional methods. Most usually, coupling of the sulphonic or sulphinic acid compounds will be via the corresponding sulphonic or sulphinic acid chlorides.

Pharmaceutically acceptable salts of the acidic or basic compounds of the invention can of course be made by conventional procedures, such as by reacting the free base or acid with at least a stoichiometric amount of the desired salt-forming acid or base.

The compounds of the invention can be administered by oral or parenteral routes, including intravenous, intramuscular, intraperitoneal, subcutaneous, rectal and topical administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch an alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the severity of the condition being treated and the weight of the patient. In general, however, the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be between 0.01 µg/kg and 50 mg/kg, especially between 10 µg/kg and 10 mg/kg, eg. between 100 µg/kg and 2 mg/kg.

The invention is now further illustrated by means of the following examples.

EXAMPLE 1

Preparation of (±)-cis-8-(3-phenylpropylaminocarbonyl)-2,3,5,6-dibenzobicyclo[2.2.2]octane-7-carboxylic acid a. 2,3,5,6-dibenzobicyclo[2.2.2]octane-7,8-dicarboxylic acid anhydride Anthracene (8.9 g, 0.05 mol) and maleic anhydride (4.9 g, 0.05 mol) were refluxed for 3 h in toluene (200 ml). Upon cooling, the title compound was obtained as white crystals which were isolated by filtration (10.2 g 74%).

b. (±)-cis-8-(3-phenylpropylaminocarbonyl)-2,3,5,6-dibenzobicyclo[2.2.2]octane-7-carboxylic acid 2,3,5,6-dibenzobicyclo[2.2.2]octane-7,8-dicarboxylic acid anhydride (107 mg, 0.39 mmol) and 1-phenyl-3-propylamine (55 mg, 0.4 mmol) were dissolved in dry THF (5 ml) and DMAP (2 mg) was introduced. The mixture was stirred at room temperature overnight during which time a thick white precipitate formed. The solid was filtered off, washed with THF and dried to give the title compound (100 mg 62%), mp 190°–1°, found: C, 78.82; H, 5.99; N, 3.40. $C_{27}H_{25}NO_3$ requires C, 78.81; H, 6.12; N, 3.38

EXAMPLE 2

Preparation of (±)-cis-8-(2-(3-indolyl)ethylaminocarbonyl)-2,3,5,6-dibenzobicyclo[2.2.2]octane-7-carboxylic acid The compound was prepared essentially as in example 1 except that tryptamine was used instead of 1-phenyl-3-propylamine in step b. Yield 84%, m.p. 137°–8°, found: C, 74.13; H, 6.12; N, 5.73. $C_{28}H_{24}N_2O_3 \cdot 0.7 H_2O \cdot 0.6$ THF requires C, 74.16; H, 6.18; N, 5.69%

EXAMPLE 3

Preparation of (±)-cis-8-(phenylmethylaminocarbonyl)-2,3,5,6-dibenzobicyclo[2.2.2]octane-7-carboxylic acid The compound was prepared essentially as in example 1 except that benzylamine was used instead of 1-phenyl-3-propylamine in step b. Yield 27%, m.p. 194°–5°, found: C, 77.35; H, 5.97; N, 3.36. $C_{25}H_{21}NO_3 \cdot 0.5$ THF requires C, 77.30; H, 6.18; N, 3.34

EXAMPLE 4

Preparation of (±)-cis-8-(1-naphthylmethylaminocarbonyl)-2,3,5,6-dibenzobicyclo[2.2.2]octane-7-carboxylic acid The compound was prepared essentially as in example 1 except that 1-naphthylmethylamine was used instead of 1-phenyl-3-propylamine in step b. Yield 35%, m.p. 135°–7°, found: C, 78.37; H, 6.07; N, 2.98. $C_{29}H_{23}NO_3 \cdot 1.0$ THF requires C, 78.39; H, 6.18; N, 2.77

EXAMPLE 5

Preparation of (±)-cis-8-(2-naphthylmethylaminocarbonyl)-2,3,5,6-dibenzobicyclo[2.2.2]octane-7-carboxylic acid The compound was prepared essentially as in example 1 except that 2-naphtylmethylamine was used instead of 1-phenyl-3-propylamine in step b. Yield 35%, m.p. 247°–8°, found: C, 80.46; H, 5.03; N, 3.32. $C_{29}H_{23}NO_3$ requires C, 80.46; H, 5.03; N, 3.23

EXAMPLE 6

Preparation of (±)-cis-8-(2-norbornylmethylaminocarbonyl)-2,3,5,6-dibenzobicyclo[2.2.2]octane-7-carboxylic acid The compound was prepared essentially as in example 1 except that 2-norbornylmethylamine was used instead of 1-phenyl-3-propylamine in step b. Yield 24%, m.p. 127°–9°, found: C, 74.93; H, 7.07; N, 3.76. $C_{26}H_{27}NO_3 \cdot 0.75 H_2O$ requires C, 75.24; H, 6.92; N, 3.38

EXAMPLE 7

Preparation of (±)-cis-8-(hexylaminocarbonyl)-2,3,5,6-dibenzobicyclo[2.2.2]octane-7-carboxylic acid The compound was prepared essentially as in example 1 except that hexylamine (2eq) was used instead of 1-phenyl-3-propylamine in step b. and the product was precipitated with 2M HCl and then filtered and washed with water. Yield 91%, m.p. 174°–6°, found: C, 76.52; H, 7.24; N, 3.98. $C_{24}H_{27}NO_3$ requires C, 76.36; H, 7.21; N, 3.71

EXAMPLE 8

Preparation of (±)-cis-8-(octylaminocarbonyl)-2,3,5,6-dibenzobicyclo[2.2.2]octane-7-carboxylic acid The compound was prepared essentially as in example 7 except that octylamine was used instead of hexylamine. Yield 89%, m.p. 116°–8°, found: C, 76.83; H, 7.70; N, 3.58. $C_{26}H_{31}NO_3$ requires C, 77.01; H, 7.71; N, 3.45

EXAMPLE 9

Preparation of (±)-cis-8-(cyclohexylmethylaminocarbonyl)-2,3,5,6-dibenzobicyclo[2.2.2]octane-7-carboxylic acid The compound was prepared essentially as in example 7 except that cyclohexylmethylamine was used instead of hexylamine. Yield 93%, m.p. 185°–7°, found: C, 76.88; H, 7.09; N, 3.69. $C_{25}H_{27}NO_3$ requires C, 77.09; H, 6.99; N, 3.60

EXAMPLE 10

Preparation of (±)-cis-8-(3,3-dimethylbutylaminocarbonyl)-2,3,5,6-dibenzobicyclo[2.2.2]octane-7-carboxylic acid The compound was prepared essentially as in example 7 except that 3,3-dimethylbutylamine was used instead of hexylamine. Yield 25%, m.p. 128°–30°, found: C, 74,56; H, 7.22; N, 3.29. $C_{24}H_{27}NO_3$. 0.2 $H_2O$ requires C, 75.64; H, 7.25; N, 3.68

EXAMPLE 11

Preparation of (±)-cis-8-(1-adamantylaminocarbonyl)-2,3,5,6-dibenzobicyclo[2.2.2]octane-7-carboxylic acid 2,3,5,6-dibenzobicyclo[2.2.2]octane-7,8-dicarboxylic acid anhydride (prepared in example 1 step a) (276 mg, 1.0 mmol) was dissolved in THF (5 ml) and 1-adamantamine (215 mg, 1.4 mmole) was added followed by triethylamine (0.16 ml). The solution was heated at a gentle reflux for 1.5 h and the clear solution on cooling was poured onto 2M HCl (20 ml). The resulting gummy solid was extracted with dichloromethane (10 ml) and the organic layer was dried, filtered and evaporated. The residue was taken up in methanol (5 ml) and diluted with water (5 ml) to precipitate a white solid. This was filtered off and dried. The product (230 mg, 54%), m.p. 234°–5°, found: C, 76.14; H, 6.72; N, 3.10. $C_{28}H_{29}NO_3$.0.75 $H_2O$ requires C, 76.25; H, 6.97; N, 3.17

EXAMPLE 12

Preparation of (±)-cis-8-(2-(1-adamantyl)ethylaminocarbonyl)-2,3,5,6-dibenzobicyclo[2.2.2]octane-7-carboxylic acid The compound was prepared essentially as in example 11 except that 1-adamantylethylamine was used instead of 1-adamantylamine. Yield 26%, m.p. 138°–40°, found: C, 77.31; H, 7.21; N, 2.70. $C_{30}H_{33}NO_3$. 0.6 $H_2O$ requires C, 77.26; H, 7.39; N, 3.00

EXAMPLE 13

Preparation of (±)-cis-8-(-1-adamantylmethyloxycarbonyl)-2,3,5,6-dibenzobicyclo[2.2.2]octane-7-carboxylic acid 2,3,5,6-dibenzobicyclo[2.2.2]octane-7,8-dicarboxylic acid anhydride (prepared in example 1 step a) (276 mg, 1.0 mmol) and 1-adamantanemethanol (166 mg, 1.0 mmol) were heated together in pyridine (2 ml) at 100° for 4 h. After cooling the solution was poured onto 2M HCl and extracted with dichloromethane (20 ml). The solution was dried filtered and evaporated to leave a white residue which was further purified by column chromatography (silica dichloromethane/ethyl acetate/methanol 9:1:0.5 as eluent). The product was further triturated with hexane to leave the title compound (110 mg, 25%), m.p. 165°, found C, 77.14; H, 6.88. $C_{29}H_{30}O_4$.0.5 $H_2O$ requires C, 77.13; H, 6.19

EXAMPLE 14

Preparation of (±)-cis-8-(1-adamantylmethylaminocarbonyl)-2,3,5,6-dibenzobicyclo[2.2.2]octane-7-carboxylic acid 2,3,5,6-dibenzobicyclo[2.2.2]octane-7,8-dicarboxylic acid anhydride (prepared in example 1 step a) (276 mg, 1.0 mmol) and 1-adamantanemethylamine (182 mg, 1.1 mmol) were dissolved in dry THF (5 ml) and refluxed for 1 h. A thick white precipitate was formed and this was isolated by filtration and washed with THF to leave the title compound (320 mg, 72%), m.p. 237°–9°, found: C,78.76; H, 7.18; N, 3.33. $C_{29}H_{31}NO_3$ requires C, 78.88; H, 7.08; N, 3.17% The compound was further characterised as the N-methyl-D-glucamine salt found: C, 63.48; H, 7.61; N, 3.79. $C_{36}H_{48}N_2O_8$. 2.5$H_2O$ requires C, 63.42; H, 7.83; N, 4.11

EXAMPLE 15

Preparation of (±)-cis-7-(methoxycarbonylmethylaminocarbonyl)-8-(1-adamantylmethylaminocarbonyl)-2,3,5,6-dibenzobicyclo[2.2.2]octane.

(±)-cis-8-(1-adamantylmethylaminocarbonyl)-2,3,5,6-dibenzobicyclo[2.2.2]octane-7-carboxylic acid prepared as in example 14 (441 mg, 1.0 mmol) was dissolved in warm DMF (5 ml) and then the solution was cooled to 0°. N-hydroxysuccinimide (115 mg, 1.0 mmol) was added followed by DCCI (206 mg, 1.0 mmol). The reaction was allowed to warm to room temperature and stirred overnight. The white precipitate was removed by filtration. Triethylamine (0.2 ml) was added to the filtrate followed by glycine methyl ester hydrochloride (125 mg, 1 mmol) and the reaction mixture was stirred for a further 24 h. The reaction mixture was poured onto a mixture of 2M HCl and ice. The white precipitate was isolated by filtration and washed well with water and dried. The solid was taken up in ethyl acetate (20 ml) and filtered through celite. The residue on evaporation was triturated with methanol leaving a white crystalline solid (125 mg, 24%), m.p. 209°–11°, found C, 74.16; H, 7.14; N, 5.53 $C_{32}H_{36}N_2O_4$ requires C, 74.19; H, 7.12; N, 5.40

EXAMPLE 16

Preparation of (±)-cis-7-(carboxymethylaminocarbonyl)-8-(1-adamantylmethylaminocarbonyl)-2,3,5,6-dibenzobicyclo[2.2.2]octane a. (±)-cis-7-(benzyloxycarbonylmethylaminocarbonyl)-8-(1-adamantylmethylaminocarbonyl)-2,3,5,6-dibenzobicyclo[2.2.2]octane (±)-Cis-8-(1-adamantylmethylaminocarbonyl)-2,3,5,6-dibenzobicyclo[2.2.2]octane-7-carboxylic acid (prepared as in example 14) (440 mg, 1 mmole) and PyBOP (520 mg, 1 mmole) were taken up in dry dichloromethane (15 ml) and Hunigs base (0.52 ml, 3 mmole) was added. The reaction mixture was stirred under an atmosphere of dry argon for 1 h. glycine benzyl ester 4-toluenesulphonic acid salt (340 mg, 1 mmole) was added and the mixture stirred overnight. The organic layer was washed with 5% potassium hydrogensulphate (15 ml), sodium hydrogencarbonate (15 ml) and saturated brine (15 ml). It was then dried, filtered and evaporated to leave the crude title compound which was further purified by column chromatography on silica using 80% ethyl acetate and 20% hexane as eluent. The title compound (510 mg, 87%) was isolated as a white solid, m.p. 130°–3° b. (±)-cis-7-(carboxymethylaminocarbonyl)-8-(1-adamantylmethylaminocarbonyl)-2,3,5,6-dibenzobicyclo[2.2.2]octane The product of step a (350 mg, 0.59 mmole) was dissolved in methanol (20 ml) and 10% palladium on charcoal (100 mg) was added. The mixture was stirred under an atmosphere of hydrogen for 3 h. The product was filtered through celite and on evaporation yielded the title compound (0.30 g, 100%). The product was characterised and tested as the N-methyl-D-glucamine salt, m.p. 110°–2°, found: C, 63.42; H, 7.55; N, 5.66. $C_{38}H_{51}N_3O_9$. 1.5 $H_2O$ requires C, 63.42; H, 7.68; N, 5.66%.

EXAMPLE 17

Preparation of methyl (±)-cis-8-(1-adamantylmethylaminocarbonyl)-2,3,5,6-dibenzobicyclo[2.2.2]octane-7-carboxylate 2,3,5,6-dibenzobicyclo[2.2.2]octane-7,8-dicarboxylic acid anhydride (prepared as in example 1 step a) (2.76 g, 6.0 mmol), methanol (0.41 ml) and DMAP (20 mg) were stirred in pyridine (5 ml). The solution was stirred and refluxed for 4 h, poured onto 2M HCl (50 ml) and extracted with dichloromethane. The organic layer was washed with mor 2M HCl and water. The solution was dried filtered and evaporated to yield the crude monoester (1.7 g). This material (308 mg, 1 mmol) and 1-adamantanemethylamine (181 mg, 1.0 mmol) were dissolved in dry dichloromethane (10 ml) and diisopropylethylamine (0.35 ml) was added followed by PyBOP (520 mg, 1 mmol). The solution was stirred at room temperature for 72 h. It was then evaporated and the residue taken up in ethyl acetate and washed successively with 5% aqueous potassium hydrogensulphate (3×40 ml), saturated aqueous sodium hydrogencarbonate (40 ml) and brine (40 ml). The organic layer was dried, filtered and evaporated to leave a foam that was purified by column chromatography (silica eluent 90% dichloromethane and 10% ethyl acetate). Further purification was achieved by recrystallisation from methanol. Yield 200 mg, 44%, m.p. 227°–30°, found: C, 79.06; H, 7.54; N, 2.94. $C_{30}H_{33}NO_3$ requires C, 79.09; H, 7.30; N, 3.07

EXAMPLE 18

Preparation of (±)-cis-8-(2-naphthylmethylaminocarbonyl)-2,3,5,6-dibenzobicyclo[2.2.2]octane-7-sulphonic acid a. Diels-Alder adduct of anthracene and 3-oxo-2,3-dihydroisothiazolone N-t-butyl-3-oxo-2,3-dihydroisothiazolone (prepared as in Helv.Chim. Acta., 1989, 72, 1416) (200 mg, 1.1 mmol) and anthracene (178 mg, 1 mmol) were suspended in dry toluene (2 ml) and a catalytic amount of anhydrous aluminium chloride was added. The reaction mixture was stirred and refluxed overnight. On cooling a white solid separated which was filtered and washed successively with toluene and pentane and air dried. The solid was then taken up in ethyl acetate and washed with dilute HCl and brine and finally dried and evaporated to leave a white solid (185 mg, 62%)

b. Alkylation of the Diels-Alder adduct

The product from step a (312 mg, 1 mmol), anhydrous potassium carbonate (138 mg, 1 mmol) and 2-bromomethylnaphthalene (225 mg, 1 mmol) were dissolved in dry DMF (3 ml) and stirred and heated to 100° for 4 h. After cooling the solution was poured onto cold water (30 ml) and the resulting white solid filtered off and dried in an oven. The solid was triturated with hexane/toluene/ethanol 9:9:2 and the solid was recrystallised from ethanol (178 mg, 39%), m.p. 184°–5° c. 8-(2-naphthylmethylaminocarbonyl)-2,3,5,6-dibenzobicyclo[2.2.2]octane-7-sulphonic acid Sodium (16 mg, 0.7 mmol) was dissolved in methanol (5 ml) and the product from step b was added (225 mg, 0.5 mmol). The reaction was stirred and refluxed for 1 h. The reaction mixture was cooled and acidified with concentrated HCl. The reaction mixture was then evaporated and the residue partitioned between water and ethyl acetate. The organic layer was dried and evaporated. The product was recrystallised from chloroform. Yield 152 mg, 32%, m.p. 245°–7° found: C, 68.74; H, 4.88; N, 2.83. $C_{28}H_{23}NO_4S$. 1.0 $H_2O$ requires C, 68.97; H, 5.16; N, 2.87

EXAMPLE 19

Preparation of (±)-cis-8-(phenylmethylaminocarbonyl)2,3,5,6-dibenzobicyclo[2.2.2]octane-7-sulphonic acid This was prepared essentially as in example 18 using benzyl bromide in step b instead of 2-bromomethylnaphthalene m.p. 245°–7° found: C, 68.764; H, 4.81; N, 3.19. $C_{24}H_{21}NO_4S$ requires C, 68.72; H, 5.05; N, 3.34

EXAMPLE 20

Preparation of (±)-cis-8-(2-naphthylmethylaminosulphonyl)-2,3,5,6-dibenzobicyclo[2.2.2]octane-7-carboxylic acid a. Diels-Alder adduct of anthracene and β-sulphoacrylic anhydride β-sulphoacrylic anhydride (prepared as in J.A.C.S. 1962, 84, 653) (184 mg, 1.0 mmol) and anthracene (178 mg, 1 mmol) were suspended in dry toluene (6 ml) and refluxed under an atmosphere of dry nitrogen for 3 h. The reaction mixture was decanted from a small amount of tarry residue and cooled in ice. White crystals that separated were filtered off and washed with a little hexane and dried. Yield 163 mg, 52% b. (±)-cis-8-(2-naphthylmethylaminosulphonyl)-2,3,5,6-dibenzobicyclo[2.2.2]octane-7-carboxylic acid The Adduct from step a (207 mg, 0.66 mmole) and 2-naphthylmethylamine (209 mg, 1.33 mmol) were dissolved in dry THF (5 ml) and DMAP (5 mg) was added. The solution was stirred at room temperature overnight and evaporated to dryness. The residue was taken up in methanol and water and stirred with Amberlite IR-120(plus) resin, filtered and evaporated. The residue was triturated with ether, to yield the title compound 215 mg, 68% m.p. 212-15 found: C, 69.78; H, 4.98; N, 2.98. $C_{28}H_{23}NO_4S$. 0.7 $H_2O$ requires C, 69.75; H, 5.10; N, 2.91

EXAMPLE 21

Preparation of (±)-cis-8-(2-(3-indolyl)ethylaminosulphonyl)-2,3,5,6-dibenzobicyclo[2.2.2]octane-7-carboxylic acid This was prepared essentially as in example 20 but using tryptamine instead of 2-naphthylmethylamine in step b, m.p.>220° found: C, 68.87; H, 5.17; N, 6.07. $C_{27}H_{24}N_2O_4S$ requires C, 68.63; H, 5.12; N, 5.92

EXAMPLE 22

Preparation of (±)-cis-8-(1-adamantylmethylaminosulphonyl)-2,3,5,6-dibenzobicyclo[2.2.2]octane-7-carboxylic acid This was prepared essentially as in example 21 but using 1-adamantylmethylamine instead of 2-naphthylmethylamine in step b, m.p. 135°–40° found: C, 69.90; H, 6.49; N, 2.68. $C_{28}H_{31}NO_4S$. 0.2 $H_2O$ requires C, 69.89; H, 6.58; N, 2.91

EXAMPLE 23

Preparation of cis-7-(1-R-carboxy-ethylaminocarbonyl)-8-(1-adamantylmethylaminocarbonyl)-2,3,5,6-dibenzobicyclo[2.2.2]octane (mixture of diastereomers)

(±)-cis-8-(1-adamantylmethylaminocarbonyl)-2,3,5,6-dibenzobicyclo[2.2.2]octane-7-carboxylic acid (prepared as in example 14) (440 mg, 1 mmol) was dissolved by warming in dry DMF (10 ml). Isopropenylsuccinimido carbonate (200 mg, 1 mmole) was then added at room temperature. A catalytic amount of DMAP was added and the reagents stirred for 4 h. Triethylamine (0.168 ml, 1.2 mmole) was added followed by D-alanine (100 mg, 1.1 mmole) and the reaction left to stir at room temperature for 60 h. The reaction mixture was poured onto 2N HCl and the white precipitate so formed was isolated by filtration. The solid was further purified by column chromatography (silica, dichloromethane to 90% dichloromethane and 10% methanol) to leave the title compound (50 mg). The compound was characterised and tested as the N-methyl-D-glucamine salt m.p. 128°–30°, found: C, 61.98; H, 7.42; N, 5.85. $C_{39}H_{53}N_3O_9$. 2.4 $H_2O$ requires C, 62.32; H, 7.75; N, 5.59

EXAMPLE 24

Preparation of cis-(±)-7-(2-methoxycarbonylethylaminocarbonyl)-8-(1-adamantylmethylaminocarbonyl)-2,3,5,6-dibenzobicyclo[2.2.2]octane This was prepared essentially as in example 23 using beta-alanine methyl ester instead of D-alanine, m.p. 207°, found: C, 74.98; H, 7.46; N, 5.27. $C_{33}H_{38}N_2O_4$ requires C, 75.26; H, 7.27; N, 5.32

EXAMPLE 25

Preparation of cis-7-(1-S-methoxycarbonyl-ethylaminocarbonyl)-8-(1-adamantylmethylaminocarbonyl)-2,3,5,6-dibenzobicyclo[2.2.2]octane (mixture of diastereomers)

(±)-cis-8-(1-adamantylmethylaminocarbonyl)-2,3,5,6-dibenzobicyclo[2.2.2]octane-7-carboxylic acid (prepared as in example 14) (440 mg, 1 mmole) and PyBOP (520 mg, 1 mmole) were taken up in dry dichloromethane (15 ml) and Hunigs base (0.52 ml, 3 mmole) was added. The reaction mixture was stirred under an atmosphere of dry argon for 1 h. L-alanine methyl ester hydrochloride (140 mg, 1 mmole) was added and the mixture stirred overnight. The organic layer was washed with 5% potassium hydrogensulphate (15 ml), sodium hydrogencarbonate (15 ml) and saturated brine (15 ml). It was then dried, filtered and evaporated to leave the crude title compound which was further purified by column chromatography on silica using 80% ethyl acetate and 20% hexane as eluent. The title compound (300 mg, 57%) was isolated as a white solid, m.p. 107°, found: C, 75.33; H, 7.25; N, 5.16. $C_{33}H_{38}N_2O_4$ requires C, 75.26; H, 7.27; N, 5.32

EXAMPLE 26

Preparation of cis-7-(1-S-methoxycarbonyl-ethylaminocarbonyl)-8-(1-adamantylmethylaminocarbonyl)-2,3,5,6-dibenzobicyclo[2.2.2]octane Diastereomer A The compound of example 25 was separated into its component diastereomers by preparative HPLC using a silica phase column and 50% ethyl acetate and 50% hexane as eluent. The title compound diastereomer A had a retention time of 18.4 minutes and was isolated as a white powder, m.p.95°–100°, $[\alpha]^D=-10.5°$ (c=1.66 in methanol), found: C, 75.32; H, 7.14; N, 5.33. $C_{33}H_{38}N_2O_4$ requires C, 75.26; H, 7.27; N, 5.32

EXAMPLE 27

Preparation of cis-7-(1-S-methoxycarbonyl-ethylaminocarbonyl)-8-(1-adamantylmethylaminocarbonyl)-2,3,5,6-dibenzobicyclo[2.2.2]octane Diastereomer B The compound of this example was the second diastereomer isolated by the HPLC technique described in example 26. The title compound diastereomer B had a retention time of 21.7 minutes and was isolated as a white powder, m.p.75°–85°, $[\alpha]^D=+3.8°$ (c=1.57 in methanol), found: C, 73.41; H, 7.37; N, 5.20. $C_{33}H_{38}N_2O_4$. 0.73 $H_2O$ requires C, 73.42; H, 7.37; N, 5.20

EXAMPLE 28

Preparation of cis-7-(1-R-methoxycarbonyl-ethylaminocarbonyl)-8-(1-adamantylmethylaminocarbonyl)-2,3,5,6-dibenzobicyclo[2.2.2]octane (mixture of diastereomers)

The reaction was performed essentially as in example 25 but using D-alanine methyl ester hydrochloride instead of the L-isomer. The title compound (300 mg, 57%) was isolated as a white solid, m.p. 113°–5°, found: C, 74.41; H, 7.42; N, 5.14. $C_{33}H_{38}N_2O_4$.0.33 $H_2O$ requires C, 74.41; H, 7.32; N, 5.26

EXAMPLE 29

Preparation of cis-(±)-7-(2-benzyloxycarbonyl-ethylaminocarbonyl)-8-(1-adamantylmethylaminocarbonyl)-2,3,5,6-dibenzobicyclo[2.2.2]octane The reaction was performed essentially as in example 25 but using the benzyl ester of beta alanine instead of L-alanine methyl ester hydrochloride. Yield 70%, m.p. 77°–8°, found: C, 76.67; H, 7.04; N, 4.52. $C_{39}H_{42}N_2O_4$.0.43 $H_2O$ requires C, 76.73; H, 7.08; N, 4.59

EXAMPLE 30

Preparation of cis-(±)-7-(2-carboxy-ethylaminocarbonyl)-8-(1-adamantylmethylaminocarbonyl)-2,3,5,6-dibenzobicyclo[2.2.2]octane The product of example 29 (370 mg, 0.6 mmole) was dissolved in ethanol (20 ml) and 10% palladium on charcoal (100 mg) was added. The mixture was stirred under an atmosphere of hydrogen overnight. The product was filtered through celite and on evaporation yielded the title compound, 56%. The product was characterised and tested as the N-methyl-D-glucamine salt, m.p. 75°–8°, found: C, 62.54; H, 7.94; N, 5.31. $C_{39}H_{53}N_3O_9$. 2.44 $H_2O$ requires C, 62.31; H, 7.76; N, 5.59

EXAMPLE 31

Preparation of cis-7-(1-S-aminocarbonyl-ethylaminocarbonyl)-8-(1-adamantylmethylaminocarbonyl)-2,3,5,6-dibenzobicyclo[2.2.2]octane (mixture of diastereomers)

The reaction was performed essentially as in example 25 but using L-alaninamide hydrochloride instead of the L-alanine methyl ester hydrochloride. Yield 81%, m.p. 175°–185°, $[\alpha]^D=-6.5°$ (c=1 in methanol), found: C, 73.13; H, 7.53; N, 7.95. $C_{32}H_{37}N_3O_3$. 0.76 $H_2O$ requires C, 73.16; H, 7.39; N, 8.00

EXAMPLE 32

Preparation of cis-7-(1-S-hydroxymethyl)-ethylaminocarbonyl)-8-(1-adamantylmethylaminocarbonyl)-2,3,5,6-dibenzobicyclo[2.2.2]octane (mixture of diastereomers)

The reaction was performed essentially as in example 25 but using L-alaninol instead of the L-alanine methyl ester hydrochloride. Yield 76%, m.p. 115°–120°, $[\alpha]^D=-4.0°$ (c=1 in methanol), found: C, 73.09; H, 7.82; N, 5.32. $C_{32}H_{38}N_2O_3$. 1.5 $H_2O$ requires C, 73.14; H, 7.86; N, 5.33

EXAMPLE 33

Preparation of cis-7-(1-S-benzyloxycarbonyl-ethylaminocarbonyl)-8-(1-adamantylmethylaminocarbonyl)-2,3,5,6-dibenzobicyclo[2.2.2]octane Diastereomer A The reaction was performed essentially as in example 25 but using the L-alanine benzyl ester of instead of L-alanine methyl ester hydrochloride. Overall yield 62%, The two diastereomers were separated by column chromatography (silica eluant 93% dichloromethane and 7% ethyl acetate). The less polar isomer has been designated diastereomer A, the title compound, Retention time HPLC silica 50% hexane and 50% ethyl acetate 7.9 min, m.p. 92°–4°, $[\alpha]^D=-5.0°$ (c=1 in chloroform), found: C, 75.49; H, 7.12; N, 4.40. $C_{39}H_{42}N_2O_4$.1.0 $H_2O$ requires C, 75.39; H, 7.15; N, 4.51

EXAMPLE 34

Preparation of cis-7-(1-S-benzyloxycarbonyl-ethylaminocarbonyl)-8-(1-adamantylmethylaminocarbonyl)-2,3,5,6-dibenzobicyclo[2.2.2]octane Diastereomer B The more polar isomer from the chromatographic separation outlined in example 33 was designated diastereomer B, Retention time HPLC silica 50% hexane and 50% ethyl acetate 10.9 min, m.p. 90°–5°, $[\alpha]^D=-1.0°$ (c=1 in chloroform), found: C, 77.66; H, 7.24; N, 4.41. $C_{39}H_{42}N_2O_4$ requires C, 77.71; H, 7.02; N, 4.65

EXAMPLE 35

Preparation of cis-7-(1-S-carboxyethylaminocarbonyl)-8-(1-adamantylmethylaminocarbonyl)-2,3,5,6-dibenzobicyclo[2.2.2]octane Diastereomer A The compound was prepared essentially as described in example 30 but using the product of example 33 instead of cis-(±)-7-(2-benzyloxycarbonyl-ethylaminocarbonyl)-8-(1-adamantylmethylaminocarbonyl)-2,3,5,6-dibenzobicyclo[2.2.2]octane (the product of example 29) as the substrate. Yield 87%, $[\alpha]^D=-16.0°$ (c=1 in methanol). The compound was further characterised and tested as the N-methyl-D-glucamine salt, m.p. 100°–105°, found: C, 60.66; H, 7.82; N, 5.74. $C_{39}H_{53}N_3O_9$. 3.4 $H_2O$ requires C, 60.93; H, 7.84; N, 5.47%.

EXAMPLE 36

Preparation of cis-7-(1-S-carboxyethylaminocarbonyl)-8-(1-adamantylmethylaminocarbonyl)-2,3,5,6-dibenzobicyclo[2.2.2]octane Diastereomer B The compound was prepared essentially as described in example 30 but using the product of example 34 instead of cis-(±)-7-(2-benzyloxycarbonyl-ethylaminocarbonyl)-8-(1-adamantylmethylaminocarbonyl)-2,3,5,6-dibenzobicyclo[2.2.2]octane (the product of example 29) as the substrate. Yield 99%, $[\alpha]^D=+3.5°$ (c=1 in methanol). The compound was further characterised and tested as the N-methyl-D-glucamine salt, m.p. 105°–110°, found: C, 61.89; H, 7.67; N, 5.72. $C_{39}H_{53}N_3O_9$. 2.6 $H_2O$ requires C, 62.03; H, 7.77; N, 5.57%.

EXAMPLE 37

Preparation of endo-cis-(±)-8-(1-adamantylmethylaminocarbonyl)-2,3-benzo-5,6-(2,5-dimethoxybenzo)bicyclo[2.2.2]octane-7-carboxylic acid a. Diels-Alder adduct of 1,4-dimethoxyanthracene Maleic anhydride (0.21 g, 2.18 mmole) and 1,4-dimethoxyanthracene (0.52 g, 2.18 mmole) were dissolved in toluene (5 ml) and heated to reflux for 4 h under an atmosphere of argon. The solvent was evaporated and the residue washed with dichloromethane affording a white powder which was recrystallised from acetone to yield the exo adduct (140 mg), used in the preparation of example 38. The endo adduct was obtained as a white solid on addition of hexane to the dichloromethane solution, which was filtered and dried (143 mg).

b. endo-cis-(±)-8-(1-adamantylmethylaminocarbonyl)-2,3-benzo-5,6-(2,5-dimethoxybenzo)bicyclo[2.2.2]octane-7-carboxylic acid The endo adduct (from step a) (132 mg, 0.39 mmole) was dissolved in THF (3 ml) and 1-adamantylmethylamine (70 mg, 0.39 mmole) was added. The reaction was stirred at room temperature under an atmosphere of argon for 15 min. The solution was evaporated and taken up in dichloromethane and precipitated with hexane. The solution was filtered and dried, dissolved in warm ether and decanted from insoluble material. Addition of hexane, cooling and filtration gave the title compound (93 mg, 48%). The compound was characterised and tested as the N-methyl-D-glucamine salt, m.p. 99°–103°, found: C, 61.63; H, 7.73; N, 3.92. $C_{38}H_{52}N_2O_{10}$. 2.3 $H_2O$ requires C, 61.76; H, 7.73; N, 3.79%.

EXAMPLE 38

Preparation of exo-cis-(±)-8-(1-adamantylmethylaminocarbonyl)-2,3-benzo-5,6-(2,5-dimethoxybenzo)bicyclo[2.2.2]octane-7-carboxylic acid The compound was prepared essentially as in example 37 step b but using the exo anhydride from example 37, step a, rather than the endo isomer. Yield 88%. The compound was characterised and tested as the N-methyl-D-glucamine salt, m.p. 109°–112°, found C, 63.07; H, 7.70; N, 3.71. $C_{38}H_{52}N_2O_{10}$. 1.5 $H_2O$ requires C, 63.04; H, 7.66; N, 3.87%.

EXAMPLE 39

Preparation of cis-(±)-8-(2-adamantylmethylaminocarbonyl)-2,3-benzo-5,6-(2,5-dimethoxybenzo)bicyclo[2.2.2]octane-7-carboxylic acid The compound was prepared essentially as in example 1 step b using 2-adamantylmethylamine instead of 1-phenyl-3-propylamine. Yield 85%. The compound was characterised and tested as the N-methyl-D-glucamine salt, found: C, 67.73; H, 7.81; N, 4.41. $C_{36}H_{48}N_2O_8$ requires C, 67.90; H, 7.60; N, 4.40%.

EXAMPLE 40

Preparation of cis-7-(1-S-dimethylaminocarbonylethylaminocarbonyl)-8-(1-adamantylmethylaminocarbonyl)-2,3,5,6-dibenzobicyclo[2.2.2]octane (mixture of diastereomers)

The reaction was performed essentially as in example 25 but using L-alanine-N,N-dimethylamide trifluoroacetate instead of the L-alanine methyl ester hydrochloride. Yield 79%, m.p. 130°–5°, $[\alpha]^D = -14°$ (c=1 in methanol) found: C, 72.58; H, 7.86; N, 7.35. $C_{34}H_{41}N_3O_3$. 1.3 $H_2O$ requires C, 72.49; H, 7.81; N, 7.46

EXAMPLE 41

Preparation of cis-7-(1-S-methoxycarbonylethylaminocarbonyl)-8-(cyclohexylmethylaminocarbonyl)-2,3,5,6-dibenzobicyclo[2.2.2]octane (mixture of diastereomers)

The reaction was performed essentially as in example 25 but using (±)-cis-8-(1-cyclohexylmethylaminocarbonyl)-2,3,5,6-dibenzobicyclo[2.2.2]octane-7-carboxylic acid (prepared in example 9) instead of (±)-cis-8-(1-adamantylmethylaminocarbonyl)- 2,3,5,6-dibenzobicyclo[2.2.2]octane-7-carboxylic acid. Yield 59%, m.p. 80°–2°, found: C, 73.10; H, 7.31; N, 5.78. $C_{29}H_{34}N_2O_4$ requires C, 73.39; H, 7.22; N, 5.90

EXAMPLE 42

Preparation of cis-7-[methoxycarbonylmethyl-(N-methyl)-aminocarbonyl]-8-(1-adamantylmethylaminocarbonyl)-2,3,5,6-dibenzobicyclo[2.2.2]octane The reaction was performed essentially as in example 25 but using the methyl ester of sarcosine hydrochloride instead of the L-alanine methyl ester hydrochloride. Yield 74%, m.p. 185°–7°, found: C, 75.47; H, 7.33; N, 5.22. $C_{33}H_{38}N_2O_4$ requires C, 75.26; H, 7.27; N, 5.32

EXAMPLE 43

Preparation of cis-7-[ethoxycarbonylmethyl-(N-methyl)-aminocarbonyl]-8-(1-adamantylmethylaminocarbonyl)-2,3,5,6-dibenzobicyclo[2.2.2]octane The reaction was performed essentially as in example 25 but using the ethyl ester of sarcosine hydrochloride instead of the L-alanine methyl ester hydrochloride. Yield 57%, found: C, 75.40; H, 7.51; N, 5.03. $C_{34}H_{40}N_2O_4$ requires C, 75.53; H, 7.46; N, 5.18

EXAMPLE 44

Preparation of (±)-trans-8-(1-adamantylmethylaminocarbonyl)-2,3,5,6-dibenzobicyclo[2.2.2]octane-7-carboxylic acid a. (±)-trans-8-ethoxycarbonyl-2,3,5,6-dibenzobicyclo[2.2.2]octane-7-carboxylic acid Anthracene (5 g, 28 mmol) and fumaric acid monoethyl ester (4.04 g, 28 mmol) were dissolved in dioxan (50 ml) and the solution heated at reflux for 3d. The reaction mixture was evaporated and the solid obtained recrystallised from hot toluene and dried (5.06 g, 56%).

b. (±)-trans-ethyl-8-(1-adamantylmethylaminocarbonyl)-2,3,5,6-dibenzobicyclo[2.2.2]octane-7-carboxylate The product of step a (0.2 g, 0.62 mmol) was stirred in anhydrous benzene (25 ml) and thionyl chloride (0.27 ml, 3.1 mmol) was added. The mixture was stirred at room temperature for 2 h. The solution was evaporated in vacuo to leave a gum. This was taken up in dry dichloromethane (25 ml) and 1-adamantylmethylamine (0.103 g, 0.62 mmol) was added followed by triethylamine (0.095 0 ml, 0.68 mmol) and the mixture stirred at room temperature for 1 h. The dichloromethane solution was washed successively with 2M hydrochloric acid, water and saturated brine and dried, filtered and evaporated to afford a colourless solid (0.28 g, 96%).

c. (±)-trans-8-(1-adamantylmethylaminocarbonyl)-2,3,5,6-dibenzobicyclo[2.2.2]octane-7-carboxylic acid The product of step b (0.28 g, 0.6 mmol) was dissolved in ethanol (20 ml) and sodium hydroxide (48 mg, 1.2 mmole) was added. The reaction mixture was heated to reflux for 2 min whereupon it was diluted with 2N hydrochloric acid, cooled to room temperature and filtered. The precipitated solid was washed successively with water, ethanol (2 ml), ether (10 ml) and dried (165 mg, 63%). The compound was characterised and tested as the N-methyl-D-glucamine salt, found: C, 67.73; H, 7.62; N, 4.22. $C_{36}H_{48}N_2O_8$ requires C, 67.90; H, 7.60; N, 4.40%.

EXAMPLE 45

Preparation of methyl cis-(±)-8-(1-adamantylmethyloxycarbonyl)-2,3,5,6-dibenzobicyclo[2.2.2]octane-7-carboxylate cis-(±)-8-(1-adamantylmethyloxycarbonyl)-2,3,5,6-dibenzobicyclo[2.2.2]octane-7-carboxylic acid prepared as in example 13 (115 mg, 0.26 mmol) was dissolved in ether (10 ml) and a solution of diazomethane in ether was added dropwise until a yellow colour persisted in solution. After 20 min at room temperature the reaction was quenched by dropwise addition of acetic acid. The reaction mixture was diluted with ether and washed sequentially with 5% sodium hydrogencarbonate solution and brine. The organic layer was dried, filtered and evaporated to give a colourless glass. Trituration with hexane then gave the desired product as a white solid (65 mg, 55%), m.p. 186°–7°, found: C, 78.86; H, 7.06. $C_{30}H_{32}O_4$ requires C, 78.92; H, 7.06

EXAMPLE 46

Preparation of cis-7-(2-R-benzyloxycarbonyl-pyrrolidinocarbonyl)-8-(1-adamantylmethylaminocarbonyl)-2,3,5,6-dibenzobicyclo[2.2.2]octane (mixture of diastereomers)

(±)-cis-8-(1-adamantylmethylaminocarbonyl)-2,3,5,6-dibenzobicyclo[2.2.2]octane-7-carboxylic acid (prepared as in example 14) (440 mg, 1 mmole) and PyBOP (520 mg, 1 mmole) were taken up in dry dichloromethane (15 ml) and Hunigs base (0.52 ml, 3 mmole) was added. The reaction mixture was stirred under an atmosphere of dry argon for 1 h. D-Proline benzyl ester hydrochloride (266 mg, 1.1 mmole) was added and the mixture stirred overnight. The organic layer was washed with 5% potassium hydrogensulphate (15 ml), sodium hydrogencarbonate (15 ml) and saturated brine (15 ml). It was then dried, filtered and evaporated to leave the crude title compound which was further purified by column chromatography on silica using a gradient elution starting with 50% ethyl acetate and 50% hexane going up to 80% ethyl acetate and 20% hexane. The title compound (580 mg, 92%) was isolated, m.p. 89°–90°, found: C, 78.14; H, 7.13; N, 4.41. $C_{41}H_{44}N_2C_4$ requires C, 78.31; H, 7.05; N, 4.45

EXAMPLE 47

Preparation of cis-7-(2-S-benzyloxycarbonyl-pyrrolidinocarbonyl)-8-(1-adamantylmethylaminocarbonyl)-2,3,5,6-dibenzobicyclo[2.2.2]octane (mixture of diastereomers)

This compound was prepared essentially as in example 46 using L-proline benzyl ester hydrochloride instead of D-proline benzyl ester hydrochloride. m.p. 91°–2°, found: C, 77.03; H, 7.12; N, 4.22. $C_{41}H_{44}N_2O_4$. 0.6 $H_2O$ requires C, 76.99; H, 7.12; N, 4.38

EXAMPLE 48

Preparation of cis-7-(2-R-carboxy-pyrrolidinocarbonyl)-8-(1-adamantylmethylaminocarbonyl)-2,3,5,6-dibenzobicyclo

[2.2]octane (mixture of diastereomers)

The product of example 46 (520 mg, 0.83 mmol) was dissolved in ethanol (20 ml) and 10% palladium on charcoal (100 mg) was added.

The reaction mixture was stirred overnight under an atmosphere of hydrogen and then filtered through celite and evaporated to yield the title compound (380 mg, 86%). The compound was characterised and tested as the N-methyl-D-glucamine salt m.p. 124°–7°, found: C, 64.58; H, 7.92; N, 5.38. $C_{41}H_{55}N_3O_9$. 1.71 $H_2O$ requires C, 64.40; H, 7.70; N, 5.47

EXAMPLE 49

Preparation of cis-7-(2-S-carboxy-pyrrolidinocarbonyl)-8-(1-adamantylmethylaminocarbonyl)-2,3,5,6-dibenzobicyclo [2.2.2]octane (mixture of diastereomers)

This compound was prepared essentially as in example 48 but using the product of example 47 as substrate rather than the product of example 46. Yield 60% The compound was characterised and tested as the N-methyl-D-glucamine salt m.p. 98°–101°, found: C, 61.12; H, 8.11; N, 5.08. $C_{41}H_{55}N_3O_9$. 3.88 $H_2O$ requires C, 61.26; H, 7.87; N, 5.23

EXAMPLE 50

Preparation of cis-7-(2-methoxycarbonyl-pyrrolidinocarbonyl)-8-(1-adamantylmethylaminocarbonyl)-2,3,5,6-dibenzobicyclo[2.2.2]octane (mixture of diastereomers)

The compound of example 46 (320 mg, 0.59 mmol) was dissolved in dioxan (10 ml) and a solution of diazomethane in ether was added dropwise until the colour persisted. After stirring for 1 h at room temperature acetic acid was added to quench the reaction and the solution was evaporated and taken up in ethyl acetate. The product was then washed with saturated sodium hydrogencarbonate solution and saturated brine. The organic phase was dried filtered and evaporated and the title compound purified on silica using 50% ethyl acetate and 50% hexane as eluent. Yield (120 mg, 37%), m.p. 112°–5°, found: C, 75.86; H, 7.43; N, 4.96. $C_{35}H_{40}N_2O_4$ requires C, 75.86; H, 7.29; N, 5.07

EXAMPLE 51

Preparation of cis-7-(2-S-methoxycarbonyl-pyrrolidinocarbonyl)-8-(1-adamantylmethylaminocarbonyl)-2,3,5,6-dibenzobicyclo[2.2.2]octane (mixture of diastereomers)

This compound was prepared essentially as in example 50 using the compound of example 47 as substrate instead of the compound of example 46. Yield 43%, m.p. 104°–6°, found: C, 74.55; H, 7.43; N, 4.88. $C_{35}H_{40}N_2O_4$. 0.6 $H_2O$ requires C, 74.57; H, 7.37; N, 4.97

EXAMPLE 52

Preparation of (±)-cis-7-(3-indolylethylaminocarbonyl)-8-(1-adamantylmethylaminocarbonyl)-2,3,5,6-dibenzobicyclo [2.2.2]octane (±)-cis-8-(1-adamantylmethylaminocarbonyl)-2,3,5,6-dibenzobicyclo[2.2.2]octane-7-carboxylic acid (prepared as in example 14) (440 mg, 1 mmole) and PyBOP (520 mg, 1 mmole) were taken up in dry dichloromethane (15 ml) and Hunigs base (0.52 ml, 3 mmole) was added. The reaction mixture was stirred under an atmosphere of dry argon for 1 h. Tryptamine hydrochloride (197 mg, 1 mmole) was added and the mixture stirred overnight. The organic layer was washed with 5% potassium hydrogensulphate (15 ml), sodium hydrogencarbonate (15 ml) and saturated brine (15 ml). It was then dried, filtered and evaporated to leave the crude title compound which was further purified by column chromatography on silica using 15% ethyl acetate and 85% dichloromethane as eluent. The title compound (432 mg, 74%) was isolated as a white solid, m.p. 130°–40°, found: C, 75.92; H, 6.98; N, 7.19. $C_{39}H_{41}N_3O_2$ requires C, 76.26; H, 7.28; N, 6.84

EXAMPLE 53

Preparation of cis-7-[R-2-(3-indolyl)-1-methoxycarbonyl-ethylaminocarbonyl]-8-(1-adamantylmethylaminocarbonyl)-2,3,5,6-dibenzobicyclo[2.2.2]octane (mixture of diastereomers)

This compound was prepared essentially as in example 52 using D-tryptophan methyl ester hydrochloride instead of tryptamine hydrochloride. Yield 78%, m.p. 135°–40°, found: C, 75.64; H, 6.81; N, 6.09. $C_{41}H_{43}N_3O_4$. 0.65 $H_2O$ requires C, 75.35; H, 6.83; N, 6.43

EXAMPLE 54

Preparation of cis-7-[2-S-(3-indolyl)-1-methoxycarbonyl-ethylaminocarbonyl]-8-(1-adamantylmethylaminocarbonyl)-2,3,5,6-dibenzobicyclo[2.2.2]octane (mixture of diastereomers)

This compound was prepared essentially as in example 52 using L-tryptophan methyl ester hydrochloride instead of tryptamine hydrochloride. Yield 80%, m.p. 135°–42°, found: C, 76.55; H, 6.95; N, 6.77. $C_{41}H_{43}N_3O_4$ requires C, 76.63; H, 6.75; N, 6.55

EXAMPLE 55

Preparation of cis-7-[2-R-(3-indolyl)-1-carboxyethylaminocarbonyl]-8-(1-adamantylmethylaminocarbonyl)-2,3,5,6-dibenzobicyclo[2.2.2]octane Diastereomer 1 a. cis-7-[2-R-(3-indolyl)-1-benzyloxycarbonyl-ethylaminocarbonyl]-8-(1-adamantylmethylaminocarbonyl)-2,3,5,6-dibenzobicyclo[2.2.2]octane and separation of diastereomers The mixture of diastereomers was prepared essentially as in example 52 using D-tryptophan benzyl ester trifluoroacetate salt instead of tryptamine hydrochloride. The diastereomers were separated by column chromatography (silica 15% ethyl acetate and 85% dichloromethane) to give a 35% yield of each component.

b. cis-7-[2-R-(3-indolyl)-1-carboxy-ethylaminocarbonyl] -8-(1-adamantylmethylaminocarbonyl)-2,3,5,6-dibenzobicyclo-[2.2.2]octane Diastereomer 1

Diastereomer 1 (from step a) (0.23 g, 0.32 mmol) was dissolved in methanol (10 ml) and a catalytic amount of 10% palladium on charcoal was added. The mixture was stirred under an atmosphere of hydrogen overnight, filtered and evaporated to leave the title compound (0.21 g, 100%). The compound was characterised and tested as the N-methyl-D-glucamine salt, m.p. 130°–5°, $[\alpha]^D=-18.5°$ (c=1 in methanol), found: C, 67.17; H, 7.36; N, 6.49. $C_{47}H_{58}N_4O_9$. $H_2O$ requires C, 67.09; H, 7.19; N, 6.65

EXAMPLE 56

Preparation of cis-7-[2-R-(3-indolyl)-1-carboxy-ethylaminocarbonyl]-8-(1-adamantylmethylaminocarbonyl)-2,3,5,6-dibenzobicyclo[2.2.2]octane Diastereomer 2

The compound was prepared essentially as in example 4 but using diastereomer 2 (isolated in example 4 step a) instead of diastereomer 1 in step b. Yield 90% The compound was further characterised and tested as the N-methyl-D-glucamine salt, m.p. 140°–5°, $[\alpha]^D=-22.0°$ (c=1 in methanol), found: C, 67.16; H, 7.18; N, 6.68. $C_{47}H_{58}N_4O_9 \cdot H_2O$ requires C, 67.09; H, 7.19; N, 6.65

EXAMPLE 57

Preparation of cis-7-[2-S-(3-indolyl)-1-carboxy-ethylaminocarbonyl]-8-(1-adamantylmethylaminocarbonyl)-2,3,5,6-dibenzobicyclo[2.2.2]octane Diastereomer 1

This was prepared essentially as in example 55 but using L-tryptophan benzyl ester trifluoracetate instead of the D-isomer in step a. Separation of diastereomers was achieved at the benzyl ester stage as indicated in example 55 step a. and diastereomer 1 used in step b. was again the isomer with the higher $R_f$. Overall yield 22% based on starting racemic carboxylic acid.

The compound was further characterised and tested as the N-methyl-D-glucamine salt, m.p. 119°–24°, $[\alpha]^D = -5.7°$ (c=0.7 in methanol), found: C, 65.07; H, 7.25; N, 6.44. $C_{47}H_{58}N_4O_9$ requires C, 65.03; H, 7.32; N, 6.45

EXAMPLE 58

Preparation of cis-7-[2-S-(3-indolyl)-1-carboxy-ethylaminocarbonyl]-8-(1-adamantylmethylaminocarbonyl)-2,3,5,6-dibenzobicyclo[2.2.2]octane Diastereomer 2

The compound was prepared essentially as in example 55 but using diastereomer 2 (isolated in example 57 step a) instead of diastereomer 1 in step b. Overall yield 26% based on starting racemic carboxylic acid. The compound was characterised and tested as the N-methyl-D-glucamine salt, m.p. 133°–8°, $[\alpha]^D = +7.6°$ (c=0.66 in methanol), found: C, 64.42; H, 7.17; N, 6.41. $C_{47}H_{58}N_4O_9 \cdot 3H_2O$ requires C, 64.37; H, 7.35; N, 6.39

EXAMPLE 59

Preparation of cis-(±)-7-(2-furanylmethylaminocarbonyl)-8-(1-adamantylmethylaminocarbonyl)-2,3,5,6-dibenzobicyclo-[2.2.2]octane The reaction was performed essentially as in Example 25 but using furfurylamine instead of L-alanine methyl ester hydrochloride. Yield 65%, m.p. 300°, found: C, 78.15; H, 6.99; N, 5.42. $C_{34}H_{36}N_2O_3$ requires C, 78.43; H, 6.97; N, 5.38

EXAMPLE 60

Preparation of cis-(±)-7-[2-(5-methyloxycarbonyl)-furanylaminocarbonyl]-8-(1-adamantylmethylaminocarbonyl)-2,3,5,6-dibenzobicyclo[2.2.2]octane The reaction was performed essentially as in Example 25 but using 5-methoxycarbonyl-2-aminofuran instead of L-alanine methyl ester hydrochloride. Yield 65%, m.p. 225°, found: C, 74.31; H. 6.54; N, 4.91. $C_{35}H_{36}N_2O_5$ requires C, 74.45; H, 6.43; N, 4.96

EXAMPLE 61

Preparation of cis-7-(1-S-benzyloxycarbonyl-2-methylpropylaminocarbonyl)-8-(1-adamantylmethylaminocarbonyl)-2,3,5,6-dibenzobicyclo[2.2.2]octane (mixture of diastereomers)

The reaction was performed essentially as in example 46 but using the p-toluenesulphonate salt of the benzyl ester of L-valine instead of D-proline benzyl ester hydrochloride. m.p. 85°–87°. Found: C, 77.99; H, 7.52; N, 4.17. $C_{41}H_{46}N_2O_4 \cdot 0.1H_2O$ requires C, 77.86; H, 7.36; N, 4.42

EXAMPLE 62

Preparation of cis-7-(1-S-carboxy-2-methyl-propylaminocarbonyl)-8-(1-adamantylmethylaminocarbonyl)-2,3,5,6-dibenzobicyclo-[2.2.2]octane (mixture of diastereomers)

The reaction was performed essentially as in example 48 but using the product of example 61 as substrate instead of the product of example 46. The compound was characterised and tested as the N-methyl-D-glucamine salt m.p 105°–8°. Found: C, 64.00; H, 8.06; N, 5.37. $C_{41}H_{57}N_3O_9 \cdot 1.8H_2O$ requires C, 64.09; H, 7.95; N, 5.46

EXAMPLE 63

Preparation of cis-7-(1-S-methoxycarbonyl-2-methyl-propylaminocarbonyl)-8-(1-adamantylmethylaminocarbonyl)-2,3,5,6-dibenzobicyclo-[2.2.2]octane (mixture of diastereomers)

cis-7-(1-S-carboxy-2-methylpropylaminocarbonyl)-8-(1-adamantylmethylaminocarbonyl)- 2,3,5,6-dibenzobicyclo-[2.2.2]octane (mixture of diastereomers) (150 mg) prepared as in example 62 was dissolved in ethyl acetate (5 ml) and a solution of diazomethane in diethyl ether was added until a yellow colour persisted in solution. After stirring the reaction mixture at room temperature for 10 min, glacial acetic acid was added and the organic layer was washed with saturated sodium hydrogencarbonate solution, dried over magnesium sulphate, filtered and evaporated. Yield 130 mg, 85%, m.p. 103°–5°. Found: C, 75.51; H, 7.67; N, 5.06. $C_{35}H_{42}N_2O_4$ requires C, 75.78; H, 7.63; N, 5.05

EXAMPLE 64

Preparation of cis-7-(1-S-2-dicarboxyethyl-aminocarbonyl)-8-(1-adamantylmethylaminocarbonyl)-2,3,5,6-dibenzobicyclo[2.2.2]octane (mixture of diastereomers)

a. cis-7-(1-S-2-dibenzyloxycarbonylethylaminocarbonyl)-8-(1-adamantylmethylaminocarbonyl)-2,3,5,6-dibenzobicyclo-[2.2.2]octane (mixture of diastereomers)

The reaction was performed essentially as in example 46 but using the dibenzyl ester of L-aspartic acid instead of D-proline benzyl ester hydrochloride. The product was used directly in step b.

b. cis-7-(1-S-2-dicarboxyethylaminocarbonyl)-8-(1-adamantylmethylaminocarbonyl)-2,3,5,6-dibenzobicyclo-[2.2.2]octane (mixture of diastereomers)

The reaction was performed essentially as in example 48 but using the product of step a. as substrate instead of the product of example 46. The compound was characterised and tested as the mono-N-methyl-D-glucamine salt, m.p 115°–7°. Found: C, 62.84; H, 7.03; N, 5.35. $C_{40}H_{53}N_3O_{11} \cdot 0.62H_2O$ requires C, 62.54; H, 7.03; N, 5.61

EXAMPLE 65

Preparation of 7-(1-S-carboxy-2-phenyl-ethyl-aminocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of phenylalanine in step a. instead of the dibenzyl ester of aspartic acid. The compound was characterised and tested as the N-methyl-D-glucamine salt, m.p. 101°–3°. Found: C, 66.13; H, 7.64; N, 5.05. $C_{45}H_{57}N_3O_9 \cdot 1.9H_2O$ requires C, 66.06; H, 7.49; N, 5.14

EXAMPLE 66

Preparation of (±)-cis-7-(1-methoxycarbonyl-1-methyl-ethylaminocarbonyl)-8-(1-adamantylmethylaminocarbonyl)-2,3,5,6-dibenzobicyclo[2.2.2]octane The reaction was performed essentially as in example 46 but using the trifluoromethylacetate salt of the methyl ester of aminoisobutyric acid instead of D-proline benzyl ester hydrochloride. m.p 120°–2°. Found: C, 75.51; H, 7.43; N, 4.90. $C_{34}H_{40}N_2O_4$ requires C, 75.53; H, 7.46; N, 5.18

EXAMPLE 67

Preparation of (±)-cis-7-(1-carboxy-1-methyl-ethylaminocarbonyl)-8-(1-adamantylmethylaminocarbonyl)-2,3,5,6-dibenzobicyclo[2.2.2]octane The reaction was performed essentially as in example 64 but using the benzyl ester of aminoisobutyric acid in step a. instead of the dibenzyl ester of aspartic acid. The compound was characterised and tested as the N-methyl-D-glucamine salt, m.p 115°–25°. Found: C, 64.71; H, 7.74; N, 5.92. $C_{40}H_{55}N_3O_9$ requires C, 64.93; H, 7.76; N, 5.68

EXAMPLE 68

Preparation of cis-7-(2-R-carboxy-4-R-hydroxy-pyrrolidinocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of cis hydroxy-D-proline in step a. instead of the dibenzyl ester of aspartic acid. The compound was characterised and tested as the N-methyl-D-glucamine salt, m.p 118°–21°. Found: C, 58.59; H, 7.48; N, 5.10. $C_{41}H_{55}N_3O_{10}$. 4.8 mol $H_2O$ requires C, 58.89; H, 7.78; N, 5.02%

EXAMPLE 69

Preparation of cis-7-(2-R-carboxy-4R-hydroxypyrrolidinocarbonyl)-8-(1-adamantylmethylaminocarbonyl)-2,3,5,6-dibenzobicyclo[2.2.2]octane Diastereomer 1

The cis-7-(2-R-benzyloxycarbonyl-4-R-hydroxy-pyrrolidino-carbonyl)-8-(1-adamantylmethylaminocarbonyl)-2,3,5,6-dibenzobicyclo[2.2.2]octane mixture of diastereomers prepared as referenced in example 68 was separated into its two diastereomeric components by repeated recrystallisation from ethyl acetate. The insoluble isomer was designated diastereomer 1. The soluble material isolated by evaporation was designated diastereomer 2. Diastereomer 1 was converted to the title compound essentially as in example 48 using it as substrate instead of the product of example 46. The compound was characterised and tested as the N-methyl-D-glucamine salt, m.p 112°–4°. Found: C, 60.81; H, 7.86; N, 4.96. $C_{41}H_{55}N_3O_{10}$. 4.4 mol $H_2O$ requires C, 60.70; H, 7.68; N, 5.18

EXAMPLE 70

Preparation of cis-7-(2-R-carboxy-4-R-hydroxypyrrolidinocarbonyl)-8-(1-adamantylmethylaminocarbonyl)-2,3,5,6-dibenzobicyclo[2.2.2]octane Diastereomer 2

Diastereomer 2 prepared as described in example 69 was converted to the title compound essentially as in example 48 using it as substrate instead of the product of example 46. The compound was characterised and tested as the N-methyl-D-glucamine salt, m.p. 132°–35°. Found: C, 63.69; H, 7.51; N, 5.04. $C_{41}H_{55}N_3O_{10}$. 1.5 mol $H_2O$ requires C, 63.40; H, 7.52; N, 5.41

EXAMPLE 71

Preparation of cis-7-(2-R-methoxycarbonyl-4-R-hydroxy-pyrrolidinocarbonyl)-8-(1-adamantylmethylaminocarbonyl)-2,3,5,6-dibenzobicyclo[2.2.2]octane Diastereomer 1

The compound was prepared essentially as in example 63 but using the product of example 69 as substrate instead of cis-7-(1-S-carboxy-2-methylpropylaminocarbonyl)-8-(1-adamantylmethylaminocarbonyl)-2,3,5,6-dibenzobicyclo [2.2.2]octane (mixture of diastereomers), m.p 133°–35°. Found: C, 72.81; H, 7.21; N, 4.88. $C_{35}H_{40}N_2O_5$. 0.5 mol $H_2O$ requires C, 72.81; H, 7.15; N, 4.85% EXAMPLE 72 Preparation of cis-7-(2-R-methoxycarbonyl-4-R-hydroxy-pyrrolidinocarbonyl)-8-(1-adamantylmethylaminocarbonyl)-2,3,5,6-dibenzobicyclo[2.2.2 ]octane Diastereomer 2

The compound was prepared essentially as in example 63 but using the product of example 70 as substrate instead of cis-7-(1-S-carboxyl-2-methylpropylaminocarbonyl)-8-(1-adamantylmethylaminocarbonyl)-2,3,5,6-dibenzobicyclo [2.2.2]octane (mixture of diastereomers), m.p 133°–35°. Found: C, 70.28; H, 7.14; N, 4.81. $C_{35}H_{40}N_2O_5$. 1.5 mol $H_2O$ requires C, 70.42; H, 7.28; N, 4.69

EXAMPLE 73

Preparation of (±)-cis-7-(3-(±)-carboxypiperidinocarbonyl)-8-(1-adamantylmethylaminocarbonyl)-2,3,5,6-dibenzobicyclo[2.2.2]octane The reaction was performed essentially as in example 46 but using the trifluoromethylacetate salt of the benzyl ester of racemic nipecotic acid instead of D-proline benzyl ester hydrochloride. The compound was characterised and tested as the N-methyl-D-glucamine salt. Found: C, 65.54; H, 8.12; N, 5.23. $C_{42}H_{57}N_3O_9$. 1.4 $H_2O$ requires C, 65.24; H, 7.80; N, 5.43

EXAMPLE 74

Preparation of (±)-cis-7-(3-(±)-methoxycarbonylpiperidinocarbonyl)-8-(1-adamantylmethylaminocarbonyl)-2,3,5,6-dibenzobicyclo[2.2.2]octane The compound was prepared essentially as in example 63 but using the product of example 73 as substrate instead of cis-7-(1-S-carboxy-2-methylpropylaminocarbonyl)-8-(1-adamantylmethylaminocarbonyl)-2,3,5,6-dibenzobicyclo [2.2.2]octane (mixture of diastereomers). Found: C, 74.24; H, 7.30; N, 4.65. $C_{36}H_{42}N_2O_4$. 0.8 $H_2O$ requires C, 74.40; H, 7.56; N, 4.82

EXAMPLE 75

Preparation of cis-7-(1-S-cyanoethylaminocarbonyl)-8-(1-adamantylmethylaminocarbonyl)-2,3,5,6-dibenzobicyclo [2.2.2]octane (mixture of disastereomers)

The compound of example 31 (0.33 g, 0.59 mmol) was dissolved in pyridine (5 ml) and cooled to 0° under an atmosphere of dry argon. Tosyl chloride (0.13 g, 0.70 mmol) was added and the reaction allowed to warm to room temperature and was then stirred overnight. The solvent was removed by evaporation and the residue partitioned between ethyl acetate and water. The organic phase was washed successively with 1M hydrochloric acid and saturated sodium hydrogen carbonate solution, dried, filtered and evaporated to leave the crude product. This material was purified by column chromatography (silica, 90% dichloromethane and 10% ethyl acetate) to leave the title compound (150 mg), m.p. 125°–8°. Found: C, 76.30; H, 7.23; N, 8.21. $C_{32}H_{35}N_3O_2$. 0.6 $H_2O$ requires C, 76.19; H, 7.23; N, 8.32

EXAMPLE 76

Preparation of cis-7-(1-S-methylcarbonylethylaminocarbonyl)-8-(1-adamantylmethylaminocarbonyl)-2,3,5,6-dibenzobicyclo[2.2.2]octane (mixture of diastereomers)

The compound of example 75 (0.25 g, 0.5 mmol) was dissolved in THF (3 ml) and cooled to 0° under an atmosphere of dry argon. Methyl magnesium bromide solution (1.4M in THF 1.4 ml, 2.0 mmol) was added. The solution was stirred at 0° for 1 h. 2M hydrochloric acid (2 ml ) was added followed by saturated ammonium chloride solution. (20 ml). The product was extracted with ethyl acetate (2×20 ml), dried, filtered and evaporated (0.25 ml). The crude product was purified by column chromatography (silica 90% dichloromethane and 10% ethyl acetate) to leave the title compound (130 mg), m.p. 105°–10°. Found: C, 76.61; H, 7.40; N, 5.25. C33H38N2O3. 0.4 H2O requires C, 76.54; H, 7.55; N, 5.41

EXAMPLE 77

Preparation of cis-7-(1-S-propyloxycarbonylethylaminocarbonyl)-8-(1-adamantylmethylaminocarbonyl)-2,3,5,6-dibenzobicyclo[2.2.2]octane (mixture of diastereomers)

The reaction was performed essentially as in example 46 but using the trifluoromethylacetate salt of the propyl ester of L-alanine (prepared from alklation of the caesium salt of BOC-L-alanine with propyl bromide followed by treatment with trifluoroacetic acid) instead of D-proline benzyl ester hydrochloride. m.p 90°–3°. Found: C, 75.33; H, 7.74; N, 4.81. $C_{35}H_{42}N_2O_4$. 0.25 $H_2O$ requires C, 75.33; H, 7.66; N, 5.01

EXAMPLE 78

Preparation of cis-7-(2-R-carboxy-pyrrolidinocarbonyl)8-(1-adamantylmethylaminocarbonyl)-2,3,5,6-dibenzobicyclo [2.2.2]octane Diastereomer 1

The compound of example 48 was separated into its constituent disastereomers by reverse phase HPLC (silica C8 column 60% acetonitrile, 40% water and 0.1% acetic acid modifier). The first compound eluted was designated diastereomer 1, the title compound. The compound was characterised and tested as the N-methyl-D-glucamine salt. Found: C, 64.23; H, 7.86; N, 5.38. $C_{41}H_{55}N_3O_{10}$. 1.8 $H_2O$ requires C, 64.22; H, 7.71; N, 5.48

EXAMPLE 79

Preparation of cis-7-(2-R-carboxy-pyrrolidinocarbonyl)-8-(1-adamantylmethylaminocarbonyl)-2,3,5,6-dibenzobicyclo [2.2.2]octane Diastereomer 2

The second compound eluted during the HPLC separation referred to in example 78 was designated diastereomer 2. The compound was characterised and tested as the N-methyl-D-glucamine salt. Found: C, 64.23; H, 7.86; N, 5.38. $C_{41}H_{55}N_3O_{10}$. 1.8 $H_2O$ requires C, 64.22; H, 7.71; N, 5.48

EXAMPLE 80

Preparation of cis-7-(2-S-methoxycarbonylpyrrolidinocarbonyl)-8-(1-adamantylmethylaminocarbonyl)-2,3,5,6-dibenzocyclo[2.2.2]octane Diastereomer 1

The compound of example 51 was separated into its constituent diastereomers by repeated recrystallisation from 80% ethyl acetate and 20% hexane. The crystals isolated were designated diastereomer 1, the title compound, m.p. 256°. Found: C, 76.07; H, 7.31; N, 4.98. $C_{35}H_{40}N_2O_4$ requires C, 76.06; H, 7.29; N, 5.07

EXAMPLE 81

Preparation of cis-7-(2-S-methoxycarbonylpyrrolidinocarbonyl)-8-(1-adamantylmethylaminocarbonyl)-2,3,5,6-dibenzobicyclo[2.2.2]octane Diastereomer 2

The mother liquors from the recrystallisation described in example 80 were concentrated to yield the other pure isomer designated diastereomer 2, m.p. 94°–6°. Found: C, 74.88; H, 7.31; N, 5.03. $C_{35}H_{40}N_2O_4$. 0.5 $H_2O$ requires C, 74.91; H, 7.35; N, 4.99

EXAMPLE 82

Preparation of cis-7-(1-S-carboxy-2-hydroxyethylaminocarbonyl)-8-(1-adamantylmethylaminocarbonyl)-2,3,5,6-dibenzobicyclo[2.2.2]octane Diastereomer 1

Step a. cis-7-(1-S-Benzyloxycarbonyl-2-hydroxyethylaminocarbonyl)-8-(1-adamantylmethylaminocarbonyl)-2,3,5,6-dibenzobicyclo [2.2.2]octane (diastereomer 1 and 2)

The reaction was performed essentially as in example 46 but using L-serine benzyl ester hydrochloride instead of D-proline benzyl ester hydrochloride. The compound was separated into its component diastereomers by column chromatography (silica 25% ethyl acetate and 75% dichloromethane). The less polar material was designated diastereomer 1 and the more polar diastereomer 2.

Step b. cis-7-(1-S-carboxy-2-hydroxyethylaminocarbonyl)-8-(1-adamantylmethylaminocarbonyl)-2,3,5,6-dibenzobicyclo[2.2.2]octane Diastereomer 1

The reaction was performed essentially as in example 48 but using the diastereomer 1 from step a. above as substrate instead of the product of example 46. The compound was characterised and tested as the N-methyl-D-glucamine salt, m.p 102°–5° found: C, 61.24; H, 7.78; N, 5.22. $C_{39}H_{53}N_3O_{10}$. 2.4 $H_2O$ requires C, 61.08; H, 7.59; N, 5.48

EXAMPLE 83

Preparation of cis-7-(1-S-carboxy-2-hydroxyethylaminocarbonyl)-8-(1-adamantylmethylaminocarbonyl)-2,3,5,6-dibenzobicyclo[2.2.2]octane Diastereomer 2

The reaction was performed essentially as in example 48 but using the diastereomer 2 from example 82 step a. as substrate instead of the product of example 46. The compound was characterised and tested and tested as the N-methyl-D-glucamine salt, m.p 107°–10° found: C, 61.27; H, 7.69; N, 5.29. $C_{39}H_{53}N_3O_{10}$. 2.3 $H_2O$ requires C, 61.19; H, 7.59; N, 5.49

EXAMPLE 84

Preparation of cis-7-(1-S-methoxycarbonyl-2-hydroxyethylaminocarbonyl)-8-(2,3,5,6-dibenzobicyclo[2.2.2]octane Diastereomer 1

Step a. cis-7-(1-S-methoxycarbonyl-2-hydroxyethylaminocarbonyl)-8-(1-adamantylmethylaminocarbonyl)-2,3,5,6-dibenzobicyclo[2.2.2]octane (mixture of diastereomers)

The reaction was performed essentially as in example 46 but using L-serine methyl ester hydrochloride instead of D-proline benzyl ester hydrochloride.

Step b. cis-7-(1-S-methoxycarbonyl-2-hydroxyethylaminocarbonyl)-8-(1-adamantylmethylaminocarbonyl)-2,3,5,6-dibenzobicyclo[2.2.2]octane Diastereomer 1

The compound prepared in step a. was separated into its component diastereomers by column chromatography (silica 30% ethyl acetate and 70% dichloromethane). The less polar material was designated diastereomer 1, the title compound, m.p 115°–20° found: C, 68.94; H, 6.95; N, 4.91. $C_{33}H_{38}N_2O_5$. 1.6 $H_2O$ requires C, 69.26; H, 7.27; N, 4.90

EXAMPLE 85

Preparation of cis-7-(1-S-methoxycarbonyl-2-hydroxyethylaminocarbonyl)-8-(1-adamantylmethylaminocarbonyl)-2,3,5,6-dibenzobicyclo[2.2.2]octane Diastereomer 2

The compound of this example was the more polar diastereomer isolated from the column chromatography described in example 84 step b, m.p 100°–10° found: C, 56.92; H, 6.03; N, 3.49. $C_{33}H_{38}N_2O_5$. 2.4 DCM requires C, 56.91; H, 5.78; N, 3.75

EXAMPLE 86

Preparation of (±)- cis-7-(1-methoxycarbonyl-1-ethyleneaminocarbonyl)-8-(1-adamantylmethylaminocarbonyl)-2,3,5,6-dibenzobicyclo[2.2.2]octane The product of example 64 step a. (270 mg, 0.5 mmol) was dissolved in THF (2 ml) and N,N-carbonyldiimidazole (80 mg, 0.5 mmol) was added followed by triethylamine (0.07 ml). The solution was stirred at room temperature overnight under an atmosphere of dry argon. The solvent was evaporated and the crude material purified by column chromatography (silica 10% ethyl acetate and 90% dichloromethane) to give the title compound as a solid (50 mg), m.p 98°–108° found: C, 73.59; H, 7.05; N, 5.06. $C_{33}H_{36}N_2O_4$. 0.8 $H_2O$ requires C, 73.55; H, 7.03; N, 5.20

EXAMPLE 87

Preparation of cis-7-(1-S-methoxycarbonyl-2-carboxyethylaminocarbonyl)-8-(1-adamantylmethylaminocarbonyl)-2,3,5,6-dibenzobicyclo[2.2.2]octane (mixture of diastereomers)

The reaction was performed essentially as in example 64 but using the alpha methyl beta benzyl diester of aspartic acid in step a. instead of the dibenzyl ester. The compound was characterised and tested as the N-methyl-D-glucamine salt, m.p 103°–5° found: C, 56.56; H, 7.70; N, 4.71. $C_{41}H_{55}N_3O_{11}$. 5.9 $H_2O$ requires C, 56.48; H, 7.72; N, 4.82

EXAMPLE 88

Preparation of cis-7-(2-R-carboxypiperidinocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of D-pipecolinic acid in step a. instead of the dibenzyl ester of aspartic acid. The compound was characterised and tested as the N-methyl-D-glucamine salt. Found: C, 65.13; H, 8.07; N, 5.64. $C_{42}H_{57}N_3O_9$. 1.5 $H_2O$ requires C, 65.10; H, 7.81; N, 5.42

EXAMPLE 89

Preparation of cis-7-(2-R-methoxycarbonylpiperidinocarbonyl)-8-(1-adamantylmethylaminocarbonyl)-2,3,5,6-dibenzobicyclo[2.2.2]octane (mixture of diastereomers)

The compound was prepared essentially as in example 63 but using the product of example 88 as substrate instead of cis-7-(1-S-carboxy-2-methylpropylaminocarbonyl)-8-(1-adamantylmethylaminocarbonyl)-2,3,5,6-dibenzobicyclo[2.2.2]octane (mixture of diastereomers). Found: C, 70.00; H, 7.18; N, 4.70. $C_{36}H_{42}N_2O_4$. 0.5 $CHCl_3$ requires C, 70.04; H, 6.78; N, 4.40

EXAMPLE 90

Preparation of cis-7-(2-S-methoxycarbonyl-4-S-hydroxypyrrolidinocarbonyl)-8-(1-adamantylmethylaminocarbonyl)-2,3,5,6-dibenzobicyclo[2.2.2]octane (mixture of diastereomers)

The reaction was performed essentially as in example 46 but using the trifluoroacetate salt of the methyl ester of cis-hydroxy-L-proline instead of D-proline benzyl ester hydrochloride. Found: C, 76.36; H, 7.24; N, 4.38. $C_{35}H_{40}N_2O_5$. 0.9 toluene requires C, 76.25; H, 7.31; N, 4.26

EXAMPLE 91

Preparation of cis-7-(2-S-methoxycarbonyl-4-R-hydroxypyrrolidinocarbonyl)-8-(1-adamantylmethylaminocarbonyl)-2,3,5,6-dibenzobicyclo[2.2.2]octane (mixture of diastereomers)

The reaction was performed essentially as in example 46 but using the trifluoroacetate salt of the methyl ester of trans-hydroxy-L-proline instead of D-proline benzyl ester hydrochloride. Found: C, 75.16; H, 7.32; N, 4.19. $C_{35}H_{40}N_2O_5$. 0.6 toluene requires C, 75.45; H, 7.24; N, 4.49

EXAMPLE 92

Preparation of cis-7-(1-S-methoxycarbonyl-2-benzylsulphenylethylaminocarbonyl)-8-(1-adamantylmethylaminocarbonyl)-2,3,5,6-dibenzobicyclo[2.2.2]octane Diastereomer 1

Step a. cis-7-(1-S-methoxycarbonyl-2-benzylsulphenylethylaminocarbonyl)-8-(1-adamantylmethylaminocarbonyl)-2,3,5,6-dibenzobicyclo[2.2.2]octane (mixture of diastereomers)

The reaction was performed essentially as in example 46 but using the benzylthioether of L-cysteine methyl ester hydrochloride instead of D-proline benzyl ester hydrochloride.

Step b. cis-7-(1-S-methoxycarbonyl-2-benzylsulphenylethylaminocarbonyl)-8-(1-adamantylmethylaminocarbonyl)-2,3,5,6-dibenzobicyclo[2.2.2]octane Diastereomer 1

The compound prepared in step a. was separated into its component diastereomers by column chromatography (silica 15% ethyl acetate and 85% dichloromethane). The more polar material ($R_f$ 0.4) was designated diastereomer 1, the title compound, m.p. 80°–1° found: C, 72.93; H, 6.88; N, 4.08. $C_{40}H_{44}N_2O_4S$. 0.5 $H_2O$ requires C, 73.04; H, 6.89; N, 4.25

EXAMPLE 93

Preparation of cis-7-(1-S-methoxycarbonyl-2-benzylsulphenylethylaminocarbonyl)-8-(1-adamantylmethylaminocarbonyl)-2,3,5,6-dibenzobicyclo[2.2.2]octane Diastereomer 2

The less polar material isolated by the chromatography ($R_f$ 0.6) described in example 92 step b. was designated as diastereomer 2, m.p. 85° found: C, 74.03; H, 7.01; N, 4.38. $C_{40}H_{44}N_2O_4S$ requires C, 74.04; H, 6.64; N, 4.32

EXAMPLE 94

Preparation of cis-7-(1-S-carboxyethyl-(N-methyl)aminocarbonyl)-8-(1-adamantylmethylaminocarbonyl)-2,3,5,6-dibenzobicyclo[2.2.2]octane (mixture of diastereomers)

The reaction was performed essentially as in example 64 but using the trifluoroacetate salt of the benzyl ester of N-methyl-L-alanine in step a. instead of the dibenzyl ester of aspartic acid. The compound was characterised and tested as the N-methyl-D-glucamine salt, m.p. 100°–10° found: C, 64.12; H, 7.89; N, 5.71. $C_{40}H_{45}N_3O_9$. 1.5 $H_2O$ requires C, 64.21; H, 7.80; N, 5.62

EXAMPLE 95

Preparation of cis-7-(1-R-carboxyethyl-(N-methyl)-aminocarbonyl)-8-(1-adamantylmethylaminocarbonyl)-2,3,5,6-dibenzobicyclo[2.2.2]octane (mixture of diastereomers)

The reaction was performed essentially as in example 64 but using the trifluoroacetate salt of the benzyl ester of N-methyl-D-alanine in step a. instead of the dibenzyl ester of aspartic acid. The compound was characterised and tested as the N-methyl-D-glucamine salt, m.p. 105°–15° found: C, 62.06; H, 7.81; N, 5.55. $C_{40}H_{55}N_3O_9$. 2.8 $H_2O$ requires C, 62.18; H, 7.91; N, 5.44

EXAMPLE 96

Preparation of cis-7-(1-S-methoxycarbonylethyl-(N-methyl)-aminocarbonyl)-8-(1-adamantylmethylaminocarbonyl)-2,3,5,6-dibenzobicyclo[2.2.2]octane (mixture of diastereomers)

The reaction was performed essentially as in example 63 but using the product of example 94 as substrate instead of cis-7-(1-S-carboxy-2-methylpropylaminocarbonyl)-8-(1-adamantylmethylaminocarbonyl)-2,3,5,6-dibenzobicyclo [2.2.2]octane (mixture of diastereomers), m.p. 96°–8° found: C, 75.55; H, 7.68; N, 5.10. $C_{34}H_{40}N_2O_4$ requires C, 75.53; H, 7.46; N, 5.18

EXAMPLE 97

Preparation of cis-7-(1-R-methoxycarbonylethyl-(N-methyl)-aminocarbonyl)-8-(1-adamantylmethylaminocarbonyl)-2,3,5,6-dibenzobicyclo[2.2.2]octane (mixture of diastereomers)

The reaction was performed essentially as in example 63 but using the product of example 95 as substrate instead of cis-7-(1-S-carboxy-2-methlpropylaminocarbonyl)-8-(1-adamantylmethylaminocarbonyl)-2,3,5,6-dibenzobicyclo [2.2.2]octane (mixture of diastereomers), m.p. 95°–105° found: C, 75.49; H, 7.53; N, 5.24. $C_{34}H_{40}N_2O_4$ requires C, 75.53; H, 7.46; N, 5.18

EXAMPLE 98

Preparation of (±)-cis-7-(pyrrolidinocarbonyl)-8-(1-adamantylmethylaminocarbonyl)-2,3,5,6-dibenzobicyclo [2.2.2]octane The reaction was performed essentially as in example 64 but using pyrrolidine in step a. instead of the dibenzyl ester of aspartic acid, m.p. 205°–7° found: C, 80.15; H, 7.77; N, 5.78. $C_{33}H_{38}N_2O_2$ requires C, 80.12; H, 7.74; N, 5.66

EXAMPLE 99

Preparation of (±)-cis-7-(methylaminocarbonyl)-8-(1-adamantylmethylaminocarbonyl)-2,3,5,6-dibenzobicyclo [2.2.2]octane The compound of example 14 (440 mg, 1 mmol) was dissolved in dichloromethane (15 ml) and diisopropylethylamine (0.52 ml) and PyBOP (520 mg) were added. The solution was stirred for 5–10 min until a clear solution was obtained. Dry methylamine gas was bubbled through the solution for 5 min until this was saturated. The solution was stirred for 1 h and then evaporated. The residue was taken up in ethyl acetate and washed successively with 5% aqueous potassium hydrogensulphate solution (2×20 ml) saturated sodium hydrogencarbonate solution (20 ml), brine (20 ml), dried, filtered and evaporated to leave a crude product which was purified by column chromatography (silica 70% dichloromethane and 30% ethyl acetate). The title compound was a white solid (240 mg), m.p. 192°–3° found: C, 79.15; H, 7.72; N, 5.91. $C_{30}H_{34}N_2O_2$ requires C, 79.26; H, 7.53; N, 6.16

EXAMPLE 100

Preparation of (±)-cis-7-(dimethylaminocarbonyl)-8-(1-adamantylmethylaminocarbonyl)-2,3,5,6-dibenzobicyclo [2.2.2]octane The compound was prepared essentially as in example 99 but using dimethylamine instead of methylamine, m.p. 253°–5° found: C, 78.86; H, 7.78; N, 5.67. $C_{31}H_{36}N_2O_2$ requires C, 78.69; H, 7.8 N, 5.92

EXAMPLE 101

Preparation of (±)-cis-7-(ethylaminocarbonyl)-8-(1-adamantylmethylaminocarbonyl)-2,3,5,6-dibenzobicyclo [2.2.2]octane The compound was prepared essentially as in example 99 but using ethylamine instead of methylamine, m.p. 200°–1° found: C, 79.82; H, 7.67; N, 5.94. $C_{31}H_{36}N_2O_2$ requires C, 79.45; H, 7.74 N, 5.98

EXAMPLE 102

Preparation of (±)-cis-7-(1-methylethylaminocarbonyl)-8-(1-adamantylmethylaminocarbonyl)-2,3,5,6-dibenzobicyclo [2.2.2]octane The compound was prepared essentially as in example 99 but using isopropylamine instead of methylamine, m.p. 122°–4° found: C, 74.80; H, 7.21; N, 5.38. $C_{32}H_{38}N_2O_2$. 0.4 DCM. 0.1 ethyl acetate requires C, 74.94; H, 7.56 N, 5.33

EXAMPLE 103

Preparation of (±)-cis-7-aminocarbonyl-8-(1-adamantylmethylaminocarbonyl)-2,3,5,6-dibenzobicyclo[2.2.2]octane The compound was prepared essentially as in example 99 but using ammonia instead of methylamine, m.p. 238°–40° found: C, 78.78; H, 7.45; N, 6.41. $C_{29}H_{32}N_2O_2$ requires C, 79.06; H, 7.32 N, 6.36

EXAMPLE 104

Preparation of (±)-cis-7-(2-benzyloxycarbonylethylaminocarbonyl)-8-(1-adamantylmethylaminocarbonyl)-1-cyano-2,3,5,6-dibenzobicyclo[2.2.2]octane Regioisomer 1

The mixture of regioisomers was prepared essentially as in example 29 but using (±)-cis-8-(1-adamantylmethylaminocarbonyl)-1-cyano-2,3,5,6-dibenzobicyclo[2.2.2]octane-7-carboxylic acid instead of (±)-cis-8-(1-adamantylmethylaminocarbonyl)-2,3,5,6-dibenzobicyclo[2.2.2]octane-7-carboxylic acid. This in turn was made by reaction of 1-adamantanemethylamine with 1-cyano-2,3,5,6-dibenzobicyclo[2.2.2]octane-7,8-dicarboxylic acid anhydride essentially as in example 14. The anhydride was prepared by reaction of maleic anhydride with 9-cyanoanthracene in refluxing toluene. The regioisomers were separated by preparative HPLC (silica, ethyl acetate 15% and dichloromethane 85%). The less polar regioisomer was designated regioisomer 1, the title compound, m.p. 205°–8° found: C, 76.55; H, 6.61; N, 6.68. $C_{40}H_{41}N_3O_4$ requires C, 76.53; H, 6.58; N, 6.69

EXAMPLE 105

Preparation of (±)-cis-7-(2-benzyloxycarbonylethylaminocarbonyl)-8-(1-adamantylmethylaminocarbonyl)-1-cyano-2,3,5,6-dibenzobicyclo[2.2.2]octane Regioisomer 2

The more polar regioisomer from the HPLC separation described in example 104 was designated regioisomer 2, the title compound, m.p. 104°–7° found: C, 76.48; H, 6.65; N, 6.59. $C_{40}H_{41}N_3O_4$ requires C, 76.53; H, 6.58; N, 6.69

EXAMPLE 106

Preparation of cis-7-(1-S-methoxycarbonylethylaminocarbonyl)-8-(neopentylaminocarbonyl)-2,3,5,6-dibenzobicyclo[2.2.2]octane (mixture of diastereomers)

a. (±)-8-(neopentylaminocarbonyl)-2,3,5,6-dibenzobicyclo[2.2.2]octane-7-carboxylic acid The material was prepared essentially as in example 14 but using neopentylamine hydrochloride as substrate instead of 1-adamantylamine.

b. cis-7-(1-S-methoxycarbonylethylaminocarbonyl)-8-(neopentylaminocarbonyl)-2,3,5,6-dibenzobicyclo[2.2.2]octane (mixture of diastereomers)

The material was prepared essentially as in example 25 but using the compound prepared in step a. above instead of (±)-cis-8-(1-adamantylmethylaminocarbonyl)-2,3,5,6-dibenzobicyclo[2.2.2]octane-7-carboxylic acid as substrate. found: C, 72.14; H, 7.32; N, 6.29. $C_{27}H_{32}N_2O_4$ requires C, 72.30; H, 7.19; N, 6.25

EXAMPLE 107

Preparation of cis-7-(2-R-carboxy-pyrrolidinocarbonyl)-8-(neopentylaminocarbonyl)-2,3,5,6-dibenzobicyclo[2.2.2]octane (mixture of diastereomers)

a. cis-7-(2-R-benzyloxycarbonylpyrrolidinocarbonyl)-8-(neopentylaminocarbonyl)-2,3,5,6-dibenzobicyclo[2.2.2]octane (mixture of diastereomers). The compound was prepared essentially as in example 46 but using the product of example 106 step a. as substrate instead of (±)-cis-8-(1-adamantylmethylaminocarbonyl)-2,3,5,6-dibenzobicyclo[2.2.2]octane-7-carboxylic acid.

b. cis-7-(2-R-carboxypyrrolidinocarbonyl)-8-(neopentylaminocarbonyl)-2,3,5,6-dibenzobicyclo[2.2.2]octane (mixture of diastereomers)

The reaction was performed essentially as in example 48 but using the product of example 107 step a. as substrate instead of the product of example 46. The compound was characterised and tested as the N-methyl-D-glucamine salt, m.p. 105°–15° found: C, 57.98; H, 7.89; N, 6.07. $C_{35}H_{49}N_3O_9$. $4.0\ H_2O$ requires C, 57.75; H, 7.89; N, 5.77%

EXAMPLE 108

Preparation of 7-(1-adamantylmethylaminocarbonyl)-2,3,5,6-dibenzobicyclo[2.2.2]oct-7,8-ene a. 7-carboxy-2,3,5,6-dibenzobicyclo[2.2.2]oct-7,8-ene 7-(methoxycarbonyl)-2,3,5,6-dibenzobicyclo[2.2.2]oct-7,8-ene (prepared as in J.C.S. Perkin I, 1984, 779) (0.5 g, 1.9 mmol) was dissolved in ethanol (20 ml) and sodium hydroxide (0.5 g) was added along with water (2 ml). The solution was stirred and refluxed for 1.5 h. The hot solution was poured onto 2M HCl (50 ml). The white precipitate formed was filtered off, washed with water and dried at 50° in vacuo. This compound was used without further purification.

b. 7-(1-adamantylmethylaminocarbonyl)-2,3,5,6-dibenzobicyclo[2.2.2]oct-7,8-ene

The acid prepared in step a. above (248 mg, 1 mmol) was dissolved in dry dichloromethane (10 ml) and diisopropylamine (0.52 g, 3 mmol) and PyBOP (0.52 g, 1 mmol) were added. After stirring at room temperature for 5 min, 1-adamantylmethylamine (180 mg) was added. After stirring for a further 30 min whereupon the reaction mixture was evaporated. The residue was taken up in ethyl acetate and washed successively with 5% aqueous potassium hydrogensulphate solution (2×20 ml), saturated sodium hydrogencarbonate solution (20 ml), brine (20 ml), dried, filtered and evaporated to leave a crude product which was recrystallised from toluene. The white solid was dried in vacuo, m.p. 254°–5° found: C, 81.28; H, 7.81; N, 3.40. $C_{28}H_{29}NO$. $H_2O$ requires C, 81.32; H, 7.50; N, 3.39

EXAMPLE 109

Preparation of (±)-7-(1-adamantylmethylaminocarbonyl)-2,3,5,6-dibenzobicyclo[2.2.2]octane a. (±)-2,3,5,6-dibenzobicyclo[2.2.2]octane-7-carboxylic acid 7-(methoxycarbonyl)-2,3,5,6-dibenzobicyclo[2.2.2]octane (prepared as in U.S. Pat. No. 5,055,468) (20 g, 80 mmol) was dissolved in methanol (220 ml) and potassium hydroxide (40 g) was added along with water (40 ml). The solution was stirred and refluxed for 4 h. The solution was cooled, filtered through charcoal and treated with concentrated HCl. The buff precipitate formed was filtered off, washed with water and recrystallised from hot benzene. This compound was used without further purification.

b. (±)-7-(1-adamantylmethylaminocarbonyl)-2,3,5,6-dibenzobicyclo[2.2.2]octane (±)-2,3,5,6-dibenzobicyclo[2.2.2]octane-7-carboxylic acid (prepared in step a. above) (1.0 g) was heated with thionyl chloride (5 ml) and DMF (2 drops) at reflux for 30 min. On cooling and evaporation the pale yellow acid chloride was isolated.

The acid chloride (267 mg, 1.0 mmol) was dissolved in dry dichloromethane (5 ml) and added with stirring to a solution of 1-adamantanemethylamine (182 mg, 1.1 mmol) and triethylamine (0.3 ml). After 30 min the solution was washed successively with 2M HCl and brine, dried, filtered and evaporated to leave a solid which was recrystallised from toluene (253 mg), m.p. 220°–1° found: C, 84.88; H, 7.81; N, 3.39. $C_{28}H_{31}NO$ requires C, 84.81; H, 7.63; N, 3.39

EXAMPLE 110

Preparation of (±)-7-(1-adamantylmethoxycarbonyl)-2,3,5,6-dibenzobicyclo[2.2.2]octane The material was prepared essentially as in example 109 except that 1-adamantanemethanol was used instead of 1-adamantanemethylamine in step b, m.p. 152°–3° found: C, 84.42; H, 7.65. $C_{28}H_{30}O_2$ requires C, 84.38; H, 7.59

EXAMPLE 111

Preparation of cis-7-(1-S-methoxycarbonylethylaminocarbonyl)-8-(1-adamantylmethoxycarbonyl)-2,3,5,6-dibenzobicyclo[2.2.2]octane (mixture of diastereomers)

The material was prepared essentially as in example 25 but using the compound prepared in example 13 instead of (±)-cis-8-(1-adamantylmethylaminocarbonyl)-2,3,5,6-dibenzobicyclo[2.2.2]octane- 7-carboxylic acid as substrate, m.p. 75°–7° found: C, 74.27; H, 7.36; N, 2.80. $C_{33}H_{37}NO_5$. 0.06 mol DCM requires C, 74.53; H, 7.02; N, 2.62

EXAMPLE 112

Preparation of cis-7-(1-R-methoxycarbonylethyl-aminocarbonyl)-8-(1-adamantylmethoxycarbonyl)-2,3,5,6-dibenzobicyclo[2.2.2]octane (mixture of diastereomers)

The material was prepared essentially as in example 111 but using D-alanine methyl ester hydrochloride instead of L-alanine methyl ester hydrochloride as substrate, m.p.

85°–7° found: C, 74.38; H, 7.29; N, 2.75. $C_{33}H_{37}NO_5$. 0.05 mol DCM requires C, 74.63; H, 7.03; N, 2.63

EXAMPLE 113

Preparation of (±)-cis-7-(2-benzyloxycarbonylethyl-aminocarbonyl)-8-(1-adamantylmethylaminocarbonyl)-1,4-dimethyl-2,3,5,6-dibenzobicyclo [2.2.2]octane The compound was prepared essentially as in example 29 but using (±)-cis-8-(1-adamantylmethylaminocarbonyl)-1,4-dimethyl-2,3,5,6-dibenzobicyclo[2.2.2]octane-7-carboxylic acid instead of (±)-cis-8-(1-adamantylmethylaminocarbonyl)-2,3,5,6-dibenzobicyclo-[2.2.2]octane-7-carboxylic acid. This in turn was made by reaction of 1-adamantanemethylamine with 1,4-dimethyl-2,3,5,6-dibenzobicyclo[2.2.2]octane-7,8-dicarboxylic acid anhydride essentially as in example 14. The anhydride was prepared by reaction of maleic anhydride with 9,10-dimethylanthracene in refluxing toluene. m.p. 170°–3° found: C, 77.89; H, 7.49; N, 4.49. $C_{41}H_{46}N_2O_4$ requires C, 78.06; H, 7.49; N, 4.44

EXAMPLE 114

Preparation of (±)-cis-7-(1-S-methoxycarbonylethyl-aminocarbonyl)-8-(1-adamantylmethylaminocarbonyl)-1-nitro-2,3,5,6-dibenzobicyclo[2.2.2]octane Diastereomer 1

The compound was prepared essentially as in example 25 but using (±)-cis-8-(1-adamantylmethylaminocarbonyl)-1-nitro-2,3,5,6-dibenzobicyclo[2.2.2]octane-7-carboxylic acid instead of (±)-cis-8-(1-adamantylmethylaminocarbonyl)-2,3,5,6-dibenzo-bicyclo[2.2.2]octane-7-carboxylic acid. This in turn was made by reaction of 1-adamantanemethylamine with 1-nitro-2,3,5,6-dibenzobicyclo-[2.2.2]octane-7,8-dicarboxylic acid anhydride essentially as in example 14. The anhydride was prepared by reaction of maleic anhydride with 9-nitroanthracene in refluxing toluene. The final mixture of diastereomers was separated into three components by HPLC (silica gradient elution of 5% ethyl acetate and 95% dichloromethane to 15% ethyl acetate and 85% dichloromethane). The least polar fraction was designated diastereomer 1. Found: C, 68.99; H, 6.78; N, 7.24. $C_{33}H_{37}N_3O_6$ requires C, 69.33; H, 6.52; N, 7.35

EXAMPLE 115

Preparation of (±)-cis-7-(1-S-methoxycarbonylethyl-aminocarbonyl)-8-(1-adamantylmethylaminocarbonyl)-1-nitro-2,3,5,6-dibenzobicyclo[2.2.2]octane Diastereomer 2

The second least polar fraction from the HPLC separation described in example 114 was designated diastereomer 2. Found: C, 69.43; H, 6.69; N, 7.37. $C_{33}H_{37}N_3O_6$ requires C, 69.33; H, 6.52; N, 7.35

EXAMPLE 116

Preparation of (±)-cis-7-(1-S-methoxycarbonylethyl-aminocarbonyl)-8-(1-adamantylmethylaminocarbonyl)-1-nitro-2,3,5,6-dibenzobicyclo[2.2.2]octane Diastereomer 3

The most polar fraction from the HPLC separation described in example 114 was designated diastereomer 3, found: C, 69.21; H, 6.80; N, 7.22. $C_{33}H_{37}N_3O_6$ requires C, 69.33; H, 6.52; N, 7.35

EXAMPLE 117

Preparation of cis-7-(1-S-methoxycarbonyl-2-(3-indolyl)ethylaminocarbonyl)-8-(neopentylaminocarbonyl)-2,3,5,6-dibenzobicyclo[2.2.2]octane (mixture of diastereomers)

The compound was prepared essentially as in example 54 but using the product of example 106 step a. as substrate instead of (±)-cis-8-(1-adamantylmethylaminocarbonyl)-2,3,5,6-dibenzobicyclo[2.2.2]octane-7-carboxylic acid. Found: C, 73.81; H, 6.49; N, 7.23. $C_{35}H_{37}N_3O_4$. 0.25 $H_2O$ requires C, 73.98; H, 6.65; N

EXAMPLE 118

Preparation of cis-7-(1-S-carboxy-2-(3-indolyl)ethylaminocarbonyl)-8-(neopentylaminocarbonyl)-2,3,5,6-dibenzobicyclo[2.2.2]octane (mixture of diastereomers)

The compound was prepared essentially as in example 107 but using the benzyl ester of L-tryptophan as substrate in step a. as substrate instead of the benzyl ester of D-proline. The compound was characterised and tested as the N-methyl-D-glucamine salt Found: C, 65.91; H, 7.01; N, 7.31. $C_{41}H_{52}N_4O_9$ requires C, 66.11; H, 7.04; N, 7.52%

EXAMPLE 119

Preparation of cis-7-(2-R-(carboxymethylamino-carbonyl)pyrrolidinocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of D-prolylglycine in step a. instead of the dibenzyl ester of aspartic acid. The compound was characterised and tested as the N-methyl-D-glucamine salt. Found: C, 61.52; H, 7.52; N, 6.81. $C_{43}H_{58}N_4O_{10}$. 2.6 $H_2O$ requires C, 61.65; H, 7.60; N, 6.69

EXAMPLE 120

Preparation of cis-7-(2-R-(carboxymethylamino-carbonyl)pyrrolidinocarbonyl)-8-(1-adamantylmethylaminocarbonyl)-2,3,5,6-dibenzobicyclo[2.2.2]octane Diastereomer 1

The benzyl ester intermediate isolated after example 119 step a. was separated into its constituent diastereomers by recrystallisation from ethyl acetate. The mother liquors on concentration gave a benzyl ester which on hydrogenolysis gave the diastereomer of this example. The compound was characterised and tested as the N-methyl-D-glucamine salt. Found: C, 65.12; H, 7.40; N, 6.95. $C_{43}H_{58}N_4O_{10}$ requires C, 65.30; H, 7.39; N, 7.08

EXAMPLE 121

Preparation of cis-7-(2-R-(carboxymethylamino-carbonyl)pyrrolidinocarbonyl)-8-(1-adamantylmethylaminocarbonyl)-2,3,5,6-dibenzobicyclo[2.2.2]octane Diastereomer 2

The crystalline material from the recrystallisation described in example 120 on hydrogenolysis gave the diastereomer of this example. The compound was characterised and tested as the N-methyl-D-glucamine salt. Found: C, 61.54; H, 7.75; N, 6.34. $C_{43}H_{58}N_4O_{10}$. 2.9 $H_2O$ requires C, 61.29; H, 7.62; N, 6.64

EXAMPLE 122

Preparation of cis-7-(2-R-(carboxyethylamino-carbonyl)pyrrolidinocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of D-prolyl-beta-alanine in step a. instead of the dibenzyl ester of aspartic acid. The compound was characterised and tested as the N-methyl-D-glucamine salt. Found: C, 63.14; H, 7.78; N, 6.60. $C_{44}H_{60}N_4O_{10}$. 1.9 $H_2O$ requires C, 63.02; H, 7.66; N, 6.68

EXAMPLE 123

Preparation of cis-7-(2-(methoxycarbonylmethylaminocarbonyl)pyrrolidinocarbonyl)-8-(1-adamantylmethylamino-carbonyl)-2,3,5,6-dibenzobicyclo[2.2.2]octane (mixture of diastereomers)

The compound was prepared essentially as in example 63 but using the compound of example 119 as substrate instead of the compound of example 62. Found: C, 69.77; H, 7.08; N, 6.58. $C_{37}H_{43}N_3O_5$. 1.4 $H_2O$ requires C, 69.97; H, 7.27; N, 6.62

EXAMPLE 124

Preparation of cis-7-(2-R-(methoxycarbonylethylaminocarbonyl)pyrrolidinocarbonyl)-8-(1-adamantylmethylaminocarbonyl)-2,3,5,6-dibenzobicyclo[2.2.2]octane (mixture of diastereomers)

The compound was prepared essentially as in example 63 but using the compound of example 122 as substrate instead of the compound of example 62. Found: C, 71.15; H, 7.40; N, 6.56. $C_{38}H_{45}N_3O_5$. $H_2O$ requires C, 71.13; H, 7.38; N, 6.54

EXAMPLE 125

Preparation of cis-7-(1-S-(carboxyethylamino-carbonyl)ethylaminocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of L-alanyl-beta-alanine in step a. instead of the dibenzyl ester of aspartic acid. The compound was characterised and tested as the N-methyl-D-glucamine salt. Found: C, 60.56; H, 7.74; N, 6.53. $C_{42}H_{58}N_4O_{10}$. 3.1 $H_2O$ requires C, 60.40; H, 7.75; N, 6.71

EXAMPLE 126

Preparation of cis-7-(1-S-(methoxycarbonylethylaminocarbonyl)ethylaminocarbonyl)-8-(1-adamantylmethylaminocarbonyl)-2,3,5,6-dibenzobicyclo[2.2.2]octane (mixture of diastereomers)

The compound was prepared essentially as in example 63 but using the compound of example 125 as substrate instead of the compound of example 62. Found: C, 69.51; H, 7.39; N, 6.49. $C_{36}H_{43}N_3O_5$. 1.4 $H_2O$ requires C, 69.35; H, 7.41; N, 6.73

EXAMPLE 127

Preparation of cis-7-(1-S-(methylaminocarbonyl)ethylaminocarbonyl)-8-(1-adamantylmethylaminocarbonyl)-2,3,5,6-dibenzobicyclo[2.2.2]octane (mixture of diastereomers)

The compound was prepared essentially as in example 25 but using the trifluoroacetate salt of N-methyl-L-alaninamide instead of L-alanine methyl ester hydrochloride. Found: C, 72.12; H, 7.37; N, 7.50. $C_{33}H_{39}N_3O_3$. 1.2 $H_2O$ requires C, 72.37; H, 7.63; N, 7.67

EXAMPLE 128

Preparation of cis-7-(1-S-(methoxycarbonyl)-ethylaminocarbonyl)-8-(1-RS-(1-adamantyl)ethylaminocarbonyl)-2,3,5,6-dibenzobicyclo[2.2.2]octane (mixture of diastereomers A)

a. 8-(1-(1-adamantyl)ethylaminocarbonyl)-2,3,5,6-dibenzobicyclo[2.2.2]octane-7-carboxylic acid (mixture of diastereomers)

This compound was prepared essentially as in example 14 but using 1-RS-(1-adamantyl)ethylamine (prepared as described in EP 178668) as substrate instead of 1-adamantanemethylamine.

b. cis-7-(1-S-(methoxycarbonyl)ethylaminocarbonyl-8-(1-RS-(1-adamantyl)ethylaminocarbonyl)-2,3,5,6-dibenzobicyclo[2.2.2]octane (mixture of diastereomers A)

This was prepared essentially as in example 25 but using the product of step a. instead of the product of example 14. The mixture of four compounds thus produced was separated into two pairs by use of preparative MPLC (silica 35% ethyl acetate and 65% hexane). The least polar pair were designated as the product of this example. found: C, 74.26; H, 7.60; N, 4.86. $C_{34}H_{40}N_2O_4$. 0.5 $H_2O$ requires C, 74.29; H, 7.52; N, 5.10

EXAMPLE 129

Preparation of cis-7-(1-S-(methoxycarbonyl)ethylaminocarbonyl)-8-(1-RS-(1-adamantyl)ethylaminocarbonyl)-2,3,5,6-dibenzobicyclo[2.2.2]octane (mixture of diastereomers B)

The most polar pair of compounds isolated after the MPLC procedure described in example 128 were designated mixture B, the compounds of this example, Found: C, 74.01; H, 7.69; N, 4.90. $C_{34}H_{40}N_2O_4$. 0.5 $H_2O$ requires C, 74.29; H, 7.52; N, 5.10

EXAMPLE 130

Preparation of cis-7-(1-S-(ethylcarbonyl)ethylaminocarbonyl)-8-(1-adamantylmethylaminocarbonyl)-2,3,5,6-dibenzobicyclo[2.2.2]octane (mixture of diastereomers)

The compound of example 75 (0.37 g, 0.74 mmol) was dissolved in THF under an atmosphere of argon and cooled to 0°. A 1M solution of ethyl magnesium bromide in THF (3 ml) was added and the solution stirred for a further 2 h before being allowed to warm to room temperature for overnight stirring. The reaction was quenched with 2M hydrochloric acid and after evaporation the product was dissolved in ethyl acetate and washed successively with saturated aqueous sodium hydrogencarbonate and with brine. The organic layer was dried, filtered and evaporated to leave the crude product which was purified by column chromatography (silica 90% dichloromethane and 10% ethyl acetate). Yield 0.19 g, 50%, m.p 105°–8°. Found: C, 77.87; H, 7.61; N, 5.22. $C_{34}H_{40}N_2O_3$ requires C, 77.83; H, 7.68; N, 5.34

EXAMPLE 131

Preparation of (±)-7-(methoxycarbonylmethyl)-cis-7-carboxy-8-(1-adamantylmethylaminocarbonyl)-2,3,5,6-dibenzobicyclo[2.2.2]octane a. Diels-Alder adduct of the methyl ester of aconitic anhydride and anthracene The methyl ester of aconitic anhydride (10.2 g, 60 mmol) was dissolved in dry dichloromenthane (200 ml) and anthracene (7.12 g, 40 mmol) was added followed by anhydrous aluminium chloride (9.0 g, 60 mmol). The solution was stirred at room temperature overnight and then poured onto a mixture of ice and hydrochloric acid. The organic layer was separated and dried, filtered and evaporated to leave an orange oil which was recrystallised from toluene after treatment with activated charcoal. The product, a buff solid, was dried in air (9.01 g) and used in the next step.

b. (±)-7-(methoxycarbonylmethyl)-cis-7-carboxy-8-(1-adamantylmethylaminocarbonyl)-2,3,5,6-dibenzobicyclo[2.2.2]octane The material was prepared essentially as in example 14 but using the material prepared in step a. above instead of (±)-2,3,5,6-dibenzobicyclo[2.2.2]octane-7,8-dicarboxylic anhydride. The compound was characterised and tested as the N-methyl-D-glucamine salt found: C, 65.72; H, 7.61; N, 3.83. $C_{39}H_{52}N_2O_{10}$ requires C, 66.08; H, 7.39; N, 3.95

EXAMPLE 132

Preparation of cis-7-(1-S-methoxycarbonyl)ethylaminocarbonyl)-8-(2-adamantylmethylaminocarbonyl)-2,3,5,6-dibenzobicyclo[2.2.2]octane (mixture of diastereomers)

The compound was prepared essentially as in example 25 but using the compound of example 39 instead of 8-(1-adamantylmethylaminocarbonyl)-2,3,5,6-dibenzobicyclo[2.2.2]octane-7-carboxylic acid as substrate, m.p. 105°–110°. Found C, 74.13; H, 7.17; N, 4.85. $C_{33}H_{38}N_2O_4 \cdot 0.5 \, H_2O$ requires C, 73.99; H, 7.33; N, 5.23

EXAMPLE 133

Preparation of cis-7-(2-R-carboxypyrrolidinocarbonyl)8-(2-adamantylmethylaminocarbonyl)-2,3,5,6-dibenzobicyclo[2.2.2]octane (mixture of diastereomers)

The benzyl ester of the compound was prepared essentially as in example 46 but using the compound of example 39 instead of 8-(1-adamantylmethylaminocarbonyl)-2,3,5,6-dibenzobicyclo[2.2.2]octane-7-carboxylic acid as substrate. The hydrogenolysis was performed as described in example 48. m.p. 105°–110°. The compound was further characterised and tested as its N-methyl-D-glucamine salt found: C, 64.86; H, 7.79; N, 5.19. $C_{41}H_{55}N_3O_9 \cdot 1.6H_2O$ requires C, 64.56; H, 7.69; N, 5.51

EXAMPLE 134

Preparation of 8-(1-adamantylmethylaminocarbonyl)-2,3,5,6-dibenzobicyclo[2.2.2]oct-7-ene-7-carboxylic acid a. dimethyl-2,3,5,6-dibenzobicyclo[2.2.2]oct-7-ene-7,8-dicarboxylate The Diels-Alder reaction between anthracene (10 g, 0.06 mol) and dimethyl acetylenedicarboxylate (8.3 ml, 0.07 mol) was performed essentially as in step a. of example 1 with the exeption that the reactants were refluxed for 24 hours.

b. 2,3,5,6,-dibenzobicyclo[2.2.2]oct-7-ene-7,8-dicarboxylic acid

To a solution of potassium hydroxide (1.05 g, 18.8 mmol) in water (30 ml) was added the solution of the product of step a. (2.0 g, 6.2 mmol) in dioxan (10 ml). The reaction mixture was heated to reflux for 20 mins, cooled to room temperature and diluted with 2N hydrochloric acid. The precipitated solid was filtered, washed with water and dried (1.42 g 78%).

c. 2,3,5,6,-dibenzobicyclo[2.2.2]oct-7-ene-7,8-dicarboxylic acid anhydride

A mixture of the product of step b (1.4 g, 4.8 mmol and acetic anhydride (36 ml) was heated at reflux for 45 mins. The solvent was evaporated and the residue was triturated with diethyl ether to afford white solid (0.73 g, 55%).

d. 8-(1-adamantylmethylaminocarbonyl)-2,3,5,6-dibenzobicyclo[2.2.2]oct-7-ene-7-carboxylic acid This was performed essentially as in example 14 using the product of step c above as substrate instead of 2,3,5,6-dibenzobicylo[2.2.2]oct-7,8-dicarboxylic anhydride. The compound was characterised and tested as the N-methyl-D-glucamine salt. Found: C, 67.79; H, 7.51; N, 4.33. $C_{36}H_{46}N_2O_8$ requires C, 68.12; H, 7.30; N, 4.41

EXAMPLE 135

Preparation of cis-7-(1-S-methoxycarbonyl-ethylaminocarbonyl)-8-(1-adamantylmethylaminocarbonyl)-2,3,5,6-dibenzobicyclo[2.2.2]oct-7-ene This was performed essentially as in example 25 using the product of example 134 as substrate instead of (±)-cis-8-(1-adamantylmethylaminocarbonyl)-2,3,5,6-dibenzobicyclo[2.2.2]oct-7-carboxylic acid found: C, 75.45; H, 6.79; N, 5.26. $C_{33}H_{36}N_2O_4$ requires C, 75.55; H, 6.92; N, 5.34

EXAMPLE 136

Preparation of cis-7-(2-R-(carboxymethylaminocarbonyl)pyrrolidinocarbonyl)-8-(1-adamantylmethylaminocarbonyl-2,3,5,6-dibenzobicyclo[2.2.2]oct-7-ene This was performed essentially as in example 119 using the product of example 134 as substrate instead of 8-(1-adamantylmethylaminocarbonyl)-2,3,5,6-dibenzobicyclo[2.2.2]oct-7-carboxylic acid. The compound was tested as the N-methyl-D-glucamine salt

EXAMPLE 137

Preparation of cis-7-(2-R-carboxy-pyrrolidinocarbonyl)-8-(1-adamantylmethylaminocarbonyl)-1,4-difluro-2,3,5,6-dibenzobicyclo[2.2.2]octane (mixture of diastereomers)

a. Diels alder reaction

This was performed essentially as in step a. of example 1 using 9,10-difluoroanthracene (prepared as in J.Org.Chem., 1989, 54, 1018) as substrate instead of anthracene.

b. (±)-cis-8-(1-adamantylmethylaminocarbonyl)-1,4-difluro-2,3,5,6-dibenzobicyclo[2.2.2]octane-7-carboxylic anhydride.

This was performed essentially as in example 14 using the product of step a. above as substrate instead of 2,3,5,6-dibenzobicyclo[2.2.2]oct-7,8-dicarboxylic anhydride c. cis -7-(2-R-benzyloxycarbonylprrolidinocarbonyl)-8-(1-adamantylmethylaminocarbonyl)-1,4-difluoro-2,3,5,6-dibenzobicyclo[2.2.2]octane (mixture of diastereomers)

This was performed essentially as in example 46 using the product of step b above as substrate instead of (±)-cis-8-(1-adamantylmethylaminocarbonyl)-2,3,5,6-dibenzobicyclo[2.2.2]oct-7-carboxylic acid d. cis-7-(2-R-carboxy-pyrrolidinocarbonyl)-8-(1-adamantylmethylaminocarbonyl)-1,4-difluoro-2,3,5,6-dibenzobicyclo[2.2.2]octane (mixture of diastereomers)

This was performed essentially as in example 48 using the product of the step c above as substrate instead of the product of example 46. The compound was characterised and tested as the N-methyl-D-glucamine salt. Found: C, 57.48; H, 7.43; N, 528. $C_{41}H_{53}F_2N_3O_9 \cdot 4.5 \, H_2O$ requires C, 57.82; H, 7.35; N, 4.93

Example 138

Preparation of cis-7-(2-R-carboxy-4-R-hydroxypyrrolidinocarbonyl)-8-(2-adamantylaminocarbonyl)-2,3,5,6-dibenzobicyclo[2.2.2]octane (mixture of diastereomers)

a. (±)-cis-8-(2-adamantylaminocarbonyl)-2,3,5,6-dibenzobicyclo[2.2.2]octane-7-carboxylic acid This was prepared essentially as in example 11 using 2-adamantamine as substrate instead of 1-adamantamine.

b. cis-7-(2-R-benzyloxycarbonyl-4-R-hydroxy-pyrrolidinocarbonyl)-8-(2-adamantylaminocarbonyl)-2,3,5,6-dibenzobicyclo[2.2.2]octane (mixture of diastereomers)

This was performed essentially as in example 46 using the product of step a. above as substrate instead of cis-8-(1-adamantylmethylaminocarbonyl)-2,3,5,6-dibenzobicyclo [2.2.2]oct-7-carboxylic acid c. 7-(2-R-carboxy-4-R-hydroxy-pyrrolidinocarbonyl)-8-(2-adamantylaminocarbonyl)-2,3,5,6-dibenzobicyclo[2.2.2] octane (mixture of diastereomers)

This was performed essentially as in example 48 using the product of step b above as substrate instead of the product of example 46. The compound was characterised and tested as the N-methyl-D-glucamine salt. Found: C, 60.86; H, 7.40; N, 5.31. $C_{40}H_{53}N_3O_{10}$. $2.9H_2O$ requires C, 60.97; H, 7.52; N, 5.33

EXAMPLE 139

Preparation of cis-7-(2-S-carboxypiperidinocarbonyl)-8-(1-adamantylmethylaminocarbonyl)-2,3,5,6-dibenzobicyclo [2.2.2]octane (mixture of diastereomers)

The reaction was performed essentially as in example 64 but using the benzyl ester of L-pipecolinic acid in step a. instead of the dibenzyl ester of aspartic acid. The compound was further characterised and tested as the N-methyl-D-glucamine salt. Found: C, 64.39; H, 7.97; N, 5.28. $C_{42}H_{57}N_3O_9$. $2.0H_2O$ requires C, 64.35; H, 7.84; N, 5.36

EXAMPLE 140

Preparation of cis-7-(4-carboxypiperidinocarbonyl)-8-(1-adamantylmethylaminocarbonyl)-2,3,5,6-dibenzobicyclo [2.2.2]octane (mixture of diastereomers)

The reaction was performed essentially as in example 64 but using the benzyl ester of 4-carboxypiperidine in step a. instead of the dibenzyl ester of aspartic acid. The compound was further characterised and tested as the N-methyl-D-glucamine salt. Found: C, 64.29; H, 8.05; N, 5.14. $C_{42}H_{57}N_3O_9$. $2.0H_2O$ requires C, 64.35; H, 7.84; N, 5.36

EXAMPLE 141

Preparation of cis-7-(2-S-(carboxymethyl)-pyrrolidinocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of 2-S-carboxymethylpyrrolidine (prepared as in WO 92/00295) in step a. instead of the dibenzyl ester of aspartic acid, $[\alpha]^D=-22.0°$ (c=1.0 in methanol). The compound was further characterised and tested as the N-methyl-D-glucamine salt. Found: C, 61.76; H, 7.89; N, 5.31. $C_{42}H_{57}N_3O_9$. $3.7H_2O$ requires C, 61.91; H, 7.97; N, 5.16

EXAMPLE 142

Preparation of cis-7-(2-R-(carboxymethyl)-pyrrolidinocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of 2-R-carboxymethylpyrrolidine (prepared as in WO 92/00295) in step a. instead of the dibenzyl ester of aspartic acid, $[\alpha]^D=+18.0°$ (c=1.0 in methanol). The compound was further characterised and tested as the N-methyl-D-glucamine salt. Found: C, 59.01; H, 8.12; N, 5.49. $C_{42}H_{57}N_3O_9$. $5.9H_2O$ requires C, 59.07; H, 8.12; N, 4.92

EXAMPLE 143

Preparation of cis-7-(2-S-(methoxycarbonylmethyl)pyrrolidinocarbonyl)-8-(1-adamantylmethylaminocarbonyl)-2,3,5, 6-dibenzobicyclo[2.2.2]octane (mixture of diastereomers)

The compound was prepared essentially as in example 63 using the product of example 141 as substrate instead of cis-7-(1-S-carboxyl-2-methylpropylaminocarbonyl)-8-(1-adamantylmethylaminocarbonyl)-2,3,5,6-dibenzobicyclo [2.2.2]octane, $[\alpha]^D=-21.0°$ (c=2.0 in CHCl3). Found: C, 75.80; H, 7.49; N, 4.62. $C_{36}H_{42}N_2O_4$. $0.3 H_2O$ requires C, 75.62; H, 7.50; N, 4.90

EXAMPLE 144

Preparation of cis-7-(2-R-(methoxycarbonylmethyl)pyrrolidinocarbonyl)-8-(1-adamantylmethylaminocarbonyl)-2,3,5, 6-dibenzobicyclo[2.2.2]octane (mixture of diastereomers)

The compound was prepared essentially as in example 63 using the product of example 142 as substrate instead of cis-7-(1-S-carboxyl-2-methylpropylaminocarbonyl)-8-(1-adamantylmethylaminocarbonyl)-2,3,5,6-dibenzobicyclo [2.2.2]octane, $[\alpha]^D=+18.0°$ (c=2.0 in CHCl$_3$). Found: C, 76.48; H, 7.46; N, 5.05. $C_{36}H_{42}N_2O_4$ requires C, 76.30; H, 7.47; N, 4.94

EXAMPLE 145

Preparation of cis-7-(2R-(1S-carboxyethylaminocarbonyl)pyrrolidinocarbonyl)-8-(1-adamantylmethylaminocarbonyl)-2,3,5,6-dibenzobicyclo[2.2.2]octane Diastereomer 1

The compound was prepared essentially as in example 64 but using the benzyl ester of D-prolyl-L-alanine in step a. instead of the dibenzyl ester of aspartic acid. The diastereomers were separated at the benzyl ester stage by column chromatography (silica 60% dichloromethane and 40% ethyl acetate). The compound with the higher $R_f$ was converted to the title compound by hydrogenation. The compound was tested as the N-methyl-D-glucamine salt

EXAMPLE 146

Preparation of cis-7-(2R-(1S-carboxyethylaminocarbonylmethyl)pyrrolidinocarbonyl)-8-(1-adamantylmethylaminocarbonyl)-2,3,5,6-dibenzobicyclo[2.2.2]octane Diastereomer 2

The compound was prepared essentially as in example 145 but using the compound with lower $R_f$ after diastereomer separation in the final hydrogenation step. The compound was tested as the N-methyl-D-glucamine salt

EXAMPLE 147

Preparation of cis-7-(2R-(1R-carboxyethylaminocarbonyl)pyrrolidinocarbonyl)-8-(1-adamantylmethylaminocarbonyl)-2,3,5,6-dibenzobicyclo[2.2.2]octane Diastereomer 1

The compound was prepared essentially as in example 64 but using the benzyl ester of D-prolyl-D-alanine in step a. instead of the dibenzyl ester of aspartic acid. The diastereomers were separated at the benzyl ester stage by column chromatography (silica 60% dichloromethane and 40% ethyl acetate). The compound with the higher $R_f$ was converted to the title compound by hydrogenation. The compound was further characterised and tested as the N-methyl-D-glucamine salt. Found: C, 59.62; H, 8.06; N, 6.23. $C_{44}H_{60}N_4O_{10}$ $4.7H_2O$ requires C, 59.45; H, 7.86; N, 6.30

EXAMPLE 148

Preparation of cis-7-(2R-(1R-carboxyethylaminocarbonyl)pyrrolidinocarbonyl)-8-(1-adamantylmethylaminocarbonyl)-2,3,5,6-dibenzobicyclo[2.2.2]octane Diastereomer 2

The compound was prepared essentially as in example 147 but using the compound with lower $R_f$ after diastereomer separation in the final hydrogenation step. The compound was tested as the N-methyl-D-glucamine salt

EXAMPLE 149

Preparation of cis-7-(2R-carboxy-4-S-hydroxypyrrolidinocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester of trans hydroxy-D-proline in step a. instead of the dibenzyl ester of aspartic acid. The compound was further characterised and tested as the N-methyl-D-glucamine salt. Found: C, 65.63; H, 7.48; N, 5.38. $C_{41}H_{55}N_3O_{10}$ requires C, 65.67; H, 7.39; N, 5.38

EXAMPLE 150

Preparation of cis-7-(3-carboxy-pyrrolidinocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester of 3-carboxypyrrolidine (prepared as in WO 92/00295) in step a. instead of the dibenzyl ester of aspartic acid. The compound was further characterised and tested as the N-methyl-D-glucamine salt. Found: C, 65.33; H, 7.67; N, 5.48. $C_{41}H_{55}N_3O_9$. 1.4 $H_2O$ requires C, 65.27; H, 7.65; N, 5.57

EXAMPLE 151

Preparation of cis-7-(3-methoxycarbonylpyrrolidinocarbonyl)-8-(1-adamantylmethylaminocarbonyl)-2,3,5,6-dibenzobicyclo[2.2.2]octane (mixture of diastereomers)

The compound was prepared essentially as in example 63 using the product of example 150 as substrate instead of cis-7-(1-S-carboxyl-2-methylpropylaminocarbonyl)-8-(1-adamantylmethylaminocarbonyl)-2,3,5,6-dibenzobicyclo[2.2.2]octane. Found: C, 75.83; H, 7.41; N, 5.08. $C_{35}H_{40}N_2O_4$ requires C, 76.06; H, 7.29; N, 5.07

EXAMPLE 152

Preparation of cis-7-(3-(+)-ethoxycarbonylpiperidinocarbonyl)-8-(1-adamantylmethylaminocarbonyl)-2,3,5,6-dibenzobicyclo[2.2.2]octane (mixture of diastereomers)

The compound was prepared essentially as in example 64 but using (+)ethyl nipecotate (prepared as described in J. Neurochem., 1976 26, 1029) in step a. instead of the dibenzyl ester of aspartic acid to give the title compound directly without the need for subsequent deprotection. Found: C, 76.69; H, 7.64; N, 4.81. $C_{37}H_{44}N_2O_4$ requires C, 76.52; H, 7.63; N, 4.82

EXAMPLE 153

Preparation of cis-7-(3-(-)-ethoxycarbonylpiperidinocarbonyl)-8-(1-adamantylmethylaminocarbonyl)-2,3,5,6-dibenzobicyclo[2.2.2]octane (mixture of diastereomers)

The compound was prepared essentially as in example 64 but using (-)ethyl nipecotate in step a. instead of the dibenzyl ester of aspartic acid to give the title compound directly without the need for subsequent deprotection. Found: C, 76.29; H, 7.61; N, 4.68. $C_{37}H_{44}N_2O_4$ requires C, 76.52; H, 7.63; N, 4.82

EXAMPLE 154

Preparation of cis-7-(3-(+)-methoxycarbonylpiperidinocarbonyl)-8-(1-adamantylmethylaminocarbonyl)-2,3,5,6-dibenzobicyclo[2.2.2]octane Diastereomer 1 a. cis-7-(3-(+)-carboxy-piperidinocarbonyl)-8-(1-adamantylmethylaminocarbonyl)- 2,3,5,6-dibenzobicyclo[2.2.2]octane (separated diastereomers)

The compound was prepared essentially as in example 64 but using (+)benzyl nipecotate (prepared by standard means from (+) ethyl nipecotate) in step a. instead of the dibenzyl ester of aspartic acid to give the carboxylic acid as a mixture of diastereomers. The two diastereomers were separated by chromatography (silica 90% dichloromethane and 10% ethyl acetate).

b. cis-7-(3-(+)-methoxycarbonyl-piperidinocarbonyl)-8-(1-adamantylmethylaminocarbonyl)-2,3,5,6-dibenzobicyclo[2.2.2]octane Diastereomer 1

The compound was prepared essentially as in example 63 using the less polar (higher $R_f$ material) isolated in step a. above as substrate instead of cis-7-(1-S-carboxyl-2-methylpropylaminocarbonyl)-8-(1-adamantylmethylaminocarbonyl)-2,3,5,6-dibenzobicyclo[2.2.2]octane

EXAMPLE 155

Preparation of cis-7-(3-(+)-methoxycarbonylpiperidinocarbonyl)-8-(1-adamantylmethylaminocarbonyl)-2,3,5,6-dibenzobicyclo[2.2.2]octane Diastereomer 2

The compound was prepared essentially as in example 63 using the more polar (lower $R_f$ material) isolated in step a. of example 154 as substrate instead of cis-7-(1-S-carboxyl-2-methylpropylaminocarbonyl)-8-(1-adamantylmethylaminocarbonyl)-2,3,5,6-dibenzobicyclo[2.2.2]octane

EXAMPLE 156

Preparation of cis-7-(3-(-)-methoxycarbonylpiperidinocarbonyl)-8-(1-adamantylmethylaminocarbonyl)-2,3,5,6-dibenzobicyclo[2.2.2]octane Diastereomer 1

The compound was prepared essentially as in example 154 but using (-) benzyl nipecotate as substrate in step a. rather than (+) benzyl nipecotate. As in that example the less polar material was converted to the title compound in step b

EXAMPLE 157

Preparation of cis-7-(3-(-)-methoxycarbonylpiperidinocarbonyl)-8-(1-adamantylmethylaminocarbonyl)-2,3,5,6-dibenzobicyclo[2.2.2]octane Diastereomer 2

The compound was prepared essentially as in example 63 using the more polar (lower $R_f$ material) isolated in step a. of example 156 as substrate instead of cis-7-(1-S-carboxyl-2-methylpropylaminocarbonyl)-8-(1-adamantylmethylaminocarbonyl)-2,3,5,6-dibenzobicyclo[2.2.2]octane

EXAMPLE 158

Preparation of cis-7-(2R-(1methyl-1-carboxycyclopropylaminocarbonyl)pyrrolidinocarbonyl)-8-(1-adamantylmethylaminocarbonyl)-2,3,5,6-dibenzobicyclo[2.2.2]octane Diastereomer 1

The compound was prepared essentially as in example 64 but using the benzyl ester of D-prolyl-cyclopropylalanine (prepared by standard means) in step a. instead of the dibenzyl ester of aspartic acid. The diastereomers were separated at the benzyl ester stage by column chromatography (silica 60% dichloromethane and 40% ethyl acetate). The compound with the higher $R_f$ was converted to the title compound by hydrogenation, $[\alpha]^D=+10.0°$ (c=1.0 in methanol). The compound was further characterised and tested as the N-methyl-D-glucamine salt. Found: C, 58.54; H, 7.44; N, 6.03. $C_{45}H_{60}N_4O_{10}$ 5.6$H_2O$ requires C, 58.92; H, 7.81; N, 6.11

EXAMPLE 159

Preparation of cis-7-(2R-(1methyl-1-carboxycyclopropylaminocarbonyl)pyrrolidinocarbonyl)-8-(1-adamantylmethylaminocarbonyl)-2,3,5,6-dibenzobicyclo[2.2.2]octane Diastereomer 2

The compound was prepared essentially as in example 158 but using the compound with lower $R_f$ after diastereomer separation in the final hydrogenation step. The compound was tested as the N-methyl-D-glucamine salt

EXAMPLE 160

Preparation of cis-7-(2-R-carboxypyrrolidinocarbonyl)-8-(1-adamantylmethylaminocarbonyl)-2,3-(2-fluorobenzo)-5,6-benzobicyclo[2.2.2]octane (mixture of isomers 1)

a. 2,3-(2-fluorobenzo)-5,6-benzobicyclo[2.2.2]octane-7,8-dicarboxylic anhydride

This was performed essentially as described in example 1 step a. except that 2-fluoroanthracene was used as reactant instead of anthracene.

b. 8-(1-adamantylmethylaminocarbonyl)-2,3-(2-fluorobenzo)-5,6-benzobicyclo[2.2.2]octane-7-carboxylic acid.

The reaction was performed essentially as described in example 14 but using the compound described in step a. above rather than 2,3,5,6-dibenzobicyclo[2.2.2]octane-7,8-dicarboxylic anhydride.

c. cis-7-(2-R-benzyloxycarbonylpyrrolidinocarbonyl)-8-(1-adamantylmethylaminocarbonyl)-2,3-(2-fluorobenzo)-5,6-benzobicyclo[2.2.2]octane.

The reaction was performed essentially as in example 46 but using the compound prepared in step b above, rather than (+)cis-8-(1-adamantylmethylaminocarbonyl)-2,3,5,6-dibenzobicyclo[2.2.2]octane-7-carboxylic acid.

d. cis-7-(2-R-carboxypyrrolidinocarbonyl)-8-(1-adamantylmethylaminocarbonyl)-2,3-(2-fluorobenzo)-5,6-benzobicyclo[2.2.2]octane (mixture of isomers 1)

The reaction was performed essentially as in example 48 but using the compound prepared in step c above, rather than cis-7-(2-R-benzyloxycarbonylpyrrolidinocarbonyl)-8-(1-adamantylmethylaminocarbonyl)-2,3,5,6-dibenzobicyclo [2.2.2]octane. The material which by this stage was a mixture of eight compounds was separated by HPLC (C8 column 60% acetonitrile, 40% water and 0.1% acetic acid) into three components. The material with a retention time of 15 min was designated the compound of this example. The compound was further characterised and tested as the N-methyl-D-glucamine salt found: C, 65.22; H, 7.38; N, 5.42. $C_{41}H_{54}FN_3O_9$ requires C, 65.49; H, 7.24; N, 5.59

EXAMPLE 161

Preparation of cis-7-(2-R-carboxypyrrolidinocarbonyl)-8-(1-adamantylmethylaminocarbonyl)-2,3-(2-fluorobenzo)-5,6-benzobicyclo[2.2.2]octane (mixture of isomers 2)

The mixture from example 160 step d with a retention time of 16 min was designated the compound of this example. The compound was further characterised and tested as the N-methyl-D-glucamine salt found: C, 64.99; H, 7.29; N, 5.59. $C_{41}H_{54}FN_3O_9$ requires C, 65.49; H, 7.24; N, 5.59

EXAMPLE 162

Preparation of cis-7-(2-R-carboxypyrrolidinocarbonyl)-8-(1-adamantylmethylaminocarbonyl)-2,3-(2-fluorobenzo)-5,6-benzobicyclo[2.2.2]octane (mixture of isomers 3)

The mixture from example 160 step d with a retention time of 22 min was designated the compound of this example. The compound was further characterised and tested as the N-methyl-D-glucamine salt found: C, 65.29; H, 7.42; N, 5.65. $C_{41}H_{54}FN_3O_9$ requires C, 65.49; H, 7.24; N, 5.59

EXAMPLE 163

Preparation of cis-7-(2R-(1-carboxy-1-methylethylaminocarbonyl)pyrrolidinocarbonyl)-8-(1-adamantylmethylaminocarbonyl)-2,3,5,6-dibenzobicyclo[2.2.2]octane Diastereomer 1

The compound was prepared essentially as in example 64 but using the benzyl ester of D-prolyl-alpha-aminobutyric acid in step a. instead of the dibenzyl ester of aspartic acid. The diastereomers were separated at the benzyl ester stage by recrystallisation from ethyl acetate and column chromatography (silica 50% hexane and 50% ethyl acetate). The compound with the lower $R_f$ was converted to the title compound by hydrogenation. The compound was further characterised and tested as the N-methyl-D-glucamine salt. Found: C, 65.91; H, 7.65; N, 6.60. $C_{45}H_{62}N_4O_{10}$ requires C, 65.99; H, 7.63; N, 6.84

EXAMPLE 164

Preparation of cis-7-(2R-(1-carboxy-1-methylethylaminocarbonyl)pyrrolidinocarbonyl)-8-(1-adamantylmethylaminocarbonyl)-2,3,5,6-dibenzobicyclo[2.2.2]octane Diastereomer 2

The compound was prepared essentially as in example 147 but using the compound with higher $R_f$ after diastereomer separation in the final hydrogenation step. The compound was tested as the N-methyl-D-glucamine salt

EXAMPLE 165

Preparation of cis-7-(2-R-carboxypyrrolidinocarbonyl)-8-(1-adamantylmethylaminocarbonyl)-8-fluoro-2,3,5,6-dibenzobicyclo[2.2.2]octane (mixture of diastereomers)

The compound was prepared essentially as described in example 160 but performing the reaction in step a. with anthracene and 2-fluoromaleic anhydride (prepared as in J.Am.Chem.Soc., 1959, 81, 2678) instead of the reagents stated. No attempt was made at separation of the diastereomers at any stage. The compound was further characterised and tested as the N-methyl-D-glucamine salt found: C, 65.59; H, 7.18; N, 5.61. $C_{41}H_{54}FN_3O_9$ requires C, 65.49; H 7.24; N, 5.59

EXAMPLE 166

Preparation of cis-7-(-N-(carboxymethyl)-N-(methoxycarbonylmethyl)aminocarbonyl)-8-(1-adamantylmethylaminocarbonyl)-2,3,5,6-dibenzobicyclo[2.2.2]octane The reaction was performed essentially as in example 25 but using methyl N-(carboxymethyl)glycine (prepared as in Tetrahedron, 1984, 40, 1151) as substrate instead of L-alanine methyl ester. The compound was further characterised and tested as the N-methyl-D-glucamine salt found: C, 64.21; H, 7.25; N, 5.22. $C_{41}H_{55}N_3O_{11}$ requires C, 64.30; H, 7.24; N, 5.49

EXAMPLE 167

Preparation of cis-7-(-N-(4-(2-oxo-N(carboxymethyl) pyrrolidine))aminocarbonyl)-8-(1-adamantylmethylaminocarbonyl)-2,3,5,6-dibenzobicyclo[2.2.2]octane Diastereomers 1 and 2

The reaction was performed essentially as in example 64 but using the benzyl ester of N-carboxymethyl-2-oxo-4-aminopyrrolidine (prepared as in Peptide Research 1991, 4, 171) in step a. instead of the dibenzyl ester of aspartic acid. The compound was separated at the end of step a. into two pairs of diastereoisomer by column chromatography the higher $R_f$ components being hydrogenated at step b to give the title compounds of this example. The compound was further characterised and tested as the N-methyl-D-glucamine salt. Found: C, 57.23; H, 7.41; N, 6.13. $C_{42}H_{56}N_4O_{10}$ 5.5$H_2O$ requires C, 57.54; H, 7.71; N, 6.39

EXAMPLE 168

Preparation of cis-7-(-N-(4-(2-oxo-N-(carboxymethyl) pyrrolidine))aminocarbonyl)-8-(1-adamantylmethylaminocarbonyl)-2,3,5,6-dibenzobicyclo[2.2.2]octane Diastereomers 3 and 4

The reaction was performed essentially as in example 167 except that the lower $R_f$ components were used in the hydrogenation step b. The compound was further characterised and tested as the N-methyl-D-glucamine salt. Found: C, 56.07; H, 7.39; N, 6.56. $C_{42}H_{56}N_4O_{10}$ 6.5$H_2O$ requires C, 56.46; H, 7.78; N, 6.27

EXAMPLE 169

Preparation of cis-7-(-N-(4-(2-oxo-N-(methoxycarbonylmethyl)pyrrolidine))aminocarbonyl)-8-(1-adamantylmethylaminocarbonyl)-2,3,5,6-dibenzobicyclo[2.2.2]octane Diastereomers 1 and 2

The compound was prepared essentially as in example 63 using the compound of example 167 as substrate instead of cis-7-(1-S-carboxyl-2-methylpropylaminocarbonyl)-8-(1-adamantylmethylaminocarbonyl)-2,3,5,6-dibenzobicyclo[2.2.2]octane. Found: C, 66.83; H, 7.21; N, 6.15. $C_{36}H_{41}N_3O_5$. 1.7$CH_3OH$ and 0.4 $Ch_2Cl_2$ requires C, 66.89; H, 7.21; N, 6.15

EXAMPLE 170

Preparation of cis-7-(-N-(4-(2-oxo-N-(methoxycarbonylmethyl)pyrrolidine))aminocarbonyl)-8-(1-adamantylmethylaminocarbonyl)-2,3,5,6-dibenzobicyclo[2.2.2]octane Diastereomers 3 and 4

The compound was prepared essentially as in example 63 using the compound of example 167 as substrate instead of cis-7-(1-S-carboxyl-2-methylpropylaminocarbonyl)-8-(1-adamantylmethylaminocarbonyl)- 2,3,5,6-dibenzobicyclo [2.2.2]octane. Found: C, 64.05; H, 6.71; N, 5.82. $C_{36}H_{41}N_3O_5$. 1.0$CH_3OH$ and 1.0 $CH_2Cl_2$ requires C, 64.04; H, 6.65; N, 5.90% H, 6.71; N, 5.82. $C_{36}H_{41}N_3O_5$. 1.0$CH_3OH$ and 1.0 $CH_2Cl_2$ requires C, 64.04; H, 6.65; N, 5.90

EXAMPLE 171

Preparation of cis-7-(1S-(carboxymethylaminocarbonyl)-2-phenylethylaminocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of L-phenylalanylglycine in step a. instead of the dibenzyl ester of aspartic acid. The compound was further characterised and tested as the N-methyl-D-glucamine salt. Found: C, 64.11; H, 7.62; N, 6.35. $C_{47}H_{60}N_4O_{10}$. 2.3$H_2O$ requires C, 63.95; H, 7.38; N, 6.35

EXAMPLE 172

Preparation of cis-7-(1S-(1R-carboxyethylaminocarbonyl)-2-phenylethylaminocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of L-phenylalanyl-D-alanine in step a. instead of the dibenzyl ester of aspartic acid. The compound was tested as the mono-N-methyl-D-glucamine salt

EXAMPLE 173

Preparation of cis-7-(1R-(carboxymethylaminocarbonyl)-2-phenylethylaminocarbonyl)-8-(1-adamantylmethylaminocarbonyl)-2,3,5,6-dibenzobicyclo[2.2.2]octane (mixture of diastereomers)

The reaction was performed essentially as in example 64 but using the benzyl ester of D-phenylalanylglycine in step a. instead of the dibenzyl ester of aspartic acid. The compound was further characterised and tested as the mono-N-methyl-D-glucamine salt. Found: C, 62.18; H, 7.48; N, 5.74. $C_{47}H_{60}N_4O_{10}$. 4.0$H_2O$ requires C, 61.86; H, 7.51; N, 6.14

EXAMPLE 174

Preparation of cis-7-(1S-(carboxymethylaminocarbonyl)-2-(3-indolyl)phenylethylaminocarbonyl)-8-(1-adamantylmethylaminocarbonyl)- 2,3,5,6-dibenzobicyclo[2.2.2]octane (mixture of diastereomers)

The reaction was performed essentially as in example 64 but using the benzyl ester of L-tryptophanylglycine in step a. instead of the dibenzyl ester of aspartic acid. The compound was further characterised and tested as the mono-N-methyl-D-glucamine salt. Found: C, 58.88; H, 7.07; N, 6.62. $C_{49}H_{61}N_5O_{10}$. 3.2$H_2O$ and 1.0 $CH_2Cl_2$ requires C, 58.73; H, 6.84; N, 6.85

EXAMPLE 175

Preparation of cis-7-(2R-(1-S-carboxy-2-carboxyethylaminocarbonyl)pyrrolidinocarbonyl)-8-(1-adamantylmethylaminocarbonyl)-2,3,5,6-dibenzobicyclo[2.2.2]octane Diastereomer 1

The compound was prepared essentially as in example 64 but using the dibenzyl ester of D-prolyl-L-aspartic acid in step a. instead of the dibenzyl ester of aspartic acid. The diastereomers were separated at the benzyl ester stage by column chromatography (silica 60% dichloromethane and 40% ethyl acetate). The compound with the higher $R_f$ was converted to the title compound by hydrogenation. Found: C, 64.46; H, 6.97; N, 5.30. $C_{38}H_{43}N_3O_7$.3.0 $H_2O$ requires C, 64.48; H, 6.97; N, 5.63% $^1H$ NM

EXAMPLE 176

Preparation of cis-7-(2R-(1-S-carboxy-2-carboxyethylaminocarbonyl)pyrrolidinocarbonyl)-8-(1-adamantylmethylaminocarbonyl)-2,3,5,6-dibenzobicyclo[2.2.2]octane Diastereomer 2

The compound was prepared essentially as in example 175 but using the compound with lower $R_f$ after diastereomer separation in the final hydrogenation step. Found: C, 69.21; H, 6.73; N, 5.93. $C_{38}H_{43}N_3O_7$. 0.5 $H_2O$ requires C, 68.86; H, 6.69; N, 6.34

EXAMPLE 177

Preparation of (±)-cis-8-(6-undecylaminocarbonyl)-2,3,5,6-dibenzobicyclo[2.2.2]octane-7-carboxylic acid The compound was prepared essentially as in example 14 but using 6-undecylamine as substrate instead of 1-adamantylmethylamine. The compound was further characterised and tested as the N-methyl-D-glucamine salt. Found: C, 65.38; H, 8.53; N, 5.33. $C_{36}H_{54}N_2O_8$. 1.0$H_2O$ requires C, 65.43; H, 8.54; N, 4.23

EXAMPLE 178

Preparation of cis-7-(-N-(3S-(2-oxo-N-(carboxymethyl)pyrrolidine))aminocarbonyl)-8-(1-adamantylmethylaminocarbonyl)-2,3,5,6-dibenzobicyclo[2.2.2]octane The reaction was performed essentially as in example 64 but using the benzyl ester of N-carboxymethyl-2-oxo-3S-aminopyrrolidine (prepared as in J. Org. Chem. 1982, 47, 105) in step a. instead of the dibenzyl ester of aspartic acid. The compound was tested as the N-methyl-D-glucamine salt

EXAMPLE 179

Preparation of cis-7-(-N-(3R-(2-oxo-N-(carboxymethyl)pyrrolidine))aminocarbonyl)-8-(1-adamantylmethylaminocarbonyl)-2,3,5,6-dibenzobicyclo[2.2.2]octane The reaction was performed essentially as in example 64 but using the benzyl ester of N-carboxymethyl-2-oxo-3R-aminopyrrolidine (prepared as in J. Org. Chem. 1982, 47, 105) in step a. instead of the dibenzyl ester of aspartic acid. The compound was tested as the N-methyl-D-glucamine salt

EXAMPLE 180

Preparation of cis-7-(2R-(carboxymethylaminocarbonyl)-2S-methyl-pyrrolidinocarbonyl)-8-(1-adamantylmethylaminocarbonyl)-2,3,5,6-dibenzobicyclo[2.2.2]octane The compound was prepared essentially as in example 64 but using the benzyl ester of α-methyl-D-prolyl-glycine (prepared as in J. Am. Chem. Soc., 1983, 105, 5390) in step a. instead of the dibenzyl ester of aspartic acid. The compound was tested as the N-methyl-D-glucamine salt

EXAMPLE 181

Preparation of cis-7-(2R-(aminocarbonylmethylaminocarbonyl)-pyrrolidinocarbonyl)-8-(1-adamantylmethylaminocarbonyl)-2,3,5,6-dibenzobicyclo[2.2.2]octane The compound was prepared essentially as in example 64 but using D-prolyl-glycinamide in step a. instead of the dibenzyl ester of aspartic acid to give the title compound directly. Obviously there was no need for a hydrogenation step. Found: C, 67.41; H, 7.01; N, 8.54. $C_{36}H_{42}N_4O_4$. 2.4$H_2O$ requires C, 67.79; H, 7.39; N, 8.78

EXAMPLE 182

Preparation of cis-7-(1R-(aminocarbonylmethylaminocarbonyl)-phenethylaminocarbonyl)-8-(1-adamantylmethylaminocarbonyl)-2,3,5,6-dibenzobicyclo[2.2.2]octane The compound was prepared essentially as in example 64 but using D-phenylalanyl-glycinamide in step a. instead of the dibenzyl ester of aspartic acid to give the title compound directly. Obviously there was no need for a hydrogenation step. Found: C, 71.76; H, 7.01; N, 8.09. $C_{40}H_{44}N_4O_4$. 1.5$H_2O$ requires C, 71.51; H, 7.05; N, 8.33

EXAMPLE 183

Preparation of cis-7-(2R-(carboxymethylaminocarbonyl)-4R-hydroxy-pyrrolidinocarbonyl)-8-(1-adamantylmethylaminocarbonyl)-2,3,5,6-dibenzobicyclo[2.2.2]octane The compound was prepared essentially as in example 64 but using the benzyl ester of cis-4-hydroxy-D-prolylglycine in step a. instead of the dibenzyl ester of aspartic acid. The compound was further characterised and tested as the N-methyl-D-glucamine salt. Found: C, 56.39; H, 7.65; N, 7.96. $C_{43}H_{58}N_4O_{11}$. 6.2$H_2O$ and 1.6 $CH_3CN$ requires C, 56.37; H, 7.70; N, 7.97

EXAMPLE 184

Preparation of cis-7-(2S-(1S-carboxyethylaminocarbonylmethyl) pyrrolidinocarbonyl)-8-(1-adamantylmethylaminocarbonyl)-2,3,5,6-dibenzobicyclo[2.2.2]octane (mixture of diastereomers)

a. cis-7-(2S-(1 1S-benzyloxycarbonylethylaminocarbonylmethyl)-pyrrolidinocarbonyl)-8-(1-adamantylmethylaminocarbonyl)-2,3,5,6-dibenzobicyclo[2.2.2]octane (mixture of diastereomers)

The compound of example 141 (250 mg, 0.45 mmol) was dissolved in dichloromethane (30 ml) and L-alanine benzyl ester p-toluenesulphonate salt (160 mg, 0.45 mmol) was added followed by PyBOP (235 mg, 0.45 mmol) and Hunigs base (240 ml, 1.35 mmol). The mixture was stirred at room temperature for 42 h and then washed with 5% potassium hydrogensulphate solution (15 ml), sodium hydrogencarbonate solution (15 ml) and saturated brine (15 ml). The solution was then dried and the product purified by chromatography (silica and ethyl acetate) to yield a colourless solid.

b. cis-7-(2S-(1S-carboxyethylaminocarbonylmethyl)-pyrrolidinocarbonyl)-8-(1-adamantylmethylaminocarbonyl)-2,3,5,6-dibenzobicyclo[2.2.2]octane (mixture of diastereomers)

The reaction was performed essentially as in example 48 but using the product of step a. as substrate instead of the product of example 46. The compound was tested as the N-methyl-D-glucamine salt

EXAMPLE 185

Preparation of cis-7-(2S-(1R-carboxyethylaminocarbonylmethyl)pyrrolidinocarbonyl)-8-(1-adamantylmethylaminocarbonyl)-2,3,5,6-dibenzobicyclo[2.2.2]octane (mixture of diastereomers)

The reaction was performed essentially as in example 184 but using D-alanine benzyl ester p-toluenesulphonate salt in step a. rather than L-alanine benzyl ester p-toluenesulphonate salt. The compound was further characterised and tested as the N-methyl-D-glucamine salt. Found: C, 59.20; H, 7.64; N, 6.11. $C_{45}H_{62}N_4O_{11}$. 4.9$H_2O$ requires C, 59.54; H, 7.98; N, 6.17

EXAMPLE 186

Preparation of cis-7-(2S-(1R-carboxyethylaminocarbonylmethyl)pyrrolidinocarbonyl)-8-(1-adamantylmethylaminocarbonyl)-2,3,5,6-dibenzobicyclo[2.2.2]octane Diastereomer 1 a. cis-7-(2S-carboxymethylpyrrolidinocarbonyl)-8-(1-adamantylmethylaminocarbonyl)-2,3,5,6-dibenzobicyclo[2.2.2]octane Diastereomer 1

The compound of example 141 was separated into its constituent diastereomers by recrystallisation from dichloromethane. The crystals isolated were the title compound. In addition the other diastereomer was isolated by concentration of the mother liquors.

b. cis-7-(2S-(1R-carboxyethylaminocarbonylmethyl)pyrrolidinocarbonyl)-8-(1-adamantylmethylaminocarbonyl)-2,3,5,6-dibenzobicyclo[2.2.2]octane Diastereomer 1

This was prepared in two steps as described in example 185 but using the product from step a. above rather than the compound of example 141 as the substrate in step a. The compound was tested as the N-methyl-D-glucamine salt

EXAMPLE 187

Preparation of cis-7-(2S-(1R-carboxyethylaminocarbonylmethyl)pyrrolidinocarbonyl)-8-(1-adamantylmethylaminocarbonyl)-2,3,5,6-dibenzobicyclo[2.2.2]octane Diastereomer 2

This was prepared essentially as in example 185 but using the dichloromethane soluble diastereomer described in example 186 step a. as substrate in step a. rather than the compound of example 141. The compound was tested as the N-methyl-D-glucamine salt

EXAMPLE 188

Preparation of cis-7-(2R-(methoxycarbonylmethylaminocarbonyl)pyrrolidinocarbonyl)-8-(1-adamantylmethylaminocarbonyl)-2,3,5,6-dibenzobicyclo[2.2.2]octane Diastereomer 1

The compound of example 123 was separated into its constituent diastereomers by chromatography (silica 30% ethyl acetate and 70% dichloromethane). The less polar material was designated the compound of this example. Found: C, 64.59; H, 6.76: N, 5.94. $C_{37}H_{43}N_3O_5 \cdot 0.3$ EtOAc and 1.1 $CH_2Cl_2$ requires C, 64.70; H, 6.58; N, 5.76

EXAMPLE 189

Preparation of cis-7-(2R-(methoxycarbonylmethylaminocarbonyl)pyrrolidinocarbonyl)-8-(1-adamantylmethylaminocarbonyl)-2,3,5,6-dibenzobicyclo[2.2.2]octane.

The more polar material isolated in example 188 was designated the compound of this example. Found: C, 70.27; H, 7.70; N, 6.63. $C_{37}H_{43}N_3O_5$ requires C, 69.97; H, 7.27; N, 6.62

EXAMPLE 190

Preparation of cis-7-(2R-(carboxymethyl(N-methyl)aminocarbonyl)pyrrolidinocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester of D-prolyl-sarcosine in step a. instead of the dibenzyl ester of aspartic acid. The compound was tested as the N-methyl-D-glucamine salt

EXAMPLE 191

Preparation of cis-7-(-N-(3R-(2-oxo-N-(methoxycarbonylmethyl)pyrrolidine))aminocarbonyl)-8-(1-adamantylmethylaminocarbonyl)-2,3,5,6-dibenzobicyclo[2.2.2]octane The reaction was performed essentially as in example 63 using the compound of example 179 as substrate instead of cis-7-(1-S-carboxyl-2-methylpropylaminocarbonyl)-8-(1-adamantylmethylaminocarbonyl)-2,3,5,6-dibenzobicyclo [2.2.2]octane. The compound was tested as the N-methyl-D-glucamine salt

EXAMPLE 192

Preparation of cis-7-(2-R-carboxy-pyrrolidinocarbonyl)-8-(1-adamantylmethylaminocarbonyl)-1,4-dimethyl-2,3,5,6-dibenzobicyclo[2.2.2]octane Diastereomer 1

The compound was prepared essentially as in example 137 but using 9,10-dimethylanthracene as substrate in step a. instead of 9,10-difluoroanthracene. In addition the mixture of diastereomers isolated after step c was separated into its constituent isomers using chromatography (silica 10% ethyl acetate and 90% dichloromethane). The less polar material was taken through to the title compound. The compound was further characterised and tested as the N-methyl-D-glucamine salt found: C, 64.71; H, 7.88; N, 5.06. $C_{43}H_{59}N_3O_9 \cdot 2.0H_2O$ requires C, 64.65; H, 7.96; N, 5.26

EXAMPLE 193

Preparation of cis-7-(2-R-carboxy-pyrrolidinocarbonyl)-8-(1-adamantylmethylaminocarbonyl)-1,4-dimethyl-2,3,5,6-dibenzobicyclo[2.2.2]octane Diastereomer 2

The more polar compound described in example 192 was hydrogenated to give the compound of this example. The compound was further characterised and tested as the N-methyl-D-glucamine salt. Found: C, 61.67; H, 7.88; N, 4.82. $C_{43}H_{59}N_3O_9 \cdot 4.0H_2O$ requires C, 61.88; H, 8.10; N, 5.0

EXAMPLE 194

Preparation of cis-7-(2S-(carboxymethylaminocarbonylmethyl)pyrrolidinocarbonyl)-8-(1-adamantylmethylaminocarbonyl)-2,3,5,6-dibenzobicyclo[2.2.2]octane (mixture of diastereomers)

The reaction was performed essentially as in example 184 but using the benzyl ester of glycine in step a. rather than L-alanine benzyl ester p-toluenesulphonate salt. The compound was further characterised and tested as the N-methyl-D-glucamine salt, HPLC; $R_T$=16.2 mins, C8 column, $CH_3CN$ 50%, 0.1% $CH_3COOH$

EXAMPLE 195

Preparation of cis-7-(2R-(1R-(2,2-dimethyl-1,3-dioxolane-4-methoxycarbonyl)-ethylaminocarbonyl)pyrrolidinocarbonyl)-8-(1-adamantylmethylaminocarbonyl)-2,3,5,6-dibenzobicyclo[2.2.2]octane The compound of example 147 (305 mg, 0.5 mmol) was dissolved in dry dichloromethane (3 ml) and solketal (66 ml, 0.5 mmol) was added. DMAP (2 mg) and DCCI (103 mg, 0.5 mmol) were added and the reaction mixture stirred at room temperature for 1 h. After filtration the solution was evaporated to leave a foam which was purified by column chromatography (silica 95% dichloromethane and 5% methanol) to leave the title compound (195 mg). Found: C, 71.42; H, 7.45; N, 5.84. $C_{43}H_{53}N_3O_7$ requires C, 71.35; H, 7.38; N, 5.81

EXAMPLE 196

Preparation of cis-7-(2R-(1R-(pivaloyloxymethoxycarbonyl)-ethylaminocarbonyl)pyrrolidinocarbonyl)-8-(1-adamantylmethylaminocarbonyl)-2,3,5,6-dibenzobicyclo [2.2.2]octane The compound of example 147 (305 mg, 0.5 mmol) was dissolved in DMF (2 ml) and pivaloyloxymethyl chloride (72 ml, 0.55 mmol) and caesium carbonate (82 mg, 0.5 mmol) was added. After gentle warming the reaction was stirred at room temperature for 1 h. The reaction mixture was poured onto brine (30 ml) and extracted with ethyl acetate (30 ml). The organic layer was washed with brine (2×30 ml) dried and evaporated. The material was completely purified by passage through a silica pad eluting with a 1:1 mixture of dichloromethane and ethyl acetate to leave the title compound (160 mg). Found: C, 71.21; H, 7.48; N, 5.62. $C_{43}H_{53}N_3O_7$ requires C, 71.35; H, 7.38; N, 5.81

EXAMPLE 197

Preparation of cis-7-(2R-aminocarbonyl)pyrrolidinocarbonyl)-8-(1-adamantylmethylaminocarbonyl)-2,3,5,6-dibenzobicyclo[2.2.2]octane (mixture of diastereomers)

The compound was prepared essentially as in example 25 but using D-prolinamide instead of the methyl ester of 1-alanine

EXAMPLE 198

Preparation of cis-7-(2R-(carboxymethylaminocarbonylmethyl)pyrrolidinocarbonyl)-8-(1-adamantylmethylaminocarbonyl)-2,3,5,6-dibenzobicyclo[2.2.2]octane Diastereomer 1 a. cis-7-(2R-carboxymethylpyrrolidinocarbonyl)-8-(1-adamantylmethylaminocarbonyl)-2,3,5,6-dibenzobicyclo [2.2.2]octane (separation of diastereomers)

The compound of example 142 was treated with dichloromethane. The dichloromethane insoluble material was designated diastereomer 1 and the soluble isomer designated diastereomer 2 b. cis-7-(2-(carboxymethylaminocarbonylmethyl)-pyrrolidinocarbonyl)-8-(1-adamantylmethylaminocarbonyl)-2,3, 5,6-dibenzobicyclo[2.2.2]octane Diastereomer 1

The compound was prepared essentially as in example 194 except that the diastereomer 1 from step a. above was used as substrate instead of the compound of example 141. The compound was tested as the N-methyl-D-glucamine salt

EXAMPLE 199

Preparation of cis-7-(2R-(carboxymethylaminocarbonylmethyl)pyrrolidinocarbonyl)-8-(1-adamantylmethylaminocarbonyl)-2,3,5,6-dibenzobicyclo[2.2.2]octane Diastereomer 2

The compound was prepared essentially as in example 194 except that the diastereomer 2 from example 198 step a. was used as substrate instead of the compound of example 141. The compound was tested as the N-methyl-D-glucamine salt

EXAMPLE 200

Preparation of cis-7-(2R-(1S-carboxyethylaminocarbonylmethyl)pyrrolidinocarbonyl)-8-(1-adamantylmethylaminocarbonyl)-2,3,5,6-dibenzobicyclo[2.2.2]octane Diastereomer 1

The compound was prepared essentially as in example 184 except that the diastereomer 1 from example 198 step a. was used as substrate instead of the compound of example 141. The compound was tested as the N-methyl-D-glucamine salt

EXAMPLE 201

Preparation of cis-7-(2R-(1S-carboxyethylaminocarbonylmethyl)pyrrolidinocarbonyl)-8-(1-adamantylmethylaminocarbonyl)-2,3,5,6-dibenzobicyclo[2.2.2]octane Diastereomer 2

The compound was prepared essentially as in example 184 except that the diastereomer 2 from example 198 step a. was used as substrate instead of the compound of example 141. The compound was tested as the N-methyl-D-glucamine salt

EXAMPLE 202

Preparation of cis-7-(2R-(1R-carboxyethylaminocarbonylmethyl)pyrrolidinocarbonyl)-8-(1-adamantylmethylaminocarbonyl)-2,3,5,6-dibenzobicyclo[2.2.2]octane Diastereomer 1

The compound was prepared essentially as in example 185 except that the diastereomer 1 from example 198 step a. was used as substrate instead of the compound of example 141. The compound was tested as the N-methyl-D-glucamine salt

EXAMPLE 203

Preparation of cis-7-(2R-(1R-carboxyethylaminocarbonylmethyl)pyrrolidinocarbonyl)-8-(1-adamantylmethylaminocarbonyl)-2,3,5,6-dibenzobicyclo[2.2.2]octane Diastereomer 2

The compound was prepared essentially as in example 185 except that the diastereomer 2 from example 198 step a. was used as substrate instead of the compound of example 141. The compound was tested as the N-methyl-D-glucamine salt

EXAMPLE 204

Preparation of cis-7-(2R-(carboxyethyl)pyrrolidinocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester of trans-3-(2R-pyrrolidino)-but-2-enoic acid (prepared from benzyl(triphenylphosphoranylidene)acetate and N-(t-butoxycarbonyl)-D-prolinal by Wittig reaction) in step a. instead of the dibenzyl ester of aspartic acid. The compound was further characterised and tested as the N-methyl-D-glucamine salt. Found: C, 64.81; H, 7.94; N, 5.14. $C_{43}H_{59}N_3O_9 \cdot 2.0H_2O$ requires C, 64.77; H, 7.96; N, 5.27

EXAMPLE 205

Preparation of cis-7-(2S-(methoxycarbonylethenyl)pyrrolidinocarbonyl)-8-(1-adamantylmethylaminocarbonyl)-2,3, 5,6-dibenzobicyclo[2.2.2]octane (mixture of diastereomers)

The compound was prepared essentially as in example 25 but using the methyl ester of trans-3-(2S-pyrrolidino)-but-2-enoic acid (prepared from methyl(triphenylphosphoranylidene)acetate and N-(t-butoxycarbonyl)-L-prolinal by Wittig reaction) instead of L-alanine methyl ester. Found: C, 76.66; H, 7.39; N, 4.73. $C_{37}H_{42}N_2O_4$ requires C, 76.79; H, 7.32; N, 4.84

EXAMPLE 206

Preparation of cis-7-(2S-(methoxycarbonylethyl)pyrrolidinocarbonyl)-8-(1-adamantylmethylaminocarbonyl)-2,3,5, 6-dibenzobicyclo[2.2.2]octane (mixture of diastereomers)

This was prepared by treating the compound of example 205 with 10% palladium on charcoal in an atmosphere of hydrogen gas. Found: C, 76.73; H, 7.79; N, 4.91. $C_{37}H_{44}N_2O_4$ requires C, 76.52; H, 7.64; N, 4.82

EXAMPLE 207

Preparation of cis-7-(1S-(aminocarbonylmethylaminocarbonyl)-2-phenylethylaminocarbonyl)-8-(1-adamantylmethylaminocarbonyl)-2,3,5,6-dibenzobicyclo[2.2.2]octane Diastereomer 1

The reaction was performed essentially as in example 25 but using L-phenylalanylglycinamide as substrate instead of L-alanine methyl ester. The mixture of diastereomers produced by this reaction was separated by column chromatography (silica and ethyl acetate). The less polar material was designated the title compound of this example. Found: C, 72.24; H, 7.02; N, 8.21. $C_{40}H_{44}N_4O_4.1.2 H_2O$ requires C, 74.50; H, 6.87; N, 8.68

EXAMPLE 208

Preparation of cis-7-(1S-(aminocarbonylmethylaminocarbonyl)-2-phenylethylaminocarbonyl)-8-(1-adamantylmethylaminocarbonyl)-2,3,5,6-dibenzobicyclo[2.2.2]octane Diastereomer 2

The more polar material isolated from the separation in example 207 was designated the compound of this example. Found: C, 72.12; H, 6.95; N, 8.39. $C_{40}H_{44}N_4O_4.1.2 H_2O$ requires C, 74.50; H, 6.87; N, 8.68

EXAMPLE 209

Preparation of (±)-7-(1-adamantylmethylaminocarbonylmethyl)-2,3,5,6-dibenzobicyclo[2.2.2]octane-7-carboxylic acid The compound was prepared essentially as in example 131 except that itaconic anhydride was used as substrate instead of the methyl ester of aconitic anhydride in step a. The compound was further characterised and tested as the N-methyl-D-glucamine salt, m.p. 115°–120°. Found: C, 68.06; H, 7.71; N, 4.37. $C_{37}H_{50}N_2O_8$ requires C, 68.29; H, 7.74; N, 4.30

EXAMPLE 210

Preparation of 7-(1S-methoxycarbonylethylaminocarbonyl)-7-(1-adamantylmethylaminocarbonylmethyl)-2,3,5,6-dibenzobicyclo[2.2.2]octane (mixture of diastereoisomers)

The compound was prepared essentially as in example 25 except that the compound of example 209 was used as substrate instead of the compound of example 14. Found: C, 75.36; H, 7.56; N, 4.99. $C_{34}H_{40}N_2O_4$ requires C, 75.53; H, 7.46; N, 5.18

EXAMPLE 211

Preparation of 7-(2R-carboxypyrrolidinocarbonyl)-7-(1-adamantylmethylaminocarbonylmethyl)-2,3,5,6-dibenzobicyclo[2.2.2]octane (mixture of diastereoisomers)

The compound was prepared essentially as in example 160 except that the compound of example 209 was used in step c as substrate instead of the compound of example 160 step b. The compound was further characterised and tested as the N-methyl-D-glucamine salt. Found: C, 67.24; H, 7.74; N, 5.81. $C_{42}H_{57}N_3O_9$ requires C, 67.45; H, 7.68; N, 5.62

EXAMPLE 212

Preparation of (±)-cis-7-(2-carboxycyclopentylaminocarbonyl)-8-(1-adamantylmethylaminocarbonyl)-2,3,5,6-dibenzobicyclo[2.2.2]octane (mixture of diastereomers 1)

The compound was prepared essentially as in example 64 but using the benzyl ester of cis 2-amino-cyclopentanoic acid in step a. instead of the dibenzyl ester of aspartic acid. The mixture of compounds after step a. was separated by column chromatography (silica 85% dichloromenthane 15% ethyl acetate) to give two pairs of diastereomers. The less polar material was hydrogenated to give the compound of this example. The compound was further characterised and tested as the N-methyl-D-glucamine salt. Found: C, 65.12; H, 7.75; N, 5.42. $C_{42}H_{57}N_3O_9.1.5 H_2O$ requires C, 65.1; H, 7.80; N, 5.42

EXAMPLE 213

Preparation of (±)-cis-7-(2-carboxycyclopentylaminocarbonyl)-8-(1-adamantylmethylaminocarbonyl)-2,3,5,6-dibenzobicyclo[2.2.2]octane (mixture of diastereomers 2)

The compound was prepared essentially as in example 212 except that the more polar material after separation was hydrogenated to give the compound of this example. The compound was further characterised and tested as the N-methyl-D-glucamine salt. Found: C, 64.88; H, 7.91; N, 5.28. $C_{42}H_{57}N_3O_9.1.7 H_2O$ requires C, 64.8; H, 7.82; N, 5.40

EXAMPLE 214

Preparation of cis-7-(2R-(1R-methoxycarbonylethylaminocarbonyl)pyrrolidinocarbonyl)-8-(1-adamantylmethylaminocarbonyl)-2,3,5,6-dibenzobicyclo[2.2.2]octane (single diastereomer)

The compound was prepared essentially as in example 63 except that the compound of example 147 was used as substrate instead of cis-7-(1-S-carboxyl-2-methylpropylaminocarbonyl)-8-(1-adamantylmethylaminocarbonyl)-2,3,5,6-dibenzobicyclo[2.2.2]octane (mixture of diastereomers). Found: C, 72.88; H, 7.51; N, 6.58. $C_{38}H_{45}N_3O_5$ requires C, 73.17; H, 7.27; N, 6.74

EXAMPLE 215

Preparation of cis-7-(2S-(carboxyethyl)pyrrolidinocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester of trans-3-(2S-pyrrolidino)-but-2-enoic acid (prepared from benzyl(triphenylphosphoranylidene)acetate and N-(t-butoxycarbonyl)-L-prolinal by Wittig reaction) in step a. instead of the dibenzyl ester of aspartic acid. The compound was further characterised and tested as the N-methyl-D-glucamine salt. Found: C, 66.64; H, 8.02; N, 5.60. $C_{43}H_{59}N_3O_9.0.6 H_2O$ requires C, 66.80; H, 7.85; N, 5.44

EXAMPLE 216

Preparation of cis-7-(1S-carboxy-(2-naphthyl)ethylaminocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester L-3-(2-naphthyl)alanine in step a. instead of the dibenzyl ester of aspartic acid. The compound was further characterised and tested as the N-methyl-D-glucamine salt. Found: C, 70.15; H, 7.33; N, 5.05. $C_{49}H_{59}N_3O_9. 0.3 H_2O$ requires C, 70.05; H, 7.16; N, 5.00

EXAMPLE 217

Preparation of cis-7-(1S-carboxy-(1-naphthyl)-ethylaminocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester L-3-(1-naphthyl)alanine in step a. instead of the dibenzyl ester of aspartic acid. The compound was further characterised and tested as the N-methyl-D-glucamine salt. Found: C, 69.94; H, 7.14; N, 5.23. $C_{49}H_{59}N_3O_9. 0.3 H_2O$ requires C, 70.05; H, 7.16; N, 5.00

EXAMPLE 218

Preparation of cis-7-(1R-(1R-carboxyethylaminocarbonyl)-2-phenylethylaminocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester D-phenylalanyl-D-alanine in step a. instead of the dibenzyl ester of aspartic acid. The compound was further characterised and tested as the N-methyl-D-glucamine salt. Found: C, 64.21; H, 7.63; N, 6.36. $C_{48}H_{62}N_4O_{10}$. 2.3 $H_2O$ requires C, 64.28; H, 7.63; N, 6.36

EXAMPLE 219

Preparation of cis-7-(3-S-carboxy-1,2,3,4-tetrahydroisoquinolinocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester 1,2,3,4-tetrahydroisoquinoline-3-S-carboxylic acid in step a. instead of the dibenzyl ester of aspartic acid. The compound was further characterised and tested as the N-methyl-D-glucamine salt. Found: C, 66.75; H, 7.37; N, 5.08. $C_{46}H_{57}N_3O_{90}$. 1.7 $H_2O$ requires C, 66.80; H, 7.37; N, 5.08

EXAMPLE 220

Preparation of 7-(2R-carboxypyrrolidinocarbonyl)-8-(1-adamantylmethyl-N-(methyl)aminocarbonyl)- 2,3,5,6-dibenzobicyclo[2.2.2]octane (mixture of diastereoisomers)

a. (±)-8-(1-adamantylmethyl-N-(methyl)aminocarbonylmethyl)-2,3,5,6-dibenzobicyclo[2.2.2]octane-7-carboxylic acid This was prepared essentially as in example 14 except that N-methyl-1-adamantanemethylamine was used as substrate instead of 1-adamantanemethylamine.

b. 7-(2R-benzyloxycarbonylpyrrolidinocarbonyl)-8-(1-adamantylmethyl-N-(methyl)aminocarbonyl)-2,3,5,6-dibenzobicyclo[2.2.2]octane (mixture of diastereoisomers)

This was prepared essentially as in example 46 except that the product of step a. was used as substrate instead of the product of example 14.

c. 7-(2R-carboxypyrrolidinocarbonyl)-8-(1-adamantylmethyl-N-(methyl)aminocarbonyl)-2,3,5,6-dibenzobicyclo [2.2.2]octane (mixture of diastereoisomers)

This was prepared essentially as in example 48 except that the product of step b above was used as substrate instead of the product of example 46. The compound was further characterised and tested as the N-methyl-D-glucamine salt. Found: C, 63.54; H, 7.87; N, 5.32. $C_{42}H_{57}N_3O_9$. 2.3 $H_2O$ requires C, 63.91; H, 7.87; N, 5.32

EXAMPLE 221

Preparation of 7-(2R-(carboxymethylaminocarbonyl)pyrrolidinocarbonyl)-8-(1-adamantylmethyl-N-(methyl)aminocarbonyl)-2,3,5,6-dibenzobicyclo[2.2.2]octane (mixture of diastereoisomers)

The compound was prepared essentially as in example 194 except that the compound of example 220 was used as substrate instead of the compound of example 141 in step a. The compound was tested as the N-methyl-D-glucamine salt

EXAMPLE 222

Preparation of 7-(2R-(1S-carboxyethylaminocarbonyl)pyrrolidinocarbonyl)-8-(1-adamantylmethyl-N-(methyl)aminocarbonyl)-2,3,5,6-dibenzobicyclo[2.2.2]octane (mixture of diastereoisomers)

The compound was prepared essentially as in example 184 except that the compound of example 220 was used as substrate instead of the compound of example 141 in step a. The compound was tested as the N-methyl-D-glucamine salt

EXAMPLE 223

Preparation of 7-(2R-(1R-carboxyethylaminocarbonyl)pyrrolidinocarbonyl)-8-(1-adamantylmethyl-N-(methyl)aminocarbonyl)-2,3,5,6-dibenzobicyclo[2.2.2]octane (mixture of diastereoisomers)

The compound was prepared essentially as in example 185 except that the compound of example 220 was used as substrate instead of the compound of example 141 in step a. The compound was tested as the N-methyl-D-glucamine salt

EXAMPLE 224

Preparation of cis-7-(2S-(1R-carboxyethylaminocarbonylmethyl)pyrrolidinocarbonyl)-8-(1-adamantylmethyl-N-(methyl)aminocarbonyl)-2,3,5,6-dibenzobicyclo[2.2.2]octane (mixture of diastereomers)

a. cis-7-(2S-(carboxymethyl)pyrrolidinocarbonyl)-8-(1-adamantylmethyl-N-(methyl)aminocarbonyl)-2,3,5,6-dibenzobicyclo[2.2.2]octane (mixture of diastereomers)

The reaction was performed essentially as in example 141 except that the compound of example 220 step a. was used instead of the compound of example 14.

b. cis-7-(2S-(1R-carboxyethylaminocarbonylmethyl)pyrrolidinocarbonyl)-8-(1-adamantylmethyl-N-(methyl)aminocarbonyl)-2,3,5,6-dibenzobicyclo[2.2.2]octane (mixture of diastereomers)

The compound was prepared essentially as in example 185 except that the compound from step a. above was used as substrate instead of the compound of example 141 in step a. The compound was tested as the N-methyl-D-glucamine salt

EXAMPLE 225

Preparation of cis-7-(2S-(1S-carboxyethylaminocarbonylmethyl)pyrrolidinocarbonyl)-8-(1-adamantylmethyl-N-(methyl)aminocarbonyl)-2,3,5,6-dibenzobicyclo[2.2.2]octane (mixture of diastereomers)

The compound was prepared essentially as in example 184 except that the compound from example 224 step a. was used as substrate instead of the compound of example 141 in step a. The compound was tested as the N-methyl-D-glucamine salt

EXAMPLE 226

Preparation of cis-7-(2R-(1S-carboxyethylaminocarbonylmethyl)pyrrolidinocarbonyl)-8-(1-adamantylmethyl-N-(methyl)aminocarbonyl)-2,3,5,6-dibenzobicyclo[2.2.2]octane (mixture of diastereomers)

a. cis-7-(2R-(carboxymethyl)pyrrolidinocarbonyl)-8-(1-adamantylmethyl-N-(methyl)aminocarbonyl)-2,3,5,6-dibenzobicyclo[2.2.2]octane (mixture of diastereomers)

The reaction was performed essentially as in example 142 except that the compound of example 220 step a. was used instead of the compound of example 14.

b. cis-7-(2R-(1S-carboxyethylaminocarbonylmethyl)pyrrolidinocarbonyl)-8-(1-adamantylmethyl-N-(methyl)aminocarbonyl)-2,3,5,6-dibenzobicyclo[2.2.2]octane (mixture of diastereomers)

The compound was prepared essentially as in example 184 except that the compound from step a. above was used as substrate instead of the compound of example 141 in step a. The compound was tested as the N-methyl-D-glucamine salt

EXAMPLE 227

Preparation of cis-7-(2S-(methoxycarbonylmethylaminocarbonyl)pyrrolidinocarbonyl)-8-(1-adamantylmethylaminocarbonyl)-2,3,5,6-dibenzobicyclo[2.2.2]octane (mixture of diastereomers)

The compound was prepared essentially as in example 25 but using the methyl ester L-prolylglycine as substrate instead of L-alanine methyl ester. Found: C, 62.87; H, 7.47; N, 5.02. $C_{37}H_{43}N_3O_5$. 1.1 EtOAc and 4.5 $H_2O$ requires C, 63.12; H, 7.78; N, 5.33

EXAMPLE 228

Preparation of cis-7-(2S-(1R-carboxyethylaminocarbonyl)pyrrolidinocarbonyl)-8-(1-adamantylmethylaminocarbonyl)-2,3,5,6-dibenzobicyclo[2.2.2]octane (mixture of diastereomers)

The compound was prepared essentially as in example 64 but using the benzyl ester L-prolyl-D-alanine in step a. instead of the dibenzyl ester of aspartic acid. The compound was further characterised and tested as the N-methyl-D-glucamine salt. Found: C, 60.11; H, 8.22; N, 6.22. $C_{44}H_{60}N_4O_{10}$. 4.4 $H_2O$ requires C, 59.81; H, 7.84; N, 6.34

EXAMPLE 229

Preparation of cis-7-(2R-(carboxymethylaminocarbonyl)-5-oxopyrrolidinocarbonyl)-8-(1-adamantylmethylaminocarbonyl)-2,3,5,6-dibenzobicyclo[2.2.2]octane Diastereomer 1

The compound was prepared essentially as in example 64 but using the benzyl ester D-pyroglutamyl-glycine in step a. instead of the dibenzyl ester of aspartic acid. The product of step a. was separated into its constituent diastereomers by chromatography (silica 30% ethyl acetate and 70% dichloromethane). The less polar material was hydrogenated to give the compound of this example. The compound was further characterised and tested as the N-methyl-D-glucamine salt. Found: C, 54.22; H, 7.26; N, 5.54. $C_{43}H_{56}N_4O_{11}$. 8.0 $H_2O$ requires C, 54.42; H, 7.60; N, 5.90

EXAMPLE 230

Preparation of cis-7-(2R-(carboxymethylaminocarbonyl)-5-oxopyrrolidinocarbonyl)-8-(1-adamantylmethylaminocarbonyl)-2,3,5,6-dibenzobicyclo[2.2.2]octane Diastereomer 2

The compound was prepared essentially as in example 229 except that the more polar material isolated after the chromatography was hydrogenated to give the compound of this example. The compound was further characterised and tested as the N-methyl-D-glucamine salt. Found: C, 54.88; H, 7.20; N, 6.11. $C_{43}H_{56}N_4O_{11}$ .8.0 $H_2O$ requires C, 54.42; H, 7.60; N, 5.90

EXAMPLE 231

Preparation of cis-7-(2R-(1R-carboxyethylaminocarbonylmethyl)pyrrolidinocarbonyl)-8-(1-adamantylmethyl-N-(methyl)aminocarbonyl)-2,3,5,6-dibenzobicyclo[2.2.2]octane (mixture of diastereomers)

The compound was prepared essentially as in example 185 except that the compound from example 226 step a. was used as substrate instead of the compound of example 141 in step a

EXAMPLE 232

Preparation of cis-7-(2S-(1R-(methoxycarbonyl)ethylaminocarbonylmethyl)-pyrrolidinocarbonyl)-8-(1-adamantylmethylaminocarbonyl)-2,3,5,6-dibenzobicyclo[2.2.2]octane (single diastereomer)

The compound was prepared essentially as in example 63 except that the compound of example 186 was used as substrate instead of cis-7-(1-S-carboxyl-2-methylpropylaminocarbonyl)-8-(1-adamantylmethylaminocarbonyl)-2, 3,5,6-dibenzobicyclo[2.2.2]octane (mixture of diastereomers

EXAMPLE 233

Preparation of cis-7-(2R-(carboxymethylaminocarbonyl)-4-thiopyrrolidinocarbonyl)-8-(1-adamantylmethylaminocarbonyl)-2,3,5,6-dibenzobicyclo[2.2.2]octane a. cis-7-(2R-(t-butoxycarboylmethylaminocarbonyl)-4-thiopyrrolidinocarbonyl)-8-(1-adamantylmethylaminocarbonyl)-2,3,5,6-dibenzobicyclo[2.2.2]octane This compound was prepared essentially as in example 25 except that 2R-(t-butoxycarbonylmethylaminocarbonyl)-4-thiopyrrolidine was used as substrate instead of L-alanine methyl ester.

b. cis-7-(2-R-(carboxymethylaminocarbonyl)-4-thiopyrrolidinocarbonyl)-8-(1-adamantylmethylaminocarbonyl)-2, 3,5,6-dibenzobicyclo[2.2.2]octane The compound of step a. above was treated with trifluoroacetic acid to give the title compound of this example

EXAMPLE 234

Preparation of cis-7-(2R-(carboxymethylaminocarbonyl)-4-oxothio-pyrrolidinocarbonyl)-8-(1-adamantylmethylaminocarbonyl)-2,3,5,6-dibenzobicyclo[2.2.2]octane This was prepared from the compound of example 233 step a. by treatment with ozone followed by treatment with trifluoroacetic acid

EXAMPLE 235

Preparation of cis-7-(2R-(carboxymethylaminocarbonyl)-4-dioxothio-pyrrolidinocarbonyl)-8-(1-adamantylmethylaminocarbonyl)-2,3,5,6-dibenzobicyclo[2.2.2]octane This was prepared from the compound of example 233 step a. by treatment with the tetrabutylammonium salt of oxone followed by treatment with trifluoroacetic acid

EXAMPLE 236

Preparation of cis-7-(2R-(3,5-dicarboxyphenylaminocarbonyl)-pyrrolidinocarbonyl)-8-(1-adamantylmethylaminocarbonyl)-2,3,5,6-dibenzobicyclo[2.2.2]octane Diastereomer 1

The compound was prepared essentially as in example 64 but using the dibenzyl ester of D-prolyl-5-aminoisophthalic acid in step a. instead of the dibenzyl ester of aspartic acid. The diastereomers were separated at the benzyl ester stage by column chromatography (silica, 92% dichloromethane and 8% ethyl acetate). The compound with the higher $R_f$ was converted to the title compound by hydrogenation. The compound was further characterised and tested as the mono-N-methyl-D-glucamine salt, HPLC; $R_T$=17.4 mins, C8 column, $CH_3CN$ 50%, 0.1% $CH_3COOH$

EXAMPLE 237

Preparation of cis-7-(2R-(3,5-dicarboxyphenylaminocarbonyl)-pyrrolidinocarbonyl)-8-(1-adamantylmethylaminocarbonyl)-2,3,5,6-dibenzobicyclo[2.2.2]octane Diastereomer 2

The compound was prepared essentially as in example 237 but using the compound with lower $R_f$ after diastereomer separation in the final hydrogenation step. The compound was further characterised and tested as the mono-N-methyl-D-glucamine salt, HPLC; $R_T$=9.4 mins, C8 column, $CH_3CN$ 60%, $H_2O$ 40%, 0.1% $CH_3COOH$

EXAMPLE 238

Preparation of cis-7-(2S-(1-R-carboxyethylaminocarbonylethyl)pyrrolidinocarbonyl)-8-(1-adamantylmethylaminocarbonyl)-2,3,5,6-dibenzobicyclo[2.2.2]octane (mixture of diastereomers)

The compound was prepared essentially as in example 185 but using the product of example 215 instead of the compound of example 141. The compound was further characterised and tested as the N-methyl-D-glucamine salt, HPLC; $R_T$=21.7 mins, C8 column, $CH_3CN$ 50%, $H_2O$ 50%, 0.1% $CH_3COOH$

EXAMPLE 239

Preparation of cis-7-(1S-(3,5-dicarboxyphenylaminocarbonyl)-2-phenylethlaminocarbonyl)-8-(1-adamantanemethylaminocarbonyl)-2,3,5,6-dibenzobicyclo[2.2.2]octane Diastereoisomer 1 a. 2,3,5,6-dibenzobicyclo[2.2.2]octane-7,8-dicarboxylic acid anhydride

Anthracene (8.9 g, 0.05 mol) and maleic anhydride (4.9 g, 0.05 mol) were refluxed for 3 h in toluene (200 ml). Upon cooling the title compound was obtained as white crystals which were isolated by filtration (10.2 g, 74%).

b. (±)-cis-8-(1-adamantanemethylaminocarbonyl)-2,3,5,6-dibenzo bicyclo[2.2.2]octane-7-carboxylic acid 2,3,5,6-dibenzobicyclo(2.2.2.)octane-7,8dicarboxylic acid anhydride (prepared in step a) (276 mg, 1.0 mmol) and 1-adamantanemethylamine (182 mg, 1.1 mmol) were dissolved in dry THF (5 ml) and refluxed for 1 h. A thick white precipitate was formed and this was isolated by filtration and washed with THF to leave the title compound (320 mg, 72%), m.p. 237°–9°, found: C, 78.76; H, 7.18; N, 3.33. $C_{29}H_{31}NO_3$ requires C, 78.88; H, 7.08; N, 3.17% c. 3,5-dibenzyloxycarbonyl-nitrobenzene 5-nitro-isophthalic acid (21.1 g, 0.1 mol), thionyl chloride (80 ml) and DMF (10 drops) were stirred and heated for about 1 h until a clear solution was obtained. Excess thionyl chloride was removed by evaporation and the residual acid chloride was coevaporated with dichloromethane (2×100 ml) to remove the last traces.

Benzyl alcohol (21.6 g, 0.2 mol) and triethylamine (30.03 g, 0.3 mol) were dissolved in dichloromethane (200 ml) and stirred at 0° under an atmosphere of dry nitrogen and a solution of the acid chloride in dichloromethane (50 ml) was added dropwise over 20 min. The solution was stirred and refluxed for 1 h, and the solution was cooled. The organic layer was washed with water (2×100 ml), saturated sodium hydrogencarbonate solution (100 ml) and dried over magnesium sulphate. The solution was filtered and evaporated to leave the title compound (39.1 g, 100%).

d. 3,5-dibenzyloxycarbonyl-aniline

The nitro compound prepared in step c above (3.91 g, 10 mol) was dissolved in ethyl acetate (50 ml) and tin (II) chloride dihydrate (11.27 g, 50 mmol) was added and the mixture stirred and heated at 70° under an atmosphere of nitrogen for 1 h. The mixture was poured carefully onto 5% sodium hydrogencarbonate solution (200 ml) and a further aliquot of ethyl acetate (100 ml) was added. After shaking the organic layer was separated and the aqueous layer was extracted with more ethyl acetate (50 ml). The combined organic layers were washed with brine, and dried, filtered and evaporated to leave a pale yellow solid (3.25 g, 90%).

e. N-tert-butyloxycarbonyl-1S-(3,5-dibenzloxycarbonylphenylaminocarbonyl)-2-phenylethylamine BOC-L-phenylalanine (8.76 g, 33 mmol) was dissolved in dry dichloromethane (200 ml) and dry diisopropylethylamine (11.48 ml, 66 mmol) was added followed by PyBROP (15.33 g, 33 mmol). The mixture was stirred at room temperature for 5 min and then the amine prepared in step d above (7.22 g, 20 mmol) was added. The solution was stirred at room temperature for a further 5 h and the solution was then washed sequentially with 2M hydrochloric acid, water, saturated sodium hydrogencarbonate solution and water and finally dried, filtered and evaporated to leave an oil. This was purified by column chromatography (90% dichloromethane and 10% ethyl acetate) to leave the title compound as a white solid (11.0 g, 90%)

f. cis-7-(1S-(3,5-dibenzyloxycarbonylphenylaminocarbonyl)-2-phenylethylaminocarbonyl)-8-(1-adamantanemethylaminocarbonyl)-2,3,5,6-dibenzobicyclo[2.2.2]octane Diastereoisomer 1

N-tert-butyloxycarbonyl-1S-(3,5-dibenzyloxycarbonylphenylaminocarbonyl)-2-phenylethylamine prepared in step e above (8.0 g, 13 mmol) was dissolved in trifluoroacetic acid (40 ml) and stirred at room temperature for 30 min. The solvent was removed by evaporation and the residue taken up in dry dichloromethane (50 ml) and basified with diisopropylethylamine.

Meanwhile (±)-cis-8-(1-adamantanemethylaminocarbonyl)-2,3,5,6-dibenzo bicyclo[2.2.2]octane-7-carboxylic acid prepared in step b above (5.75 g, 13 mmol) was suspended in dry dichloromethane (150 ml) and diisopropylethylamine (4.6 ml, 26 mmol) was added followed by PyBOP (6.76 g, 13 mmol). The solution was stirred until a clear solution was obtained and the solution of amine prepared above was added. After stirring at room temperature for 3 h, the solution was washed sequentially with 2M hydrochloric acid and water, dried, filtered and evaporated. The residual oil was purified by column chromatography (90% dichloromethane and 10% ethyl acetate) to leave two compounds. The less polar was material was designated the title compound (4.65 g).

g. cis-7-(1S-(3,5-dicarboxyphenylaminocarbonyl)-2-phenylethylaminocarbonyl)-8-(1-adamantanemethylaminocarbonyl)-2,3,5,6-dibenzobicyclo[2.2.2]octane Diastereoisomer 1

The dibenzylester prepared in step f above (4.65 g, 5.0 mmol) was dissolved in 1:1 methanolic THF (40 ml). 10% palladium on charcoal (400 mg) was added and the reaction was stirred under an atmosphere of hydrogen overnight. The catalyst was removed by filtration through celite and the product isolated by evaporation (3.53 g).

The compound was further characterised and tested as the di-N-methyl-D-glucamine salt found: C, 61.38; H, 7.54 ; N, 4.24. $C_{60}H_{79}N_5O_{17}$. 4.2 mol dioxan requires C, 60.99; H, 7.51; N, 4.63

EXAMPLE 240

Preparation of cis-7-(1S-(3,5-dicarboxyphenylaminocarbonyl)-2-phenylethylaminocarbonyl)-8-(1-adamantanemethylaminocarbonyl)-2,3,5,6-dibenzobicyclo[2.2.2]octane Diastereoisomer 2

The compound was prepared essentially as in example 239 except that the more polar material from the chromatography described in step f was used in the final hydrogenation.

The compound was further characterised and tested as the N-methyl-D-glucamine salt found: C, 64.34; H, 6.64; N, 4.70. $C_{53}H_{62}N_4O_{12}$. 1.7 mol dioxan. 0.8 $H_2O$ requires C, 64.63; H, 7.00; N, 5.04

EXAMPLE 241

Preparation of cis-7-(1R-(3,5-dicarboxyphenylaminocarbonyl)-2-phenylethylaminocarbonyl)-8-(1-adamantanemethylaminocarbonyl)-2,3,5,6-dibenzobicyclo[2.2.2]octane Diastereoisomer 1

The compound was prepared essentially as in example 239 except that BOC-D-phenylalanine was used in step e instead of BOC-L-phenylalanine.

The compound was further characterised and tested as the N-methyl-D-glucamine salt found: C, 65.66; H, 6.68; N, 5.46. $C_{53}H_{62}N_4O_{12}$. 1.3 $H_2O$ requires C, 65.55; H, 6.71; N, 5.76

EXAMPLE 242

Preparation of cis-7-(1R-(3,5-dicarboxyphenylaminocarbonyl)-2-phenylethylaminocarbonyl)-8-(1-adamantanemethylaminocarbonyl)-2,3,5,6-dibenzobicyclo[2.2.2]octane Diastereoisomer 2

The compound was prepared essentially as in example 241 except that the more polar material from the chromatography described in step f was used in the final hydrogenation.

The compound was further characterised and tested as the N-methyl-D-glucamine salt found: C, 64.77; H, 7.00; N, 5.90. $C_{53}H_{62}N_4O_{12}$. 2.0 $H_2O$ requires C, 64.75; H, 6.76; N, 5.69

EXAMPLE 243

Preparation of cis-7-(1S-(3,5-dicarboxyphenylaminocarbonyl)-2-cyclohexylethylaminocarbonyl)-8-(1-adamantanemethylaminocarbonyl)-2,3,5,6-dibenzobicyclo[2.2.2]octane (mixture of diastereomers)

The compound was prepared essentially as in example 239 except that BOC-L-2-cyclohexylalanine was used in step e instead of BOC-L-phenylalanine and no attempt was made to separate the diastereomers in step.

The compound was further characterised and tested as the di-N-methyl-D-glucamine salt found: C, 60.31; H, 8.00; N, 5.84. $C_{60}H_{85}N_5O_{17}$. 2.5 $H_2O$ requires C, 60.38; H, 7.60; N, 5.86

EXAMPLE 244

Preparation of cis-7-(1S-(3,5-dicarboxyphenylaminocarbonyl)-2-(2-thiophenyl)-ethylaminocarbonyl)-8-(1-adamantanemethylaminocarbonyl)-2,3,5,6-dibenzobicyclo[2.2.2]octane Diastereoisomer 1

The compound was prepared essentially as in example 239 except that BOC-L-2-thiophenylalanine was used in step e instead of BOC-L-phenylalanine.

The compound was further characterised and tested as the N-methyl-D-glucamine salt found: C, 58.61; H, 6.43; N, 5.00. $C_{51}H_{60}N_4O_{12}S$. 5.0 $H_2O$ requires C, 58.72; H, 6.76; N, 5.37

EXAMPLE 245

Preparation of cis-7-(1S-(3,5-dicarboxyphenylaminocarbonyl)-2-thiophenyl)ethylaminocarbonyl)-8-(1-adamantanemethylaminocarbonyl)-2,3,5,6-dibenzobicyclo[2.2.2]octane Diastereoisomer 2

The compound was prepared essentially as in example 244 except that the more polar material from the chromatography described in step f was used in the final hydrogenation.

The compound was further characterised and tested as the N-methyl-D-glucamine salt found: C, 59.26; H, 6.66; N, 5.00. $C_{51}H_{60}N_4O_{12}S$. 4.5 $H_2O$ requires C, 59.23; H, 6.73; N, 5.40

EXAMPLE 246

Preparation of cis-7-(1S-(3,5-dicarboxyphenylaminocarbonyl)-2-(4-fluorophenyl)-ethylaminocarbonyl)-8-(1-adamantanemethylaminocarbonyl)-2,3,5,6-dibenzobicyclo[2.2.2]octane Diastereoisomer 1

The compound was prepared essentially as in example 239 except that BOC-L-4-fluorophenylalanine was used in step e instead of BOC-L-phenylalanine.

The compound was further characterised and tested as the di-N-methyl-D-glucamine salt found: C, 59.38; H, 7.19; N, 5.92. $C_{60}H_{78}N_5O_{17}F$. 3.1 $H_2O$ requires C, 59.24; H, 6.98; N, 5.76

EXAMPLE 247

Preparation of cis-7-(1S-(3,5-dicarboxyphenylaminocarbonyl)-2-(4-fluorophenyl)ethylaminocarbonyl)-8-(1-adamantanemethylaminocarbonyl)-2,3,5,6-dibenzobicyclo[2.2.2]octane Diastereoisomer 2

The compound was prepared essentially as in example 246 except that the more polar material from the chromatography described in step f was used in the final hydrogenation.

The compound was further characterised and tested as the di-N-methyl-D-glucamine salt found: C, 60.18; H, 7.21; N, 6.01. $C_{60}H_{78}N_5O_{17}F$. 2.3 $H_2O$ requires C, 59.94; H, 6.93; N, 5.83

EXAMPLE 248

Preparation of cis-7-(1S-(3,5-dicarboxyphenylaminocarbonyl)-2-(4-chlorophenyl)-ethylaminocarbonyl)-8-(1-adamantanemethylaminocarbonyl)-2,3,5,6-dibenzobicyclo[2.2.2]octane Diastereoisomer 1

The compound was prepared essentially as in example 239 except that BOC-L-4-chlorophenylalanine was used in step e instead of BOC-L-phenylalanine.

The compound was further characterised and tested as the di-N-methyl-D-glucamine salt found: C, 59.16; H, 7.04; N, 5.72. $C_{60}H_{78}N_5O_{17}Cl$. 1.9 $H_2O$ requires C, 59.49; H, 6.81; N, 5.78

EXAMPLE 249

Preparation of cis-7-(1S-(3,5-dicarboxyphenylaminocarbonyl)-2-(4-chlorophenyl)ethylaminocarbonyl)-8-(1-adamantanemethylaminocarbonyl)-2,3,5,6-dibenzobicyclo[2.2.2]octane Diastereoisomer 2

The compound was prepared essentially as in example 248 except that the more polar material from the chromatography described in step f was used in the final hydrogenation.

The compound was further characterised and tested as the di-N-methyl-D-glucamine salt found: C, 59.08; H, 6.97; N, 5.43. $C_{60}H_{78}N_5O_{17}Cl$. 2.7 $H_2O$ requires C, 58.85; H, 6.86; N, 5.72

EXAMPLE 250

Preparation of cis-7-(1S-(3,5-dicarboxyphenylaminocarbonyl)-2-(4-methoxyphenyl)-ethylaminocarbonyl)-8-(1-adamantanemethylaminocarbonyl)-2,3,5,6-dibenzobicyclo[2.2.2]octane Diastereoisomer 1

The compound was prepared essentially as in example 239 except that BOC-L-4-methoxyphenylalanine was used in step e instead of BOC-L-phenylalanine.

The compound was further characterised and tested as the di-N-methyl-D-glucamine salt found: C, 59.36; H, 7.28; N, 5.77. $C_{61}H_{81}N_5O_{18}$. 3.3 $H_2O$ requires C, 59.45; H, 7.17; N, 5.68

EXAMPLE 251

Preparation of cis-7-(1S-(3,5-dicarboxyphenylaminocarbonyl)-2-(4-methoxyphenyl)ethylaminocarbonyl)-8-(1-adamantanemethylaminocarbonyl)-2,3,5,6-dibenzobicyclo[2.2.2]octane Diastereoisomer 2

The compound was prepared essentially as in example 250 except that the more polar material from the chromatography described in step f was used in the final hydrogenation.

The compound was further characterised and tested as the di-N-methyl-D-glucamine salt found: C, 57.14; H, 7.26; N, 5.32. $C_{61}H_{81}N_5O_{18}$. 6.3 $H_2O$ requires C, 57.01; H, 7.34; N, 5.45

EXAMPLE 252

Preparation of cis-7-(1S-(3,5-dicarboxyphenylaminocarbonyl)-2-(2-naphthyl)-ethylaminocarbonyl)-8-(1-adamantanemethylaminocarbonyl)-2,3,5,6-dibenzobicyclo[2.2.2]octane Diastereoisomer 1

The compound was prepared essentially as in example 239 except that BOC-L-3-(2-naphthyl)alanine was used in step e instead of BOC-L-phenylalanine.

The compound was further characterised and tested as the di-N-methyl-D-glucamine salt found: C, 61.14 H, 7.03; N, 5.64. $C_{64}H_{81}N_5O_{17}$. 3.5 $H_2O$ requires C, 61.20; H, 7.07; N, 5.58

EXAMPLE 253

Preparation of cis-7-(1S-(3,5-dicarboxyphenylaminocarbonyl)-2-(2-naphthyl)ethylaminocarbonyl)-8-(1-adamantanemethylaminocarbonyl)-2,3,5,6-dibenzobicyclo[2.2.2]octane Diastereoisomer 2

The compound was prepared essentially as in example 252 except that the more polar material from the chromatography described in step f was used in the final hydrogenation.

The compound was further characterised and tested as the di-N-methyl-D-glucamine salt found: C, 61.59; H, 7.11; N, 5.52. $C_{64}H_{81}N_5O_{17}$. 4.2 $H_2O$ requires C, 61.59; H, 7.11; N, 5.52

EXAMPLE 254

Preparation of cis-7-(1S-(3,5-dicarboxyphenylaminocarbonyl)-2-(2-fluorophenyl)-ethylaminocarbonyl)-8-(1-adamantanemethylaminocarbonyl)-2,3,5,6-dibenzobicyclo[2.2.2]octane Diastereoisomer 1

The compound was prepared essentially as in example 239 except that BOC-L-2-fluorophenylalanine was used in step e instead of BOC-L-phenylalanine.

The compound was further characterised and tested as the di-N-methyl-D-glucamine salt found: C, 58.63; H, 6.99; N, 5.49. $C_{60}H_{78}N_5O_{17}F$. 4.0 $H_2O$ requires C, 58.44; H, 7.04; N, 5.68

EXAMPLE 255

Preparation of cis-7-(1S-(3,5-dicarboxyphenylaminocarbonyl)-2-(2-fluorophenyl) ethylaminocarbonyl)-8-(1-adamantanemethylaminocarbonyl)-2,3,5,6-dibenzobicyclo[2.2.2]octane Diastereoisomer 2

The compound was prepared essentially as in example 254 except that the more polar material from the chromatography described in step f was used in the final hydrogenation.

The compound was further characterised and tested as the di-N-methyl-D-glucamine salt found: C, 58.49; H, 7.00; N, 5.67. $C_{60}N_{78}N_5O_{17}F$. 4.2 $H_2O$ requires C, 58.34; H, 7.04; N, 5.67

EXAMPLE 256

Preparation of cis-7-(1S-(3,5-dicarboxyphenylaminocarbonyl)-2-(3-fluorophenyl)-ethylaminocarbonyl)-8-(1-adamantanemethylaminocarbonyl)-2,3,5,6-dibenzobicyclo[2.2.2]octane Diastereoisomer 1

The compound was prepared essentially as in example 239 except that BOC-L-3-fluorophenylalanine was used in step e instead of BOC-L-phenylalanine.

The compound was further characterised and tested as the di-N-methyl-D-glucamine salt found: C, 58.60; H, 7.04; N, 5.62. $C_{60}H_{78}N_5O_{17}F$. 3.9 $H_2O$ requires C, 58.55; H, 7.038; N, 5.69

EXAMPLE 257

Preparation of cis-7-(1S-(3,5-dicarboxyphenylaminocarbonyl)-2-(3-fluorophenyl)ethylaminocarbonyl)-8-(1-adamantanemethylaminocarbonyl)-2,3,5,6-dibenzobicyclo[2.2.2]octane Diastereoisomer 2

The compound was prepared essentially as in example 256 except that the more polar material from the chromatography described in step f was used in the final hydrogenation.

The compound was further characterised and tested as the di-N-methyl-D-glucamine salt found: C, 58.49; H, 7.09; N, 5.69

EXAMPLE 258

Preparation of cis-7-(1S-(3,5-dicarboxyphenylaminocarbonyl)-2-(2-chlorophenyl)-ethylaminocarbonyl)-8-(1-adamantanemethylaminocarbonyl)-2,3,5,6-dibenzobicyclo[2.2.2]octane (mixture of diastereomers)

The compound was prepared essentially as in example 239 except that BOC-L-2-chlorophenylalanine was used in step e instead of BOC-L-phenylalanine and no attempt was made to separate the diastereomers in step f.

The compound was further characterised and tested as the di-N-methyl-D-glucamine salt found: C, 57.69; H, 7.05; N, 5.55. $C_{60}H_{78}N_5O_{17}Cl$. 4.1 $H_2O$ requires C, 57.59; H, 6.95; N, 5.55

EXAMPLE 259

Preparation of cis-7-(1R-(3,5-dicarboxyphenylaminocarbonyl)-2-(2-thiophenyl)ethylaminocarbonyl)-8-(1-adamantanemethylaminocarbonyl)-2,3,5,6-dibenzobicyclo[2.2.2]

octane Diastereoisomer 2

The compound was prepared essentially as in example 245 except that except that BOC-D-2-thiophenylalanine was used in step e instead of BOC-L-phenylalanine.

The compound was further characterised and tested as the di-N-methyl-D-glucamine sal

EXAMPLE 260

Preparation of cis-7-(1S-(phenylaminocarbonyl)-2-phenylethylaminocarbonyl)-8-(1-adamantanemethylaminocarbonyl)- 2,3,5,6-dibenzobicyclo[2.2.2]octane Diastereoisomer 1

The compound was prepared essentially as in example 239 step f except that N-tert-butyloxycarbonyl-1S-(phenylaminocarbonyl)-2-phenylethylamine was used instead of N-tert-butyloxycarbonyl-1S-(3,5-dibenzyloxycarbonylphenylaminocarbonyl)-2-phenylethylamine. As before, the less polar compound after chromatography was designated the compound of this example. found: C, 78.33; H, 6.94; N, 6.05 $C_{44}H_{45}N_3O_3$. 0.4 ethyl acetate requires C, 78.49; H, 6.94; N, 6.05

EXAMPLE 261

Preparation of cis-7-(1S-(phenylaminocarbonyl)-2-phenylethylaminocarbonyl)-8-(1-adamantanemethylaminocarbonyl)-2,3,5,6-dibenzobicyclo[2.2.2]octane Diastereoisomer 2

The compound was prepared essentially as in example 260 except that the more polar material from the chromatography was designated as the compound of this example found: C, 79.37; H, 6.96; N, 6.24 $C_{44}H_{45}N_3O_3$ requires C, 79.61; H, 6.83; N, 6.33

EXAMPLE 262

Preparation of cis-7-(1S-(3,5-dicarboxyphenylaminocarbonyl)-2-(4-hydroxyphenyl)-ethylaminocarbonyl)-8-(1-adamantanemethylaminocarbonyl)-2,3,5,6-dibenzobicyclo [2.2.2]octane Diastereoisomer 2

The compound was prepared essentially as in example 239 except that BOC-L-tyrosine was used in step e instead of BOC-L-phenylalanine.

The compound was further characterised and tested as the di-N-methyl-D-glucamine sal

EXAMPLE 263

Preparation of cis-7-(1S-(3,5-dicarboxyphenylaminocarbonyl)-2-(4-hydroxyphenyl)ethylaminocarbonyl)-8-(1-adamantanemethylaminocarbonyl)-2,3,5,6-dibenzobicyclo [2.2.2]octane Diastereoisomer 2

The compound was prepared essentially as in example 262 except that the more polar material from the chromatography described in step f was used in the final hydrogenation.

The compound was further characterised and tested as the di-N-methyl-D-glucamine salt found: C, 57.11; H, 7.46; N, 5.79. $C_{60}H_{79}N_5O_{18}$. 6.0 $H_2O$ requires C, 56.95; H, 7.24; N, 5.53

EXAMPLE 264

Preparation of cis-7-(1R-(3.5-dicarboxyphenylaminocarbonyl)-2-(4-hydroxyphenyl)-ethylaminocarbonyl)-8-(1-adamantanemethylaminocarbonyl)-2,3,5,6-dibenzobicyclo [2.2.2]octane Diastereoisomer 1

The compound was prepared essentially as in example 239 except that BOC-D-tyrosine was used in step e instead of BOC-L-phenylalanine.

The compound was further characterised and tested as the di-N-methyl-D-glucamine salt found: C, 57.05; H, 7.09; N, 5.23. $C_{60}H_{79}N_5O_{18}$. 6.1 $H_2O$ requires C, 56.79; H, 7.25; N, 5.52

EXAMPLE 265

Preparation of cis-7-(1R-(3,5-dicarboxyphenylaminocarbonyl)-2-(4-hydroxyphenyl)ethylaminocarbonyl)-8-(1-adamantanemethylaminocarbonyl)-2,3,5,6-dibenzobicyclo [2.2.2]octane Diastereoisomer 2

The compound was prepared essentially as in example 26 except that the more polar material from the chromatography described in step f was used in the final hydrogenation

EXAMPLE 266

Preparation of cis-7-(1S-(3,5-dicarboxyphenylaminocarbonyl)-2-phenylethylaminocarbonyl)-8-(1-cycloheptanemethylaminocarbonyl)-2,3,5,6-dibenzobicyclo[2.2.2]octane Diastereoisomer 1

The compound was prepared essentially as in example 239 except that cycloheptanemethylamine was used in step b instead of 1-adamantanemethylamine.

The compound was further characterised and tested as the di-N-methyl-D-glucamine salt found: C, 59.25; H, 7.17; N, 5.94. $C_{57}H_{77}N_5O_{17}$. 2.9 $H_2O$ requires C, 59.14; H, 7.22; N, 6.06

EXAMPLE 267

Preparation of cis-7-(1S-(3,5-dicarboxyphenylaminocarbonyl)-2-phenylethylaminocarbonyl)-8-(cycloheptanemethylaminocarbonyl)-2,3,5,6-dibenzobicyclo[2.2.2]octane Diastereoisomer 2

The compound was prepared essentially as in example 266 except that the more polar material from the chromatography described in step f was used in the final hydrogenation.

The compound was further characterised and tested as the di-N-methyl-D-glucamine salt found: C, 59.14; H, 7.15; N, 6.10. $C_{57}H_{77}N_5O_{17}$. 2.9 $H_2O$ requires C, 59.14; H, 7.22; N, 6.06

EXAMPLE 268

Preparation of cis-7-(1S-(3,5-dicarboxyphenylaminocarbonyl)-2-phenylethylaminocarbonyl)-8-(1-cyclohexanemethylaminocarbonyl)-2,3,5,6-dibenzobicyclo[2.2.2]octane Diastereoisomer 1

The compound was prepared essentially as in example 239 except that cyclohexanemethylamine was used in step b instead of 1-adamantanemethylamine.

The compound was further characterised and tested as the di-N-methyl-D-glucamine salt found: C, 58.75; H, 7.11; N, 5.85. $C_{56}H_{75}N_5O_{17}$. 3.2 $H_2O$ requires C, 58.58; H, 7.15; N, 6.06

EXAMPLE 269

Preparation of cis-7-(1S-(3,5-dicarboxyphenylaminocarbonyl)-2-phenylethylaminocarbonyl)-8-(cyclohexanemethylaminocarbonyl)-2,3,5,6-dibenzobicyclo[2.2.2]octane Diastereoisomer 2

The compound was prepared essentially as in example 268 except that the more polar material from the chromatography described in step f was used in the final hydrogenation.

The compound was further characterised and tested as the di-N-methyl-D-glucamine salt found: C, 58.61; H, 7.19; N, 6.18. $C_{56}H_{75}N_5O_{17}$. 3.1 $H_2O$ requires C, 58.69; H, 7.14; N, 6.11

EXAMPLE 270

Preparation of cis-7-(1S-(3,5-dicarboxyphenylaminocarbonyl)-2-phenylethylaminocarbonyl)-8-(1-naphthalenemethylaminocarbonyl)-2,3,5,6-dibenzobicyclo[2.2.2]octane Diastereoisomer 1

The compound was prepared essentially as in example 239 except that 1-naphthalenemethylamine was used in step b instead of 1-adamantanemethylamine.

The compound was further characterised and tested as the di-N-methyl-D-glucamine salt found: C, 59.82; H, 6.70; N, 6.04. $C_{60}H_{71}N_5O_{17}$. 3.7 $H_2O$ requires C, 60.03; H, 6.58; N, 5.83

EXAMPLE 271

Preparation of cis-7-(1S-(3,5-dicarboxyphenylaminocarbonyl)-2-phenylethylaminocarbonyl)-8-(1-naphthalenemethylaminocarbonyl)-2,3,5,6-dibenzobicyclo[2.2.2]octane Diastereoisomer 2

The compound was prepared essentially as in example 270 except that the more polar material from the chromatography described in step f was used in the final hydrogenation.

The compound was further characterised and tested as the di-N-methyl-D-glucamine salt found: C, 58.02; H, 6.84; N, 5.96. $C_{60}H_{71}N_5O_{17}$. 5.6 $H_2O$ requires C, 58.31; H, 6.71; N, 5.67

EXAMPLE 272

Preparation of cis-7-(1S-(3,5-dicarboxyphenylaminocarbonyl)-2-phenylethylaminocarbonyl)-8-(3,4-dichlorophenylmethylaminocarbonyl)-2,3,5,6-dibenzobicyclo[2.2.2]octane Diastereoisomer 1

The compound was prepared essentially as in example 239 except that 3,4-dichlorobenzylamine was used in step b instead of 1-adamantanemethylamine.

The compound was further characterised and tested as the di-N-methyl-D-glucamine salt found: C, 56.58; H, 6.27; N, 5.90. $C_{56}H_{67}Cl_2N_5O_{17}$. 1.9$H_2O$ requires C, 56.65; H, 6.01; N, 5.89

EXAMPLE 273

Preparation of cis-7-(1S-(3,5 -dicarboxyphenylaminocarbonyl)-2-phenylethylaminocarbonyl)-8-(3,4-dichlorophenylmethylaminocarbonyl)-2,3,5,6-dibenzobicyclo[2.2.2]octane Diastereoisomer 2

The compound was prepared essentially as in example 272 except that the more polar material from the chromatography described in step f was used in the final hydrogenation.

The compound was further characterised and tested as the di-N-methyl-D-glucamine salt found: C, 56.98; H, 6.04; N, 6.05. $C_{56}H_{67}Cl_2N_5O_{17}$. 1.4 $H_2O$ requires C, 57.08; H, 5.97; N, 5.94

EXAMPLE 274

Preparation of cis-7-(1S-(3,5-dicarboxyphenylaminocarbonyl)-3-phenylpropylaminocarbonyl)-8-(1-adamantanemethylaminocarbonyl)-2,3,5,6-dibenzobicyclo[2.2.2]octane (mixture of diastereomers)

The compound was prepared essentially as in example 239 except that 2S-(tert-butyloxycarbonylamino)-4-phenylbutanoic acid was used in step e instead of BOC-L-phenylalanine and no attempt was made to separate the diastereomers in step f.

The compound was further characterised and tested as the di-N-methyl-D-glucamine salt found: C, 59.76; H, 7.03; N, 5.79. $C_{61}H_{81}N_5O_{17}$. 3.6 $H_2O$ requires C, 60.01; H, 7.28; N, 5.74

EXAMPLE 275

Preparation of cis-7-(1R-(3,5-dicarboxyphenylaminocarbonyl)-3-phenylpropylaminocarbonyl)-8-(1adamantanemethylaminocarbonyl)-2,3,5,6-dibenzobicyclo[2.2.2]octane (mixture of diastereomers)

The compound was prepared essentially as in example 239 except that 2R-(tert-butyloxycarbonylamino)-4-phenylbutanoic acid was used in step e instead of BOC-L-phenylalanine and no attempt was made to separate the diastereomers in step f.

The compound was further characterised and tested as the di-N-methyl-D-glucamine salt found: C, 59.65; H, 7.01; N, 5.51. $C_{61}H_{81}N_5O_{17}$. 3.7 $H_2O$ requires C, 59.93; H, 7.28; N, 5.73

EXAMPLE 276 preparation of cis-7-(1S-(3,5-dicarboxyphenylaminocarbonyl)-2-phenylethyl-N (methyl)-aminocarbonyl)-8-(1-adamantanemethylaminocarbonyl)-2,3,5,6-dibenzobicyclo[2.2.2]octane (mixture of diastereomers)

The compound was prepared essentially as in example 239 except that N-methyl-BOC-L-phenylalanine was used in step e instead of BOC-L-phenylalanine and no attempt was made to separate the diastereomers in step f.

The compound was further characterised and tested as the di-N-methyl-D-glucamine salt found: C, 58.78; H, 7.09; N, 5.70. $C_{61}H_{81}N_5O_{17}$. 4.7 $H_2O$ requires C, 59.04; H, 7.34; N, 5.64

EXAMPLE 277

Preparation of cis-7-(1S-(3,5-dicarboxyphenylaminocarbonyl)-3-phenylmethylaminocarbonyl)-8-(1-adamantanemethylaminocarbonyl)-2,3,5,6-dibenzobicyclo[2.2.2]octane (mixture of diastereomers)

The compound was prepared essentially as in example 239 except that BOC-L-phenylglycine was used in step e instead of BOC-L-phenylalanine and no attempt was made to separate the diastereomers in step f.

The compound was further characterised and tested as the N-methyl-D-glucamine salt found: C, 64.20; H, 6.75; N, 5.80. $C_{52}H_{60}N_4O_{12}$. 2.2 $H_2O$ requires C, 64.21; H, 6.67; N, 5.76

EXAMPLE 278

Preparation of cis-7-(1S-(3-carboxyphenylaminocarbonyl)-2-phenylethylaminocarbonyl)-8-(1-adamantanemethylaminocarbonyl)-2,3,5,6,-dibenzobicyclo[2.2.2]octane Diastereoisomer 1

The compound was prepared essentially as in example 239 steps f and g except that N-tert-butyloxycarbonyl-1S-(3-benzyloxycarbonylphenylaminocarbonyl)-2-phenylethylamine was used instead of N-tert-butyloxycarbonyl-1S-(3,5-dibenzyloxycarbonyl-phenyl aminocarbonyl)-2-phenylethylamine in step f. As before, the less polar compound after chromatography in step f was taken through to the compound of this example.

The compound was further characterised and tested as the N-methyl-D-glucamine salt found: C, 69.70; H, 7.00; N, 5.96. $C_{52}H_{62}N_4O_{10}$. 0.7 $H_2O$ requires C, 69.45; H, 7.10; N, 6.23

EXAMPLE 279

Preparation of cis-7-(1S-(3-carboxyphenylaminocarbonyl)-2-phenylethylaminocarbonyl)-8-(1-adamantanemethylaminocarbonyl)-2,3,5,6-dibenzobicyclo[2.2.2]octane Diastereoisomer 2

The compound was prepared essentially as in example 278 except that the more polar.

The compound was further characterised and tested as the N-methyl-D-glucamine salt found: C, 66.60; H, 7.21; N, 6.06. $C_{52}H_{62}N_4O_{10}$. 1.9 $H_2O$ requires C, 66.57; H, 7.08; N, 5.97

EXAMPLE 280

Preparation of cis-7-(1S-(3-carboxy-5-methoxycarbonylphenylaminocarbonyl)-2-phenylethylaminocarbonyl)-8-(1-adamantanemethylaminocarbonyl)-2,3,5,6-dibenzobicyclo[2.2.2]octane (mixture of diastereomers)

The compound was prepared essentially as in example 239 expect that 3-methoxycarbonyl-5-nitrobenzoic acid was used in step c instead of 5-nitro-isophthalic acid.

The compound was further characterised and tested as the N-methyl-D-glucamine salt found: C, 65.81; H, 6.93; N, 5.79. $C_{54}H_{64}N_4O_{12}$. 1.5 $H_2O$ requires C, 65.70; H, 6.83; N, 5.67

EXAMPLE 281

Preparation of cis-7-(1S-(3,4-dicarboxyphenylaminocarbonyl)-2-phenylethylaminocarbonyl)-8-(1-adamantanemethylaminocarbonyl)-2,3,5,6-dibenzobicyclo[2.2.2]octane (mixture of diastereomers)

The compound was prepared essentially as in example 239 except that 4-nitrophthalic acid was used in step c instead of 5-nitroisophthalic acid.

The compound was further characterised and tested as the di-N-methyl-D-glucamine salt found: C, 60.31; H, 7.22; N, 5.76. $C_{60}H_{79}N_5O_{17}$. 1.5 $H_2O$ requires C, 60.29; H, 7.16; N, 5.86

EXAMPLE 282

Preparation of cis-7-(1S-(3,5-ditetrazolylphenylaminocarbonyl)-2-phenylethylaminocarbonyl)-8-(1-adamantanemethylaminocarbonyl)-2,3,5,6-dibenzobicyclo[2.2.2]octane (mixture of diastereomers)

The compound was prepared essentially as in example 239 except that the bis pivaloyloxymethyl (POM) derivative of N-tert-butyloxycarbonyl-1S-(3,5-ditetrazolylphenylaminocarbonyl)-2-phenylethylamine was used instead of N-tert-butyloxycarbonyl-1S-(3,5-dibenzyloxycarbonylphenylaminocarbonyl)-2-phenylethylamine in step f and the deprotection in step g was performed with methanolic ammonia solution

EXAMPLE 283

Preparation of cis-7-(1S-(2-carboxyphenylaminocarbonyl)-2-phenylethylaminocarbonyl)-8-(1-adamantanemethylaminocarbonyl)-2,3,5,6-dibenzobicyclo[2.2.2]octane (mixture of diastereomers)

The compound was prepared essentially as in example 239 steps f and g except that N-tert-butyloxycarbonyl-1S-(2-benzyloxycarbonylphenylaminocarbonyl)-2-phenylethylamine was used instead of N-tert-butyloxycarbonyl-1S-(3,5-dibenzyloxycarbonylphenylaminocarbonyl)-2-phenylethylamine in step f. No attempt was made to separate diastereoisomers.

The compound was further characterised and tested as the N-methyl-D-glucamine salt found: C, 63.51; H, 7.00; N, 5.52, $C_{52}H_{62}N_4O_{10}$. 4.2 $H_2O$ requires C, 63.77; H, 7.25; N, 5.72%

EXAMPLE 284

Preparation of cis-7-(1S-(4-carboxyphenylaminocarbonyl)-2-phenylethylaminocarbonyl)-8-(1-adamantanemethylaminocarbonyl)-2,3,5,6-dibenzobicyclo[2.2.2]octane Diastereomer 1

The compound was prepared essentially as in example 239 steps f and g except that N-tert-butyloxycarbonyl-1S-(2-benzyloxycarbonylphenylaminocarbonyl)-2-phenylethylamine was used instead of N-tert-butyloxycarbonyl-1S-(3,5-dibenzyloxycarbonylphenylaminocarbonyl)-2-phenylethylamine in step f. The less polar material described from the chromatography in step f was taken through to the title compound of this example.

The compound was further characterised and tested as the N-methyl-D-glucamine salt found: C, 66.60; H, 7.21; N, 6.06. $C_{52}H_{62}N_4O_{10}$. 1.9 $H_2O$ requires C, 66.57; H, 7.08; N, 5.97%

EXAMPLE 285

Preparation of cis-7-(1S-(4-carboxyphenylaminocarbonyl)-2-phenylaminocarbonyl-8-(1-adamantanemethylaminocarbonyl)-2,3,5,6-dibenzobicyclo[2.2.2]octane Diastereomer 2

The more polar diastereomer described in example 284 was taken through as the title compound of this example.

The compound was further characterised and tested as the N-methyl-D-glucamine salt found: C, 62.98; H, 7.26; N, 6.02. $C_{52}H_{62}N_4O_{10}$ 4.6 $H_2O$ requires C, 63.32; H, 7.28; N, 5.68%. $H_2O$ requires C, 63.32; H, 7.28; N, 5.68%

EXAMPLE 286

Preparation of cis-7-(1S-(3,5-dimethoxycarbonylphenylaminocarbonyl)-2-phenylethylamino-carbonyl-8-(1-adamantanemethylaminocarbonyl)-2,3,5,6-dibenzobicyclo[2.2.2]octane Diastereomer 1

The compound of example 239 was treated with an excess of diazomethane to leave the title compound after quenching and evaporation found: C, 74.00; H, 6.40; N, 5.32. $C_{48}H_{49}N_3O_7$ requires C, 73.92; H, 6.33; N, 5.39

EXAMPLE 287

Preparation of cis-7-(1S-(3,5-dicarboxyphenylaminocarbonyl)-2-phenylethylaminocarbonyl)-8-(1-(1-adamantane)-1-methylethylaminocarbonyl)-2,3,5,6-dibenzobicyclo[2.2.2]octane (mixture of diastereomers)

The compound was prepared essentially as in example 239 except that 1-(1-adamantane)-1-methylethylamine was used in step b instead of 1-adamantanemethylamine and no attempt was made to separate the diastereomers described in step f. m.p 195–°8°.

The compound was further characterised and tested as the di N-methyl-D-glucamine salt found: C, 58.96; H, 7.33; N, 5.59. $C_{62}H_{83}N_5O_{17}$. 5 $H_2O$ requires C, 659.08; H, 7.43; N, 5.56

EXAMPLE 288

Preparation of cis-7-(1S-(3,5-dicarboxyphenylaminocarbonyl)-2-phenylethylaminocarbonyl)-8-(3-indolylethylaminocarbonyl)-2,3,5,6-dibenzobicyclo[2.2.2]octane Diastereoisomer 1

The compound was prepared essentially as in example 239 except that 3-indolylethylamine was used in step b instead of 1-adamantanemethylamine.

The compound was further characterised and tested as the di N-methyl-D-glucamine salt found: C, 58.37; H, 6.44; N, 7.04. $C_{59}H_{72}N_6O_{17}$. 4 $H_2O$ requires C, 58.60; H, 6.67; N, 5.95

EXAMPLE 289

Preparation of cis-7-(1S-(3,5-dicarboxyphenylaminocarbonyl)-2-phenylethylaminocarbonyl)-8-(3-indolylethylaminocarbonyl)-2,3,5,6-dibenzobicyclo[2.2.2]octane Diastereoisomer 2

The compound was prepared essentially as in example 288 except that the more polar material from the chromatography described in step f was used in the final hydrogenation.

The compound was further characterised and tested as the di N-methyl-D-glucamine salt found: C, 59.83; H, 6.20; N, 6.76. $C_{59}H_{72}N_6O_{17}$. 2.4 $H_2O$ requires C, 60.03; H, 6.56; N, 7.12

EXAMPLE 290

Preparation of cis-7-(1S-(3,5-dicarboxyphenylaminocarbonyl)-2-phenylethylaminocarbonyl)-8-(2-thiophenylmethylaminocarbonyl)-2,3,5,6-dibenzobicyclo[2.2.2]octane (mixture of diastereomers)

The compound was prepared essentially as in example 239 except that 2-thiophenylmethylethylamine was used in step b instead of 1-adamantanemethylamine and no attempt was made to separate the diastereomers described in step f.

The compound was further characterised and tested as the di N-methyl-D-glucamine salt found: C, 52.68; H, 6.43; N, 5.67. $C_{54}H_{67}N_6O_{17}S$. 7.4 $H_2O$ requires C, 52.99; H, 6.74; N, 5.72

EXAMPLE 291

Preparation of cis-7-(1S-(3,5-dicarboxyphenylaminocarbonyl)-2-phenylethylaminocarbonyl)-8-(2-phenylethylaminocarbonyl)-2,3,5,6-dibenzobicyclo[2.2.2]octane (mixture of diastereomers)

The compound was prepared essentially as in example 239 except that 2-phenylethylamine was used in step b instead of 1-adamantanemethylamine and no attempt was made to separate the diastereomers described in step f.

The compound was further characterised and tested as the di N-methyl-D-glucamine salt found: C, 59.15; H, 6.83; N, 5.81. $C_{57}H_{71}N_5O_{17}$. 3.5 $H_2O$ requires C, 58.95; H, 6.77; N, 6.03

EXAMPLE 292

Preparation of cis-7-(1S-(3,5-dicarboxyphenylaminocarbonyl)-2-phenylethylaminocarbonyl)-8-(2-phenylpropylaminocarbonyl)-2,3,5,6-dibenzobicyclo[2.2.2]octane (mixture of diastereomers)

The compound was prepared essentially as in example 239 except that 3-phenylpropylamine was used in step b instead of 1-adamantanemethylamine and no attempt was made to separate the diastereomers described in step f.

The compound was further characterised and tested as the di N-methyl-D-glucamine salt found: C, 59.39; H, 6.79; N, 5.90. $C_{58}H_{73}N_5O_{17}$. 3.8 $H_2O$ requires C, 59.38; H, 6.85; N, 5.96

EXAMPLE 293

Preparation of cis-7-(1S-(3-carboxyphenylaminocarbonyl)-2-(2-thiophenyl)ethylaminocarbonyl)-8-(1-adamantanemethylaminocarbonyl)-2,3,5,6-dibenzobicyclo[2.2.2]octane Diastereomer 1

The compound was prepared essentially as in example 239 except that step e was carried out using BOC-L-3-(2-thiophenyl)alanine instead of BOC-L-phenylalanine and 3-benzyloxycarbonylaniline instead of 3,5-dibenzyloxycarbonylaniline. The product of this reaction was used in step f instead of N-tert-butyloxycarbonyl-1S-(3,5-dibenzyloxycarbonylphenylaminocarbonyl)-2-phenylethylamine.

The compound was further characterised and tested as the N-methyl-D-glucamine salt found: C, 66.21; H, 6.62; N, 5.87. $C_{50}H_{60}N_4O_{10}S$ requires C, 66.06; H, 6.65; N, 6.16

EXAMPLE 294

Preparation of cis-7-(1S-(3-carboxyphenylaminocarbonyl)-2-(2-thiophenyl)ethylaminocarbonyl)-8-(1-adamantanemethylaminocarbonyl)-2,3,5,6-dibenzobicyclo[2.2.2.]octane Diastereomer 2

The compound was prepared essentially as in example 293 except that the more polar material from the chromatography described in step f was used in the final hydrogenation.

The compound was further characterised and tested as the N-methyl-D-glucamine salt found: C, 66.32; H, 6.81; N, 5.88. $C_{50}H_{60}N_4O_{10}S$ requires C, 66.06; H, 6.65; N, 6.16

EXAMPLE 295

Preparation of cis-7-(1S-(3-carboxyphenylaminocarbonyl)-2-(2-thiophenyl)ethylaminocarbonyl)-8-(1-naphthalenemethylaminocarbonyl)-2,3,5,6-dibenzobicyclo[2.2.2]octane Diastereomer 1

The compound was prepared essentially as in example 293 except that 1-naphthalenemethylamine was used in step b instead of 1-adamantanemethylamine.

The compound was further characterised and tested as the N-methyl-D-glucamine salt found: C, 58.71; H, 6.21; N, 5.85. $C_{50}H_{52}N_4O_{10}S$. 6.4 $H_2O$ requires C, 59.06; H, 6.43; N, 5.51

EXAMPLE 296

Preparation of cis-7-(1S-(3-carboxyphenylaminocarbonyl)-2-(2-thiophenyl)ethylaminocarbonyl)-8-(1-naphthalenemethylaminocarbonyl)-2,3,5,6-dibenzobicyclo[2.2.2]octane Diastereomer 2

The compound was prepared essentially as in example 295 except that the more polar material from the chromatography described in step f was used in the final hydrogenation. f was used in the final hydrogenation.

The compound was tested as the N-methyl-D-glucamine salt

EXAMPLE 297

Preparation of cis-7-(1S-(3-carboxyphenylaminocarbonyl)-2-phenylethylaminocarbonyl)-8-(1-naphthalenemethylaminocarbonyl)-2,3,5,6-dibenzobicyclo[2.2.2]octane Diastereomer 1

The compound was prepared essentially as in example 295 except that BOC-L-phenylalanine was used in step e instead of BOC-L-3-(2-thiophenyl)alanine.

The compound was further characterised and tested as the N-methyl-D-glucamine salt found: C, 58.71; H, 6.21; N, 5.85. $C_{50}H_{52}N_4O_{10}S$. 6.4 $H_2O$ requires C, 59.06; H, 6.43; N, 5.51

EXAMPLE 298

Preparation of cis-7-(1S-(3-carboxyphenylaminocarbonyl)-2-phenylethylaminocarbonyl)-8-(1-naphthalenemethylaminocarbonyl)-2,3,5,6-dibenzobicyclo[2.2.2]octane Diastereomer 2

The compound was prepared essentially as in example 297 except that the more polar material from the chromatography described in step f was used in the final hydrogenation.

The compound was tested as the N-methyl-D-glucamine salt

EXAMPLE 299

Preparation of cis-7-(1S-(3,5-discarboxyphenyl-methylaminocarbonyl)-2-phenylethylaminocarbonyl)-8-(1-adamantanemethylaminocarbonyl)-2,3,5,6-dibenzobicyclo[2.2.2]octane Diastereoisomer 1

The compound was prepared essentially as in example 239 except that 3,5-dibenzyloxycarbonylbenzylamine was used in step e instead of 3,5-dibenzyloxycarbonylaniline.

The compound was further characterised and tested as the N-methyl-D-glucamine salt found: C, 64.72; H, 6.96; N, 5.88. $C_{54}H_{64}N_4O_{12}$. 2 $H_2O$ requires C, 64.99; H, 6.88; N, 5.61

EXAMPLE 300

Preparation of cis-7-(1S-(3,5-dicarboxyphenylmethylaminocarbonyl)-2-phenylethylaminocarbonyl)-8-(1-adamantanemethylaminocarbonyl)-2,3,5,6-dibenzobicyclo[2.2.2]octane Diastereoisomer 2

The compound was prepared essentially as in example 299 except that the more polar material from the chromatography described in step f was used in the final hydrogenation.

The compound was further characterised and tested as the N-methyl-D-glucamine salt found: C, 64.99; H, 6.95; N, 5.65. $C_{54}H_{64}N_4O_{12}$. 2 $H_2O$ requires C, 64.99; H, 6.88; N, 5.61

EXAMPLE 301

Preparation of cis-7-(1S-(3,5-dicarboxyphenylaminocarbonyl)-2-phenylethylaminocarbonyl)-8-(2-napthalenemethylaminocarbonyl)-2,3,5,6-dibenzobicyclo[2.2.2]octane Diastereoisomer 1

The compound was prepared essentially as in example 239 except that 2-naphthalenemethylamine was used in step b instead of 1-adamantanemethylamine, found: C, 73.99; H, 5.26; N, 5.41. $C_{46}H_{37}N_3O_7$. requires C, 74.28; H, 5.01; N, 5.65%

The compound was tested as the di N-methyl-D-glucamine salt

EXAMPLE 302

Preparation of cis-7-(1S-(3,5-dicarboxyphenylaminocarbonyl)-2-phenylethylaminocarbonyl)- 8-(2-naphthalenemethylaminocarbonyl)-2,3,5,6-dibenzobicyclo[2.2.2]octane Diastereoisomer 2

The compound was prepared essentially as in example 301 except that the more polar material from the chromatography described in step f was used in the final hydrogenation found: C, 72.76; H, 5.18; N, 5.42. $C_{46}H_{37}N_3O_7$. 1.1 $H_2O$ requires C, 72.30; H, 5.18; N, 5.50%

The compound was tested as the di N-methyl-D-glucamine salt.

The following $^1H$ NMR data were obtained for the compounds described in the Examples:

Ex.1a. ($d^6$-DMSO) δ7.5 (2H, m), 7.3 (2H, m), 7.2 (4H, m), 4.8 (2H, s), 3.6 (2H, s).

Ex.1b. ($d^6$-DMSO) δ11.6 (1H, br s), 7.9 (1H, t), 7.4–6.9 (13H, m), 4.5 (1H, s), 4.4 (1H, s), 3.1 (1H, d), 2.9 (2H, m), 2.8 (1H, d), 2.5 (2H, t), 1.6 (2H, m).

Ex.2 ($d^6$-DMSO) δ11.6 (1H, br s), 10.8 (1H, s), 8.0 (1H, t), 7.6–6.8 (13H, m), 4.5 (1H, s), 4.3 (1H, d), 3.3–3.0 (3H, d), 2.2–2.4 (3H, m).

Ex.3 ($d^6$-DMSO) δ8.4 (1H, br s), 8.4 (1H, t), 7.4–6.8 (13H, m), 4.4 (2H, d), 4.1 (2H, m), 3.2 (1H, d), 2.8 (1H, d).

Ex.4 ($d^6$-DMSO) δ8.4 (1H, t), 8.0–6.9 (15H, m), 4.7 (1H, dd), 4.5 (1H, dd), 4.5 and 4.3 (2H, 2xs), 3.3 (1H, d), 2.8 (1H, d).

Ex.5 ($d^6$-DMSO) δ8.5 (1H, t), 8.0–6.9 (15H, m), 4.5 (2H, d), 4.3 (2H, m), 3.2 (1H, d), 2.8 (1H, d).

Ex.6 ($d^6$-DMSO) δ11.6 (1H, br s), 7.8 (1H, m), 7.4–6.9 (8H, m), 4.5 (1H, s), 4.4 (1H, s), 3.2–2.6 (4H, m), 2.2–0.9 (11H, m).

Ex.7 ($d^6$-DMSO) δ11.6 (1H, br s), 7.8 (1H, m), 7.4–6.9 (8H, m), 4.5 (1H, s), 4.4 (1H, s), 3.2 (1H, dd), 3.0–2.8 (2H, m), 2.8 (1H, dd) 1.2 (8H, m), 0.9 (3H, t).

Ex.8 ($d^6$-DMSO) δ11.6 (1H, br s), 7.8 (1H, t), 7.4–6.9 (8H, m), 4.5 (1H, d), 4.4 (1H, d), 3.1 (1H, dd), 3.0–2.8 (2H, m), 2.7 (1H, dd) 1.3 (12H, m), 0.9 (3H, t).

Ex.9 ($d^6$-DMSO) δ11.6 (1H, br s), 7.8 (1H, t), 7.4–6.9 (8H, m), 4.5 (1H, d), 4.4 (1H, d), 3.1 (1H, dd), 2.8–2.6 (3H, m), 1.8–0.7 (11H, m).

Ex.10 ($d^6$-DMSO) δ12.6 (1H, br s), 7.7 (1H, t), 7.4–6.9 (8H, m), 4.5 (1H, d), 4.4 (1H, d), 3.0 (1H, dd), 2.9 (2H, m), 2.8 (1H, dd), 1.3 (2H, m), 0.9 (9H, s).

Ex.11 ($d^6$-DMSO) δ7.3 (3H, m), 7.2 (1H, m), 7.1 (5H, m), 4.5 (1H, d), 4.4 (1H, d), 3.1 (1H, dd), 2.7 (1H, dd), 1.9 (3H, s), 1.8 (6H, m), 1.6 (6H, m).

Ex.12 ($d^6$-DMSO) δ7.6 (1H, t), 7.4–6.9 (8H, m), 4.5 (1H, d), 4.4 (1H, d), 3.0 (1H, dd), 2.9 (2H, m), 2.8 (1H, dd), 1.9 (3H, s), 1.6 (6H, m), 1.4 (6H, m), 1.1 (2H, t).

Ex.13 ($d^6$-DMSO) δ12.2 (1H br s), 7.4–7.0 (8H, m), 4.6 (1H, dd), 3.4 (1H, d), 3.3 (1H, d), 3.1 (1H, d), 1.9 (3H, s), 1.6 (6H, m), 1.4 (6H, m).

Ex.14 ($d^7$-DMF) δ7.7 (1H, t), 7.4 (3H, m), 7.2 (3H, m), 7.1 (2H, m), 4.7 (1H, d), 4.6 (1H, d), 3.5 (1H, dd), 3.0 (1H, dd), 2.9 (1H, dd), 2.7 (1H, dd), 2.0 (3H, s), 1.7 (6H, m), 1.5 (6H, s).

Ex.15 ($d^6$-DMSO) δ7.9 (1H, t), 7.0–7.4 (8H, m), 6.6 (1H, t), 4.5 (2H, d), 3.8–3.5 (2H, 2xdd), 3.6 (3H, s), 3.2 (1H, d), 3.0 (1H, dd), 2.5 (1H, dd), 1.9 (3H, b s), 1.2–1.7 (12H, m).

Ex.16a ($d^6$DMSO) δ8.0 (1H, m), 7.4–7.0 (13, m), 6.6 (1H, m), 5.1 (2H, s), 4.4 (2H, s), 3.8 (1H, dd), 3.6 (1H, dd), 3.1 (1H, m), 3.0 (1H, d), 2.5 (2H, m), 1.9 (3H, s), 1.6 (6H, q), 1.3 (6H, d).

Ex.16b ($d^6$-DMSO) δ7.8 (1H, m), 7.3–7.0 (8H, m), 6.6 (1H, m), 4.5 (2H, s), 3.7 (1H, dd), 3.4 (1H, m), 3.1 (1H, d), 2.9 (1H, d), 2.5 (2H, m), 1.9 (3H, s), 1.6 (6H, q), 1.2 (6H, d).

Ex.17 (CDCl$_3$) δ7.6 (1H, d), 7.1–7.4 (7H, m), 4.9 (1H, t), 4.6 (1H, d), 4.5 (1H, d), 3.6 (3H, s), 3.3 (1H, dd), 3.2 (1H, dd), 2.9 (1H, m), 2.6 (1H, m), 2.0 (3H, s), 1.6 (6H, m), 1.3 (6H, s).

Ex.18a (CDCl$_3$) δ7.6–7.1 (8H, m), 6.0 (1H, d), 5.9 (1H, d), 4.0 (1H, dd), 3.8 (1H, dd).

Ex.18b (CDCl$_3$) δ7.8–6.9 (15H, m), 4.9 (2H, d), 4.6 (1H, d), 4.4 (1H, d), 4.0 (1H, dd),3.8 (1H, dd).

Ex.18c (d$^6$-DMSO) δ9.0 (1H, bs), 7.9–7.0 (15H, m), 5.4 (1H, s), 4.6 (2H, d), 4.4 (1H, m), 4.3 (1H, m), 3.1 (1H, m), 2.9 (1H, m).

Ex.19 (d$^6$-DMSO) δ8.9 (1H, bs), 7.4–6.8 (13H, m), 4.6 (2H, s), 4.3 (1H, dd), 4.1 (1H, dd), 3.5 (1H, m), 3.0 (1H, dd), 2.8 (1H, dd).

Ex.20a (CDCl$_3$) δ7.6–7.1 (8H, m), 5.0 (1H, d), 4.9 (1H, d), 4.2 (1H, dd), 4.1 (1H, dd)

Ex.20b (d$^6$-DMSO) δ8.2 (1H, bs), 7.9–6.9 (15H, m), 4.7 and 4.5 (2H, 2×s), 4.2 (1H, d), 4.1 (1H, d), 3.1 (2H, m).

Ex.21 (d$^6$-DMSO) δ10.8 (1H, s), 8.0 (1H, bs), 7.5–6.8 (13H, m), 4.7 and 4.4 (2H, 2×s), 3.2–2.9 (6H, m).

Ex.22 (d$^6$-DMSO) δ7.7 (1H, bs), 7.4–6.9 (8H, m), 4.7 and 4.4 (2H, 2×s), 3.1 (2H, m), 2.7 (1H, dd), 2.3 (1H, d), 1.8 (3H, s), 1.6 (6H, m), 1.2 (6H, m).

Ex.23 (d$^6$-DMSO) δ8.0 (1H, t), 7.9 (1H, m), 7.4–7.0 (8H, m), 4.6 (2H, d), 3.9 (1H, m), 3.2 (1H, m), 3.1 (1H, m), 2.9 (1H, m), 2.5 (1H, m), 1.9 (3H, s), 1.6 (6H, q), 1.4 (6H, s), 1.2 (3H, dd).

Ex.24 (CDCl$_3$) δ7.5–7.1 (8H, m), 6.2 (1H, t), 5.3 (1H, t), 4.5 (2H, s), 3.7 (3H, s), 3.3 (2H, m) 3.2 (2H, q), 2.7 (2H, ddd), 2.4 (2H, t), 1.9 (3H, s), 1.4 (6H, q), 1.2 (6H, s).

Ex.25 (CDCl$_3$) δ7.5–7.1 (8H, m), 5.9 and 5.7 (1H, 2×d), 5.3 and 5.1 (1H, 2×t), 4.6 (2H, m), 4.3 (1H, m), 3.7 (3H, s), 3.3–3.1 (2H, dd), 2.9–2.5 (2H, m), 1.9 (3H, s), 1.7 (6H, q), 1.3 (6H, d), 1.2 and 0.9 (3H, d).

Ex.26 (CDCl$_3$) δ7.5–7.1 (8H, m), 5.7 (1H, d), 5.3 (1H, t), 4.6 (2H, m), 4.3 (1H, m), 3.7 (3H, s), 3.2 (2H, s), 2.8–2.6 (2H, dd), 1.9 (3H, s), 1.7 (6H, q), 1.3 (6H, d), 1.1 (3H, d).

Ex.27 (CDCl$_3$) δ7.5–7.1 (8H, m), 6.1 (1H, t), 5.2 (1H, d), 4.6 (2H, m), 4.2 (1H, m), 3.7 (3H, s), 3.2 (2H, dd), 2.8–2.5 (2H, dd), 1.9 (3H, s), 1.6 (6H, q), 1.3 (6H, d), 0.9 (3H, d).

Ex.28 (CDCl$_3$) δ7.5–7.1 (8H, m), 6.1 and 5.9 (1H, 2×d), 5.4 and 5.2 (1H, 2×t), 4.6 (2H, d), 4.3 (1H, m), 3.7 (3H, s), 3.2 (2H, ddd), 2.9–2.5 (2H, m), 2.0 (3H, s), 1.7 (6H, q), 1.3 (6H, d), 1.2 (3H, d).

Ex.29 (CDCl$_3$) δ7.5–7.1 (13H, m), 5.8 (1H, t), 5.2 (2H, s), 5.1(1H, t) 4.6 (2H, d), 3.3 (2H, q), 3.3–3.0 (2H, q), 2.8–2.6 (2H, ddd), 2.4 (2H, q), 1.8 (3H, s), 1.7 (6H, q), 1.3 (6H, d).

Ex.30 (CDCl$_3$) δ7.6 (2H, d), 7.3–7.1 (7H, m), 4.8(1H, t) 4.6 (1H, d), 4.5 (1H, d), 3.5 (1H, m), 3.3 (1H, d), 3.1 (2H, m), 2.9 (1H, q), 2.4 (3H, m), 1.9 (3H, s), 1.6 (6H, q), 1.2 (6H, d).

Ex.31 (d$^6$-DMSO) δ7.5–6.8 (12H, m), 4.5 (2H, m), 4.0 (1H, m), 3.3–2.5 (4H, m), 1.9 (3H, s), 1.6 (6H, m), 1.4 and 1.3 (6H, 2×s), 1.1 and 1.0 (3H, 2×d).

Ex.32 (d$^6$-DMSO) δ7.3 (4H, m), 7.1 (4H, m), 6.9–6.6 (2H, m), 4.5 and 4.3 (1H, 2×t), 4.5 (2H, m), 3.6 (1H, m), 3.2 (1H, m), 3.0–2.8 (3H, m), 2.5 (2H, m), 1.9 (3H, s), 1.6 (6H, m), 1.3 (6H, m), 0.9 and 0.8 (3H, 2×d).

Ex.33 (CDCl$_3$) δ7.4–7.1 (13H, m), 5.7 (1H, d), 5.3 (1H, t), 5.1 (2H, s), 4.6 (1H, s), 4.5 (1H, s), 4.3 (1H, m), 3.2 (2H, s), 2.8 (1H, dd), 2.6 (1H, dd), 1.9 (3H, s), 1.6 (6H, q), 1.3 (6H, d), 1.1 (3H, d).

Ex.34 (CDCl$_3$) δ7.5–7.1 (13H, m), 6.0 (1H, d), 5.1 (3H, m), 4.6 (2H, m), 4.4 (1H, m), 3.3 (1H, dd), 3.2 (1H, dd), 2.9 (1H, dd), 2.5 (1H, dd), 2.0 (3H, s), 1.7 (6H, q), 1.3 (9H, m).

Ex.35 (d$^6$-DMSO) δ7.5 (1H, d), 7.4–7.2 (4H, m), 7.0 (4H, m), 6.8 (1H, t), 4.5 (2H, s), 4.0 (1H, m), 3.0 (2H, m), 2.5 (2H, m), 1.8 (3H, s), 1.6 (6H, q), 1.2 (6H, m), 1.1 (3H, d).

Ex.36 (d$^6$-DMSO) δ7.7 (1H, d), 7.3 (2H, m), 7.2 (2H, m), 7.1 (2H, m), 7.0 (2H, m), 6.6 (1H, t), 4.5 (2H, s), 4.0 (1H, m), 3.0 (1H, d), 2.9 (1H, d), 2.6 (2H, m), 1.9 (3H, s), 1.6 (6H, q), 1.3 (6H, m), 1.1 (3H, d).

Ex.37b (d$^6$-DMSO) δ7.6 (1H, t), 7.3 (2H, m), 7.0 (4H, m), 4.8 (1H, d), 4.6 (1H, d), 3.7 (6H, 2×s), 3.1 (1H, dd), 2.7–2.4 (3H, m), 1.9 (3H, s), 1.6 (6H, q), 1.4 (6H, m).

Ex.38 (d$^6$-DMSO) δ7.4 (1H, t), 7.3 (2H, m), 7.0 (2H, m), 6.6 (2H, m), 4.8 (1H, d), 4.7 (1H, d), 3.7 (6H, 2×s), 3.1 (1H, dd), 2.7–2.4 (3H, m), 1.9 (3H, s), 1.6 (6H, q), 1.4 (6H, m).

Ex.39 (d$^6$-DMSO) δ11.6 (1H, bs), 7.8 (1H, t), 7.3 (3H, m), 7.0 (5H, m), 4.5 (1H, d), 4.4 (1H, d), 3.1 (2H, m), 2.9 (1H, m), 2.7 (1H, dd), 2.0–1.4 (15H, m).

Ex.40 (d$^6$-DMSO) δ7.7 and 7.5 (1H, 2×d), 7.4–7.0 (8H, m), 6.8 and 6.7 (1H, 2×t), 4.5 (1H, m), 4.4 (2H, s), 3.0–2.7 (8H, m), 2.5 (2H, m), 1.9 (3H, s), 1.6 (6H, m), 1.3 (6H, 2×s), 1.1 and 1.0 (3H, 2×d).

Ex.41 (CDCl$_3$) δ7.5–7.1 (8H, m), 6.0 and 5.7 (1H, 2×d), 5.4 and 5.0 (1H, 2×t), 4.6 (2H, m), 4.3 (1H, m), 3.7 (3H, s), 3.3–3.1 (2H, m), 3.0–2.6 (2H, m), 1.6–1.4 (5H, m), 1.2–1.1 (7H, m), 0.7 (2H, m).

Ex.42 (CDCl$_3$) δ7.6 (1H, m), 7.3–7.0 (7H, m), 4.6 (3H, m), 4.3 (1H, m), 3.7 (3H, s), 3.5–3.3 (3H, m), 3.0 and 2.8 (3H, 2×s), 2.8 (1H, m), 2.3 (1H, m), 1.9 (3H, s), 1.6 (6H, q), 1.1 (6H, d).

Ex.43 (CDCl$_3$) δ7.6 (1H, m), 7.3–7.0 (7H, m), 4.6 (3H, m), 4.3 (1H, m), 4.2 (2H, m), 3.5–3.3 (3H, m), 3.0 and 2.8 (3H, 2×s), 2.8 (1H, m), 2.4 (1H, m), 1.9 (3H, s), 1.6 (6H, q), 1.3 (3H, m), 1.1 (6H, d).

Ex.44a (d$^6$-DMSO) δ12.7 (1H, s), 7.4–7.1 (8H, m) 4.8 (2H, m), 4.0 (2H, m) 3.2 (1H, dd), 3.15 (1H, dd), 1.43 (3H, t).

Ex.44b (d$^6$-DMSO) δ8.1 (1H, t), 7.4–7.0 (8H, m), 4.7 (1H, d), 4.65 (1H, d), 4.0 (2H, m), 3.4 (1H, dd), 3.1 (1H, dd), 2.9 (1H, dd), 2.6 (1H, dd), 1.9–1.4 (15H, m), 1.1 (3H, t).

Ex.44c (d$^6$-DMSO) δ15–13 (1H, br s), 7.5–7.0 (9H, m), 4.8 (2H, s), 3.2 (2H, s), 2.7 (2H, s), 1.7–0.9 (15H, m).

Ex.45 (CDCl$_3$) δ7.3 (4H, m), 7.1 (4H, m), 4.6 (2H, m), 3.5 (3H, s), 3.4–3.6 (2H, m), 3.2 (1H, 2×s), 2.0 (3H, br s), 1.7 (6H, q), 1.4 (6H, d).

Ex.46 (CDCl$_3$) δ7.6 (1H, m), 7.3 (13H, m), 5.4–5.0 (2H, m), 4.9–4.4 (3H, m), 3.7–3.1 (4H, m), 3.0–2.2 (2H, m), 2.2–1.8 (7H, m), 1.6 (6H, q), 1.2 (6H, m).

Ex.47 (CDCl$_3$) δ7.6 (1H, m), 7.3 (13H, m), 5.4–5.0 (2H, m), 4.9–4.4 (3H, m), 3.7–3.1 (4H, m), 3.0–2.2 (2H, m), 2.2–1.8 (7H, m), 1.6 (6H, q), 1.2 (6H, m).

Ex.48 (CDCl$_3$) δ7.6 (1H, m), 7.3 (7H, m), 5.3 (1H, br s), 4.7–4.2 (3H, m), 3.8–3.2 (5H, m), 3.1 and 2.8 (1H, m) 2.3 (2H, m), 2.0 (5H, m), 1.6 (6H, q), 1.2 (6H, m).

Ex.49 (CDCl$_3$) δ7.6 (1H, m), 7.3 (7H, m), 5.3 (1H br s), 4.7–4.2 (3H, m), 3.8–3.2 (5H, m), 3.1 and 2.8 (1H, m) 2.3 (2H, m), 2.0 (5H, m), 1.6 (6H, q), 1.2 (6H, m).

Ex.50 (CDCl$_3$) δ7.6 (1H, m), 7.3 (7H, m), 4.7–4.3 (4H, m), 3.8–3.2 (7H, m), 3.0 and 2.8 (1H, m), 2.4–1.8 (8H, m), 1.6 (6H, q), 1.2 (6H, m).

Ex.51 (CDCl$_3$) δ7.6 (1H, m), 7.3 (7H, m), 4.7–4.3 (4H, m), 3.8–3.2 (7H, m), 3.0 and 2.8 (1H, m), 2.4–1.8 (8H, m), 1.6 (6H, q), 1.2 (6H, m).

Ex.52 (d6-DMSO) δ10.8 (1H,s), 7.5 (1H, d), 7.3 (6H, m), 7.0 (7H, m), 6.5 (1H, m), 4.5 (1H, m), 4.4 (1H, m), 3.1 (2H, s), 3.0 (1H, dd), 2.9 (1H, dd), 2.7 (2H, m), 2.5 (2H, m), 1.8 (3H, s), 1.6 (6H, q), 1.3 (6H, d).

Ex.53 (d6-DMSO) δ10.9 (1H, 2×s), 7.9 and 7.6 (1H, 2×d), 7.5–7.2 (6H, m), 7.1 (7H, m), 6.6 (1H, m), 4.5 (2H, m), 4.3 (1H, m), 3.5 (3H, s), 3.0 (4H, dd), 2.5 (2H, m), 1.8 (3H, s), 1.6 (6H, q), 1.2 (6H, d).

Ex.54 (d$^6$-DMSO) δ10.9 (1H, 2×s), 7.9 and 7.6 (1H, 2×d), 7.5–7.2 (6H, m), 7.1 (7H, m), 6.6 (1H, m), 4.5 (2H, m), 4.3

(1H, m), 3.5 (3H, s), 3.0 (4H, dd), 2.5 (2H, m), 1.8 (3H, s), 1.6 (6H, q), 1.2 (6H, d).

Ex.55a (diastereomer 1, higher $R_f$) (d$^6$-DMSO) δ10.9 (1H, s), 7.5–6.9 (19H, m), 6.7 (1H, m), 4.9 (2H, m), 4.5 (2H, m), 4.3 (1H, m), 3.0 (4H, m), 2.5 (2H, m), 1.8 (3H, s), 1.6 (6H, q), 1.2 (6H, d).

Ex.55a (diastereomer 2, lower $R_f$) (d$^6$-DMSO) δ10.8 (1H, s), 7.9 (1H, d), 7.4–6.9 (18H, m), 6.6 (1H, m), 5.0 (2H, m), 4.5 (1H, m), 4.42 (1H, s), 4.38 (1H, m), 3.1–2.9 (4H, m), 2.5 (2H, m), 1.8 (3H, s), 1.6 (6H, q), 1.2 (6H, d).

Ex.55b (d$^6$-DMSO) δ10.9 (1H, s), 7.5 (2H, m), 7.4–6.9 (12H, m), 6.6 (1H, t), 4.4 (2H, m), 4.2 (1H, s), 3.0 (4H, m), 2.5 (2H, m), 1.9 (3H, s), 1.6 (6H, q), 1.2 (6H, m).

Ex.56 (d$^6$-DMSO) δ10.8 (1H, s), 7.8 (1H, d), 7.4–6.9 (13H, m), 6.5 (1H, t), 4.5 (1H, s), 4.4 (1H, s), 4.3 (1H, m), 3.1 (1H, m), 3.0 (1H, dd), 2.9 (2H, m), 2.4 (2H, m), 1.8 (3H, s), 1.6 (6H, q), 1.2 (6H, m).

Ex.57 (d$^6$-DMSO) δ10.9 (1H, s), 7.6 (2H, m), 7.4–6.9 (12H, m), 6.6 (1H, t), 4.4 (2H, m), 4.2 (1H, s), 3.0 (4H, m), 2.5 (2H, m), 1.8 (3H, s), 1.6 (6H, q), 1.2 (6H, m).

Ex.58 (CDCl$_3$) δ8.1 (1H, s), 7.6 (1H, d), 7.4–6.9 (11H, m), 6.6 (1H, m), 6.5 (1H, m), 5.5 (1H, m), 4.8 (1H, m), 4.4 (1H, s), 4.2 (1H, m), 3.2 (4H, m), 2.7 (1H, m), 2.3 (1H, m), 2.0 (3H, s), 1.6 (6H, q), 1.2 (6H, m).

Ex.59 (d$^6$-DMSO) δ8.6 (1H, t), 7.3–7.0 (9H, m), 6.4 (1H, d), 6.2 (1H, d), 4.6 (2H, dd), 4.2 (2H, m), 3.2 (2H, d), 2.9 (1H, m), 2.5 (1H, m), 1.9 (3H, s), 1.6 (6H, q), 1.4 (6H, d).

Ex.60 (CDCl$_3$) δ7.7 (1H, d), 7.4 (1H, d), 7.3–7.0 (9H, m), 4.9 (1H, s), 4.7 (1H, d), 4.6 (1H, t), 3.9 (3H, m), 3.3 (2H, s), 2.6 (1H, q), 2.2 (1H, q), 1.7 (3H, s), 1.5 (6H, q), 0.9 (6H, s).

Ex.61 (CDCl$_3$) δ7.6–7.0 (13H, m), 6.1 and 5.8 (1H 2×d), 5.5 and 5.3 (1H, 2×t), 5.1 (2H, m), 4.6–4.2 (3H, m), 3.3–3.1 (2H, m), 2.9 (1H, m), 2.6 (1H, m), 1.9 (4H, s), 1.6 (6H, m), 0.8–0.6 (6H, m).

Ex.62 (CDCl$_3$) δ7.5–7.1 (8H, m), 6.9 and 6.5 (1H 2×m), 5.5 and 5.4 (1H, 2×m), 4.5 (2H, m), 4.3 and 4.2 (1H, m), 3.3 (2H, m), 3.0–2.4 (2H, m), 2.0 (4H, s), 1.6 (6H, m), 1.3 (6H, m), 0.8 (6H, m).

Ex.63 (CDCl$_3$) δ7.5–7.2 (8H, m), 5.9 and 5.7 (1H 2×d), 5.3 and 5.2 (1H, m), 4.6 (2H, bt), 4.2 (1H, m), 3.7 (3H, d), 3.3 (2H, m), 2.9 and 2.6 (2H, m), 1.9 (4H, s), 1.6 (6H, m), 1.3 (6H, m), 0.98–0.76 (6H, m).

Ex.64b (d$^6$-DMSO) δ12.4 (1H, br s), 7.8–6.8 (11H, m), 4.4 (2H, m), 4.2 (1H, m), 3.0 (2H, m), 2.6–2.3 (4H, m), 1.9 (3H, s), 1.6 (6H, m), 1.3 (6H, m).

Ex.65 (d$^6$-DMSO) δ12.6 (1H, br s), 7.9–6.9 (14H, m), 6.6 and 6.5 (1H, 2×t), 4.5 (2H, m), 4.4 (1H, m), 3.0 (2H, m), 2.8–2.3 (4H, m), 1.9 (3H, s), 1.6 (6H, m), 1.3 (6H, m).

Ex.66 (d$^6$-DMSO) δ7.3–7.0 (10H, m), 4.5 (1H, s), 4.4 (1H, s), 3.6 (3H, s), 3.0 (2H, m), 2.7 (1H, m), 2.5 (1H, m), 1.9 (3H, s), 1.6 (6H, m), 1.3 (6H, m), 1.1 (6H, 2×s).

Ex.67 (d$^6$-DMSO) δ7.4–7.0 (10H, m), 4.5 (1H, s), 4.4 (1H, s), 3.1 (1H, m), 2.9 (1H, m), 2.7 (1H, m), 2.5 (1H, m), 1.9 (3H, s), 1.6 (6H, m), 1.3 (6H, m), 1.1 (6H, 2×s).

Ex.68 (CDCl$_3$) δ7.6 (1H, m), 7.4–7.0 (7H, m), 5.8 (1H, br s), 4.9–4.3 (5H, m), 3.7–3.1 (4H, m), 2.9–2.1 (4H, m), 2.0 (3H, s), 1.6 (6H, m), 1.3 (6H, m).

Ex.69 (CDCl$_3$) δ7.6 (1H, d), 7.4–7.1 (8H, m), 4.7 (1H, t), 4.6 (1H, d), 4.5 (1H, d), 4.4 (2H, m), 3.8 (1H, m), 3.6 (1H, d), 3.4 (1H, dd), 3.2 (1H, d), 2.8 (1H, dd), 2.4 (2H, m), 2.2 (1H, m), 2.0 (3H, s), 1.6 (6H, m), 1.3 (6H, m).

Ex.70 (CDCl$_3$) δ7.6 (1H, m), 7.4–7.0 (7H, m), 5.8 (1H, br s), 4.9–4.3 (5H, m), 3.7–3.1 (4H, m), 2.9–2.1 (4H, m), 2.0 (3H, s), 1.6 (6H, m), 1.3 (6H, m).

Ex.71 (CDCl$_3$) δ7.6 (1H, d), 7.4–7.1 (8H, m), 4.7 (1H, d), 4.6 (1H, d), 4.4 (3H, m), 3.8 (3H, s), 3.7 (1H, m), 3.6–3.2 (4H, m), 2.8 (1H, dd), 2.4 (1H, dd), 2.1 (1H, m), 1.9 (3H, s), 1.6 (6H, m), 1.2 (6H, m).

Ex.72 (CDCl$_3$) δ7.6 (1H, m), 7.4–7.0 (8H, m), 4.8–4.4 (5H, m), 3.9–3.1 (8H, m), 2.9–2.1 (3H, m), 2.0 (3H, s), 1.6 (6H, m), 1.3 (6H, m).

Ex.73 (CDCl$_3$) δ7.6 (1H, m), 7.4–7.0 (8H, m), 4.8–4.4 (4H, m), 3.9–3.7 (3H, m), 3.3–2.6 (3H, m), 2.5–2.1 (3H, m), 2.0 (3H, s), 1.6 (8H, m), 1.1 (6H, m).

Ex.74 (CDCl$_3$) δ7.6 (1H, m), 7.4–7.0 (8H, m), 4.8–4.2 (4H, m), 3.9–2.1 (12H, m), 2.0 (3H, s), 1.6 (8H, m), 1.1 (6H, m).

Ex.75 (CDCl$_3$) δ7.5–7.1 (8H, m), 6.2 and 6.1 (1H, 2×d), 5.4 and 5.3 (1H, 2×t), 4.5 (3H, s), 3.3–3.1 (2H, m), 2.7 (2H, m), 1.9 (3H, s), 1.7 (6H, m), 1.3 (9H, m).

Ex.76 (CDCl$_3$) δ7.5–7.1 (8H, m), 6.2 and 5.9 (1H, 2×d), 5.4 and 5.2 (1H, 2×t), 4.6 (2H, m), 4.3 (1H, m), 3.2 (2H, m), 2.9–2.4 (2H, m), 2.1 (3H, s), 1.9 (3H, s), 1.7 (6H, m), 1.3 (9H, m).

Ex.77 (CDCl$_3$) δ7.5–7.0 (8H, m), 6.2 and 5.8 (1H, 2×d), 5.4 and 5.1 (1H, 2×t), 4.6 (2H, m), 4.3 (1H, m), 4.1 (2H, m), 3.5–3.2 (2H, m), 2.8 (1H, m), 2.6 (1H, m), 1.9 (3H, s), 1.7 (8H, m), 1.2 (9H, m), 0.9 (3H, m).

Ex.78 (CDCl$_3$) δ7.6 (1H, d), 7.4–7.1 (8H, m), 4.6–4.2 (3H, m), 3.6–3.2 (5H, m), 2.8 (1H, dd), 2.4 (2H, m), 2.0 (5H, m), 1.6 (6H, m), 1.3 (6H, m).

Ex.79 (CDCl$_3$) δ7.6–7.1 (8H, m), 5.4 (1H, br s), 4.86–4.4 (3H, m), 3.7–2.8 (6H, m), 2.4 (2H, m), 2.0 (5H, m), 1.6 (6H, m), 1.3 (6H, m).

Ex.80 (CDCl$_3$) δ7.6 (1H, d), 7.4–7.1 (7H, m), 4.6–4.3 (4H, m), 3.8 (3H, s), 3.5 (3H, m), 3.2 (1H, dd), 2.8 (1H, dd), 2.4 (1H, dd), 2.0 (7H, m), 1.6 (6H, m), 1.2 (6H, s).

Ex.81 (CDCl$_3$) δ7.6–7.1 (8H, m), 4.8–4.4 (4H, m), 3.7 and 3.6 (3H, 2×s), 3.5–2.9 (5H, m), 2.4–1.8 (8H, m), 1.6 (6H, m), 1.2 (6H, m).

Ex.82 (d$^6$-DMSO) δ7.6–6.9 (8H, m), 4.5 (2H, m), 4.1 (1H, m), 3.7–3.3 (2H, m), 3.1 (2H, m), 2.5 (2H, m), 1.9 (3H, s), 1.6 (6H, m), 1.2 (6H, m).

Ex.83 (d$^6$-DMSO) δ7.7–6.9 (8H, m), 4.5 (2H, m), 4.1 (1H, m), 3.6–3.3 (2H, m), 3.1 (2H, m), 2.6 (2H, m), 1.9 (3H, s), 1.6 (6H, m), 1.2 (6H, m).

Ex.84 (CDCl$_3$) δ7.6 (1H, d), 7.3–7.1 (7H, m), 6.6 (1H, d), 5.9 (1H, t), 4.6 (1H, d), 4.4 (2H, m), 3.8 (3H, s), 3.7 (2H, m), 3.6 (1H, m) 3.2 (1H, dd), 3.0 (1H, dd), 2.9 (1H, dd), 2.7 (1H, dd), 2.0 (3H, s), 1.7 (6H, m), 1.4 (6H, m).

Ex.85 (CDCl$_3$) δ7.5–7.1 (8H, m), 6.5 (1H, d), 5.6 (1H, t), 4.5 (2H, 2×s), 4.4 (1H, m), 3.7 (6H, m), 3.3 (1H, dd), 3.2 (1H, dd), 2.9 (1H, dd), 2.5 (1H, dd), 2.0 (3H, s), 1.7 (6H, m), 1.3 (6H, m).

Ex.86 (CDCl$_3$) δ7.7–7.1 (8H, m), 6.4 (1H, s), 5.8 (1H, s), 5.3 (1H, s), 5.0 (1H, t), 4.6 (1H, d), 4.5 (1H, d), 3.8 (3H, s), 3.4 (1H, dd), 3.2 (1H, dd), 2.7 (1H, dd), 2.5 (1H, dd), 1.9 (3H, s), 1.6 (6H, m), 1.2 (6H, s).

Ex.87 (d$^6$-DMSO) δ8.0–6.9 (9H, m), 4.9 amd 4.8 (1H, 2×m), 4.6–4.3 (3H, m), 3.5–2.7 (7H, m), 2.5–2.2 (2H, m), 1.8 (3H, s), 1.5 (6H, m), 1.1 (6H, m).

Ex.88 (CDCl$_3$) δ7.6 (1H, m), 7.4–7.0 (8H, m), 5.5–5.2 (1H, m), 4.6–4.4 (3H, m), 3.7–3.2 (3H, m), 3.1–2.6 (2H, m), 2.3 (2H, m), 1.9 (3H, m), 1.6 (6H, m), 1.4 (5H, m), 1.2 (6H, m).

Ex.89 (CDCl$_3$) δ7.6 (1H, m), 7.4–7.0 (7H, m), 5.3–4.3 (4H, m), 3.8–2.6 (8H, m), 2.3 (2H, m), 1.9 (3H, m), 1.6 (6H, m), 1.4 (5H, m), 1.2 (6H, m).

Ex.90 (d$^6$-DMSO) δ8.1–6.9 (9H, m), 4.9–4.1 (5H, m), 3.7–3.1 (7H, m), 2.9–2.1 (4H, m), 2.0 (3H, s), 1.6 (6H, m), 1.3 (6H, m).

Ex.91 (d$^6$-DMSO) δ8.1–6.9 (9H, m), 4.9–4.1 (5H, m), 3.8–3.1 (7H, m), 2.9–2.1 (4H, m), 2.0 (3H, s), 1.6 (6H, m), 1.1 (6H, m).

Ex.92 (d$^6$-DMSO) δ7.5–7.0 (13H, m), 6.4 (1H, d), 5.2 (1H, t), 4.5 (3H, m), 3.7 (3H, s), 3.6 (2H, s), 3.2 (2H, dd), 2.6 (4H, m), 2.0 (3H, s), 1.6 (6H, m), 1.2 (6H, s).

Ex.93 (CDCl$_3$) δ7.4–6.9 (13H, m), 6.3 (1H, d), 5.2 (1H, t), 4.5 (3H, m), 3.6 (3H, s), 3.5 (2H, s), 3.1 (2H, dd), 2.6 (4H, m), 1.9 (3H, s), 1.6 (6H, m), 1.2 (6H, s).

Ex.94 (d$^6$-DMSO) δ7.3 (3H, m), 7.1 (6H, m), 4.9–4.5 (3H, m), 3.3 (1H, m), 3.0 (1H, m), 2.8–2.5 (5H, m), 1.9 (3H, s), 1.6 (6H, m), 1.4 (6H, m), 1.1 (3H, m).

Ex.95 (d$^6$-DMSO) δ7.3 (3H, m) 7.1–6.9 (6H, m), 4.9–4.5 (3H, m), 3.3 (1H, m), 3.0 (1H, m), 2.8–2.5 (5H, m), 1.9 (3H, s), 1.6 (6H m), 1.4 (6H, m), 1.1 (3H, m).

Ex.96 (d$^6$-DMSO) δ7.4 (3H, m), 7.1 (5H, m), 5.0–4.4 (3H, m), 3.6 and 3.5 (3H, 2×s), 3.2 (1H, m), 3.0 (1H, m), 2.8 and 2.7 (3H, 2×s), 2.5 (2H, m), 1.9 (3H, s), 1.6 (6H, m), 1.3 (6H, m), 1.2–0.9 (3H, m).

Ex.97 (d$^6$-DMSO) δ7.4 (3H, m), 7.1–6.9 (5H, m), 5.0–4.3 (3H, m), 3.6 and 3.5 (3H, 2×s), 3.3 (1H, m),3.0 (1H, m), 2.8–2.5 (5H, m), 1.9 (3H, s), 1.6 (6H, m), 1.3–1.0 (9H, m).

Ex.98 (CDCl$_3$) δ7.7 (1H, d), 7.4–7.1 (7H, m), 4.6 (2H, m), 4.5 (1H, t), 3.5 (1H, m), 3.4 (2H, m), 3.3 (2H, m), 3.1 (1H, m), 2.7 (1H, q), 2.4 (1H, q), 1.9 (3H, s), 1.9–1.8 (4H, m), 1.6 (6H, m), 1.2 (6H, m).

Ex.99 (d$^6$-DMSO) δ7.4–7.0 (9H, m), 6.4 (1H, t), 4.4 (2H, m), 3.3 (1H, d), 3.1 (1H, dd), 2.9 (1H, dd), 2.5 (1H, q), 2.4 (3H, d), 1.9 (3H, s), 1.6 (6H, m), 1.2 (6H, m).

Ex.100 (CDCl$_3$) δ7.7 (1H, d), 7.4–7.1 (7H, m), 4.6 (2H, m), 4.4 (1H, t), 3.5 (1H, d), 3.1 (1H, dd), 2.9 (6H, 2×s), 2.7 (1H, dd), 2.5 (1H, dd), 1.9 (3H, s), 1.6 (6H, m), 1.2 (6H, m).

Ex.101 (CDCl$_3$) δ7.4 (2H, m), 7.3–7.1 (6H, m), 5.9 (1H, m), 5.7 (1H, m), 4.5 (2H, m), 3.2 (2H, d), 3.0 (2H, m), 2.6 (2H, m), 1.9 (3H, s), 1.6 (6H, m), 1.2 (6H, m), 0.9 (3H, t).

Ex.102 (CDCl$_3$) δ7.5–7.1 (8H, m), 5.9 (1H, t), 5.3 (1H, d), 4.5 (2H, d), 3.7 (2H, m), 3.1 (2H, s), 2.8 (1H, m), 2.6 (1H, m), 1.9 (3H, s), 1.6 (6H, m), 1.2 (6H, m), 0.8 (6H, d).

Ex.103 (d$^6$-DMSO) δ7.4–7.0 (8H, m), 6.7 (1H, m), 6.6 (2H, m), 4.5 (2H, d), 3.0 (1H, d), 2.9 (1H, d), 2.6 (1H, m), 2.5 (1H, m), 1.9 (3H, s), 1.6 (6H, m), 1.3 (6H, m).

Ex.104 (CDCl$_3$) δ7.7 (1H, m), 7.6 (1H, m), 7.4 (1H, m), 7.4–7.2 (10H, m), 6.0 (1H, t), 5.3 (1H, t), 5.1 (2H, s), 4.5 (1H, d), 3.4 (1H, m), 3.3 (2H, dt), 3.1 (1H, dd), 2.8 (1H, dd), 2.7 (1H, dd), 2.4 (2H, t), 1.9 (3H, s), 1.6 (6H, m), 1.3 (6H, s).

Ex.105 (CDCl$_3$) δ7.8 (1H, m), 7.7 (1H, m), 7.4 (1H, m), 7.4–7.2 (10H, m), 6.3 (1H, t), 5.2 (1H, t), 5.1 (2H, s), 4.6 (1H, d), 3.4 (1H, m), 3.3 (2H, dd), 3.2 (1H, d), 2.8 (1H, dd), 2.7 (1H, dd), 2.4 (2H, t), 1.9 (3H, s), 1.6 (6H, m), 1.3 (6H, m).

Ex.106 (CDCl$_3$) δ7.5–7.1 (8H, m), 6.3–6.0 (1H, 2×d), 5.6 and 5.3 (1H, 2×t), 4.6 (2H, m), 4.3 (1H, m), 3.7 (3H, m), 3.3 (2H, m), 2.9 (1H, m), 2.7 (1H, m), 1.2 (3H, dd), 0.8 (9H, d).

Ex.107 (d$^6$-DMSO) δ8.0–6.9 (9H, m), 4.5–3.9 (3H, m), 3.5–2.6 (6H, m), 2.2–1.6 (4H, m), 0.8 (9H, d).

Ex.108 (CDCl$_3$) δ7.4 (4H, m), 7.0 (4H, m), 5.7 (2H, d), 5.2 (1H, d), 3.0 (2H, d), 2.0 (3H, s), 1.7 (6H, q), 1.5 (6H, s).

Ex.109 (CDCl$_3$) δ7.4–7.1 (8H, m), 5.0 (1H, t), 4.6 (1H, d), 4.4 (1H, d), 2.8 (3H, m), 2.2 (1H, m), 1.9 (4H, m), 1.6 (6H, m), 1.3 (6H, s).

Ex.110 (CDCl$_3$) δ7.4–7.0 (8H, m), 4.7 (1H, d), 4.4 (1H, t), 3.6 (2H, dd), 3.0 (1H, m), 2.2 (1H, m), 2.1 (1H, m), 2.0 (3H, s), 1.7 (6H, m), 1.5 (6H, q).

Ex.111 (CDCl$_3$) δ7.5–7.1 (8H, m), 5.6 (1H, t), 4.6 (1H, s), 4.5 (1H, dd), 4.3 (1H, m), 3.7 (3H, 2×s), 3.6 (1H, t), 3.4–3.1 (3H, m), 1.9 (3H, m), 1.7 (6H, q), 1.4 (6H, s), 1.2 (3H, dd).

Ex.112 (CDCl$_3$) δ7.5–7.1 (8H, m), 5.6 (1H, t), 4.6 (1H, s), 4.5 (1H, dd), 4.3 (1H, m), 3.8 (3H, 2×s), 3.6 (1H, t), 3.4–3.1 (3H, m), 1.9 (3H, m), 1.7 (6H, q), 1.4 (6H, s), 1.2 (3H, dd)

Ex.113 (d$^6$-DMSO) δ7.4 (5H, m), 7.3 (4H, m), 7.1 (4H, m), 5.1 (2H, q), 3.1 (2H, m), 2.8 (2H, q), 2.4 (2H, m), 1.8 (3H, s), 1.6 (6H, m), 1.2 (6H, s).

Ex.114 (d$^6$-DMSO) δ7.7–6.8 (10 H, m), 4.6 (1H, s), 4.1 (1H, m), 3.6 (4H, m), 3.4 (1H, m), 2.7 (1H, q), 2.3 (1H, m), 1.8 (3H, s), 1.6 (6H, m), 1.3 (6H, s), 1.2 (3H, d).

Ex.115 (d$^6$-DMSO) δ8.1–6.8 (10H, m), 4.6 (1H, s), 4.0 (1H, m), 3.6 (4H, m), 3.4 (1H, m), 2.7 (1H, q), 2.3 (1H, m), 1.8 (3H, s), 1.6 (6H, m), 1.3 (6H, s), 1.2 (3H, m).

Ex.116 (d$^6$-DMSO) δ8.0–6.8 (10 H, m), 4.5 (1H, s), 4.0 (1H, m), 3.6 (4H, m), 3.4 (1H, m), 2.6 (1H, q), 2.3 (1H, m), 1.9 (3H, s), 1.6 (6H, m), 1.4 (6H, s), 1.0 (3H, d).

Ex.117 (CDCl$_3$) δ8.6 and 8.2 (1H, 2×s), 7.5–7.1 (13H, m), 6.3 and 6.0 (1H, 2×d), 5.4 and 5.2 (1H, 2×t), 4.8–4.4 (3H, m), 3.6 (3H, s), 3.3–2.3 (6H, m), 0.8 (9H, 2×s).

Ex.118 (CDCl$_3$) δ8.2 –6.8 (15H, m), 5.6 and 5.4 (1H, 2×t), 4.8–4.2 (3H, m), 3.3–2.5 (6H, m), 0.8 (9H, 2×s).

Ex.119 (CDCl$_3$) δ7.6–7.0 (10H, m), 6.4 (1H, m), 5.0 (1H, m), 4.6–4.4 (2H, m), 4.3–4.0 (2H, m), 3.9–3.2 (3H, m), 2.9–2.6 (2H, m), 2.3 (1H, m), 2.1–1.9 (7H, m), 1.6 (6H, m), 1.4 and 1.2 (6H, 2×s).

Ex.120 (CDCl$_3$) δ7.6–7.0 (10H, m), 6.1 (1H, m), 5.0–4.4 (3H, m), 4.2 (2H, m), 3.9–3.2 (3H, m), 2.9–2.6 (2H, m), 2.1–1.9 (8H, m), 1.6 (6H, m), 1.2 (6H, s).

Ex.121 (CDCl$_3$) δ7.6–7.0 (10H, m), 6.1 (1H, s), 4.8–4.4 (3H, m), 4.2–3.3 (5H, m), 2.9 (2H, m), 2.3 (1H, m), 2.1–1.9 (7H, m), 1.6 (6H, m), 1.2 (6H, s).

Ex.122 (CDCl$_3$) δ7.6–7.1 (10H, m), 6.0 (1H, m), 4.8–4.3 (3H, m), 3.8–3.2 (7H, m), 2.9 (1H, m), 2.6 (2H, m), 2.1–1.9 (7H, m), 1.6 (6H, m), 1.2 (6H, s).

Ex.123 (CDCl$_3$ δ7.6–7.1 (9H, m), 6.0 (1H, m), 4.6–4.0 (5H, m), 3.9–3.2 (6H, m), 2.9–2.3 (3H, m), 2.1–1.9 (7H, m), 1.6 (6H, m), 1.4 and 1.2 (6H, 2×s).

Ex.124 (CDCl$_3$) δ7.6–7.1 (9H, m), 5.9 (1H, m), 4.6–4.2 (3H, m), 3.8–3.1 (8H, m), 3.0–2.2 (5H, m), 2.1–1.9 (7H, m), 1.6 (6H, m), 1.4 and 1.2 (6H, 2×s).

Ex.125 (d$^6$-DMSO) δ7.7–7.5 (2H, m), 7.4–6.9 (9H, m), 4.5 (2H, m), 4.0 (1H, m), 3.8–3.2 (4H, m), 2.8–2.6 (2H, m), 2.3 (2H, m), 1.9 (3H, m), 1.6 (6H, m), 1.3 (6H, 2×s), 1.1 (3H, 2×d).

Ex.126 (CDCl$_3$) δ7.4–6.9 (9H, m), 5.9 (1H, m), 5.6 (1H, m), 4.5 (2H, m), 4.2 (2H, m), 3.7 (3H, s), 3.4 (4H, m), 2.8 (2H, m), 2.5 (2H, m), 2.0 (3H, s), 1.7 (6H, m), 1.3 (6H, 2×s), 1.1 (3H, 2×d).

Ex.127 (CDCl$_3$) δ7.5–7.1 (8H, m), 6.8 (1H, m), 6.1 and 5.9 (2H, m), 4.5 (2H, m), 4.3 (1H, m), 3.2 (2H, s), 2.9–2.5 (5H, m), 2.0 (3H, s), 1.6 (6H, m), 1.3 (9H, m).

Ex.128b (CDCl$_3$) δ7.5–7.1 (8H, m), 6.0 and 5.4 and 5.3 and 5.2 (2H, 4×d), 4.6 (2H, m), 4.3 (1H, m), 3.7 (3H, 2×d), 3.5 (1H m), 3.2 (2H, m), 2.0 (3H, s), 1.6–0.9 (15H, m), 0.8 (3H, 2×d).

Ex.129 (CDCl$_3$) δ7.5–7.1 (8H, m), 6.2 and 6.0 and 5.3 and 5.2 (2H, 4×d), 4.6 (2H, m), 4.4 (1H, m), 3.7 (3H, 2×s), 3.5 (1H, m), 3.2 (2H, m), 2.0 (3H, m), 1.8–0.9 (15H, m), 0.8 (3H, 2×d).

Ex.130 (CDCl$_3$) δ7.5–7.1 (8H, m), 6.2 and 6.0 (1H, 2×d), 5.4 and 5.2 (1H, 2×t), 4.6 (2H, m), 4.3 (1H, m), 3.3–3.1 (2H, m), 2.9–2.3 (4H, m), 2.0 (3H, s), 1.6 (6H, m),1.3 (6H, 2×s), 1.1 (6H, m).

Ex.131b (d$^6$-DMSO) δ7.6–6.9 (9H, m), 4.6 (1H, s), 4.3 (1H, m), 3.6 (3H, s), 3.5 (1H, m), 2.9–2.5 (4H, m), 2.0 (3H, s), 1.6 (6H, m),1.3 (6H, s).

Ex.132 (d$^6$-DMSO) δ7.9 and 7.5 (1H, 2×d), 7.4–6.9 (9H, m), 4.4 (2H, m), 4.2–4.0 (1H, m), 3.6 (3H, 2×s), 3.0 (4H, m), 2.0 (3H, s), 1.6 (6H, m),1.3 (6H, 2×s), 1.2 (3H, m).

Ex.133 (CDCl$_3$) δ7.6–7.1 (9H, m), 5.3 (2H, m), 4.6–4.2 (3H, m), 3.6–3.1 (4H, m), 2.7 (1H, m), 2.1–1.2 (18H, m).

Ex.134d (d$^6$-DMSO) δ13.5–12.5 (1H, br s), 8.3 (1H, t), 7.4–7.0 (8H, m), 5.7 (1H, s), 5.4 (1H, m), 2.8 (2H, m), 1.9 (3H, s), 1.6 (6H, m), 1.4 (6H, m).

Ex.135 (d$^6$-DMSO) δ8.8 (1H, d), 8.1 (1H, t), 7.5–7.0 (8H, m), 5.59 (1H, s), 5.56 (1H, s), 4.4 (1H, m), 3.6 (3H, s), 2.9 (2H, d), 1.9 (3H, s), 1.6 (6H, m), 1.4 (6H, m), 1.3 (3H, d).

Ex.136 (d$^6$-DMSO) δ12.6 (1H, br s),8.4 (1H, t), 8.1 (1H, t), 7.5–6.9 (8H, m), 5.8 (1H, s), 5.4 (1H, s), 4.4 (1H, m), 3.9–3.5 (2H, m), 3.3–2.5 (4H, m), 2.1–1.4 (13H, m), 1.3 (6H, m).

Ex.137d (CDCl$_3$) δ7.8 (4H, m), 7.3 (4H, m), 6.1 and 5.5 (1H, br s), 4.6 and 4.33 (1H, dd), 3.9–2.3 (7H, m), 2.0 (6H, m), 1.7 (6H, m), 1.4 (6H, m).

Ex.138c (CDCl$_3$) δ7.6–7.0 (8H, m), 5.9 and 5.0 (1H, 2×d), 4.6–4.3 (5H, m), 3.8–3.1 (4H, m), 2.4–1.9 (2H, m), 1.8–1.0 (15H, m).

Ex.139 (CDCl$_3$) δ7.7–7.0 (8H, m), 4.6–4.3 (3H, m), 3.8–2.8 (7H, m), 2.3 (2H, m), 1.9–1.0 (19H, m).

Ex.140 (CDCl$_3$) δ7.7–7.0 (8H, m), 4.6–4.0 (4H, m), 3.8–2.2 (8H, m), 1.9 (4H, m), 1.6 (9H, m), 1.0 (6H, m).

Ex.141 (CDCl$_3$) δ7.6–7.0 (8H, m), 5.0–4.5 (3H, m), 4.3 and 4.2 (1H, 2×m), 3.6–3.0 (5H, m), 2.7 (1H, m), 2.4 (1H, m), 2.2 (1H, m), 1.8 (7H, m), 1.6 (6H, m), 1.2 (6H, m).

Ex.142 (CDCl$_3$) δ7.6 (1H, m), 7.2 (7H, m), 5.0–4.6 (3H, m), 4.3 and 4.1 (1H, 2×m), 3.6–3.0 (5H, m), 2.9 (1H, m), 2.7 (1H, m), 2.4 (1H, m), 2.2 (1H, m), 1.9 (6H, m), 1.6 (6H, m), 1.2 (6H, m).

Ex.143 (CDCl$_3$) δ7.6 (1H, m), 7.2 (7H, m), 4.6 (3H, m), 4.4 and 4.2 (1H, 2m), 3.65 and 3.6 (3H, 2s), 3.5–3.0 (5H, m), 2.7 (1H, m), 2.3 (1H, m), 2.1–1.4 (14H, m), 1.2 (6H, m).

Ex.144 (CDCl$_3$) δ7.6–7.1 (8H, m), 4.8–4.5 (3H, m), 4.4 and 4.2 (1H, 2m), 3.6 (3H, m), 3.5–2.0 (7H, m), 2.0–1.4 (14H, m), 1.2 (6H, m).

Ex.145 (CDCl$_3$) δ7.6–6.9 (8H, m), 5.5 (1H, m), 4.7 (1H, t), 4.5 (2H, m), 4.2 (1H, m), 3.7–3.2 (5H, m), 2.9 (1H, m), 2.7 (1H, m), 2.2–1.7 (7H, m), 1.5 (9H, m), 1.2 (6H, m).

Ex.146 (CDCl$_3$) δ7.6–7.0 (8H, m), 6.3 (1H, m), 4.5 (2H, d), 4.3 (2H, m), 3.8–3.2 (5H, m), 2.9 (1H, m), 2.6 (1H, m), 2.0 (7H, m), 1.7 (6H, m), 1.4 (9H, m).

Ex.147 (CDCl$_3$) δ7.6–7.0 (8H, m), 6.1 (1H, m), 4.8–4.2 (4H, m), 3.6–3.2 (5H, m), 2.9 (1H, m), 2.3 (1H, m), 2.2–1.8 (7H, m), 1.6 (9H, m), 1.2 (6H, m).

Ex.148 (CDCl$_3$) δ7.8–7.0 (8H, m), 4.8–4.2 (5H, m), 3.7–3.3 (3H, m), 3.2 (1H, m), 2.7 (1H, d), 2.6 (1H, m), 2.4 (1H, m), 2.2–1.2 (13H, m), 1.1 (6H, m), 0.8 (3H, d).

Ex.149 (d$^6$-DMSO) δ12.5 (1H, br s), 7.4–6.8 (9H, m), 5.1–4.1 (5H, m), 3.9 (1H, m), 3.7 (1H, m), 3.3–2.9 (4H, m), 2.5 (2H, m), 1.9 (3H, s), 1.6 (6H, m), 1.3 (6H, m).

Ex.150 (d$^6$-DMSO) δ7.3 (3H, m), 7.1 (5H, m), 6.8–6.3 (1H, m), 4.5 (2H, s), 3.7–2.7 (5H, m), 2.5 (2H, m), 1.9 (5H, m), 1.6 (6H, m), 1.2 (6H, s).

Ex.151 (CDCl$_3$) δ7.7–7.1 (8H, m), 4.6 (2H, br,s), 4.5 (1H, m), 3.7 (3H, m), 3.65–2.0 (9H, m), 1.9 (3H, br,s), 1.6 (7H, m), 1.3 (1H, m), 1.1 (6H, s).

Ex.152 (CDCl$_3$) δ7.6 (1H, d), 7.2 (7H, m), 4,8–4.2 (3H, m), 4.1 (2H, m), 3.9–2.0 (9H, m), 1.9 (3H, s), 1.6 (10H, m), 1.2 (3H, m), 1.1 (6H, s).

Ex.153 (CDCl$_3$) δ7.6 (1H, d), 7.2 (7H, m), 4.8–4.2 (3H, m), 4.1 (2H, m), 3.9–2.0 (9H, m), 1.9 (3H, s), 1.6 (10H, m), 1.2 (3H, m), 1.1 (6H, s).

Ex.154b (CDCl$_3$) δ7.7 (1H, m), 7.2 (7H, m), 4.8–4.2 (3H, m), 3.8 (1H, m), 3.62 and 3.64 (3H, 2×s), 3.6–2.0 (8H, m), 1.9 (3H, s), 1.6 (8H, m), 1.2 (2H, m), 1.1 (6H, s).

Ex.155 (CDCl$_3$) δ7.7 (1H, m), 7.2 (7H, m), 4.6–4.2 (3H, m), 3.8 (1H, m), 3.63 and 3.65 (3H, 2×s), 3.6–2.0 (8H, m), 1.9 (3H, s), 1.6 (10H, m), 1.1 (6H, s).

Ex.156 (CDCl$_3$) δ7.7 (1H, m), 7.2 (7H, m), 4.8–4.2 (3H, m), 3.8 (1H, m), 3.63 and 3.65 (3H, 2×s), 3.6–2.0 (8H, m), 1.9 (3H, s), 1.6 (8H, m), 1.3 (2H, m), 1.1 (6H, s).

Ex.157 (CDCl$_3$) δ7.6 (1H, d), 7.2 (7H, m), 4.8–4.3 (3H, m), 3.8 (1H, m), 3.63 and 3.65 (3H, 2×s), 3.6–2.0 (8H, m), 1.9 (3H, s), 1.6 (10H, m), 1.1 (6H, s).

Ex.158 (d$^6$-DMSO) δ8.2 (1H, s), 7.3 (3H, m), 7.0 (5H, m), 6.7 (1H, t), 4.47 and 4.48 (2H, 2×s), 3.9 (1H, m), 3.5–2.9 (4H, m), 2.6 (1H, m), 2.4 (1H, m), 1.8 (4H, m), 1.6 (9H, m), 1.3 (8H, m), 1.0 (2H,s).

Ex.159 (d$^6$-DMSO) δ8.3 (1H, s), 7.3 (3H, m), 7.0 (5H, m), 4.50 and 4.52 (2H, 2×s), 4.1 (1H, t), 3.4 (2H, m), 3.1 (1H, m), 2.9 (1H, d), 2.7 (2H, m), 1.9 (4H, m), 1.6 (9H, m), 1.3 (6H, m), 1.2(1H, m), 0.9 (1H, m), 0.7 (2H,m).

Ex.160d (CDCl$_3$) δ7.7 (1H, d), 7.4–7.1 (6H, m), 6.9 (1H, m), 5.0 (1H, d), 4.6 (1H, s), 4.3 (1H, m), 3.5 (3H, m), 3.3 (1H, m), 2.9 (1H, m), 2.5–1.4 (14H, m), 1.2 (6H, m).

Ex.161 (CDCl$_3$) δ7.6 (1H, d), 7.4–7.0 (6H, m), 6.9 (1H, m), 5.0 (1H, s), 4.6 (2H, m), 4.3 (1H, m), 3.5 (3H, m), 3.2 (2H, m), 2.8–1.4 (13H, m), 1.2 (6H, m).

Ex.162 (CDCl$_3$) δ7.7 (1H, d), 7.4–7.1 (6H, m), 6.9 (1H, m), 5.0 (1H, m), 4.6 (1H, m), 4.3 (1H, m), 3.5 (3H, m), 3.3 (1H, m), 2.9 (1H, m), 2.5–1.4 (14H, m), 1.2 (6H, m).

Ex.163 (d$^6$-DMSO) δ8.2 (1H, t), 7.5 (1H, s), 7.3 (3H, m), 7.0 (5H, m), 4.5 (2H, d), 4.0 (1H, m), 3.1–3.4 (2H, m), 3.0 (1H, m), 2.9 (1H, d), 2.8–2.6 (2H, m), 1.9–1.3 (19H, m), 1.08 and 1.13 (6H, 2×s).

Ex.164 (d$^6$-DMSO) δ7.9(1H, s), 7.3–6.8 (1H, t), 4.5 (2H, s), 4.0 (1H, m), 3.1–3.4 (3H, m), 3.0 (1H, m), 2.85 (2H, m), 2.1 (1H, m), 2.0–1.0 (24H, m).

Ex.165 (CDCl$_3$) δ7.7–6.9 (8H, m), 5.7 (1H, m), 5.4 (1H, m), 4.9–4.4 (2H, m), 3.8–2.4 (5H, m), 2.2–1.2 (19H, m).

Ex.166 (CDCl$_3$) δ7.5 (1H, m), 7.4–7.1 (7H, m), 5.4 and 5.1 (1H, 2×br,s), 4.5 (2H, m), 4.4 (2H, m), 3.75 and 3.72 (3H, 2×s), 3.5 (2H, m), 2.8 (1H, m), 2.5 (1H, m), 1.9 (3H, br, s), 1.6 (6H, m), 1.2 (6H, m).

Ex.167 (d$^6$-DMSO) δ12.8 (1H, br s), 7.5 (1H, d), 7.4–6.9 (9H, m), 4.4 (2H, s), 4.1 (1H, m), 3.8 (2H, m), 3.4 and 3.0 (2H, 2×dd), 3.1 and 2.8 (2H, 2×dd), 2.5 (2H, m), 2.45 and 2.0 (2H, 2×dd), 1.9 (3H, s), 1.6 (6H, m), 1.3 (6H, s).

Ex.168 (d$^6$-DMSO) δ12.8 (1H, br s), 7.7 (1H, d), 7.4–6.9 (8H, m), 6.8 (1H, t), 4.4 (2H, s), 4.1 (1H, m), 3.9 (2H, m), 3.5 and 3.1 (2H, 2×dd), 2.9 (2H, 2×dd), 2.6 (2H, m), 2.4 and 1.9 (2H, 2×dd), 1.85 (3H, s), 1.6 (6H, m), 1.3 (6H, s).

Ex.169 (d$^6$-DMSO) δ7.5 (1H, d), 7.4–6.9 (9H, m), 4.4 (2H, s), 4.2–3.8 (3H, m), 3.6 (3H, s), 3.5–2.9 (4H, m), 2.8 (1H, d), 2.5 (2H, m), 2.0 (1H, m), 1.9 (3H, s), 1.6 (6H, m), 1.3 (6H, s).

Ex.170 (d$^6$-DMSO) δ7.6 (1H, d), 7.4–6.9 (8H, m) 6.8 (1H, t), 4.4 (2H, s), 4.0 (3H, m), 3.6 (3H, s), 3.6–1.95 (8H, m), 1.9 (3H, s), 1.6 (6H, m), 1.3 (6H, s).

Ex.171 -DMSO) δ8.1 (1H, m), 7.9 and 7.5 (1H, 2×m), 7.4–6.9 (14H, m), 4.6–4.2 (3H, m), 3.8–2.4 (8H, m), 1.9 (3H, br,s), 1.6 (6H, m), 1.3 (6H, m).

Ex.172 (d$^6$-DMSO) δ8.0–6.8 (16H, m), 4.5–4.0 (4H, m), 3.4–2.4 (6H, m), 1.8 (3H, m), 1.6 (6H, m), 1.2 (6H, m), 1.1 (3H, d).

Ex.173 (d$^6$-DMSO) δ8.0–6.9 (16H, m), 4.5–4.0 (3H, m), 3.3–2.5 (8H, m), 1.8 (3H, m), 1.6 (6H, m), 1.2 (6H, m).

Ex.174 (d$^6$-DMSO) δ10.85 and 10.8 (1H, 2×s), 8.1 (1H, m), 7.7–6.7 (15H, m), 4.5–4.1 (3H, m), 3.8–2.3 (8H, m), 1.9 (3H, m), 1.6 (6H, m), 1.2 (6H, m).

Ex.175 (CDCl$_3$) δ7.6–7.0 (8H, m), 4.8 (2H, m), 4.6 (2H, m), 4.3 (1H, m), 3.6–2.2 (9H, m), 2.1–1.4 (13H, m), 1.2 (6H, s).

Ex.176 (CDCl$_3$) δ7.6–6.7 (8H, m), 4.8–4.0 (5H, m), 3.3–2.0 (9H, m), 1.8–0.8 (19H, m).

Ex.177 (CDCl$_3$) δ7.1 (1H, m), 7.0–6.6 (8H, m), 5.6 (1H, br,s), 4.3 (1H, s), 4.1 (1H, s), 3.3 (1H, m), 2.9 (1H, d), 2.7 (1H, d), 0.9 (16H, m), 0.6 (6H, t).

Ex.178 (d$^6$-DMSO) δ12.8 (1H, br s), 7.7 (1H, m), 7.4–6.9 (8H, m), 6.7 and 6.6 (1H, 2×m), 4.4 (2H, s), 4.3–3.8 (3H, m), 3.4–2.8 (4H, m) 2.5 (2H, m), 2.1 (1H, m), 1.9 (3H, s), 1.6 (7H, m), 1.3 (6H, m).

Ex.179 (d$^6$-DMSO) δ12.8 (1H, br s), 7.7 (1H, m), 7.5–7.0 (8H, m), 6.7 and 6.6 (1H, 2×m), 4.4 (2H, m), 4.3–3.5 (3H, m), 3.4–2.9 (4H, m), 2.5 (2H, m), 2.1 (1H, m), 1.9 (3H, s), 1.6 (7H, m), 1.3 (6H, m).

Ex.180 (d$^6$-DMSO) δ8.3–6.9 (10H, m), 4.5 (2H, m), 4.0–2.5 (8H, m), 1.9 (4H, m), 1.7 (9H, m), 1.4–1.2 (9H, m).

Ex.181 (d$^6$-DMSO) δ8.3 and 8.25 (1H, 2t), 7.7–6.9 (10H, m), 6.6 and 6.5 (1H, 2s), 4.5 (2H, m), 4.1 and 3.8 (1H, 2m), 3.6–2.4 (8H, m), 2.0–1.5 (13H, m), 1.4 and 1.3 (6H, m).

Ex.182 (d$^6$-DMSO) δ8.1–6.8 (18H, m), 4.5–4.1 (3H, m), 3.6–2.4 (8H, m), 1.9 (3H, sm), 1.6 (6H, m), 1.3 (6H, m).

Ex.183 (d$^6$-DMSO) δ12.0 (1H, br s), 7.9 (1H, m), 7.4 (4H, m), 7.1–6.8 (5H, m), 4.6–4.3 (3H, m), 3.9 (1H, m), 3.7 (2H, m), 3.5–2.9 (5H, m), 2.6 (2H, m), 1.9–1.5 (11H, m), 1.3 (6H, m).

Ex.184b (d$^6$-DMSO) δ12.6 (1H, br s), 8.1 and 6.3 (1H, 2×t), 7.4–6.9 (9H, m), 4.5 (2H, m), 4.2–3.9 (2H, m), 3.5–2.8 (6H, m), 2.6 (2H, m), 2.1–1.5 (13H, m), 1.4–1.1 (9H, m).

Ex.185 (d$^6$-DMSO) δ12.6 (1H, br s), 8.0 and 6.3 (1H, 2×m), 7.4–6.9 (9H, m), 4.5 (2H, m), 4.2–3.9 (2H, m), 3.5–2.8 (6H, m), 2.6 (2H, m), 2.1–1.5 (13H, m), 1.4–1.1 (9H, m).

Ex.186b (d$^6$-DMSO) δ12.5 (1H, br s), 8.2 and 8.0 (1H, 2×d), 7.4–6.9 (9H, m), 4.5 (2H, m), 4.1 (2H, m), 3.5–2.3 (8H, m), 2.2–1.5 (13H, m), 1.4–1.1 (9H, m).

Ex.187 (d$^6$-DMSO) δ12.4 (1H, br s), 8.1 (1H, d), 7.3 (3H, m), 7.1 (5H, m), 4.5 (2H, d), 4.1 (1H, m), 3.9 (1H, m), 3.3–2.9 (6H, m), 2.5 (2H, m), 2.1–1.4 (13H, m), 1.2 (9H, m).

Ex.188 (CDCl$_3$) δ9.1 and 6.0 (1H, 2×t), 7.6–7.0 (8H, m), 4.6–4.3 (3H, m), 4.1 (1H, m), 3.8 and 3.3 (3H, 2×s), 3.6–3.1 (6H, m), 2.9 (1H, m), 2.7–2.2 (2H, m), 2.0–1.6 (12H, m), 1.4 and 1.2 (6H, 2×s).

Ex.189 (CDCl$_3$) δ7.6–7.0 (8H, m), 5.9 (1H, m), 4.5 (3H, m), 4.1 (1H, m), 3.7 (3H, s), 3.6–3.4 (4H, m), 3.3 (2H, s), 2.8 (1H, m), 2.6 (1H, m), 2.3 (1H, m), 2.0–1.6 (12H, m), 1.4 (6H, s).

Ex.190 (d$^6$-DMSO) δ7.4–6.9 (8H, m), 6.8 (1H, t), 4.8–4.1 (3H, m), 3.6–2.6 (9H, m), 2.5 (2H, m), 1.9–1.4 (13H, m), 1.2 (6H, d).

Ex.191 (d$^6$-DMSO) δ7.8 (1H, t), 7.5–6.9 (8H, m), 6.8 and 6.7 (1H, 2×t), 4.8–3.8 (5H, m), 3.6 (3H, m), 3.4–2.9 (4H, m), 2.5 (2H, m), 2.1 (1H, m), 1.9 (3H, br s), 1.7–1.2 (13H, m).

Ex.192 (CDCl$_3$) δ7.6–7.1 (8H, m), 5.1 and 4.7 (1H 2×m), 4.5 and 4.3 (1H, 2×d), 3.5 (2H, m), 3.4–2.8 (4H, m), 2.4–1.1 (25H, m).

Ex.193 (CDCl$_3$) δ7.5 (1H, d), 7.4–7.1 (7H, m), 4.6 (1H, m), 4.2 (1H, m), 3.5 (2H, m), 3.2 (2H, m), 2.9 (1H, m), 2.3 (1H, m), 2.2–1.8 (13H, m), 1.6 (6H, m), 1.2 (6H, m).

Ex.194 (d$^6$-DMSO) δ12.5 (1H, br s), 8.1 (1H, t), 7.3 (3H, m), 7.0 (5H, m), 6.3 (1H, t), 4.5 (2H, m), 3.9 (1H, m), 3.7 (2H, m), 3.4–2.9 (4H, m), 2.7–2.3 (4H, m), 2.1 (1H, m), 1.8 (3H, s), 1.6 (9H, m), 1.3 (6H, s).

Ex.195 (CDCl$_3$) δ7.7–7.1 (8H, m), 6.9 and 6.0 (1H 2×t), 4.6(3H, m), 4.4–4.0 (3H, m), 3.8 (1H, m), 3.5 (4H, m), 3.2 (2H, m), 2.8 (1H, m), 2.3 (2H, m), 1.9 (6H, m), 1.8–1.2 (22H, m).

Ex.196 (CDCl$_3$) δ7.6 (1H, d), 7.5–7.1 (7H, m), 6.9 (1H, d), 5.8 and 5.2 (2H, dd), 4.5(3H, m), 4.3 (1H, m), 3.5 (4H, m), 3.2 (1H, d), 2.9 (1H, m), 2.5–2.1 (2H, m), 2.0–1.1 (30H, m).

Ex.197 (d$^6$-DMSO) δ8.2 and 6.7 (1H,2×m), 7.4–6.8 (10H, m), 4.5 (2H, m), 4.1 and 3.8 (1H, 2×m), 3.6–2.5 (6H, m), 1.9 (3H, m), 1.8–1.5 (10H, m), 1.4 and 1.2 (6H, 2×s).

Ex.198b (d$^6$-DMSO) δ12.6 (1H, br s), 8.0 (1H, t), 7.4 (3H, m), 7.0 (6H, m), 4.5 (2H, d), 4.1 (1H, m), 3.6 (2H, m), 3.4–2.8 (4H, m), 2.6–2.2 (4H, m), 1.9 (3H, s), 1.6 (10H, m), 1.35 (6H, s).

Ex.199 (d$^6$-DMSO) δ12.6 (1H, br s), 8.1 (1H, t), 7.3 (3H, m), 7.0 (5H, m), 6.4 (1H, t), 4.5 (2H, m), 3.9 (1H, m), 3.6 (2H, m), 3.4–2.9 (4H, m), 2.6–2.4 (4H, m), 2.1 (1H, m), 1.8 (3H, s), 1.6 (9H, m), 1.2 (6H, s).

Ex.200 (d$^6$-DMSO) δ12.6 (1H, br s), 8.0 (1H, d), 7.3 (3H, m), 7.0 (6H, m), 4.5 (2H, m), 4.0 (2H, m), 3.4–2.8 (4H, m), 2.6–2.1 (5H, m), 1.9 (3H, s), 1.6 (9H, m), 1.2 (9H, m).

Ex.201 (d$^6$-DMSO) δ12.6 (1H, br s), 8.0 (1H, d), 7.3 (3H, m), 7.0 (5H, m), 6.3 (1H, t), 4.5 (2H, d), 4.1 (1H, m), 3.9 (1H, m), 3.4–2.9 (4H, m), 2.6–2.4 (4H, m), 2.0 (1H, m), 1.9 (3H, s), 1.6 (9H, m), 1.2 (9H, m).

Ex.202 (d$^6$-DMSO) δ12.6 (1H, br s), 8.0 (1H, d), 7.3 (3H, m), 7.0 (6H, m), 4.5 (2H, m), 4.1 (2H, m), 3.5–2.8 (4H, m), 2.7–2.2 (5H, m), 1.9 (3H, s), 1.6 (9H, m), 1.4–1.1 (9H, m).

Ex.203 (d$^6$-DMSO) δ12.6 (1H, br s), 8.1 (1H, d), 7.3 (3H, m), 7.0 (5H, m), 6.4 (1H, t), 4.5 (2H, d), 4.1 (1H, m), 3.9 (1H, m), 3.4–2.9 (4H, m), 2.7–2.3 (4H, m), 2.0 (1H, m), 1.8 (3H, s), 1.6 (9H, m), 1.2 (9H, m).

Ex.204 (CDCl$_3$) δ7.6–7.1 (8H, m), 5.1–4.5 (3H, m), 4.0 (1H, m), 3.6–2.2 (10H, m), 2.0–1.4 (13H, m), 1.2 (6H, m).

Ex.205 (CDCl$_3$) δ7.6 (1H, m), 7.4–7.0 (7H, m), 6.8 (1H, m), 5.8 (1H, dd), 4.7–4.4 (4H, m), 3.8 and 3.75 (3H, 2×s), 3.6–2.2 (6H, m), 2.0–1.4 (13H, m), 1.2 (6H, m).

Ex.206 (CDCl$_3$) δ7.7–7.1 (8H, m), 4.5 (3H, m), 3.9 (1H, m), 3.7 and 3.6 (3H, 2×s), 3.5–2.1 (10H, m), 2.0–1.5 (13H, m), 1.2 (6H, m).

Ex.207 (d$^6$-DMSO) δ8.0 (1H, t), 7.5 (1H, d), 7.4–6.8 (16H, m), 4.4 (2H, s), 4.1 (1H, m), 3.6–3.1 (3H, m), 2.9 (3H, m), 2.5 (2H, m), 1.9 (3H, s), 1.6 (6H, m), 1.3 (6H, s).

Ex.208 (d$^6$-DMSO) δ8.0 (1H, t), 7.8 (1H, d), 7.5 (1H, t), 7.4–6.9 (15H, m), 4.5 (1H, s), 4.3 (1H, m), 4.2 (1H, s), 3.6–3.0 (4H, m), 2.7 (2H, m), 2.5 (2H, m), 1.9 (3H, s), 1.6 (6H, m), 1.3 (6H, m).

Ex.209 (CDCl$_3$) δ7.4–7.0 (8H, m), 5.6 (1H, t), 4.6 (1H, s), 4.4 (1H, s), 2.9 (3H, m), 2.3 (2H, dd), 2.0 (3H, s), 1.6 (6H, m), 1.3 (1H, d), 1.2 (6H, s).

Ex.210 (CDCl$_3$) δ7.2 (8H, m), 7.1 and 6.2 (1H, 2×d), 5.7 and 5.6 (1H, 2×t), 4.7–4.2 (3H, m), 3.7 (3H, s), 3.0–2.2 (5H, m), 2.0 (3H, s), 1.7 (7H, m), 1.43 and 1.40 (6H, 2×s), 1.3 and 1.1 (3H, 2×d).

Ex.211 (CDCl$_3$) δ7.5–7.0 (8H, m), 5.8 and 5.6 (1H, 2×t), 4.8–4.3 (3H, m), 3.9–3.2 (3H, m), 3.0 (3H, m), 2.6–1.0 (21H, m).

Ex.212 (CDCl$_3$) δ7.5 (1H, d), 7.4–7.1 (7H, m), 6.2 (1H, d), 5.8 (1H, t), 4.5 (2H, d), 3.8 (1H, m), 3.2 (2H, dd), 2.8 (1H, m), 2.7 (1H, m), 2.4 (1H, m), 2.0 (3H, s), 1.8–1.1 (18H, m).

Ex.213 (CDCl$_3$) δ7.5–7.1 (8H, m), 6.3 (1H, d), 5.7 (1H, t), 4.5 (2H, d), 3.8 (1H, m), 3.2 (2H, dd), 2.8 (1H, m), 2.7 (1H, m), 2.5 (1H, m), 2.0 (3H, s), 1.8–1.1 (18H, m).

Ex.214 (CDCl$_3$) δ7.6–6.8 (9H, m), 6.0 (1H, m), 4.8–4.2 (4H, m), 3.8 (3H, s), 3.6–2.1 (7H, m), 2.0–1.1 (21H, m).

Ex.215 (CDCl$_3$) δ7.6–7.1 (8H, m), 5.1–4.5 (3H, m), 4.0 (1H, m), 3.6–2.2 (10H, m), 2.0–1.4 (13H, m), 1.2 (6H, m).

Ex.216 (d$^6$-DMSO) δ8.0–7.0 (15H, m), 6.8–6.5 (2H, m), 4.5–4.0 (3H, m), 3.4–3.0 (4H, m), 2.5 (2H, m), 1.82 and 1.78 (3H, 2×s), 1.6 (6H, m), 1.1 and 1.2 (6H, 2×s).

Ex.217 (d$^6$-DMSO) δ8.2–6.8 (16H, m), 6.5 (1H, t), 4.5–4.1 (3H, m), 3.4–2.2 (6H, m), 1.8 and 1.7 (3H, 2×s), 1.6 (6H, m), 1.1 and 1.2 (6H, 2×s).

Ex.218 (d$^6$-DMSO) δ8.0 (1H, t), 7.7 (1H, d), 7.4–6.7 (14H, m), 4.5–4.0 (4H, m), 3.6–2.3 (6H, m), 1.8 (3H, s), 1.6 (6H, m), 1.3–1.0 (9H, m).

Ex.219 (d$^6$-DMSO) δ12.6 (1H, br s), 7.4–6.9 (13H, m), 5.0–4.0 (4H, m), 3.6–3.0 (3H, m), 2.8–2.1 (4H, m), 1.7 (3H, br s), 1.6 (6H, m), 1.1 and 1.08 (6H, 2×s).

Ex.220c (CDCl$_3$) δ7.6–7.0 (8H, m), 4.8–4.3 (3H, m), 3.8–2.3 (9H, m), 2.2–1.4 (19H, m).

Ex.221 (CDCl$_3$) δ7.6–7.0 (8H, m), 6.4 (1H, m), 4.6–4.4 (2H, m), 4.3–4.0 (1H, m), 3.9–3.1 (9H, m), 2.9–2.6 (2H, m), 2.3 (1H, m), 2.1–1.9 (6H, m), 1.6 (6H, m), 1.4 and 1.2 (6H, 2×s).

Ex.222 (CDCl$_3$) δ7.6–6.9 (8H, m), 5.5 (1H, m), 4.5 (2H, m), 4.2 (1H, m), 3.7–3.1 (8H, m), 2.9 (1H, m), 2.7 (1H, m), 2.2–1.7 (7H, m), 1.5 (9H, m), 1.2 (6H, m).

Ex.223 (CDCl$_3$) δ7.6–7.0 (8H, m), 6.1 (1H, m), 4.7–4.2 (3H, m), 3.6–3.1 (8H, m), 2.9 (1H, m), 2.3 (1H, m), 2.2–1.8 (7H, m), 1.6 (9H, m), 1.2 (6H, m).

Ex.224b (d$^6$-DMSO) δ12.6 (1H, br s), 7.4–6.9 (9H, m), 4.5 (2H, m), 4.2–3.9 (2H, m), 3.5–2.8 (9H, m), 2.6 (2H, m), 2.1–1.5 (13H, m), 1.4–1.1 (9H, m).

Ex.225 (d$^6$-DMSO) δ12.6 (1H, br s), 7.4–6.9 (9H, m), 4.5 (2H, m), 4.2–3.9 (2H, m), 3.5–2.8 (9H, m), 2.6 (2H, m), 2.1–1.5 (13H, m), 1.4–1.1 (9H, m).

Ex.226b (d$^6$-DMSO) δ12.6 (1H, br s), 8.0 (1H, d), 7.3 (3H, m), 7.0 (5H, m), 4.5 (2H, d), 4.1 (1H, m), 3.9 (1H, m), 3.4–2.9 (7H, m), 2.6–2.4 (4H, m), 2.0 (1H, m), 1.9 (3H, s), 1.6 (9H, m), 1.2 (9H, m).

Ex.227 (CDCl$_3$) δ7.6–7.0 (9H, m), 6.0 (1H, m), 4.6–4.0 (5H, m), 3.8–3.2 (6H, m), 2.9–2.2 (3H, m), 2.0–1.2 (19H, m).

Ex.228 (CDCl$_3$) δ7.8–7.1 (9H, m), 6.6 (1H, m), 4.6–4.2 (4H, m), 3.6–3.0 (4H, m), 2.9–2.0 (3H, m), 2.0–1.2 (21H, m).

Ex.229 (CDCl$_3$) δ8.1 (1H, t), 7.6 (1H, d), 7.4–7.1 (7H, m), 6.0 (1H, t), 4.8 (1H, m), 4.6 (1H, s), 4.4 (1H, s), 4.1 (1H, dd), 3.8 (1H, dd), 3.5 (2H, m), 2.9–2.2 (6H, m), 2.0 (3H, s), 1.6 (6H, m), 1.4 (6H, s).

Ex.230 (CDCl$_3$) δ7.6–6.9 (9H, m), 5.8 (1H, m), 4.5 (2H, m), 4.2–3.6 (3H, m), 3.2 (2H, m), 2.5 (2H, m), 2.2–1.2 (19H, m).

Ex.231 (d$^6$-DMSO) δ12.6 (1H, br s), 8.1 (1H, d), 7.3 (3H, m), 7.0 (5H, m), 4.5 (2H, d), 4.1 (1H, m), 3.9 (1H, m), 3.4–2.9 (7H, m), 2.7–2.3 (4H, m), 2.0 (1H, m), 1.8 (3H, s), 1.6 (9H, m), 1.2 (9H, m).

Ex.232 (d$^6$-DMSO) δ12.5 (1H, br s), 8.2 and 8.0 (1H, 2×d), 7.4–6.9 (9H, m), 4.5 (2H, m), 4.1 (2H, m), 3.7 (3H, s), 3.5–2.3 (8H, m), 2.2–1.5 (13H, m), 1.4–1.1 (9H, m).

Ex.233 (d$^6$-DMSO) δ12.6 (1H, br s), 8.6 and 8.4 (1H, 2×t), 8.2 and 7.8 (1H, 2×t), 7.6 (1H,m), 7.3 (3H, m), 7.0 (4H, m), 5.0 and 4.7 (1H, 2×d), 4.55 (2H, d), 4.5–4.1 (2H, m), 3.9–3.5 (4H, m), 3.3–2.4 (4H, m), 1.9 (3H, s), 1.6 (6H, m), 1.3 (6H, m).

Ex.234 (d$^6$-DMSO) δ12.6 (1H, br s), 8.9 and 8.3 (1H, 2×m), 7.6 (1H, t), 7.3 (3H, m), 7.0 (5H, m), 5.1 and 4.6 (1H, 2×m), 4.5 (1H, s), 4.4 (1H, s), 4.3–3.6 (6H, m), 3.4–2.2 (4H, m), 1.9 (3H, s), 1.6–1.3 (12H, m).

Ex.235 (d$^6$-DMSO) δ12.7 (1H, br s), 9.0 (1H, m), 8.6–8.2 (3H, m), 7.7–6.9 (6H, m), 4.9–3.0 (9H, m), 2.8–2.2 (4H, m), 1.9 (3H, m), 1.6–1.3 (12H, m).

Ex.236 (d$^6$-DMSO) δ9.4 (1H, s), 8.4 (2H, s), 8.3 (1H, t), 8.1 (1H, s), 7.3 (3H, m), 7.1 (3H, m), 6.9 (2H, m), 4.6 (2H, s), 4.3 (1H, m), 3.5 (2H, m), 3.1 and 3.0 (2H, 2×d), 2.8 and 2.6 (2H, m), 2.1–1.2 (19H, m).

Ex.237 (d$^6$-DMSO) δ11.7 (1H, s), 10.2 (1H, s), 8.44 (2H, s), 8.4 (1H, t), 8.1 (1H, s), 7.3 (3H, m), 7.1 (3H, m), 6.9 (2H, m), 4.5 (2H, s), 4.0 (1H, m), 3.5 (2H, m), 3.1 and 3.0 (2H, 2×d), 2.8–2.5 (2H, m), 2.0–1.1 (19H, m).

Ex.238 (d$^6$-DMSO) δ8.1 and 8.0 (1H, 2×d), 7.3 (3H, m), 7.0 (5H, m), 7.0 and 6.3 (1H, 2×t), 4.5 (2H, m), 4.2–2.1 (12H, m), 2.0–1.1 (22H, m).

Ex.239a (d$^6$-DMSO) δ7.5 (2H, m), 7.3 (2H, m), 7.2 (4H, m), 4.8 (2H, s), 3.6 (2H, s)

Ex.239b (d$^7$-DMF) δ7.7 (1H, t), 7.4 (3H, m), 7.2 (3H,m), 7.1 (2H, m), 4.7 (1H, d), 4.6 (1H, d), 3.5 (1H, dd), 3.0 (1H, dd), 2.9 (1H, dd), 2.7 (1H, dd), 2.0 (3H, s), 1.7 (6H, m), 1.5 (6H, s)

Ex.239c (CDCl$_3$) δ9.0 (3H, d), 7.5 (10H, m), 5.5 (4H, s)

Ex.239d (CDCl$_3$) δ8.1 (1H, d), 7.5 (12H, m), 5.4 (4H, s), 3.8 (2H, bs)

Ex.239e (d$^6$-DMSO) δ10.5 (1H, s), 8.5 (2H, s), 8.2 (1H, s), 7.3 (15H, m), 5.4 (4H, s), 4.3 (1H, m), 2.9 (2H, m), 1.3 (9H,s)

Ex.239g (d$^6$-DMSO) δ9.8 (1H, s), 8.4 (2H, s), 8.1 (1H, s), 8.0 (1H, d), 7.1 (14H, m), 4.5 (2H, s), 4.2 (1H, s), 3.1 (2H, m), 2.8 (2H, m), 2.6 (1H, m), 2.2 (1H, m), 1.7 (3H, s), 1.5 (6H, m), 1.1 (6H, s)

Ex.240 (d$^6$-DMSO) δ9.9 (1H, s), 8.3(2H, s), 8.1 (1H, s), 7.1 (15H, m), 4.4 (3H, m), 3.1 (2H, m), 2.8 (2H, m),2.6 (1H, m), 2.2 (1H, m), 1.8 (3H, s), 1.5 (6H, m), 1.2 (6H, s)

Ex.241 (d$^6$-DMSO) δ9.8 (1H, s), 8.4 (2H, s), 8.1 (1H, s), 8.0 (1H, d), 7.1 (14H, m), 4.5 (2H, s), 4.2 (1H, s), 3.1 (2H, m), 2.8 (2H, m), 2.6 (1H, m), 2.2 (1H, m), 1.7 (3H, s), 1.5 (6H, m), 1.1 (6H, s)

Ex.242 (d$^6$-DMSO) δ9.9 (1H, s), 8.3 (2H, s), 8.1 (1H, s), 7.1 (15H, m), 4.4 (3H, m), 3.1 (2H, m), 2.8 (2H, m), 2.6 (1H, m), 2.2 (1H, m), 1.8 (3H, s), 1.5 (6H, m), 1.2 (6H, s)

Ex.243 (d$^6$-DMSO) δ10.1 and 9.8 (1H, 2×s), 8.4 (2H, d), 8.1 (1H, m), 7.7 and 7.4 (1H, 2×m), 7.1 (9H, m), 4.5 (2H, m), 4.2 (1H, m), 3.2 (2H, m), 2.9 (1H, m), 2.6 (1H, m), 2.2 (1H, m), 1.8–0.8 (28H, m)

Ex.244 (d$^6$-DMSO) δ9.8 (1H, s), 8.4 (2H, s), 8.1 (2H, s), 7.2 (12H, m), 4.4 (3H, m), 3.0 (4H, m), 2.6 (1H, m), 2.2 (1H, m), 1.7 (3H, s), 1.5 (6H, m), 1.1 (6H, s)

Ex.245 (d$^6$-DMSO) δ9.9 (1H, s), 8.3 (2H, s), 8.1 (1H, s), 7.1 (13H, m), 4.5 (3H, m), 3.1 (2H, m), 2.8 (2H, m), 2.6 (1H, m), 2.2 (1H, m), 1.8 (3H, s), 1.6 (6H, m), 1.2 (6H, m)

Ex.246 (d$^6$-DMSO) δ9.8 (1H, s), 8.4 (2H, s), 8.1 (1H, s), 8.0 (1H, d), 7.2 (13H, m), 4.5 (2H, m), 4.2 (1H, s), 3.1 (2H, m), 2.8 (2H, m), 2.6 (1H, m), 2.2 (1H, m), 1.7 (3H, s), 1.5 (6H, m), 1.1 (6H, s)

Ex.247 (d$^6$-DMSO) δ9.9 (1H, s), 8.3 (2H, s), 8.1 (1H, s), 7.1 (14H, m), 4.5 (3H, m), 3.1 (2H, m), 2.8 (3H, m), 2.4 (2H, m), 1.8 (3H, s), 1.5 (6H, m), 1.2 (6H, m)

Ex.248 (d$^6$-DMSO) δ9.8 (1H, s), 8.4 (2H, s), 8.1 (1H, s), 8.0 (1H, d), 7.2 (13H, m), 4.5 (2H, m), 4.2 (1H, m), 3.1 (2H, m), 3.1 (2H, m), 2.6 (1H, m), 2.2 (1H, m), 1.7 (3H, s), 1.5 (6H, m), 1.1 (6H, s)

Ex.249 (d$^6$-DMSO) δ9.9 (1H, s), 8.3 (2H, s), 8.1 (1H, s), 7.1 (14H, m), 4.5 (3H, m), 3.1 (1H, m), 2.9 (3H, m), 2.4 (2H, m), 1.8 (3H, s), 1.5 (6H, m), 1.2 (6H, m)

Ex.250 (d$^6$-DMSO) δ9.8 (1H, s), 8.4 (2H, s), 8.1 (1H, s), 7.9 (1H, d), 7.2 (13H, m), 4.4 (2H, m), 4.2 (1H, m), 3.7 (3H, s), 3.0 (4H, m), 2.6 (1H, m), 2.2 (1H, m), 1.7 (3H, s), 1.5 (6H, m), 1.1 (6H, s)

Ex.251 (d$^6$-DMSO) δ9.9 (1H, s), 8.3 (2H, s), 8.1 (1H, s), 7.1 (14H, m), 4.4 (3H, m), 3.7 (3H, s), 3.1 (2H, m), 2.4 (2H, m), 1.8 (3H, s), 1.6 (6H, m), 1.2 (6H, m)

Ex.252 (d$^6$-DMSO) δ13.2 (2H, br s), 9.9 (1H, s), 8.4 (2H, s), 8.1 (1H, s), 8.0 (1H, d), 7.9–6.8 (16H, m), 4.5 (2H, m), 4.0 (1H, s), 3.1 (2H, m), 2.8 (2H, m), 2.6 (1H, m), 2.2 (1H, m), 1.7 (3H, s), 1.5 (6H, m), 1.1 (6H, s)

Ex.253 (d$^6$-DMSO) δ13.1 (2H, br s), 9.9 (1H, s), 8.3 (2H, s), 8.1 (1H, s), 7.9–6.8 (17H, m), 4.5 (3H, m), 3.1 (1H, m), 2.8 (3H, m), 2.4 (2H, m), 1.8 (3H, s), 1.5 (6H, m), 1.2 (6H, m)

Ex.254 (d$^6$-DMSO) δ13.2 (2H, br s), 9.8 (1H, s), 8.4 (2H, s), 8.1 (1H, s), 8.0 (1H, d), 7.2 (13H, m), 4.5 (2H, m), 4.2 (1H, s), 3.1 (2H, m), 2.8 (2H, m), 2.6 (1H, m), 2.2 (1H, m), 1.7 (3H, s), 1.5 (6H, m), 1.1 (6H, s)

Ex.255 (d$^6$-DMSO) δ13.2 (2H, br s), 9.9 (1H, s), 8.3 (2H, s), 8.1 (1H, s), 7.1 (14H, m), 4.5 (3H, m), 3.1 (1H, m), 2.8 (3H, m), 2.4 (2H, m), 1.8 (3H, s), 1.5 (6H, m), 1.2 (6H, m)

Ex.256 (d⁶-DMSO) δ13.2 (2H, br s), 9.8 (1H, s), 8.4 (2H, s), 8.1 (1H, s), 8.0 (1H, d), 7.2 (13H, m), 4.5 (2H, m), 4.2 (1H, s), 3.1 (2H, m), 2.8 (2H, m), 2.6 (1H, m), 2.2 (1H, m), 1.7 (3H, s), 1.5 (6H, m), 1.1 (6H, s)

Ex.257 (d⁶-DMSO) δ13.2 (2H, br s), 9.9 (1H, s), 8.3 (2H, s), 8.1 (1H, s), 7.1 (14H, m), 4.5 (3H, m), 3.1 (1H, m), 2.8 (3H, m), 2.4 (2H, m), 1.8 (3H, s), 1.5 (6H, m), 1.2 (6H, m)

Ex.258 (d⁶-DMSO) δ13.2 (2H, br s), 11.1 and 9.8 (1H, 2×s), 8.2 (4H, m), 7.2 (13H, m), 4.5–4.2 (3H, m), 3.2–2.4 (6H, mm), 17–1.1 (15H, m)

Ex.259 (d⁶-DMSO) δ9.9 (1H, s), 8.3 (2H, s), 8.1 (1H, s), 7.1 (13H, m), 4.5 (3H, m), 3.1 (2H, m), 2.8 (2H, m), 2.6 (1H, m), 2.2 (1H, m), 1.8 (3H, s), 1.6 (6H, m), 1.2 (6H, m)

Ex.260 (CDCl₃) δ8.6 (1H, s), 7.6 (2H, d), 7.2 (16H, m), 5.8 (1H, m), 5.6 (1H, m), 4.8 (1H, s), 4.5 (1H, d), 4.2 (1H, d), 3.2 (3H, m), 3.0 (1H, dd), 2.6 (1H, m), 2.4 (1H, m), 1.9 (3H, s), 1.6 (6H, m), 1.2 (6H, s)

Ex.261 (CDCl₃) δ8.8 (1H, s), 7.3 (18H, m), 6.1 (1H, m), 6.0 (1H, m), 5.0 (1H, m), 4.4 (1H, d), 4.1 (1H, d), 3.7 (1H, dd), 3.2 (1H, m), 3.1–2.8 (3H, m), 2.4 (1H, m), 2.0 (3H, s), 1.7 (6H, m), 1.3 (6H, s)

Ex.262 (d⁶-DMSO) δ9.8 (1H, s), 9.2 (1H, br s), 8.4 (2H, s), 8.1 (1H, s), 8.0 (1H, d), 7.2 (11H, m), 6.6 (2H, d), 4.5 (1H, s), 4.4 (1H, m), 4.2 (1H, s), 3.1 (2H, m), 2.8 (2H, m), 2.6 (1H, m), 2.2 (1H, m), 1.7 (3H, s), 1.5 (6H, m), 1.1 (6H, s)

Ex.263 (d⁶-DMSO) δ9.8 (1H, s), 9.2 (1H, s), 8.3 (2H, s), 8.1 (1H, s), 7.1 (12H, m), 6.6 (2H, d), 4.4 (3H, m), 3.1 (1H, m), 2.8 (3H, m), 2.4 (2H, m), 1.8 (3H, s), 1.5 (6H, m), 1.2 (6H, m)

Ex.264 (d⁶-DMSO) δ9.8 (1H, s), 9.2 (1H, br s), 8.4 (2H, s), 8.1 (1H, s), 8.0 (1H, d), 7.2 (11H, m), 6.6 (2H, d), 4.5 (1H, s), 4.4 (1H, m), 4.2 (1H, s), 3.1 (2H, m), 2.8 (2H, m), 2.6 (1H, m), 2.2 (1H, m), 1.7 (3H, s), 1.5 (6H, m), 1.1 (6H, s)

Ex.265 (d⁶-DMSO) δ9.8 (1H, s), 9.2 (1H, br s), 8.4 (2H, s), 8.1 (1H, s), 8.0 (1H, d), 7.2 (11H, m), 6.6 (2H, d), 4.5 (1H, s), 4.4 (1H, m), 4.2 (1H, s), 3.1 (2H, m), 2.8 (2H, m), 2.6 (1H, m), 2.2 (1H, m), 1.7 (3H, s), 1.5 (6H, m), 1.1 (6H, s)

Ex.266 (d⁶-DMSO) δ9.8 (1H, s), 8.4 (2H, s), 8.1 (1H, d), 7.1 (14H, m), 4.5 (2H, m), 4.2 (1H, s), 3.1 (3H, m), 2.7 (3H, m), 1.4–0.7 (13H, m)

Ex.267 (d⁶-DMSO) δ9.9 (1H, s), 8.3 (2H, s), 8.1 (1H, s), 7.1 (15H, m), 4.5 (3H, m), 3.1 (4H, m), 2.6 (2H, m), 1.4–0.7 (13H, m)

Ex.268 (d⁶-DMSO) δ9.8 (1H, s), 8.4 (2H, s), 8.1 (1H, s), 8.0 (1H, d), 7.1 (14H, m), 4.5 (2H, m), 4.2 (1H, s), 3.1 (3H, m), 2.7 (3H, m), 1.4–0.7 (11H, m)

Ex.269 (d⁶-DMSO) δ9.9 (1H, s), 8.3 (2H, s), 8.1 (1H, s), 7.1 (15H, m), 4.5 (3H, m), 3.0 (4H, m), 2.6 (2H, m), 1.6–0.6 (11H, m)

Ex.270 (d⁶-DMSO) δ13.1 (2H, br s), 9.8 (1H, s), 8.4 (2H, s), 8.3–6.8 (23H, m), 4.7–4.2 (3H, m), 3.2 (4H, m), 2.7 (2H, m)

Ex.271 (d⁶-DMSO) δ13.2 (2H, br s), 10.0 (1H, s), 8.3 (2H, s), 8.2–6.8 (23H, m), 4.5 (3H, m), 3.2 (3H, m), 2.7 (3H, m)

Ex.272 (d⁶-DMSO) δ9.6 (1H, s), 8.4–6.8 (21H, m), 4.7–4.1 (3H, m), 3.2 (4H, m), 2.8 (2H, m)

Ex.273 (d⁶-DMSO) δ9.8 (1H, s), 8.3–6.7 (21H, m), 4.5–4.1 (3H, m), 3.2 (4H, m), 2.9 (2H, m)

Ex.274 (d⁶-DMSO) δ13.1 (2H, br s), 10.1–9.7 (1H, (1H, 333 s), 8.4–7.0 (18H, m), 4.5–4.1 (3H, m), 3.1 (2H, m), 2.8 (2H, m), 2.6 (2H, m), 2.0 (2H, m), 1.7 (3H, s), 1.5 (6H, m), 1.1 (6H, )

Ex.275 (d⁶-DMSO) δ13.1 (2H, br s), 10.1–9.7 (1H, 3×s), 8.4–7.0 (18H, m), 4.5–4.1 (3H, m), 3.1 (2H, m), 2.8 (2H, m), 2.6 (2H, m) 2.0 (2H, m), 1.7 (3H, s), 1.5 (6H, m), 1.1 (6H, m)

Ex.276 (d⁶-DMSO) δ13.2 (2H, br s), 11.0 and 10.9 (1H, 2×s), 9.9 and 9.7 (1H, 2×s), 8.4–6.8 (15H, m), 6.5 and 6.3 (1H, 2×t), 4.5–4.1 (3H, m), 3.2 (5H, m), 2.8 (2H, m), 2.6 (1H, m), 2.2 (1H, m), 1.7 (3H, m), 1.5 (6H, m), 1.1 (6H, m)

Ex.277 (d⁶-DMSO) δ10.5 and 10.3 (1H, 2×s), 8.4–8.0 (3H, m), 7.2 (13H, m), 5.3 (1H, d), 4.5 (2H, m), 3.1 (2H, m), 2.5 (2H, m), 1.8 (3H, m), 1.5 (6H, m), 1.2 (6H, m)

Ex.278 (d⁶-DMSO) δ9.7 (1H, s), 8.2 (1H, s), 8.0 (1H, m), 7.8–6.9 (17H, m), 4.5 (1H, s), 4.4 (1H, s), 3.5–3.2 (2H, m), 2.9 (2H, m), 2.6 (1H, m), 2.3 (1H, m), 1.7 (3H, s), 1.5 (6H, m), 1.4 (6H, s)

Ex.279 (d⁶-DMSO) δ12.9 (1H, s), 9.7 (1H, s), 8.2 (1H, s), 7.6 (2H, t), 7.4–7.2 (11H, m), 7.1 (2H, m), 7.0 (2H, q), 6.8 (1H, t), 4.5 (3H, m), 3.2 (1H, dd), 3.0 (2H, m), 2.9 (1H, dd), 2.6 (1H, dd), 2.4 (1H, dd), 1.8 (3H, s), 1.6 (6H, m), 1.3 (6H, s)

Ex.280 (d⁶-DMSO) δ9.2–7.7 (5H, m), 7.3 (13H, m), 7.0 and 6.8 (1H, 2×t), 5.0–4.2 (3H, m), 3.8 (3H, m), 3.4–2.5 (6H, m) 1.9 (3H, m), 1.5 (6H, m), 1.1 (6H, m)

Ex.281 (d⁶-DMSO) δ13.0 (2H, br s), 9.8 (1H, d), 8.0 (1H, d), 7.9–6.8 (17H, m), 4.5–4.2 (3H, m), 3.1 (2H, m), 2.8 (2H, m), 2.6 (1H, m), 2.3 (1H, m), 1.8 (3H, m), 1.5 (6H, m), 1.1 (6H, m)

Ex.282 (d⁶-DMSO) δ9.8 (1H, m), 8.4–8.0 (3H, m), 7.1 (14H, m), 4.5 (3H, m), 3.0 (4H, m), 2.6 (1H, m), 2.2 (1H, m), 1.8 (3H, m), 1.5 (6H, m), 1.1 (6H, s)

Ex.283 (d⁶-DMSO) δ13.7 (1H, br s), 8.5 (2H, m), 8.2–7.9 (2H, m), 7.6–6.4 (16H, m), 4.5 (1H, m), 4.4 (1H, m), 4.2 (1H, s), 3.5–3.2 (2H, m), 2.9 (2H, m), 2.6 (1H, m), 2.3 (1H, m), 1.7 (3H, m), 1.5 (6H, m), 1.0 (6H, m)

Ex.284 (d⁶-DMSO) δ12.9 (1H, br s), 9.7 (1H, s), 8.2 (1H, s), 7.6–7.0 (17H, m), 6.8 (1H, t), 4.5 (3H, m), 3.2 (1H, m), 3.0 (2H, m), 2.9 (1H, m), 2.4 (1H, m), 1.8 (3H, m), 1.5 (6H, m), 1.3 (6H, m)

Ex.285 (d⁶-DMSO) δ9.8 (1H, s), 8.0 (1H, s), 7.9 (1H, d), 7.8–6.9 (17H, m), 4.5 (2H, m), 4.2 (1H, m), 3.4–3.1 (2H, m), 2.8 (1H, d), 2.7–2.3 (3H, m), 1.9 (3H, m), 1.5 (6H, m), 1.2 (6H, m)

Ex.286 (d⁶-DMSO) δ9.8 (1H, s), 8.4 (2H, s), 8.1 (1H, s), 8.0 (1H, d), 7.1 (14H, m), 4.5 (2H, s), 4.2 (1H, s), 3.9 (6H, s), 3.1 (2H, m), 2.8 (2H, m), 2.6 (1H, m), 2.2 (1H, m), 1.7 (3H, s), 1.5 (6H, m), 1.1 (6H, s)

Ex.287 (CDCl₃) δ9.2 and 9.1 (1H, 2×s), 8.4–8.0 (4H, m), 7.1 (14H, m), 4.8 (1H, m), 4.5 (3H, m), 3.6–2.6 2.6 (4H, m), 1.7 (3H, m), 1.5 (6H, m), 1.1 (6H, m), 0.7 (6H, m)

Ex.288 (d⁶-DMSO) δ10.5 (1H, s), 9.9 (1H, s), 8.5 (2H, s), 8.1 (1H, s), 7.9 (1H, d), 7.7 (1H, br t), 7.4–6.7 (18H, m), 4.6 (1H, m), 4.4 (1H, s), 4.1 (1H, s), 3.3 (2H, m), 3.0 (2H, m), 2.9–2.7 (2H, m), 2.6 (2H, m)

Ex.289 (d⁶-DMSO) δ13.2 (2H, br s), 10.8 (1H, s), 10.0 (1H, s), 8.3 (2H, d), 8.1 (1H, d), 7.6 (1H, br t), 7.5–6.8 (19H, m), 4.5 (1H, m), 4.45 (1H, d), 4.37 (1H, d), 3.3–2.8 (6H, m), 2.7 (2H, m)

Ex.290 (d⁶-DMSO) δ9.9 (1H, s), 8.5 (2H, s), 8.2 (1H, br s), 8.1 (1H, s), 7.4–6.7 (17H, m), 4.5 (2H, m), 4.2 (3H, m), 3.0 (4H, m)

Ex.291 (d⁶-DMSO) δ13.2 (2H, br s), 10.0 (1H, br s), 8.5 (2H, s), 8.2 (1H, br s), 8.1 (1H, s), 7.7 (1H, br s), 7.5–6.8 (18H, m), 4.5 (3H, m), 3.0 (6H, m), 2.5 (2H, m)

Ex.292 (d⁶-DMSO) δ13.2 (2H, br s), 10.0 (1H, 2×s), 8.3 (2H, s), 8.1 (1H, br s), 8.0 (1H, d), 7.5–6.8 (19H, m), 4.5 (3H, m), 3.0 (6H, m), 2.0 (2H, m), 1.5 (2H, t)

Ex.293 (d⁶-DMSO) δ13.2 (1H, br s), 9.7 (1H, s), 8.2 (1H, s), 8.0 (1H, br s), 7.8 (1H, d), 7.6 (1H, d), 7.4–6.9 (13H, m), 4.5 (3H, m), 3.0 (4H, m), 2.4 (2H, m), 1.8 (3H, d), 1.5 (6H, m), 1.2 (6H, m)

Ex.294 (d⁶-DMSO) δ13.0 (1H, br s), 9.7 (1H, s), 8.2 (1H, s), 7.6 (2H, s), 7.4–6.8 (14H, m), 4.5 (3H, m), 3.0 (4H, m), 2.4 (2H, m), 1.8 (3H, s), 1.5 (6H, q), 1.2 (6H, s)

Ex.295 (d⁶-DMSO) δ13.0 (1H, br s), 9.7 (1H, s), 8.3 (1H, s), 8.2 (1H, br s), 8.0–6.9 (22H, m), 4.7–4.2 (5H, m), 3.0 (4H, m)

Ex.296 (d⁶-DMSO) δ13.0 (1H, br s), 9.8 (1H, s), 8.2 (2H, br s), 8.0–6.9 (22H, m), 4.7–4.2 (5H, m), 3.0 (4H, m)

Ex.297 (d⁶-DMSO) δ12.8 (1H, br s), 9.8 (1H, s), 8.3 (1H, br s), 8.2 (1H, s), 8.0–6.9 (24H, m), 4.7–4.2 (5H, m), 3.0 (4H, m)

Ex.298 (d⁶-DMSO) δ12.8 (1H, br s), 9.8 (1H, s), 8.4 (1H, br s), 8.3 (1H, s), 8.0–6.9 (24H, m), 4.7–4.2 (5H, m), 3.0 (4H, m)

Ex.299 (d⁶-DMSO) δ8.3 (2H, m), 8.0 (2H, s), 7.8 (1H, d), 7.4 (1H, t), 7.3–6.9 (13H, m), 4.5 (1H, s), 4.3 (3H, m), 4.1 (1H, s), 3.2–2.4 (6H, m), 1.8 (3H, m), 1.5 (6H, m), 1.2 (6H, m)

Ex.300 (d⁶-DMSO) δ8.3 (2H, m), 8.0 (2H, s), 7.4–7.0 (12H, t), 6.9 (3H, m), 4.4 (2H, 2×s), 4.3 (1H, m), 4.2 (2H, m), 3.2–2.4 (6H, m), 1.8 (3H, m), 1.6 (6H, m), 1.2 (6H, m)

Ex.301 (d⁶-DMSO) δ13.2 (2H, br s), 9.8 (1H, s), 8.4 (2H, s), 8.3 (1H, m), 8.1 (2H, m), 7.7 (3H, m), 7.5 (1H, s), 7.3 (9H, m), 7.2 (2H, m), 7.1 (2H, m), 6.9 (3H, s), 4.6 (1H, s), 4.55 (1H, m), 4.4 (1H, m), 4.3 (1H, s), 4.1 (1H, m), 3.2 (2H, m), 2.9 (1H, m), 2.8 (1H, m)

Ex.302 (d⁶-DMSO) δ13.2 (2H, br s), 9.9 (1H, s), 8.4 (2H, s), 8.3 (1H, m), 8.1 (2H, m), 7.7 (3H, m), 7.5 (1H, s), 7.3 (9H, m), 7.2 (2H, m), 7.1 (2H, m), 6.9 (3H, s), 4.6 (1H, s), 4.55 (1H, m), 4.4 (1H, m), 4.3 (1H, s), 4.1 (1H, m), 3.2 (2H, m), 2.9 (1H, m), 2.8 (1H, m)

The compounds of the examples were tested for binding at the CCK$_B$ receptor in mouse cortical membranes by means of a radioligand binding assay. The procedure was as follows:

The whole brains from male mice (CD1 22–25 g; Charles River) were removed and placed in ice-cold buffer (pH 7.2@21°±3° C.) of the following composition (mM); 10 HEPES, 130 NaCl, 4.7 KCl, 5 MgCl$_2$, 1 EDTA and containing 0.25 g.l$^{-1}$ bacitracin. The cortex was dissected, weighed and homogenised in 40 ml ice-cold buffer using a Teflon-in-glass homogeniser. The homogenate was centrifuged at 39,800 g for 20 min at 4° C., the supernatant discarded and the pellet resuspended by homogenisation in fresh buffer. The homogenate was recentrifuged (39,800 g; 20 min @4° C.) and the final pellet was resuspended in HEPES buffer to give a tissue concentration of 2 mg.ml$^{-1}$ (original wet weight).

The membranes (400 ml) were incubated for 150 min at 21°±3° C. in a final volume of 0.5 ml with HEPES buffer containing [$^{125}$I]-CCK8S (0.05 ml; 200 pM NEN 2200 Ci.mmol$^{-1}$) and competing compound. Total and non-specific binding of [$^{125}$I]-CCK8S were defined using 0.05 ml of buffer and 0.05 ml of 10 mM L-365,260, respectively. The assay was terminated by rapid filtration through pre-soaked Whatman GF/B filters using a Brandell Cell harvester. The filters were washed (3×3 ml) with ice-cold 50 mM Tris-HCl (pH 7.4 @4° C.) and bound radioactivity determined by counting (1 min.) in a gamma-counter.

The results obtained from the CCK$_B$ assays are set out in Table 1.

TABLE 1

| Example | CCK$_B$ pK$_i$ | Example | CCK$_B$ pK$_i$ |
|---|---|---|---|
| 1 | 5.0 | 32 | 5.5 |
| 2 | 5.1 | 33 | 6.0 |
| 3 | 4.8 | 34 | 6.6 |
| 4 | 5.6 | 35 | 5.1 |
| 5 | 5.3 | 36 | 6.1 |
| 6 | 5.3 | 37 | 6.6 |
| 7 | 4.8 | 38 | 6.0 |
| 8 | 5.2 | 39 | 5.8 |
| 9 | 5.0 | 40 | 6.0 |
| 10 | 4.8 | 42 | 6.8 |
| 11 | 5.0 | 43 | 6.2 |
| 12 | 6.2 | 44 | 5.3 |
| 13 | 6.0 | 45 | 5.2 |
| 14 | 6.3 | 46 | 6.1 |
| 15 | 5.8 | 47 | 6.3 |
| 16 | 5.7 | 48 | 6.0 |
| 17 | 5.7 | 49 | 5.9 |
| 19 | 4.5 | 50 | 6.6 |
| 20 | 5.5 | 51 | 7.2 |
| 21 | 5.2 | 52 | 6.6 |
| 23 | 5.5 | 53 | 6.5 |
| 24 | 5.9 | 54 | 6.1 |
| 25 | 6.7 | 55 | 6.1 |
| 26 | 5.5 | 56 | 6.6 |
| 27 | 6.9 | 57 | 6.7 |
| 28 | 5.9 | 58 | 6.6 |
| 29 | 5.9 | 59 | 5.6 |
| 30 | 5.7 | 60 | 6.4 |
| 31 | 5.5 | 61 | 5.9 |
| 62 | 5.6 | 94 | 5.2 |
| 63 | 5.9 | 95 | 5.5 |
| 64 | 5.3 | 96 | 6.7 |
| 65 | 6.5 | 97 | 5.9 |
| 66 | 6.2 | 98 | 6.7 |
| 67 | 5.6 | 99 | 5.5 |
| 68 | 5.9 | 100 | 6.2 |
| 69 | 6.2 | 101 | 5.6 |
| 70 | 5.0 | 102 | 5.6 |
| 71 | 5.8 | 103 | 5.2 |
| 72 | 5.8 | 104 | 4.9 |
| 73 | 5.3 | 105 | 6.2 |
| 74 | 7.3 | 106 | 4.5 |
| 75 | 5.9 | 107 | 4.2 |
| 76 | 5.7 | 108 | 4.7 |
| 77 | 6.5 | 110 | 4.9 |
| 78 | 6.2 | 111 | 7.0 |
| 79 | 5.5 | 112 | 5.7 |
| 80 | 5.8 | 113 | 5.6 |
| 81 | 7.3 | 114 | 5.3 |
| 82 | 5.1 | 115 | 6.0 |
| 83 | 5.1 | 116 | 5.7 |
| 84 | 5.2 | 117 | 5.3 |
| 85 | 5.8 | 118 | 6.1 |
| 86 | 6.2 | 119 | 6.7 |
| 87 | 5.3 | 120 | 7.0 |
| 88 | 5.3 | 121 | 4.8 |
| 89 | 6.1 | 122 | 6.2 |
| 92 | 5.6 | 123 | 5.8 |
| 93 | 5.3 | 124 | 5.8 |
| 125 | 5.5 | 156 | 7.3 |
| 126 | 5.4 | 157 | 6.7 |
| 127 | 5.3 | 158 | 5.7 |
| 128 | 5.8 | 159 | 4.6 |
| 129 | 6.5 | 160 | 6.4 |
| 130 | 6.3 | 161 | 6.2 |
| 131 | 7.4 | 162 | 5.6 |
| 132 | 6.5 | 163 | 5.0 |
| 133 | 6.1 | 164 | 6.3 |
| 134 | 5.9 | 165 | 6.0 |
| 135 | 6.3 | 166 | 6.0 |
| 136 | 6.3 | 167 | 5.0 |
| 137 | 5.8 | 168 | 5.1 |
| 138 | 4.6 | 169 | 5.1 |
| 139 | 5.3 | 170 | 5.4 |
| 140 | 5.0 | 171 | 6.7 |
| 141 | 5.8 | 172 | 5.8 |
| 142 | 5.9 | 173 | 6.1 |
| 143 | 7.2 | 174 | 6.1 |
| 144 | 6.2 | 175 | 6.1 |
| 145 | 6.2 | 176 | 5.2 |

TABLE 1-continued

| Example | CCK$_B$ pK$_i$ | Example | CCK$_B$ pK$_i$ |
|---|---|---|---|
| 147 | 6.3 | 177 | 5.5 |
| 148 | 5.2 | 178 | 5.3 |
| 149 | 6.1 | 179 | 5.2 |
| 150 | 5.4 | 180 | 6.3 |
| 151 | 6.6 | 181 | 5.5 |
| 152 | 6.0 | 182 | 5.5 |
| 153 | 6.2 | 183 | 6.3 |
| 154 | 6.5 | 184 | 6.2 |
| 155 | 6.5 | 185 | 6.8 |
| 186 | 7.1 | 216 | 6.3 |
| 187 | 6.2 | 217 | 6.3 |
| 188 | 6.2 | 218 | 6.4 |
| 189 | 5.7 | 219 | 6.2 |
| 190 | 5.8 | 220 | 7.0 |
| 191 | 5.2 | 227 | 5.0 |
| 192 | 5.3 | 228 | 5.4 |
| 193 | 5.5 | 229 | 5.5 |
| 194 | 5.8 | 230 | 5.3 |
| 195 | 6.1 | 233 | 6.5 |
| 196 | 6.2 | 234 | 6.5 |
| 197 | 4.5 | 236 | 6.7 |
| 198 | 5.1 | 237 | 6.7 |
| 199 | 6.1 | 238 | 7.6 |
| 200 | 5.0 | 239 | 8.8 |
| 201 | 6.5 | 240 | 7.8 |
| 202 | 5.2 | 241 | 8.0 |
| 203 | 5.9 | 242 | 7.8 |
| 204 | 6.0 | 243 | 7.6 |
| 205 | 6.7 | 244 | 8.6 |
| 206 | 6.9 | 245 | 7.3 |
| 207 | 5.5 | 246 | 7.9 |
| 208 | 6.2 | 247 | 7.3 |
| 209 | 6.5 | 248 | 8.0 |
| 210 | 5.2 | 249 | 6.6 |
| 211 | 5.8 | 250 | 7.0 |
| 212 | 6.1 | 251 | 6.3 |
| 213 | 5.8 | 252 | 6.5 |
| 214 | 5.7 | 253 | 6.7 |
| 215 | 6.1 | 254 | 8.5 |
| 255 | 8.2 | 280 | 7.5 |
| 256 | 8.5 | 281 | 7.0 |
| 257 | 8.0 | 282 | 6.5 |
| 258 | 8.0 | 283 | 6.7 |
| 259 | 7.3 | 284 | 6.8 |
| 260 | 5.4 | 285 | 6.9 |
| 261 | 5.4 | 286 | 5.0 |
| 262 | 8.8 | 287 | 7.2 |
| 265 | 7.8 | 288 | 7.8 |
| 266 | 8.4 | 289 | 7.1 |
| 267 | 7.4 | 290 | 7.3 |
| 268 | 7.7 | 291 | 8.4 |
| 269 | 6.7 | 292 | 7.5 |
| 270 | 8.0 | 293 | 8.2 |
| 271 | 6.5 | 294 | 7.6 |
| 272 | 7.4 | 295 | 7.2 |
| 273 | 6.8 | 296 | 6.3 |
| 274 | 7.2 | 297 | 7.2 |
| 275 | 7.0 | 298 | 6.4 |
| 276 | 7.3 | 299 | 7.5 |
| 277 | 6.3 | 300 | 7.4 |
| 278 | 7.8 | 301 | 8.6 |
| 279 | 6.8 | 302 | 8.3 |

The compounds of the examples were also tested for gastrin antagonist activity in an immature rat stomach assay. The procedure was as follows: The oesophagus of immature rats (33–50 g, ca. 21 days old) was ligated at the level of the cardiac sphincter and the duodenal sphincter was cannulated. The stomach was excised and flushed with ca. 1 ml of unbuffered physiological saline solution. The fundus was punctured and cannulated. A further 4–5 ml of unbuffered solution was flushed through the stomach to ensure the preparation was not leaking. The stomach was lowered into a jacketed organ bath containing 40 ml of buffered solution containing $3\times10^{-8}$M 5-methylfurmethide, maintained at 37° and gassed vigorously with 95% $O_2$/5% $Co_2$. The stomach was continuously perfused at a rate of 1 ml min$^{-1}$ with unbuffered solution gassed with 100% $O_2$ with the perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et.al., Br. J. Pharmacol., 1985, 86, 581.

The results obtained from the gastrin assays are set out in Table 2.

TABLE 2

| Example | Gastrin pK$_B$ | Example | Gastrin pK$_B$ |
|---|---|---|---|
| 12 | 4.8 | 78 | 6.9 |
| 13 | 5.8 | 79 | 5.6 |
| 14 | 5.9 | 81 | 5.9 |
| 15 | 5.7 | 83 | 5.4 |
| 16 | 5.6 | 84 | 5.6 |
| 22 | 5.2 | 85 | 6.2 |
| 23 | 5.2 | 90 | 4.6 |
| 24 | 5.7 | 91 | 4.6 |
| 25 | 6.7 | 94 | 4.9 |
| 27 | 6.5 | 99 | 5.6 |
| 28 | 6.0 | 103 | 5.9 |
| 29 | 5.8 | 109 | 5.6 |
| 35 | 5.7 | 112 | 6.2 |
| 36 | 5.5 | 113 | 4.9 |
| 39 | 4.7 | 119 | 6.9 |
| 41 | 5.5 | 120 | 6.9 |
| 48 | 6.6 | 122 | 6.7 |
| 49 | 5.8 | 123 | 7.2 |
| 50 | 6.1 | 124 | 6.5 |
| 51 | 5.6 | 129 | 6.7 |
| 56 | 5.2 | 131 | 6.0 |
| 62 | 5.3 | 132 | 5.7 |
| 64 | 5.2 | 133 | 6.9 |
| 65 | 5.4 | 136 | 6.0 |
| 67 | 5.1 | 142 | 6.1 |
| 68 | 6.5 | 143 | 6.9 |
| 69 | 7.1 | 144 | 5.6 |
| 70 | 5.7 | 145 | 6.3 |
| 71 | 5.7 | 147 | 6.9 |
| 73 | 5.8 | 149 | 6.2 |
| 151 | 5.9 | 206 | 6.0 |
| 156 | 5.7 | 209 | 5.7 |
| 158 | 6.4 | 210 | 5.1 |
| 160 | 7.0 | 211 | 6.0 |
| 161 | 6.6 | 213 | 6.1 |
| 162 | 6.1 | 214 | 6.6 |
| 164 | 6.6 | 215 | 5.5 |
| 165 | 5.9 | 220 | 7.3 |
| 166 | 5.7 | 227 | 6.2 |
| 167 | 5.5 | 228 | 5.8 |
| 171 | 6.5 | 229 | 6.4 |
| 172 | 5.4 | 230 | 5.8 |
| 173 | 5.8 | 233 | 6.4 |
| 180 | 6.2 | 234 | 5.5 |
| 181 | 5.7 | 236 | 6.9 |
| 183 | 6.5 | 237 | 6.8 |
| 184 | 6.6 | 239 | 8.8 |
| 185 | 7.1 | 240 | 7.8 |
| 186 | 7.3 | 241 | 8.0 |
| 187 | 6.9 | 242 | 7.8 |
| 188 | 7.3 | 243 | 7.6 |
| 189 | 6.9 | 244 | 8.6 |
| 195 | 6.9 | 245 | 7.3 |
| 196 | 7.0 | 246 | 7.9 |
| 198 | 5.2 | 247 | 7.3 |
| 199 | 6.3 | 248 | 8.0 |
| 201 | 7.0 | 249 | 6.6 |
| 203 | 6.4 | 250 | 7.0 |
| 204 | 6.1 | 251 | 6.3 |
| 205 | 6.2 | 252 | 6.5 |
| 253 | 5.8 | 273 | 6.0 |

TABLE 2-continued

| Example | Gastrin pK$_B$ | Example | Gastrin pK$_B$ |
|---|---|---|---|
| 254 | 8.6 | 274 | 7.5 |
| 255 | 8.0 | 275 | 7.2 |
| 256 | 8.4 | 276 | 7.1 |
| 257 | 7.6 | 277 | 6.4 |
| 258 | 8.2 | 278 | 5.7 |
| 259 | 7.2 | 279 | 5.7 |
| 261 | 6.6 | 280 | 5.8 |
| 262 | 8.9 | 281 | 6.1 |
| 263 | 7.2 | 282 | 6.9 |
| 264 | 6.8 | 284 | 5.7 |
| 265 | 8.1 | 287 | 8.0 |
| 266 | 8.4 | 291 | 7.1 |
| 267 | 7.0 | 299 | 7.4 |
| 268 | 7.3 | 300 | 7.2 |
| 269 | 6.6 | 301 | 7.4 |
| 270 | 7.6 | 302 | 6.5 |
| 272 | 6.5 | | |

The compounds of the examples were also tested in a CCK$_A$ binding assay as follows:

The pancreatata were removed from male guinea-pigs (200–300 g; Dunkin Hartley) and placed in ice-cold HEPES buffer (pH 7.2 @21±3°). The pancreatata were homogenised in 40 ml ice-cold HEPES buffer using a polytron (Brinkmann, PT10, setting 10) 4×1 second. The homogenate was centrifuged at 39,800 g for 15 min at 4°. The supernatant was discarded and the pellet re-suspended using a Teflon-in-glass homogeniser in 20 volumes of fresh buffer and re-centrifuged as above. The final pellet was re-suspended using a Teflon-in-glass homogeniser to a tissue concentration of 1 mg.ml$^{-1}$ (original wet weight), and filtered through 500 μm pore-size Nytex mesh.

The membranes (400 μl; containing 0.375 μM PD134, 308) are incubated for 150 minutes at 21±3° in a final volume of 0.5 ml with HEPES buffer containing [$^{125}$I]-CCK$_8$(S) (50 μl; 200 pM) and competing compound. Total and non-specific binding of [$^{125}$I]-CCK$_8$(S) are defined using 50 μl of buffer and 50 μl of 100 nM L-364,718 respectively. The assay is terminated by rapid filtration through pre-soaked Whatman GF/B filters using a Brandell Cell Harvester. The filters were washed (3×3 ml) with ice-cold 50 mM Tris HCl (pH 7.4 at 4°) and bound radioactivity is determined by counting (1 min) in a gamma counter.

The results are set out in Table 3.

TABLE 3

| Example | CCK$_A$ pK$_i$ | Example | CCK$_A$ pK$_i$ |
|---|---|---|---|
| 3 | 5.3 | 52 | 6.0 |
| 6 | 4.8 | 53 | 5.3 |
| 7 | 5.4 | 54 | 5.9 |
| 8 | 5.3 | 55 | 6.6 |
| 9 | 5.1 | 57 | 6.7 |
| 11 | 4.9 | 58 | 6.4 |
| 12 | 5.7 | 60 | 5.2 |
| 13 | 5.5 | 61 | 5.3 |
| 14 | 5.1 | 62 | 4.8 |
| 15 | 4.7 | 63 | 5.1 |
| 22 | 5.3 | 64 | 5.1 |
| 24 | 5.2 | 65 | 5.9 |
| 27 | 5.4 | 66 | 5.4 |
| 28 | 5.0 | 67 | 5.0 |
| 30 | 4.6 | 69 | 5.1 |
| 32 | 4.7 | 70 | 4.8 |
| 33 | 4.9 | 71 | 4.9 |
| 34 | 5.5 | 73 | 5.4 |
| 35 | 4.9 | 74 | 4.9 |
| 36 | 5.5 | 75 | 5.4 |
| 37 | 5.1 | 76 | 5.3 |
| 38 | 5.2 | 77 | 5.2 |
| 39 | 4.9 | 78 | 5.1 |
| 40 | 5.1 | 79 | 5.1 |
| 41 | 4.8 | 80 | 4.8 |
| 42 | 4.8 | 81 | 5.3 |
| 44 | 5.1 | 82 | 5.3 |
| 45 | 5.3 | 83 | 4.9 |
| 48 | 5.1 | 84 | 4.9 |
| 49 | 4.9 | 85 | 5.0 |
| 51 | 5.5 | 86 | 5.6 |
| 87 | 5.0 | 122 | 5.1 |
| 88 | 4.9 | 123 | 5.6 |
| 89 | 5.3 | 124 | 5.3 |
| 90 | 4.8 | 125 | 4.9 |
| 91 | 4.7 | 126 | 5.3 |
| 92 | 5.8 | 127 | 4.8 |
| 93 | 5.8 | 128 | 5.1 |
| 94 | 5.2 | 129 | 4.9 |
| 95 | 5.1 | 130 | 5.0 |
| 96 | 5.5 | 131 | 5.0 |
| 97 | 5.1 | 132 | 5.0 |
| 98 | 5.2 | 133 | 5.2 |
| 99 | 5.0 | 134 | 5.4 |
| 100 | 5.3 | 135 | 5.1 |
| 101 | 4.9 | 137 | 5.2 |
| 102 | 5.3 | 138 | 5.2 |
| 103 | 5.2 | 139 | 5.2 |
| 104 | 5.2 | 140 | 5.2 |
| 105 | 5.3 | 141 | 4.8 |
| 107 | 4.5 | 142 | 5.4 |
| 108 | 5.5 | 143 | 5.3 |
| 111 | 5.6 | 144 | 5.6 |
| 112 | 5.9 | 145 | 5.2 |
| 113 | 5.4 | 146 | 4.9 |
| 114 | 5.5 | 147 | 5.3 |
| 115 | 5.3 | 148 | 5.7 |
| 117 | 5.7 | 149 | 5.2 |
| 118 | 5.6 | 150 | 5.1 |
| 119 | 4.8 | 151 | 5.5 |
| 120 | 5.4 | 152 | 5.5 |
| 121 | 5.0 | 153 | 5.5 |
| 154 | 5.5 | 186 | 4.6 |
| 155 | 5.2 | 187 | 5.2 |
| 156 | 5.3 | 189 | 5.9 |
| 157 | 5.7 | 190 | 4.9 |
| 158 | 5.1 | 191 | 5.1 |
| 159 | 5.7 | 192 | 5.0 |
| 160 | 5.1 | 193 | 5.2 |
| 162 | 5.6 | 194 | 5.1 |
| 163 | 5.9 | 195 | 5.9 |
| 164 | 4.4 | 196 | 5.9 |
| 165 | 5.3 | 197 | 5.7 |
| 166 | 5.2 | 199 | 5.9 |
| 167 | 5.0 | 200 | 5.5 |
| 168 | 4.8 | 201 | 5.1 |
| 169 | 5.7 | 202 | 4.9 |
| 170 | 5.2 | 203 | 5.2 |
| 171 | 5.8 | 205 | 5.3 |
| 172 | 5.6 | 206 | 5.7 |
| 173 | 5.4 | 207 | 6.6 |
| 174 | 6.2 | 208 | 5.7 |
| 175 | 5.3 | 209 | 5.3 |
| 176 | 4.7 | 210 | 5.1 |
| 177 | 5.8 | 212 | 5.1 |
| 178 | 4.9 | 213 | 5.1 |
| 179 | 5.0 | 214 | 5.5 |
| 180 | 4.4 | 215 | 4.5 |
| 181 | 4.9 | 219 | 5.6 |
| 182 | 5.3 | 220 | 6.3 |
| 183 | 5.1 | 227 | 6.3 |
| 184 | 5.1 | 228 | 5.4 |
| 185 | 4.9 | 229 | 5.5 |
| 239 | 5.7 | 271 | 5.9 |
| 240 | 6.3 | 272 | 6.6 |
| 241 | 5.6 | 273 | 5.9 |
| 242 | 5.9 | 274 | 5.7 |

TABLE 3-continued

| Example | CCK$_A$ pK$_i$ | Example | CCK$_A$ pK$_i$ |
| --- | --- | --- | --- |
| 243 | 6.0 | 275 | 5.7 |
| 244 | 5.7 | 276 | 6.5 |
| 245 | 6.3 | 277 | 5.6 |
| 246 | 6.0 | 278 | 6.0 |
| 247 | 6.4 | 279 | 6.0 |
| 248 | 6.1 | 280 | 5.7 |
| 249 | 7.3 | 281 | 5.9 |
| 250 | 5.8 | 283 | 5.9 |
| 251 | 5.7 | 287 | 5.6 |
| 252 | 6.1 | 288 | 6.4 |
| 253 | 7.0 | 289 | 5.8 |
| 254 | 6.0 | 290 | 6.8 |
| 255 | 6.1 | 291 | 5.5 |
| 256 | 6.5 | 292 | 5.8 |
| 257 | 6.4 | 293 | 6.1 |
| 258 | 5.7 | 294 | 6.0 |
| 259 | 5.9 | 299 | 5.6 |
| 260 | 5.9 | 300 | 5.6 |
| 268 | 5.4 | 301 | 5.8 |
| 269 | 5.9 | 302 | 5.8 |
| 270 | 6.3 | | |

We claim:

1. A compound of the formula

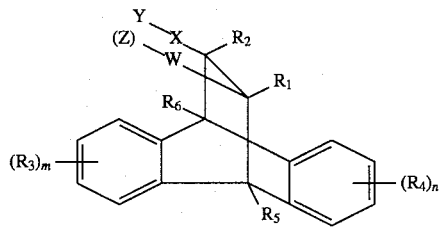

wherein

W is a carbonyl, sulphonyl or sulphinyl group, or, W is H when Z is absent and X is a carbonyl, sulphonyl or sulphinyl group or —C(O)—CH$_2$— (in which the carbonyl group is bonded to Y), provided that at least one of W and X contains carbonyl, Y is R$_7$—O— or R$_7$—N(R$_8$)— (wherein R$_7$ is H or C$_1$ to C$_{15}$ hydrocarbyl, up to two carbon atoms of the hydrocarbyl moiety optionally being replaced by a nitrogen, oxygen or sulphur atom provided that Y does not contain a —O—O— group, and R$_8$ is H, C$_1$ to C$_3$ alkyl, carboxymethyl or esterified carboxymethyl), Z is selected from i) —O—R$_9$ wherein R$_9$ is H, C$_1$ to C$_5$ alkyl, phenyl, substituted phenyl, benzyl or substituted benzyl;

ii)

wherein Q is H, C$_1$ to C$_5$ hydrocarbyl, or —R$_{10}$—U, wherein R$_{10}$ is a bond or C$_1$ to C$_3$ alkylene and U is aryl, substituted aryl, heterocyclic, substituted heterocyclic or cycloalkyl;

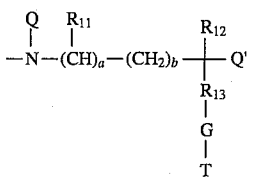

iii)

wherein a is 0 or 1 and b is from 0 to 3,

R$_{11}$ is H or methyl,

R$_{12}$ is H or C$_1$ to C$_3$ alkyl; or R$_{12}$ is CH$_2$= and Q' is absent; or R$_{11}$ and R$_{12}$ are linked to form a 3- to 7-membered ring, R$_{13}$ is a bond or C$_1$ to C$_5$ hydrocarbylene, G is a bond, —CHOH— or —C(O)—

Q' is as recited above for Q or —R$_{10}$—(C(O))$_d$—L—(C(O))$_e$—R$_9$ (wherein R$_9$ and R$_{10}$ are as defined above, L is O, S or —N(R$_{14}$)—, in which R$_{14}$ is as defined above for R$_8$, and d and e are 0 or 1, provided that d+e<2); or Q' and R$_{12}$, together with the carbon atom to which they are attached, form a 3- to 7-membered ring, Q is as defined above; or Q and R$_{12}$ together form a group of the formula —(CH$_2$)$_f$—V—(CH$_2$)$_g$— wherein V is —S—, —S(O)—, —S(O)$_2$—, —CH$_2$—, or —C(O)—, f is from 0 to 2 and g is from 0 to 3; or, when Q' is —R$_{10}$—U and U is an aromatic group, Q may additionally represent a methylene link to U, which link is ortho to the R$_{10}$ link to U, T is H, cyano, C$_1$ to C$_4$ alkyl, —CH$_2$OH, carboxy, esterified carboxy or amidated carboxy; or iv)

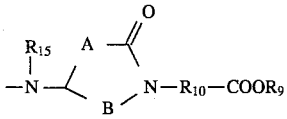

wherein A and B are independently a bond or C$_1$ to C$_3$ alkylene, provided that A and B together provide from 2 to 4 carbon atoms in the ring, R$_9$ and R$_{10}$ are as defined above, and R$_{15}$ is as defined above for R$_8$ or Z is absent and W is H, R$_1$ is H, methyl, halo, carboxy, esterified carboxy, amidated carboxy, carboxymethyl, esterified carboxymethyl or amidated carboxymethyl, R$_2$ is selected from the groups recited above for R$_1$; or, when Z is absent and W is H, R$_2$ may additionally represent —C(O)—Z' wherein Z' is selected from the groups recited above for Z; or R$_1$ and R$_2$ together form a second bond between the carbon atoms to which they are attached, R$_3$ and R$_4$ (or each R$_3$ and R$_4$ group, when m or n is 2 or more) are independently selected from halo, amino, nitro, cyano, sulphamoyl, sulphonyl, trifluoromethyl, C$_1$ to C$_3$ alkyl, C$_1$ to C$_3$ alkoxy, hydroxy, C$_1$ to C$_3$ hydroxyalkyl, C$_1$ to C$_3$ alkylcarboxyamino, carboxy, esterified carboxy and amidated carboxy, R$_5$ and R$_6$ are independently selected from H and the groups recited above for R$_3$ m is from 0 to 4, provided that m is not more than 2 unless R$_1$ is exclusively halo, n is from 0 to 4, provided that n is not more than 2 unless R$_4$ is exclusively halo, or a pharmaceutically acceptable salt thereof, provided that
if one (but only one) of $R_1$ and $R_2$ is methyl, m and n are not both 0, Z is not hydroxy or methoxy when Y is hydroxy or methoxy, Z and Y are not trans to each other when Z is $R_8$—O— and Y is $R_7$—O—, —X—Y is not equal to —W—Z when $R_1$=$R_2$=H and m=n=0, and if Z is absent and $R_1$ and $R_2$ are both H or form part of a double bond, Y is not $R_7$—O—, and further provided that said compound is not 7-(N,N-dimethylaminocarbonyl)-8-methyl-2,3,5,6-dibenzobicyclo[2.2.2]octane or 7-(N-methyl-N-phenylaminocarbonyl)-8-methyl-2,3,5,6-dibenzobicyclo[2.2.2]octane.

2. A compound according to claim 1 wherein $R_7$ is $C_6$ to $C_8$ straight or branched chain alkyl, or $R_{25}$-$(CH_2)_p$-, wherein $R_{25}$ is selected from phenyl, 1-naphthyl, 2-naphthyl, indoyl, norbornyl, adamantyl or cyclohexyl, and p is from 0 to 3.

3. A compound according to claim 1 wherein W is carbonyl and X is sulphonyl.

4. A compound according to claim 1 wherein W is carbonyl and X is carbonyl.

5. A compound according to claim 1 wherein W is sulphonyl and X is carbonyl.

6. A compound according to claim 1 wherein $R_1$ and $R_2$ are both H.

7. A compound according to claim 1 wherein m and n are both 0.

8. A compound according to claim 1 of the formula

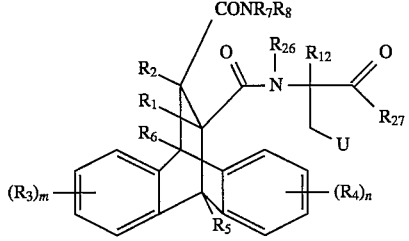

wherein $R_1$, $R_2$, $R_3$, $R_4$, $R_5$, $R_6$, $R_7$, $R_8$, $R_{12}$ and U are as defined in claim 1, $R_{26}$ is H or $C_1$ to $C_3$ alkyl, and $R_{27}$ is

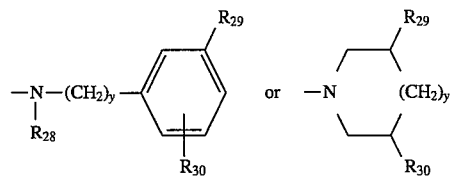

(wherein $R_{28}$ is H or $C_1$ to $C_3$ alkyl, $R_{29}$ is —$CO_2H$ or tetrazolyl, $R_{30}$ is H, —$CO_2H$, tetrazolyl, —$CH_2OH$, —$CO_2Me$ or —$CONH_2$, and y is from 0 to 2), or a pharmaceutically acceptable salt thereof.

9. A pharmaceutical composition comprising a compound according to claim 8, together with a pharmaceutically acceptable diluent or carrier.

10. A pharmaceutical composition comprising a compound according to claim 1, together with a pharmaceutically acceptable diluent or carrier.

11. A compound according to claim 1 of the formula

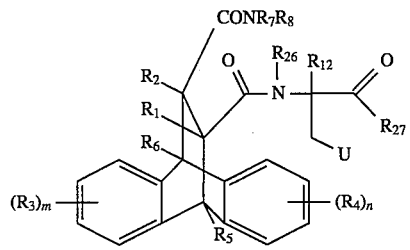

wherein $R_1$, $R_2$, $R_3$, $R_4$, $R_5$, $R_6$, $R_7$, $R_8$, $R_{12}$ and U are as defined in claim 1, $R_{26}$ is H or $C_1$ to $C_3$ alkyl and $R_{27}$ is

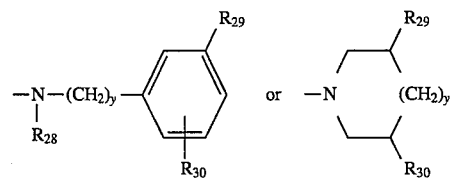

wherein $R_{28}$ is H or $C_1$ to $C_3$ alkyl, $R_{29}$ is esterified carboxy or amidated carboxy and $R_{30}$ is H, —$CO_2H$, esterified carboxy, amidated carboxy, tetrazolyl or —$CH_2OH$, or $R_{29}$ is —$CO_2H$ or tetrazolyl and $R_{30}$ is esterified carboxy or amidated carboxy, and y is 0, 1 or 2, or a pharmaceutically acceptable salt thereof.

12. A method for counteracting an effect of cholecystokinin or gastrin in a patient, said method comprising administering to said patient an effective amount of a compound of the formula

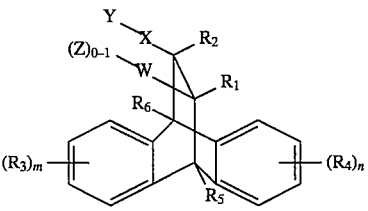

wherein

W is a carbonyl, sulphonyl or sulphinyl group, or, W is H when Z is absent and X is a carbonyl, sulphonyl or sulphinyl group or —C(O)—$CH_2$—(in which the carbonyl group is bonded to Y), provided that at least one of W and X contains carbonyl, Y is $R_7$—O— or $R_7$—N($R_8$)— (wherein $R_7$ is H or $C_1$ to $C_{15}$ hydrocarbyl, up to two carbon atoms of the hydrocarbyl moiety optionally being replaced by a nitrogen, oxygen or sulphur atom provided that Y does not contain a —O—O— group, and $R_8$ is H, $C_1$ to $C_3$ alkyl, carboxymethyl or esterified carboxymethyl), Z is selected from
i) —O—$R_9$
wherein
$R_9$ is H, $C_1$ to $C_5$ alkyl, phenyl, substituted phenyl, benzyl or substituted benzyl;

ii)

wherein Q is H, $C_1$ to $C_5$ hydrocarbyl, or $-R_{10}-U$, wherein $R_{10}$ is a bond or $C_1$ to $C_3$ alkylene and U is aryl, substituted aryl, heterocyclic, substituted heterocyclic or cycloalkyl;

iii)

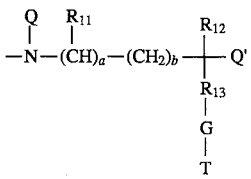

wherein a is 0 or 1 and b is from 0 to 3,
$R_{11}$ is H or methyl,
$R_{12}$ is H or $C_1$ to $C_3$ alkyl; or $R_{12}$ is $CH_2=$ and Q' is absent; or $R_{11}$ and $R_{12}$ are linked to form a 3- to 7- membered ring,
$R_{13}$ is a bond or $C_1$ to $C_5$ hydrocarbylene, G is a bond, —CHOH— or —C(O)—
Q' is as recited above for Q or $-R_{10}-(C(O))_d-$L$-(C(O))_e-R_9$ (wherein $R_9$ and $R_{10}$ are as defined above, L is O, S or $-N(R_{14})-$, in which $R_{14}$ is as defined above for $R_8$, and d and e are 0 or 1, provided that d+e<2); or Q' and $R_{12}$, together with the carbon atom to which they are attached, form a 3- to 7-membered ring,
Q is as defined above; or Q and $R_{12}$ together form a group of the formula $-(CH_2)_f-V-(CH_2)_g-$ wherein V is —S—, —S(O)—, $-S(O)_2-$, $-CH_2-$, —CHOH— or —C(O)—, f is from 0 to 2 and g is from 0 to 3; or, when Q' is $-R_{10}-U$ and U is an aromatic group, Q may additionally represent a methylene link to U, which link is ortho to the $R_{10}$ link to U,
T is H, cyano, $C_1$ to $C_4$ alkyl, $-CH_2OH$, carboxy, esterified carboxy or amidated carboxy; or iv)

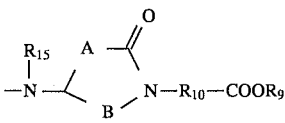

wherein A and B are independently a bond or $C_1$ to $C_3$ alkylene, provided that A and B together provide from 2 to 4 carbon atoms in the ring, $R_9$ and $R_{10}$ are as defined above, and $R_{15}$ is as defined above for $R_8$
or Z is absent and W is H,
$R_1$ is H, methyl, halo, carboxy, esterified carboxy, amidated carboxy, carboxymethyl, esterified carboxymethyl or amidated carboxymethyl,
$R_2$ is selected from the groups recited above for $R_1$; or, when Z is absent and W is H, $R_2$ may additionally represent $-C(O)-Z'$ wherein Z' is selected from the groups recited above for Z; or $R_1$ and $R_2$ together form a second bond between the carbon atoms to which they are attached, $R_3$ and $R_4$ (or each $R_3$ and $R_4$ group, when m or n is 2 or more) are independently selected from halo, amino, nitro, cyano, sulphamoyl, sulphonyl, trifluoromethyl, $C_1$ to $C_3$ alkyl, $C_1$ to $C_3$ alkoxy, hydroxy, $C_1$ to $C_3$ hydroxyalkyl, $C_1$ to $C_3$ alkylcarboxyamino, carboxy, esterified carboxy and amidated carboxy
$R_5$ and $R_6$ are independently selected from H and the groups recited above for $R_3$
m is from 0 to 4, provided that m is not more than 2 unless $R_3$ is exclusively halo,
n is from 0 to 4, provided that n is not more than 2 unless $R_4$ is exclusively halo,
or a pharmaceutically acceptable salt thereof.

13. A method according to claim 12 wherein $R_7$ is $C_6$ to $C_8$ straight or branched chain alkyl or cycloalkyl, or $R_{25}-(CH_2)_p-$, wherein $R_{25}$ is selected from phenyl, 1-naphthyl, 2-naphthyl, indolyl, norbornyl, 1-adamantyl, 2-adamantyl, cyclohexyl or cycloheptyl, and p is from 0 to 3.

14. A method according to claim 12 wherein W is carbonyl and X is sulphonyl.

15. A method according to claim 12 wherein W is carbonyl and X is carbonyl.

16. A method according to claim 12 wherein W is sulphonyl and X is carbonyl.

17. A method according to claim 12 wherein $R_1$ and $R_2$ are both H.

18. A method according to claim 12 wherein m and n are both 0.

19. A method according to claim 12 comprising administering to said patient an effective amount of a compound of the formula

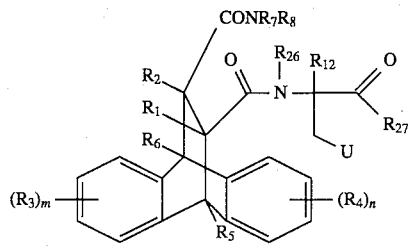

wherein
$R_1$, $R_2$, $R_3$, $R_4$, $R_5$, $R_6$, $R_7$, $R_8$, $R_{12}$ and U are as defined in claim 12,
$R_{26}$ is H or $C_1$ to $C_3$ alkyl, and
$R_{27}$ is

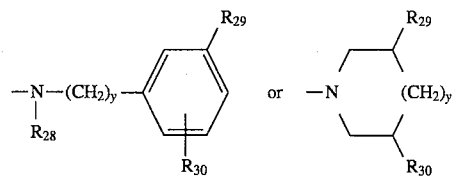

(wherein $R_{28}$ is H or $C_1$ to $C_3$ alkyl, $R_{29}$ is $-CO_2H$ or tetrazolyl, $R_{30}$ is H, $-CO_2H$, tetrazolyl, $-CH_2OH$, $-CO_2Me$ or $-CONH_2$, and y is from 0 to 2).

* * * * *